US010874625B2

(12) United States Patent
Turano et al.

(10) Patent No.: US 10,874,625 B2
(45) Date of Patent: *Dec. 29, 2020

(54) METHODS FOR THE BIOSYNTHESIS OF TAURINE OR HYPOTAURINE IN CELLS

(71) Applicant: PLANT SENSORY SYSTEMS LLC, Baltimore, MD (US)

(72) Inventors: Frank J. Turano, Baltimore, MD (US); Kathleen A. Turano, Baltimore, MD (US); Peter S. Carlson, Baltimore, MD (US); Alan M. Kinnersley, Baltimore, MD (US)

(73) Assignee: PLANT SENSORY SYSTEMS, LLC, Baltimore, MD (US)

( * ) Notice: Subject to any disclaimer, the term of this patent is extended or adjusted under 35 U.S.C. 154(b) by 158 days.

This patent is subject to a terminal disclaimer.

(21) Appl. No.: 16/154,204

(22) Filed: Oct. 8, 2018

(65) Prior Publication Data

US 2019/0060256 A1 Feb. 28, 2019

Related U.S. Application Data

(63) Continuation-in-part of application No. 14/993,519, filed on Jan. 12, 2016, now Pat. No. 10,092,527, which is a continuation of application No. 13/505,415, filed as application No. PCT/US2010/054664 on Oct. 29, 2010, now Pat. No. 9,267,148.

(60) Provisional application No. 61/263,548, filed on Nov. 23, 2009, provisional application No. 61/257,240, filed on Nov. 2, 2009.

(51) Int. Cl.
| C12N 15/70 | (2006.01) |
| A61K 31/145 | (2006.01) |
| C12N 15/82 | (2006.01) |
| A61K 31/185 | (2006.01) |
| A23K 20/10 | (2016.01) |
| A23K 10/12 | (2016.01) |
| C12N 9/02 | (2006.01) |
| C12P 13/00 | (2006.01) |
| A23L 33/10 | (2016.01) |
| A23L 33/175 | (2016.01) |
| C12P 11/00 | (2006.01) |

(52) U.S. Cl.
CPC .......... A61K 31/145 (2013.01); A23K 10/12 (2016.05); A23K 20/10 (2016.05); A23L 33/10 (2016.08); A23L 33/175 (2016.08); A61K 31/185 (2013.01); C12N 9/0069 (2013.01); C12N 15/8243 (2013.01); C12N 15/8251 (2013.01); C12N 15/8253 (2013.01); C12N 15/8261 (2013.01); C12N 15/8271 (2013.01); C12N 15/8273 (2013.01); C12N 15/8279 (2013.01); C12P 11/00 (2013.01); C12P 13/001 (2013.01); A23V 2002/00 (2013.01); C12Y 113/1102 (2013.01); Y02A 40/146 (2018.01); Y02A 50/30 (2018.01)

(58) Field of Classification Search
CPC .................................................. A61K 31/145
See application file for complete search history.

(56) References Cited

U.S. PATENT DOCUMENTS

| 6,998,422 B2 * | 2/2006 | Ohsawa ................. A61K 31/22 514/548 |
| 10,092,527 B2 * | 10/2018 | Turano ................. A61K 31/185 |
| 2009/0183270 A1 | 7/2009 | Adams et al. |

FOREIGN PATENT DOCUMENTS

| WO | 02/38736 A2 | 5/2002 |
| WO | 2007044043 A2 | 4/2007 |
| WO | 2009009142 A2 | 1/2009 |

OTHER PUBLICATIONS

Gaylord, T.G. et al. Aquaculture (2007) vol. 269, pp. 514-524. (Year: 2007).*
Honjoh et al., Amino Acids 38:1173-1183, 2009 (Year: 2009).*
Honjoh, K. et al., "Enhancement of Menadione Stress Tolerance in Yeast by Accumulation of Hypotaurine and Taurine: Co-expression of cDNA Clones, from Cyprinus Carpio, for Cysteine Dioxygenase and Cysteine Sulfinate Decarboxlase in *Saccharomyces cerevisiae*," Amino Acids, 2010, vol. 38, pp. 1173-1183, © Springer-Verlag 2009.
Stipanuk, M.H. et al., "Mammalian Cysteine Metabolism: New Insights into Regulation of Cysteine Metabolism," Journal of Nutrition, vol. 136, No. 6, Suppl. S, Jun. 2006, pp. 1652S-1659S, XP-002626793, © 2006 American Society for Nutrition.

(Continued)

Primary Examiner — Russell Kallis
(74) Attorney, Agent, or Firm — Rothwell, Figg, Ernst & Manbeck, P.C.

(57) ABSTRACT

The present invention describes an approach to increase taurine or hypotaurine production in prokaryotes. More particularly, the invention relates to genetic transformation of organisms with genes that encode proteins that catalyze the conversion of cysteine to taurine, methionine to taurine, cysteamine to taurine, or alanine to taurine. The invention describes methods for the use of polynucleotides that encode cysteine dioxygenase (CDO) and sulfinoalanine decarboxylase (SAD) polypeptides in prokaryotes to increase taurine, hypotaurine or taurine precursor production. The preferred embodiment of the invention is in plants but other organisms may be used. Increased taurine production in prokaryotes could be used as nutraceutical, pharmaceutical, or therapeutic compounds or as a supplement in animal feed.

15 Claims, 1 Drawing Sheet
Specification includes a Sequence Listing.

(56) References Cited

OTHER PUBLICATIONS

De La Rosa, J. et al., "Evidence for a Rate-Limiting Role of Cysteinesulfinate Decarboxylase Activity in Taurine Biosynthesis In Vivo," Comparative Biochemistry and Physiology, B. Comparative Biochemistry, vol. 81, No. 3, pp. 565-571, ©1985 Pergamon Press Ltd.
Flinn, J.E. et al., "Green Plants as Biofactories for Drugs," Biopharm International, Advanstar Communications, Duluth, MN, US, vol. 17, No. 8, Aug. 1, 2004, pp. 42-49, XP009109706.
Beyer, P., "Golden Rice: Introducing the β-Carotene Biosynthesis Pathway into Rice Endosperm by Genetic Engineering to Defeat Vitamin A Deficiency," Journal of Nutrition, vol. 132, No. 3, Mar. 1, 2002, pp. 506S-510S, XP001069128, © 2002 American Society for Nutritional Services.
Lahdesmaki, P., "Determination of Taurine and Other Acidic Amino-Acids in Plants," Phytochemistry (Oxford), vol. 25, No. 10, 1986, pp. 2409-2411, XP002626795, Pergamon Journals Ltd.
Stintzing, F.C., "Amino Acid Composition and Betaxanthin Formation in Fruits From Opuntia ficus-Indica," Planta Medica, vol. 65, No. 7, Oct. 1999, pp. 632-635, XP002626796, © Georg Thieme Verlag Stutgart-New York.
Haas. F. et al., Plant Physiology (Oct. 2008) vol. 148, pp. 1055-1067.
Feugang, J.M. et al., Frontiers in Bioscience (Sep. 1, 2006), vol. 11, pp. 2574-2589.
Tevatia, R. et al., Algal Research 2015, vol. 9, pp. 21-26.
Agnello, G. et al., ACS Chem Biol. Oct. 18, 2013; vol. 8, No. 10 pp. 1-17.
Gaylord, T.G. et al. Aquaculture (2007) vol. 269, pp. 514-524.

\* cited by examiner

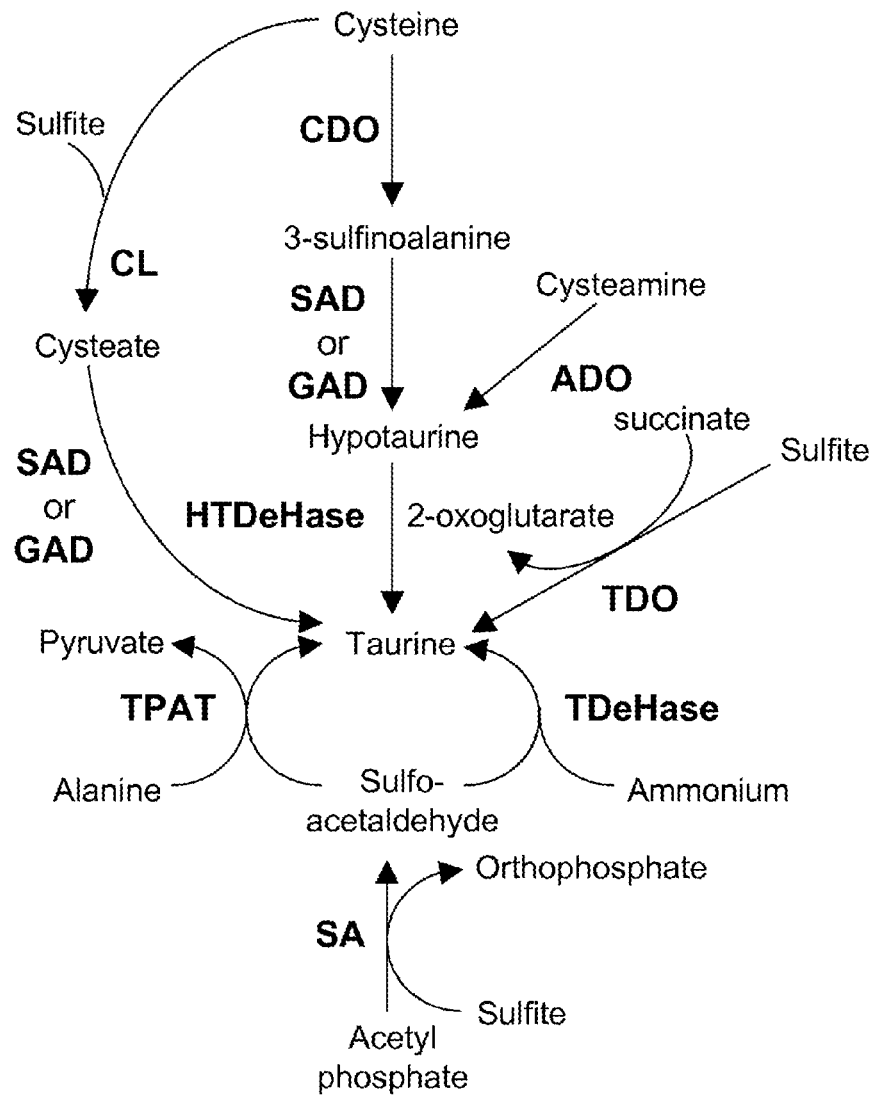

SEQUENCE LISTING

<160> NUMBER OF SEQ ID NOS: 128

<210> SEQ ID NO 1
<211> LENGTH: 603
<212> TYPE: DNA
<213> ORGANISM: Bos taurus

<400> SEQUENCE: 1

```
atggagcgga ccgaggtgct aaagcccgc accctggccg atctgatccg cgtcctgcac      60
cagctcttcg ccggcgagga gatcaacgtg gaggaagtgc aggccgtcat ggaagcctat     120
gagagcaacc ccgccgagtg ggcagtgtac gccaagttcg accagtacag gtatactcga     180
aatcttgtgg atcaaggaaa tggaaagttt aatctcatga ttctatgctg gggtgaagga     240
catggcagca gtatccatga tcacaccgac tcccactgct ttctgaagat gctgcaggga     300
aatctaaagg agacattgtt tgcctggcct gacaagaaat ccaatgagat gatcaagaag     360
tctgaaagaa tcttgaggga aaaccagtgt gcctacatca tgattccat ggcttacat      420 cgagtagaga atattagcca tacagagcct gccgtgagcc ttcacttgta tagtccgcct     480
tttgacacat gccacgcctt tgatcaaaga acaggacata aaaacaaagt catcatgaca     540
ttccatagca aatttggaat caagactcca tttacaactt caggatccct ggagaacaac     600
taa                                                                   603

<210> SEQ ID NO 2
<211> LENGTH: 606
<212> TYPE: DNA
<213> ORGANISM: Zebrafish

<400> SEQUENCE: 2
atggagcaga ctgaagtcat gaagcccgag actctggagg atctgatcaa aactctgcat      60
cagatcttcc agagcgactc catcaatgtg gaggaggtgc agaacctgat ggagtcctac     120
cagagcaacc cgcaggactg gatgaagttc gccaagttcg accagtacag gtacaccagg     180
aacctcgtgg atgaaggaaa cggaaagttc aacctgatga tcctgtgctg ggtgaagga      240 cacggcagca gcatccatga ccacacagac tcgcactgct tcctgaagct gctgcagggt     300
cagctgaagg agacgctgtt cgactggccc gaccgcaagc tgcagagcgg catgaagccc     360
cgcggccaga gcgtgctgca ggagaaccag tgcgcgtaca tcaacgactc tctgggactc     420
caccgtgtgg agaatgtgag ccacacagag ccggccgtga gtctgcacct ttacagtcct     480
ccgttccaga gctgccgcac gtttgaccag cgcaccggac accacaacac cgtcaagatg     540
accttctgga gcaaatatgg cgagaggacg ccctatgagc tgagcgtctc gcaggagaat     600
aactga                                                                606

<210> SEQ ID NO 3
<211> LENGTH: 200
<212> TYPE: PRT
<213> ORGANISM: Bos taurus

<400> SEQUENCE: 3

Met Glu Arg Thr Glu Val Leu Lys Pro Arg Thr Leu Ala Asp Leu Ile
1               5                   10                  15

Arg Val Leu His Gln Leu Phe Ala Gly Glu Glu Ile Asn Val Glu Glu
                20                  25                  30

Val Gln Ala Val Met Glu Ala Tyr Glu Ser Asn Pro Ala Glu Trp Ala
            35                  40                  45

Val Tyr Ala Lys Phe Asp Gln Tyr Arg Tyr Thr Arg Asn Leu Val Asp
        50                  55                  60

Gln Gly Asn Gly Lys Phe Asn Leu Met Ile Leu Cys Trp Gly Glu Gly
65                  70                  75                  80

His Gly Ser Ser Ile His Asp His Thr Asp Ser His Cys Phe Leu Lys
                85                  90                  95

Met Leu Gln Gly Asn Leu Lys Glu Thr Leu Phe Ala Trp Pro Asp Lys
```

```
            100                 105                 110
Lys Ser Asn Glu Met Ile Lys Lys Ser Glu Arg Ile Leu Arg Glu Asn
        115                 120                 125

Gln Cys Ala Tyr Ile Asn Asp Ser Ile Gly Leu His Arg Val Glu Asn
        130                 135                 140

Ile Ser His Thr Glu Pro Ala Val Ser Leu His Leu Tyr Ser Pro Pro
145                 150                 155                 160

Phe Asp Thr Cys His Ala Phe Asp Gln Arg Thr Gly His Lys Asn Lys
                165                 170                 175

Val Ile Met Thr Phe His Ser Lys Phe Gly Ile Lys Thr Pro Phe Thr
                    180                 185                 190

Thr Ser Gly Ser Leu Glu Asn Asn
        195                 200

<210> SEQ ID NO 4
<211> LENGTH: 201
<212> TYPE: PRT
<213> ORGANISM: Zebrafish

<400> SEQUENCE: 4

Met Glu Gln Thr Glu Val Met Lys Pro Glu Thr Leu Glu Asp Leu Ile
1               5                   10                  15

Lys Thr Leu His Gln Ile Phe Gln Ser Asp Ser Ile Asn Val Glu Glu
            20                  25                  30

Val Gln Asn Leu Met Glu Ser Tyr Gln Ser Asn Pro Gln Asp Trp Met
        35                  40                  45

Lys Phe Ala Lys Phe Asp Gln Tyr Arg Tyr Thr Arg Asn Leu Val Asp
    50                  55                  60

Glu Gly Asn Gly Lys Phe Asn Leu Met Ile Leu Cys Trp Gly Glu Gly
65                  70                  75                  80

His Gly Ser Ser Ile His Asp His Thr Asp Ser His Cys Phe Leu Lys
                85                  90                  95

Leu Leu Gln Gly Gln Leu Lys Glu Thr Leu Phe Asp Trp Pro Asp Arg
            100                 105                 110

Lys Leu Gln Ser Gly Met Lys Pro Arg Gly Gln Ser Val Leu Gln Glu
        115                 120                 125

Asn Gln Cys Ala Tyr Ile Asn Asp Ser Leu Gly Leu His Arg Val Glu
    130                 135                 140

Asn Val Ser His Thr Glu Pro Ala Val Ser Leu His Leu Tyr Ser Pro
145                 150                 155                 160

Pro Phe Gln Ser Cys Arg Thr Phe Asp Gln Arg Thr Gly His His Asn
                165                 170                 175

Thr Val Lys Met Thr Phe Trp Ser Lys Tyr Gly Glu Arg Thr Pro Tyr
                180                 185                 190

Glu Leu Ser Val Ser Gln Glu Asn Asn
        195                 200

<210> SEQ ID NO 5
<211> LENGTH: 1482
<212> TYPE: DNA
<213> ORGANISM: Equus

<400> SEQUENCE: 5
atggctgact ctgaaccgct cctctcccct gatggggacc ccgtggctgc agaagccttg      60
ctccgggatg tgtttgggat cattgtggat gaggtcattc ggaaagggac cagtgcctcc     120
```

-continued

| | | |
|---|---|---|
| gagaaggtct gcgagtggaa ggagccggag gagctgaagc agctgctgga tttggagctg | 180 |
| cggagccatg gggagtcacg ggagcagatc ctggagcggt gccgggctgt catccgctac | 240 |
| agcgtgaaga cctgtcaccc tcacttcttc aaccagctct tctcagggtt ggatccccac | 300 |
| gctctggccg ggcgcattgt caccgagagc cttaacacca gccagtacac ttatgaaatc | 360 |
| gcccccgtgt ttgtgctcat ggaagaagag gtcctgaaga aactccgggc gctggtgggc | 420 |
| tggagctctg gcgatggggt cttctgccct ggtggctcca tctccaacat gtatgctgtg | 480 |
| aacctggccc gctatcagcg ctaccggat tgcaagcaga ggggcctccg ggcactgccg | 540 |
| cccctggccc tcttcacatc gaaggagtgt cattactcca tcaagaaggg agctgctttt | 600 |
| ctgggacttg gcactgacag tgtccgagtg gtcaaggcag atgagagagg gaaaatgatc | 660 |
| cctgaggatc tggagaggca gatcagtctg gccgaggcgg agggtgctgt gccattcctg | 720 |
| gtcactgcca cctctggcac gaccgtgctg ggggcctttg atcccctgga ggcgattgct | 780 |
| gatgtgtgcc agcgtcatgg gctgtggctg catgtggacg ccgcctgggg tgggagtgtc | 840 |
| ctgctctcac agacacacag acatctcctg gctgggatcc agagggcgga ctccgtggcc | 900 |
| tggaatcccc acaagctcct cacagcaggc ctgcagtgct cagctctcct gctccgggat | 960 |
| acctcgaacc tgctcaagcg ctgccacggg tcccaggcca gctacctctt ccagcaggac | 1020 |
| aagttctacg acgtggctct ggacacagga gacaaggtgg tgcagtgcgg ccgccgcgtg | 1080 |
| gactgtctga gctgtggct catgtggaag gcccagggcg ggcaagggct ggagcagcga | 1140 |
| gtggaccagg ccttcgccct tgcccggtac ctggtggagg aattgaagaa gcgggaagga | 1200 |
| tttgagttgg ttatggagcc tgagtttgtc aacgtgtgtt tctggttcgt cccgcccagc | 1260 |
| ctgcggggga acaggggag tccagattat gctgaaaggc ttgccaaggt ggccccggta | 1320 |
| cttaaagagc gcatggtgaa ggagggctcc atgatggttg gctaccagcc ccacgggacc | 1380 |
| cggggcaact ttttccgcat ggttgtggcc aacccggctc tgacccaggc tgatatggac | 1440 |
| ttcttcctca atgagctgga acggctaggc caggacctct ga | 1482 |

<210> SEQ ID NO 6
<211> LENGTH: 1449
<212> TYPE: DNA
<213> ORGANISM: Zebrafish

<400> SEQUENCE: 6

| | | |
|---|---|---|
| atggacgagt ctgatgggaa gctgttcctt actgaggctt caacataat catggaagaa | 60 |
| attcttaaca aggaaggga cttgaaggag aaggtttgtg agtggaaaga tccagatcag | 120 |
| ctgagatctc tcctggacct cgaacttcgg gatcatggag aatgtcatga aagctgctg | 180 |
| cagagggttc gagatgtggc caaatacagc gtaaaaactt gtcatcctcg gttcttcaat | 240 |
| cagctgtttg ctggcgtgga ctatcatgca ctgacaggac ggctcatcac tgaaaccctc | 300 |
| aataccagcc aatacaccta tgaagtggct ccagtgtttg tcctgatgga ggaggaagtg | 360 |
| atcagtaagc ttcgctctct ggttggctgg tcagaaggag atgggatctt tgtcctgga | 420 |
| ggatccatgt ctaacatgta tgccattaac gtcgctcggt actgggcttt tcctcaagtg | 480 |
| aagacaaaag gcttgtgggc cgcaccacgg atggctatat ttacatcaca acagagtcat | 540 |
| tactccgtga aaaaggagc tgcgtttctt ggtattggaa cagaaaatgt tttcattgtg | 600 |
| caagtggatg agagcggcag catgatacca gaagacctgg aggcaaaaat tgtgcaggca | 660 |
| aaatcccaag acgctgttcc gttttttcgta aacgccacag ccggaaccac agtgcaggga | 720 |
| gccttttgacc ctctgaagcg catagctgac atatgtgaaa gaaacggcat gtggatgcat | 780 |

```
gttgacgccg catggggagg aagcgtgctg ttttccaaaa agcacagaca tctggttgca      840
ggaatagaaa gagcaaactc ggtgacttgg aatcctcaca aaatgcttct gacgggactg      900
cagtgctctg tgattttgtt cagagatact acgaatttgc tcatgcactg tcacagtgcc      960
aaagccacat acttgttcca gcaagacaag ttctacgaca caagtctgga cacgggcgac     1020
aaatccatcc agtgtggccg aaggtggat tgcctcaagc tctggctcat gtggaaggca      1080
atcggagcta gtggtctttc acagcgtgtc gataaggcct ttgccctcac taggtattta     1140
gttgaagaaa tggagaaacg ggagaatttc cagctggtct gtaagggggcc gtttgtgaac    1200 gtttgcttct ggtttattcc acccagtctg aaaggaaagg agaacagccc agattaccag     1260
gaaagactat ccaaggtggc gccagtcatt aaagagagga tgatgaagcg aggaacgatg     1320
atggtgggat atcagccaat ggatgaacac gtcaacttct ccgcatggt ggttgtttct      1380 ccacagctca aaccaaaga catggatttc ttccttgatg agatggagaa actcgggaag     1440
gatctatga                                                             1449
```

<210> SEQ ID NO 7
<211> LENGTH: 493
<212> TYPE: PRT
<213> ORGANISM: Equus

<400> SEQUENCE: 7

```
Met Ala Asp Ser Glu Pro Leu Leu Ser Leu Asp Gly Asp Pro Val Ala
1               5                   10                  15

Ala Glu Ala Leu Leu Arg Asp Val Phe Gly Ile Ile Val Asp Glu Val
            20                  25                  30

Ile Arg Lys Gly Thr Ser Ala Ser Glu Lys Val Cys Glu Trp Lys Glu
        35                  40                  45

Pro Glu Glu Leu Lys Gln Leu Leu Asp Leu Glu Leu Arg Ser His Gly
    50                  55                  60

Glu Ser Arg Glu Gln Ile Leu Glu Arg Cys Arg Ala Val Ile Arg Tyr
65                  70                  75                  80

Ser Val Lys Thr Cys His Pro His Phe Phe Asn Gln Leu Phe Ser Gly
                85                  90                  95

Leu Asp Pro His Ala Leu Ala Gly Arg Ile Val Thr Glu Ser Leu Asn
            100                 105                 110

Thr Ser Gln Tyr Thr Tyr Glu Ile Ala Pro Val Phe Val Leu Met Glu
        115                 120                 125

Glu Glu Val Leu Lys Lys Leu Arg Ala Leu Val Gly Trp Ser Ser Gly
    130                 135                 140

Asp Gly Val Phe Cys Pro Gly Gly Ser Ile Ser Asn Met Tyr Ala Val
145                 150                 155                 160

Asn Leu Ala Arg Tyr Gln Arg Tyr Pro Asp Cys Lys Gln Arg Gly Leu
                165                 170                 175

Arg Ala Leu Pro Pro Leu Ala Leu Phe Thr Ser Lys Glu Cys His Tyr
            180                 185                 190

Ser Ile Lys Lys Gly Ala Ala Phe Leu Gly Leu Gly Thr Asp Ser Val
        195                 200                 205

Arg Val Val Lys Ala Asp Glu Arg Gly Lys Met Ile Pro Glu Asp Leu
    210                 215                 220

Glu Arg Gln Ile Ser Leu Ala Glu Ala Glu Gly Ala Val Pro Phe Leu
225                 230                 235                 240

Val Thr Ala Thr Ser Gly Thr Thr Val Leu Gly Ala Phe Asp Pro Leu
```

```
                    245                 250                 255
Glu Ala Ile Ala Asp Val Cys Gln Arg His Gly Leu Trp Leu His Val
                260                 265                 270

Asp Ala Ala Trp Gly Gly Ser Val Leu Leu Ser Gln Thr His Arg His
            275                 280                 285

Leu Leu Ala Gly Ile Gln Arg Ala Asp Ser Val Ala Trp Asn Pro His
        290                 295                 300

Lys Leu Leu Thr Ala Gly Leu Gln Cys Ser Ala Leu Leu Leu Arg Asp
305                 310                 315                 320

Thr Ser Asn Leu Leu Lys Arg Cys His Gly Ser Gln Ala Ser Tyr Leu
                325                 330                 335

Phe Gln Gln Asp Lys Phe Tyr Asp Val Ala Leu Asp Thr Gly Asp Lys
            340                 345                 350

Val Val Gln Cys Gly Arg Arg Val Asp Cys Leu Lys Leu Trp Leu Met
        355                 360                 365

Trp Lys Ala Gln Gly Gly Gln Gly Leu Glu Gln Arg Val Asp Gln Ala
370                 375                 380

Phe Ala Leu Ala Arg Tyr Leu Val Glu Glu Leu Lys Lys Arg Glu Gly
385                 390                 395                 400

Phe Glu Leu Val Met Glu Pro Glu Phe Val Asn Val Cys Phe Trp Phe
                405                 410                 415

Val Pro Pro Ser Leu Arg Gly Lys Gln Gly Ser Pro Asp Tyr Ala Glu
            420                 425                 430

Arg Leu Ala Lys Val Ala Pro Val Leu Lys Glu Arg Met Val Lys Glu
        435                 440                 445

Gly Ser Met Met Val Gly Tyr Gln Pro His Gly Thr Arg Gly Asn Phe
    450                 455                 460

Phe Arg Met Val Val Ala Asn Pro Ala Leu Thr Gln Ala Asp Met Asp
465                 470                 475                 480

Phe Phe Leu Asn Glu Leu Glu Arg Leu Gly Gln Asp Leu
                485                 490

<210> SEQ ID NO 8
<211> LENGTH: 482
<212> TYPE: PRT
<213> ORGANISM: Zebrafish

<400> SEQUENCE: 8

Met Asp Glu Ser Asp Gly Lys Leu Phe Leu Thr Glu Ala Phe Asn Ile
1               5                   10                  15

Ile Met Glu Glu Ile Leu Asn Lys Gly Arg Asp Leu Lys Glu Lys Val
                20                  25                  30

Cys Glu Trp Lys Asp Pro Asp Gln Leu Arg Ser Leu Leu Asp Leu Glu
            35                  40                  45

Leu Arg Asp His Gly Glu Cys His Glu Lys Leu Leu Gln Arg Val Arg
        50                  55                  60

Asp Val Ala Lys Tyr Ser Val Lys Thr Cys His Pro Arg Phe Phe Asn
65                  70                  75                  80

Gln Leu Phe Ala Gly Val Asp Tyr His Ala Leu Thr Gly Arg Leu Ile
                85                  90                  95

Thr Glu Thr Leu Asn Thr Ser Gln Tyr Thr Tyr Glu Val Ala Pro Val
            100                 105                 110

Phe Val Leu Met Glu Glu Val Ile Ser Lys Leu Arg Ser Leu Val
        115                 120                 125
```

-continued

Gly Trp Ser Glu Gly Asp Gly Ile Phe Cys Pro Gly Gly Ser Met Ser
130                 135                 140

Asn Met Tyr Ala Ile Asn Val Ala Arg Tyr Trp Ala Phe Pro Gln Val
145                 150                 155                 160

Lys Thr Lys Gly Leu Trp Ala Ala Pro Arg Met Ala Ile Phe Thr Ser
            165                 170                 175

Gln Gln Ser His Tyr Ser Val Lys Lys Gly Ala Ala Phe Leu Gly Ile
            180                 185                 190

Gly Thr Glu Asn Val Phe Ile Val Gln Val Asp Glu Ser Gly Ser Met
            195                 200                 205

Ile Pro Glu Asp Leu Glu Ala Lys Ile Val Gln Ala Lys Ser Gln Asp
210                 215                 220

Ala Val Pro Phe Phe Val Asn Ala Thr Ala Gly Thr Thr Val Gln Gly
225                 230                 235                 240

Ala Phe Asp Pro Leu Lys Arg Ile Ala Asp Ile Cys Glu Arg Asn Gly
            245                 250                 255

Met Trp Met His Val Asp Ala Ala Trp Gly Gly Ser Val Leu Phe Ser
            260                 265                 270

Lys Lys His Arg His Leu Val Ala Gly Ile Glu Arg Ala Asn Ser Val
            275                 280                 285

Thr Trp Asn Pro His Lys Met Leu Leu Thr Gly Leu Gln Cys Ser Val
290                 295                 300

Ile Leu Phe Arg Asp Thr Thr Asn Leu Leu Met His Cys His Ser Ala
305                 310                 315                 320

Lys Ala Thr Tyr Leu Phe Gln Gln Asp Lys Phe Tyr Asp Thr Ser Leu
            325                 330                 335

Asp Thr Gly Asp Lys Ser Ile Gln Cys Gly Arg Lys Val Asp Cys Leu
            340                 345                 350

Lys Leu Trp Leu Met Trp Lys Ala Ile Gly Ala Ser Gly Leu Ser Gln
            355                 360                 365

Arg Val Asp Lys Ala Phe Ala Leu Thr Arg Tyr Leu Val Glu Glu Met
            370                 375                 380

Glu Lys Arg Glu Asn Phe Gln Leu Val Cys Lys Gly Pro Phe Val Asn
385                 390                 395                 400

Val Cys Phe Trp Phe Ile Pro Pro Ser Leu Lys Gly Lys Glu Asn Ser
            405                 410                 415

Pro Asp Tyr Gln Glu Arg Leu Ser Lys Val Ala Pro Val Ile Lys Glu
            420                 425                 430

Arg Met Met Lys Arg Gly Thr Met Met Val Gly Tyr Gln Pro Met Asp
            435                 440                 445

Glu His Val Asn Phe Phe Arg Met Val Val Ser Pro Gln Leu Thr
            450                 455                 460

Thr Lys Asp Met Asp Phe Phe Leu Asp Glu Met Glu Lys Leu Gly Lys
465                 470                 475                 480

Asp Leu

<210> SEQ ID NO 9
<211> LENGTH: 1401
<212> TYPE: DNA
<213> ORGANISM: E. coli

<400> SEQUENCE: 9
atggataaga agcaagtaac ggatttaagg tcggaactac tcgattcacg ttttggtgcg      60
aagtctattt ccactatcgc agaatcaaaa cgttttccgc tgcacgaaat gcgcgacgat     120

```
gtcgcattcc agattatcaa tgacgaatta tatcttgatg caacgctcg tcagaacctg      180 gccactttct gccagacctg ggacgacgaa aatgtccaca aattgatgga tttatccatt    240
aacaaaaact ggatcgacaa agaagaatat ccgcaatccg cagccatcga cctgcgttgc    300
gtaaatatgg ttgccgatct gtggcatgcg cctgcgccga aaatggtca ggccgttggc     360 accaacacca ttggttcttc cgaggcctgt atgctcggcg ggatggcgat gaaatggcgt    420
tggcgcaagc gtatggaagc tgcaggcaaa ccaacggata aaccaaacct ggtgtgcggt    480
ccggtacaaa tctgctggca taaattcgcc cgctactggg atgtggagct gcgtgagatc    540
cctatgcgcc ccggtcagtt gtttatggac ccgaaacgca tgattgaagc ctgtgacgaa    600
aacaccatcg gcgtggtgcc gactttcggc gtgacctaca ctggtaacta tgagttccca    660
caaccgctgc acgatgcgct ggataaattc caggccgata ccggtatcga catcgacatg    720
cacatcgacg ctgccagcgg tggcttcctg gcaccgttcg tcgccccgga tatcgtctgg    780
gacttccgcc tgccgcgtgt gaaatcgatc agtgcttcag gccataaatt cggtctggct    840
ccgctgggct gcggctgggt tatctggcgt gacgaagaag cgctgccgca ggaactggtg    900
ttcaacgttg actacctggg tggtcaaatt ggtacttttg ccatcaactt ctcccgcccg    960
gcgggtcagg taattgcaca gtactatgaa ttcctgcgcc tcggtcgtga aggctatacc   1020
aaagtacaga cgcctctta ccaggttgcc gcttatctgg cggatgaaat cgccaaactg    1080
gggccgtatg agttcatctg tacgggtcgc ccggacgaag gcatcccggc ggtttgcttc    1140
aaactgaaag atggtgaaga tccgggatac accctgtatg acctctctga acgtctgcgt    1200
ctgcgcggct ggcaggttcc ggccttcact ctcggcggtg aagccaccga catcgtggtg    1260
atgcgcatta tgtgtcgtcg cggcttcgaa atggactttg ctgaactgtt gctggaagac    1320
tacaaagcct ccctgaaata tctcagcgat cacccgaaac tgcagggtat tgcccaacag    1380
aacagcttta aacatacctg a                                              1401

<210> SEQ ID NO 10
<211> LENGTH: 1485
<212> TYPE: DNA
<213> ORGANISM: Arabidopsis

<400> SEQUENCE: 10
atggttttga caaaaaccgc aacgaatgat gaatctgtct gcaccatgtt cggatctcgc     60
tatgttcgca ctacacttcc caagtatgag attggtgaga attcgatacc gaaagacgct   120
gcatatcaga tcataaaaga tgagctgatg cttgatggta acccgaggct taacctagct   180
tcgtttgtga ctacatggat ggaaccagag tgtgacaaac tcatcatgga ctctatcaac   240
aagaactacg ttgatatgga tgagtaccct gtcacaactg agctccagaa ccgatgtgta   300
aacattatag ctcgactgtt caatgcgcca ctcgaggaat ctgagacggc ggtgggagta   360
gggacagttg gttcttcaga agccatcatg ttagccggat tggccttcaa agaaaatgg    420 cagaacaaac gcaaggctga gggtaaaccc tatgacaaac ccaacattgt cactggagcc    480
aatgttcaag tttgctggga gaaattcgct cggtacttcg aggtggagct aaaggaagta    540
aacctaagtg aaggttacta cgtgatggat ccagacaaag cagcagaaat ggtagacgag    600
aacacaatct gtgtcgcagc catattggga tccacactca cggtgagtt cgaagacgtg     660 aaacgtctca atgacttgct agtcaagaaa aacgaggaga ctggttggaa cacaccgatc    720
cacgtggatg cagcaagtgg agggttcata gctccgtttta tctatcctga attagaatgg    780
```

```
gactttagac ttcctttggt taagagtatc aacgtgagtg gtcacaagta tggactggtc    840
tatgctggta ttggttgggt cgtgtggagg gcagcagagg atttgcctga agagcttatc    900
tttcatatta attatcttgg tgctgatcaa cccactttca ctctcaattt ctccaaggga    960
tcgagccaaa ttattgctca atactaccag ctcattcgtc ttggattcga ggggtacaaa   1020
aatgtgatgg agaattgcat agagaacatg gtggttctca agaagggat agagaaaaca    1080 gagcgtttca acatagtctc aaaggaccaa ggagtgccag tcgtagcctt ctctctcaag   1140
gaccatagtt tccacaacga gttcgagatc tctgagatgc tacgtcgttt tggctggatc   1200
gtcccagctt acactatgcc tgccgatgca cagcacatca cggttctgcg tgttgtcatc   1260
agggaagatt tctcaagaac actcgcggag agacttgttg ctgatatttc gaaggtgctt   1320
catgagctag ataccttgcc ttccaagata tctaagaaga tgggaataga agggatcgcg   1380
gaaaatgtaa aggagaagaa gatggagaag gagattctga tggaagttat tgttggatgg   1440
aggaagtttg tgaaggagag gaagaagatg aatggtgtgt gctaa                  1485
```

<210> SEQ ID NO 11
<211> LENGTH: 466
<212> TYPE: PRT
<213> ORGANISM: E. coli

<400> SEQUENCE: 11

```
Met Asp Lys Lys Gln Val Thr Asp Leu Arg Ser Glu Leu Leu Asp Ser
1               5                   10                  15

Arg Phe Gly Ala Lys Ser Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Arg Lys Arg
    130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255
```

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
            275                 280                 285

Trp Arg Asp Glu Glu Ala Leu Pro Gln Glu Leu Val Phe Asn Val Asp
290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
            325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
            355                 360                 365

Gly Arg Pro Asp Glu Gly Ile Pro Ala Val Cys Phe Lys Leu Lys Asp
            370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
            405                 410                 415

Asp Ile Val Val Met Arg Ile Met Cys Arg Arg Gly Phe Glu Met Asp
            420                 425                 430

Phe Ala Glu Leu Leu Leu Glu Asp Tyr Lys Ala Ser Leu Lys Tyr Leu
            435                 440                 445

Ser Asp His Pro Lys Leu Gln Gly Ile Ala Gln Gln Asn Ser Phe Lys
            450                 455                 460

His Thr
465

<210> SEQ ID NO 12
<211> LENGTH: 494
<212> TYPE: PRT
<213> ORGANISM: Arabidopsis

<400> SEQUENCE: 12

Met Val Leu Thr Lys Thr Ala Thr Asn Asp Glu Ser Val Cys Thr Met
1               5                   10                  15

Phe Gly Ser Arg Tyr Val Arg Thr Thr Leu Pro Lys Tyr Glu Ile Gly
            20                  25                  30

Glu Asn Ser Ile Pro Lys Asp Ala Ala Tyr Gln Ile Ile Lys Asp Glu
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Ile Met Asp Ser Ile Asn
65              70                  75                  80

Lys Asn Tyr Val Asp Met Asp Glu Tyr Pro Val Thr Thr Glu Leu Gln
            85                  90                  95

Asn Arg Cys Val Asn Ile Ile Ala Arg Leu Phe Asn Ala Pro Leu Glu
            100                 105                 110

Glu Ser Glu Thr Ala Val Gly Val Gly Thr Val Gly Ser Ser Glu Ala
            115                 120                 125

Ile Met Leu Ala Gly Leu Ala Phe Lys Arg Lys Trp Gln Asn Lys Arg
        130                 135                 140

Lys Ala Glu Gly Lys Pro Tyr Asp Lys Pro Asn Ile Val Thr Gly Ala

```
                    145                 150                 155                 160
Asn Val Gln Val Cys Trp Glu Lys Phe Ala Arg Tyr Phe Glu Val Glu
                165                 170                 175

Leu Lys Glu Val Asn Leu Ser Glu Gly Tyr Tyr Val Met Asp Pro Asp
                180                 185                 190

Lys Ala Ala Glu Met Val Asp Glu Asn Thr Ile Cys Val Ala Ala Ile
                195                 200                 205

Leu Gly Ser Thr Leu Asn Gly Glu Phe Glu Asp Val Lys Arg Leu Asn
            210                 215                 220

Asp Leu Leu Val Lys Lys Asn Glu Glu Thr Gly Trp Asn Thr Pro Ile
225                 230                 235                 240

His Val Asp Ala Ala Ser Gly Gly Phe Ile Ala Pro Phe Ile Tyr Pro
                245                 250                 255

Glu Leu Glu Trp Asp Phe Arg Leu Pro Leu Val Lys Ser Ile Asn Val
                260                 265                 270

Ser Gly His Lys Tyr Gly Leu Val Tyr Ala Gly Ile Gly Trp Val Val
                275                 280                 285

Trp Arg Ala Ala Glu Asp Leu Pro Glu Glu Leu Ile Phe His Ile Asn
            290                 295                 300

Tyr Leu Gly Ala Asp Gln Pro Thr Phe Thr Leu Asn Phe Ser Lys Gly
305                 310                 315                 320

Ser Ser Gln Ile Ile Ala Gln Tyr Tyr Gln Leu Ile Arg Leu Gly Phe
                325                 330                 335

Glu Gly Tyr Lys Asn Val Met Glu Asn Cys Ile Glu Asn Met Val Val
                340                 345                 350

Leu Lys Glu Gly Ile Glu Lys Thr Glu Arg Phe Asn Ile Val Ser Lys
                355                 360                 365

Asp Gln Gly Val Pro Val Val Ala Phe Ser Leu Lys Asp His Ser Phe
            370                 375                 380

His Asn Glu Phe Glu Ile Ser Glu Met Leu Arg Arg Phe Gly Trp Ile
385                 390                 395                 400

Val Pro Ala Tyr Thr Met Pro Ala Asp Ala Gln His Ile Thr Val Leu
                405                 410                 415

Arg Val Val Ile Arg Glu Asp Phe Ser Arg Thr Leu Ala Glu Arg Leu
                420                 425                 430

Val Ala Asp Ile Ser Lys Val Leu His Glu Leu Asp Thr Leu Pro Ser
            435                 440                 445

Lys Ile Ser Lys Lys Met Gly Ile Gly Ile Ala Glu Asn Val Lys
        450                 455                 460

Glu Lys Lys Met Glu Lys Glu Ile Leu Met Glu Val Ile Val Gly Trp
465                 470                 475                 480

Arg Lys Phe Val Lys Glu Arg Lys Lys Met Asn Gly Val Cys
                485                 490

<210> SEQ ID NO 13
<211> LENGTH: 813
<212> TYPE: DNA
<213> ORGANISM: Suis

<400> SEQUENCE: 13
atgccccgag acaacatggc ctccctgatc caacggatcg cccgccaggc atgcctcacc      60
ttccggggca gcgggggcgg ccgcagctct tccgatcgcg gcgcggcgcc aggccctgag     120
gcgcctgtgc cgcagggctt cccggagaac ctgagcaagc tgaagagcct gctgacacag     180
```

```
gtccgcgcag aggacctgaa catctccccg cgcaaggcca cgctgcagcc gttgccaccc      240
aacctgccgc ccgtcaccta tatgcacatc tacgagactg acggcttcag cctcggcgtg      300
ttcttgctta agagcggcac atccatcccg ctccacgacc accctggcat gcatggcatg      360
ctcaaggtgc tctatggcac cgtgcgcatc agctgcatgg acaagctgga ggcaggcagc      420
gggcaacggc cgcgggcccc gccaccagag cagcagttcg aaccgccgct gctggcccgg      480
gagcgggacg cggtgcggcc gggagtgctg cgctcgcggg ccgagtacac tgaggccagc      540
ggtccctgcg tcctcacgcc gcaccgggac aacctgcacc agatcgacgc tgtggatggg      600
cctgccgcct tcttggatat cctggccccg ccctacgacc cggacgacgg ccgggactgt      660
cactattacc gggtgctgga gcctgtcagg gccaaagagg cctccgactc ggcctgtgac      720
ctgccccgag aggtgtggct tctggagacc ccgcaggccg atgacttttg gtgcgagggg      780
gagccctatc caggtcccag ggtcttccct tga                                   813

<210> SEQ ID NO 14
<211> LENGTH: 750
<212> TYPE: DNA
<213> ORGANISM: Zebrafish

<400> SEQUENCE: 14
atgacttcca cagtccagaa aatcgccaaa caggccctcg caacattccg aaacccgtct      60
gtcatcggcg agcacaacaa agtgttttg gagaaccaaa gcaagctgaa aagcctcttg       120
gcggaggtca gagcggcgga cttgaagatc gcagcccgga cccccgagag cgccccggtg      180
ccgcatcagc gcatcgctcc tcccgtcaca tacatgcata tctgcgagac cgactccttc      240
agcatggggg tgtttctgct gaaaacgggg gcttcgatac ccctgcacga ccatccgggg      300
atgtacggca tgctgaaggt gatctacggg aaggtgcgga tcagttgttt cgaccgcctg      360
gataaaccga gagacggcgc cagcggcgtg cagttcaacc ctccgctcat gcccttccag      420
aggggctcct acggccctc agtgctgaag tccgtcgggg agttcacaga ggacagcagc      480
ccgtgtgtgc tctcacccca gcaggacaat atccaccaga tagacgctgt tgacggaccc      540
accgctttcc tggacatctt agcacccccg tacgacccag acgaagggag agactgccat      600
tattataaag ttttgcaagc tcattcagag gctgcagata aaaagagtga agtccaggat      660
caaggggacg tgtggctaat ggaaataccc cagcctagtg aattttggtg tggtggtgaa      720
ccatacccag ggcctaaagt gaccctctga                                       750

<210> SEQ ID NO 15
<211> LENGTH: 270
<212> TYPE: PRT
<213> ORGANISM: Suis

<400> SEQUENCE: 15

Met Pro Arg Asp Asn Met Ala Ser Leu Ile Gln Arg Ile Ala Arg Gln
1               5                   10                  15

Ala Cys Leu Thr Phe Arg Gly Ser Gly Gly Arg Ser Ser Ser Asp
            20                  25                  30

Arg Gly Ala Ala Pro Gly Pro Glu Ala Pro Val Pro Gln Gly Phe Pro
        35                  40                  45

Glu Asn Leu Ser Lys Leu Lys Ser Leu Leu Thr Gln Val Arg Ala Glu
    50                  55                  60

Asp Leu Asn Ile Ser Pro Arg Lys Ala Thr Leu Gln Pro Leu Pro Pro
65                  70                  75                  80
```

```
Asn Leu Pro Pro Val Thr Tyr Met His Ile Tyr Glu Thr Asp Gly Phe
                85                  90                  95

Ser Leu Gly Val Phe Leu Leu Lys Ser Gly Thr Ser Ile Pro Leu His
            100                 105                 110

Asp His Pro Gly Met His Gly Met Leu Lys Val Leu Tyr Gly Thr Val
        115                 120                 125

Arg Ile Ser Cys Met Asp Lys Leu Glu Ala Gly Ser Gly Gln Arg Pro
    130                 135                 140

Arg Ala Pro Pro Pro Glu Gln Gln Phe Glu Pro Leu Leu Ala Arg
145                 150                 155                 160

Glu Arg Asp Ala Val Arg Pro Gly Val Leu Arg Ser Arg Ala Glu Tyr
                165                 170                 175

Thr Glu Ala Ser Gly Pro Cys Val Leu Thr Pro His Arg Asp Asn Leu
            180                 185                 190

His Gln Ile Asp Ala Val Asp Gly Pro Ala Ala Phe Leu Asp Ile Leu
        195                 200                 205

Ala Pro Pro Tyr Asp Pro Asp Gly Arg Asp Cys His Tyr Tyr Arg
    210                 215                 220

Val Leu Glu Pro Val Arg Ala Lys Glu Ala Ser Asp Ser Ala Cys Asp
225                 230                 235                 240

Leu Pro Arg Glu Val Trp Leu Leu Glu Thr Pro Gln Ala Asp Asp Phe
                245                 250                 255

Trp Cys Glu Gly Glu Pro Tyr Pro Gly Pro Arg Val Phe Pro
            260                 265                 270

<210> SEQ ID NO 16
<211> LENGTH: 249
<212> TYPE: PRT
<213> ORGANISM: Zebrafish

<400> SEQUENCE: 16

Met Thr Ser Thr Val Gln Lys Ile Ala Lys Gln Ala Leu Ala Thr Phe
1               5                   10                  15

Arg Asn Pro Ser Val Ile Gly Glu His Asn Lys Val Phe Leu Glu Asn
                20                  25                  30

Gln Ser Lys Leu Lys Ser Leu Leu Ala Glu Val Arg Ala Ala Asp Leu
            35                  40                  45

Lys Ile Ala Ala Arg Thr Pro Glu Ser Ala Pro Val Pro His Gln Arg
    50                  55                  60

Ile Ala Pro Pro Val Thr Tyr Met His Ile Cys Glu Thr Asp Ser Phe
65                  70                  75                  80

Ser Met Gly Val Phe Leu Leu Lys Thr Gly Ala Ser Ile Pro Leu His
                85                  90                  95

Asp His Pro Gly Met Tyr Gly Met Leu Lys Val Ile Tyr Gly Lys Val
            100                 105                 110

Arg Ile Ser Cys Phe Asp Arg Leu Asp Lys Pro Arg Asp Gly Ala Ser
        115                 120                 125

Gly Val Gln Phe Asn Pro Pro Leu Met Pro Phe Gln Arg Gly Ser Leu
    130                 135                 140

Arg Pro Ser Val Leu Lys Ser Val Gly Glu Phe Thr Glu Asp Ser Ser
145                 150                 155                 160

Pro Cys Val Leu Ser Pro Gln Gln Asp Asn Ile His Gln Ile Asp Ala
                165                 170                 175

Val Asp Gly Pro Thr Ala Phe Leu Asp Ile Leu Ala Pro Pro Tyr Asp
            180                 185                 190
```

Pro Asp Glu Gly Arg Asp Cys His Tyr Tyr Lys Val Leu Gln Ala His
        195                 200                 205

Ser Glu Ala Ala Asp Lys Lys Ser Glu Val Gln Asp Gln Gly Asp Val
    210                 215                 220

Trp Leu Met Glu Ile Pro Gln Pro Ser Glu Phe Trp Cys Gly Gly Glu
225                 230                 235                 240

Pro Tyr Pro Gly Pro Lys Val Thr Leu
                245

<210> SEQ ID NO 17
<211> LENGTH: 1392
<212> TYPE: DNA
<213> ORGANISM: Roseobacter denitrificans

<400> SEQUENCE: 17

| | |
|---|---|
| atggacggca atttcaatga aaatgatatc tcccgcgtcg tcgaagcaga ccgcgcgcat | 60 |
| atctggcacc atctgagcca gcacaaacct tacgagacaa cagacccgcg catcattgtc | 120 |
| gaaggcaagg gcatgaaggt ttgggaccag aagggcaaag agcatcttga tgccgtctcc | 180 |
| ggtggggtct ggaccgtcaa tgtcggctat ggccgcgaac gcatcgccaa cgccgtgcgg | 240 |
| gaccagttgg tcaagttgaa ctatttcgcc ggctccgcag gctccatccc cggtgccatg | 300 |
| ttcgccgagc gtctgatcga aagatgccg gggctgagcc gcgtttatta ctgcaattcc | 360 |
| ggctccgagg cgaatgaaaa agccttcaag atggtccgcc agatcgcgca caaacgctat | 420 |
| ggcggcaaaa agcacaaggt gctttatcgc gagcgtgact atcacggcac caccatttcc | 480 |
| gcccttccg caggcgggca ggacgaacgg aacgcacaat atggcccctt cacgcccggt | 540 |
| ttcgtgcgcg tgccccattg ccttgaatac cgcgcctttg aacaggaagg ggcgccacag | 600 |
| gaaaactacg gtgtctgggc ggcggatcag atcgaaaagg taatcctcgc cgaagggccc | 660 |
| gataccgtgg gcggcctgtg ccttgaaccg gtcactgcag gtggcggggt gatcacgccc | 720 |
| cccgatggct actgggagcg tgtgcaggaa atctgccaca atacgacat cctgctgcat | 780 |
| atcgacgagg tcgtatgcgg cgtcggtcgg accggcacat ggttcggcta tcagcactac | 840 |
| ggcatccagc cggatatggt cacgatggcc aagggtgtcg cgtccggtta cgcggcgatc | 900 |
| gcctgccttg tgaccaatga aaaagtcttc gacatgttca aggatgacgc ctcggatccg | 960 |
| ctgaactact tccgcgacat ctcgaccttt ggggctgca cggcgggtcc ggcagctgcg | 1020 |
| ctggaaaacc tgtcgatcat cgaagaagaa ggcctgctgg acaacaccac ggaacagggg | 1080 |
| gcctatatgc tcgactgtct gggcggcttg atggacaagc acaagatcat cggccaggtg | 1140 |
| cgcggcaagg ggctgttcct cggtgccgaa ctggtcgagg atcgcgacac gcgcaaaccg | 1200 |
| gttgacgaaa ggctcgcgca agcggtggtc gcggactgca tgcaacaggg tgtgatcatc | 1260 |
| ggcgtgacca accgctctct gccgggcaag aacaacacgc tgtgtttctc gcccgccctg | 1320 |
| atcgccagca aggatgacat tgaccacatc tgcgacgcgg tggacggtgc gctgtcgcgc | 1380 |
| gttttcggct aa | 1392 |

<210> SEQ ID NO 18
<211> LENGTH: 463
<212> TYPE: PRT
<213> ORGANISM: Roseobacter denitrificans

<400> SEQUENCE: 18

Met Asp Gly Asn Phe Asn Glu Asn Asp Ile Ser Arg Val Val Glu Ala
1               5                   10                  15

Asp Arg Ala His Ile Trp His His Leu Ser Gln His Lys Pro Tyr Glu
            20                  25                  30

Thr Thr Asp Pro Arg Ile Ile Val Glu Gly Lys Gly Met Lys Val Trp
            35                  40                  45

Asp Gln Lys Gly Lys Glu His Leu Asp Ala Val Ser Gly Gly Val Trp
50                  55                  60

Thr Val Asn Val Gly Tyr Gly Arg Glu Arg Ile Ala Asn Ala Val Arg
65                  70                  75                  80

Asp Gln Leu Val Lys Leu Asn Tyr Phe Ala Gly Ser Ala Gly Ser Ile
                85                  90                  95

Pro Gly Ala Met Phe Ala Glu Arg Leu Ile Glu Lys Met Pro Gly Leu
            100                 105                 110

Ser Arg Val Tyr Tyr Cys Asn Ser Gly Ser Glu Ala Asn Glu Lys Ala
            115                 120                 125

Phe Lys Met Val Arg Gln Ile Ala His Lys Arg Tyr Gly Gly Lys Lys
            130                 135                 140

His Lys Val Leu Tyr Arg Glu Arg Asp Tyr His Gly Thr Thr Ile Ser
145                 150                 155                 160

Ala Leu Ser Ala Gly Gly Gln Asp Glu Arg Asn Ala Gln Tyr Gly Pro
                165                 170                 175

Phe Thr Pro Gly Phe Val Arg Val Pro His Cys Leu Glu Tyr Arg Ala
            180                 185                 190

Phe Glu Gln Glu Gly Ala Pro Gln Glu Asn Tyr Gly Val Trp Ala Ala
            195                 200                 205

Asp Gln Ile Glu Lys Val Ile Leu Ala Glu Gly Pro Asp Thr Val Gly
            210                 215                 220

Gly Leu Cys Leu Glu Pro Val Thr Ala Gly Gly Val Ile Thr Pro
225                 230                 235                 240

Pro Asp Gly Tyr Trp Glu Arg Val Gln Glu Ile Cys His Lys Tyr Asp
                245                 250                 255

Ile Leu Leu His Ile Asp Glu Val Val Cys Gly Val Gly Arg Thr Gly
            260                 265                 270

Thr Trp Phe Gly Tyr Gln His Tyr Gly Ile Gln Pro Asp Met Val Thr
            275                 280                 285

Met Ala Lys Gly Val Ala Ser Gly Tyr Ala Ala Ile Ala Cys Leu Val
290                 295                 300

Thr Asn Glu Lys Val Phe Asp Met Phe Lys Asp Asp Ala Ser Asp Pro
305                 310                 315                 320

Leu Asn Tyr Phe Arg Asp Ile Ser Thr Phe Gly Gly Cys Thr Ala Gly
                325                 330                 335

Pro Ala Ala Ala Leu Glu Asn Leu Ser Ile Ile Glu Glu Gly Leu
            340                 345                 350

Leu Asp Asn Thr Thr Glu Gln Gly Ala Tyr Met Leu Asp Cys Leu Gly
            355                 360                 365

Gly Leu Met Asp Lys His Lys Ile Ile Gly Gln Val Arg Gly Lys Gly
            370                 375                 380

Leu Phe Leu Gly Ala Glu Leu Val Glu Asp Arg Asp Thr Arg Lys Pro
385                 390                 395                 400

Val Asp Glu Arg Leu Ala Gln Ala Val Val Ala Asp Cys Met Gln Gln
                405                 410                 415

Gly Val Ile Ile Gly Val Thr Asn Arg Ser Leu Pro Gly Lys Asn Asn
            420                 425                 430

```
Thr Leu Cys Phe Ser Pro Ala Leu Ile Ala Ser Lys Asp Asp Ile Asp
        435                 440                 445

His Ile Cys Asp Ala Val Asp Gly Ala Leu Ser Arg Val Phe Gly
    450                 455                 460

<210> SEQ ID NO 19
<211> LENGTH: 1779
<212> TYPE: DNA
<213> ORGANISM: Roseobacter denitrificans

<400> SEQUENCE: 19
atgaaaatga ccactgaaga agcctttgta aaaaccctgc aagcgcatgg tatcgaacac      60
gccttcggga ttatcggctc ggccatgatg ccgatctccg acattttccc cgatgcgggc     120
atcaaattct gggactgcgc gcatgaaggt tccgcaggca tgatgtctga cggttacacc     180
cgcgccaccg gcaaagtgtc gatgatgatc gcgcagaacg gccccggcat caccaatttc     240
gtgaccgccg tcaaaaccgc ctactggaac cacacgccgc ttctgctcgt gacgccgcaa     300
gccgcgaaca agaccatcgg tcagggcggt tttcaggaag tcgaacagat gaaactcttc     360
gaggacatgg tcgcttatca ggaagaggtg cgcgacccga cccgtgtggc cgaggtcctg     420
acccgcgtga ttgccaaggc aaaacgcctc agcggcccgg cgcagatcaa catcccgcgt     480
gatttctgga cgcaggtggt cgacatcgaa atccccgacc cgattgaatt cgaagcctcc     540
ccgggcggtg aaaactccgt tgcgcaagcc gccgagatgc tctccaacgc caagaatccg     600
gtgatcctga cggggcgggc gtggtcctg tcaaaaggcg gcatcgacgc ctcccgcctt     660
ctggcagaac gtctggatgc ccccgtctgc gtgggctatc agcacaatga cgcctttccc     720
ggcaaccatc cgctctttgc cggaccactt ggatacaacg gttccaaagc gggcatgcag     780
ctgatcaagg aagccgacgt ggttctgtgc ctcggcacgc gtctcaaccc gttttcgacc     840
ctgcccggct atggcatcga ctattggccc gcagatgcga aaatcattca ggtggacatc     900 aacccccgacc ggatcggcct gaccaagaag gtctcggtcg ggatcgtcgg cgatgcagca     960
aaggtggcca aggggatcct gtcgcagctc tcggacaccg caggcgacga gggccgcgag    1020
gcgcgcaaag cccatatcgc ccagacaaaa tccgcatggg cgcaggagtt gacctcgctc    1080
acccacgagc aggacgatcc gggcaccgac tggaacgtgc gcgcacgcgc ggccaagcct    1140
gactggatga cccccgcat ggcgtggcgc gcaatccaga gcgcgctgcc ggtggaggcg    1200
atcatttcat ccgacatcgg caacaactgc gccatcggca cgcctacccc ggccttcgaa    1260 gagggggcgca agtatctcgc cgcgggtctc ttcggtccct cggctacgg cctgcccgcc    1320 attgtcggcg ccaagatcgg tcagccccat gtgccggttg tgggtttcgc aggtgacggg    1380
gcctttggca tcgccgtcaa cgaattgacc gccatcggcc gtggtgagtg gcccgcgatc    1440
acgcagatcg tgttccgcaa ctaccagtgg ggcgctgaaa agcgcaactc gaccctgtgg    1500
ttcgaagaca acttcgtcgg caccgagctt gacgaggaag tctcctacgc tggcatcgcc    1560
aatgcgtgcg gcctcaaagg cgtcgtcgcc cgcacgcagg aggaactgac agatgccctc    1620
aacgaggcga tcaaggacca gatggaaaac ggcatcacca cgctgatcga ggccatgatc    1680
aatcaggaac tcggcgatcc cttccgccgc gacgcgatga aaaagcctgt tcaggttgct    1740
gggatcagca aatccgacat gcgtccacag actgtctga                           1779

<210> SEQ ID NO 20
<211> LENGTH: 592
<212> TYPE: PRT
<213> ORGANISM: Roseobacter denitrificans
```

<400> SEQUENCE: 20

Met Lys Met Thr Thr Glu Glu Ala Phe Val Lys Thr Leu Gln Ala His
1               5                   10                  15

Gly Ile Glu His Ala Phe Gly Ile Ile Gly Ser Ala Met Met Pro Ile
            20                  25                  30

Ser Asp Ile Phe Pro Asp Ala Gly Ile Lys Phe Trp Asp Cys Ala His
        35                  40                  45

Glu Gly Ser Ala Gly Met Met Ser Asp Gly Tyr Thr Arg Ala Thr Gly
    50                  55                  60

Lys Val Ser Met Met Ile Ala Gln Asn Gly Pro Gly Ile Thr Asn Phe
65                  70                  75                  80

Val Thr Ala Val Lys Thr Ala Tyr Trp Asn His Thr Pro Leu Leu Leu
                85                  90                  95

Val Thr Pro Gln Ala Ala Asn Lys Thr Ile Gly Gln Gly Gly Phe Gln
            100                 105                 110

Glu Val Glu Gln Met Lys Leu Phe Glu Asp Met Val Ala Tyr Gln Glu
        115                 120                 125

Glu Val Arg Asp Pro Thr Arg Val Ala Glu Val Leu Thr Arg Val Ile
    130                 135                 140

Ala Lys Ala Lys Arg Leu Ser Gly Pro Ala Gln Ile Asn Ile Pro Arg
145                 150                 155                 160

Asp Phe Trp Thr Gln Val Val Asp Ile Glu Ile Pro Asp Pro Ile Glu
                165                 170                 175

Phe Glu Ala Ser Pro Gly Gly Glu Asn Ser Val Ala Gln Ala Ala Glu
            180                 185                 190

Met Leu Ser Asn Ala Lys Asn Pro Val Ile Leu Asn Gly Ala Gly Val
        195                 200                 205

Val Leu Ser Lys Gly Gly Ile Asp Ala Ser Arg Leu Leu Ala Glu Arg
    210                 215                 220

Leu Asp Ala Pro Val Cys Val Gly Tyr Gln His Asn Asp Ala Phe Pro
225                 230                 235                 240

Gly Asn His Pro Leu Phe Ala Gly Pro Leu Gly Tyr Asn Gly Ser Lys
                245                 250                 255

Ala Gly Met Gln Leu Ile Lys Glu Ala Asp Val Val Leu Cys Leu Gly
            260                 265                 270

Thr Arg Leu Asn Pro Phe Ser Thr Leu Pro Gly Tyr Gly Ile Asp Tyr
        275                 280                 285

Trp Pro Ala Asp Ala Lys Ile Ile Gln Val Asp Ile Asn Pro Asp Arg
    290                 295                 300

Ile Gly Leu Thr Lys Lys Val Ser Val Gly Ile Val Gly Asp Ala Ala
305                 310                 315                 320

Lys Val Ala Lys Gly Ile Leu Ser Gln Leu Ser Asp Thr Ala Gly Asp
                325                 330                 335

Glu Gly Arg Glu Ala Arg Lys Ala His Ile Ala Gln Thr Lys Ser Ala
            340                 345                 350

Trp Ala Gln Glu Leu Thr Ser Leu Thr His Glu Gln Asp Asp Pro Gly
        355                 360                 365

Thr Asp Trp Asn Val Arg Ala Arg Ala Lys Pro Asp Trp Met Ser
    370                 375                 380

Pro Arg Met Ala Trp Arg Ala Ile Gln Ser Ala Leu Pro Val Glu Ala
385                 390                 395                 400

Ile Ile Ser Ser Asp Ile Gly Asn Asn Cys Ala Ile Gly Asn Ala Tyr

```
            405                 410                 415
Pro Ala Phe Glu Glu Gly Arg Lys Tyr Leu Ala Pro Gly Leu Phe Gly
            420                 425                 430

Pro Cys Gly Tyr Gly Leu Pro Ala Ile Val Gly Ala Lys Ile Gly Gln
        435                 440                 445

Pro His Val Pro Val Val Gly Phe Ala Gly Asp Gly Ala Phe Gly Ile
    450                 455                 460

Ala Val Asn Glu Leu Thr Ala Ile Gly Arg Gly Glu Trp Pro Ala Ile
465                 470                 475                 480

Thr Gln Ile Val Phe Arg Asn Tyr Gln Trp Gly Ala Glu Lys Arg Asn
                485                 490                 495

Ser Thr Leu Trp Phe Glu Asp Asn Phe Val Gly Thr Glu Leu Asp Glu
            500                 505                 510

Glu Val Ser Tyr Ala Gly Ile Ala Asn Ala Cys Gly Leu Lys Gly Val
        515                 520                 525

Val Ala Arg Thr Gln Glu Glu Leu Thr Asp Ala Leu Asn Glu Ala Ile
    530                 535                 540

Lys Asp Gln Met Glu Asn Gly Ile Thr Thr Leu Ile Glu Ala Met Ile
545                 550                 555                 560

Asn Gln Glu Leu Gly Asp Pro Phe Arg Arg Asp Ala Met Lys Lys Pro
                565                 570                 575

Val Gln Val Ala Gly Ile Ser Lys Ser Asp Met Arg Pro Gln Thr Val
            580                 585                 590

<210> SEQ ID NO 21
<211> LENGTH: 387
<212> TYPE: DNA
<213> ORGANISM: Roseobacter denitrificans

<400> SEQUENCE: 21
atgaccaaaa cactgacagc tcaggacttg tccgacacct ttgacgcctt caatcgccat    60
gacgttgatg gcgtcatgac acatttcgcc gatgattgcg tgttctacac cgtgggcggg   120
gatgaagcct atggcgccaa agtcgaaggc gcagaagcga ttgccaaagc attctctgcc   180
gtctgggcgg gcatgaagga cgcccattgg gatcatcaca gccactttgt gcatggggat   240
cgcgccgtat ccgaatggac gttctccgga actggcgcgg acggcatgcg catcgaagca   300
cagggcgctg acctctttac cctgcgcgac ggcaagatca tcgtgaaaca ggccctgcgc   360
aaatcccgcc gcccttcaa ggcttaa                                        387

<210> SEQ ID NO 22
<211> LENGTH: 128
<212> TYPE: PRT
<213> ORGANISM: Roseobacter denitrificans

<400> SEQUENCE: 22

Met Thr Lys Thr Leu Thr Ala Gln Asp Leu Ser Asp Thr Phe Asp Ala
1               5                   10                  15

Phe Asn Arg His Asp Val Asp Gly Val Met Thr His Phe Ala Asp Asp
                20                  25                  30

Cys Val Phe Tyr Thr Val Gly Gly Asp Glu Ala Tyr Gly Ala Lys Val
            35                  40                  45

Glu Gly Ala Glu Ala Ile Ala Lys Ala Phe Ser Ala Val Trp Ala Gly
        50                  55                  60

Met Lys Asp Ala His Trp Asp His His Ser His Phe Val His Gly Asp
65                  70                  75                  80
```

Arg Ala Val Ser Glu Trp Thr Phe Ser Gly Thr Gly Ala Asp Gly Met
                85                  90                  95

Arg Ile Glu Ala Gln Gly Ala Asp Leu Phe Thr Leu Arg Asp Gly Lys
            100                 105                 110

Ile Ile Val Lys Gln Ala Leu Arg Lys Ser Arg Pro Pro Phe Lys Ala
        115                 120                 125

<210> SEQ ID NO 23
<211> LENGTH: 1395
<212> TYPE: DNA
<213> ORGANISM: Roseobacter denitrificans

<400> SEQUENCE: 23

```
atgccacata gaccaaagca ctggcccaag gccagctacg atcccaaata cgatcctatc      60
gtcgacgcgg gtcccggtca caaccgggac cacgcaccga cctattggat tggtacggcg     120
gggacgccac ctgaagatga cgggccggtg tcgggtgaca tcgatgcgga tgtcgtcgtt     180
gtcggctctg gctatacagg tctgtctacc gcaatccacc tggcgaagga ccacggcatc     240
aaggcgcatg tccttgaagc caacacagtc gcctggggct gttccacccg caatggcggg     300
caggcacaga tttcttccgg tcgtctcaag cggtcggagt ggatcaagcg gtggggcgtg     360
gatgtcgcca aaggcatgca cgccgaggtc tgtgaagcct cgaactgtt caatgatctg      420
atcgggtcag atgacattga ttgcgacccg caaaccgggg gccatttcta tattgcccac     480
cgcgaaaagg tcatggcgaa gctggaaaag gaatgtgccg tcctgaacga cacgtttggc     540
tatggctctc gcattctgtc gcgcgacgaa ctacacgaaa aatacgtgcg ggatcaggaa     600
gcacacggtg cccttgggga accggacggg acctcgatcc acgcggcaaa actggccttc     660
agctacgtgc gtcttgcgcg caaactcggc gccaagatcc acacggccag cccggtcatg     720
gggtggaaga ccgtgaacgg tgtgcatcac ctcaccacgc ccggtggcac ggtgcgcgca     780
cgtgccgtgg ccttggcgac agcgggctac acaccgccgg ggctgaacga aaagaccaag     840
caccggctca tgccgatcct gtcaaactcc atcgtgacgc gtccgctgag cgatgaggaa     900
aaggcgggat gcggttttca ggtgaaatct ccgctgactg acacgcgcac cttgcggcac     960
tactaccgct atctgcccga cggacgggtc cagatcggca gccgcagtgc gattacaggt    1020
cgagacgcag agaaccccag acatctggag cttctgcaga aaggtctcta tcgcaagttc    1080
cccgtgctcg aaggcattga actggattac tcctggtggg gatgggtgga tgtcagccat    1140
gacatgatgc cacgcatttt ccagccaaac ccgaagcaaa caatcttta tgcgatgggc     1200
tacggcggca acggggtgat gtattccgca caggccggca agcgcatggc gcaaatggtt    1260
gcgggcgaag gcaaggacct caaacttccg atcttcacct cgcaactgcc aagccacggt    1320
gttctgacac ccttccgcag gttgggccag cgcatggcct accctacta ctaccttcgc     1380
gatgaaattc tctga                                                     1395
```

<210> SEQ ID NO 24
<211> LENGTH: 464
<212> TYPE: PRT
<213> ORGANISM: Roseobacter denitrificans

<400> SEQUENCE: 24

Met Pro His Arg Pro Lys His Trp Pro Lys Ala Ser Tyr Asp Pro Lys
1               5                   10                  15

Tyr Asp Pro Ile Val Asp Ala Gly Pro Gly His Asn Arg Asp His Ala
            20                  25                  30

```
Pro Thr Tyr Trp Ile Gly Thr Ala Gly Thr Pro Pro Glu Asp Asp Gly
            35                  40                  45

Pro Val Ser Gly Asp Ile Asp Ala Asp Val Val Val Gly Ser Gly
 50                  55                  60

Tyr Thr Gly Leu Ser Thr Ala Ile His Leu Ala Lys Asp His Gly Ile
 65                  70                  75                  80

Lys Ala His Val Leu Glu Ala Asn Thr Val Ala Trp Gly Cys Ser Thr
                 85                  90                  95

Arg Asn Gly Gly Gln Ala Gln Ile Ser Ser Gly Arg Leu Lys Arg Ser
                100                 105                 110

Glu Trp Ile Lys Arg Trp Gly Val Asp Val Ala Lys Gly Met His Ala
                115                 120                 125

Glu Val Cys Glu Ala Phe Glu Leu Phe Asn Asp Leu Ile Gly Ser Asp
           130                 135                 140

Asp Ile Asp Cys Asp Pro Gln Thr Gly Gly His Phe Tyr Ile Ala His
145                 150                 155                 160

Arg Glu Lys Val Met Ala Lys Leu Glu Lys Glu Cys Ala Val Leu Asn
                165                 170                 175

Asp Thr Phe Gly Tyr Gly Ser Arg Ile Leu Ser Arg Asp Glu Leu His
           180                 185                 190

Glu Lys Tyr Val Arg Asp Gln Glu Ala His Gly Ala Leu Trp Glu Pro
           195                 200                 205

Asp Gly Thr Ser Ile His Ala Ala Lys Leu Ala Phe Ser Tyr Val Arg
210                 215                 220

Leu Ala Arg Lys Leu Gly Ala Lys Ile His Thr Ala Ser Pro Val Met
225                 230                 235                 240

Gly Trp Lys Thr Val Asn Gly Val His His Leu Thr Thr Pro Gly Gly
                245                 250                 255

Thr Val Arg Ala Arg Ala Val Ala Leu Ala Thr Ala Gly Tyr Thr Pro
           260                 265                 270

Pro Gly Leu Asn Glu Lys Thr Lys His Arg Leu Met Pro Ile Leu Ser
           275                 280                 285

Asn Ser Ile Val Thr Arg Pro Leu Ser Asp Glu Lys Ala Gly Cys
290                 295                 300

Gly Phe Gln Val Lys Ser Pro Leu Thr Asp Thr Arg Thr Leu Arg His
305                 310                 315                 320

Tyr Tyr Arg Tyr Leu Pro Asp Gly Arg Val Gln Ile Gly Ser Arg Ser
                325                 330                 335

Ala Ile Thr Gly Arg Asp Ala Glu Asn Pro Arg His Leu Glu Leu Leu
           340                 345                 350

Gln Lys Gly Leu Tyr Arg Lys Phe Pro Val Leu Glu Gly Ile Glu Leu
           355                 360                 365

Asp Tyr Ser Trp Trp Gly Trp Val Asp Val Ser His Asp Met Met Pro
370                 375                 380

Arg Ile Phe Gln Pro Asn Pro Lys Gln Thr Ile Phe Tyr Ala Met Gly
385                 390                 395                 400

Tyr Gly Gly Asn Gly Val Met Tyr Ser Ala Gln Ala Gly Lys Arg Met
                405                 410                 415

Ala Gln Met Val Ala Gly Glu Gly Lys Asp Leu Lys Leu Pro Ile Phe
                420                 425                 430

Thr Ser Gln Leu Pro Ser His Gly Val Leu Thr Pro Phe Arg Arg Leu
           435                 440                 445
```

Gly Gln Arg Met Ala Tyr Pro Tyr Tyr Tyr Leu Arg Asp Glu Ile Leu
            450                 455                 460

<210> SEQ ID NO 25
<211> LENGTH: 852
<212> TYPE: DNA
<213> ORGANISM: E. coli

<400> SEQUENCE: 25

| | |
|---|---|
| atgagtgaac gtctgagcat taccccgctg gggccgtata tcggcgcaca aatttcgggt | 60 |
| gccgacctga cgcgcccgtt aagcgataat cagtttgaac agctttacca tgcggtgctg | 120 |
| cgccatcagg tggtgtttct acgcgatcaa gctattacgc cgcagcagca acgcgcgctg | 180 |
| gcccagcgtt ttggcgaatt gcatattcac cctgtttacc cgcatgccga aggggttgac | 240 |
| gagatcatcg tgctggatac ccataacgat aatccgccag ataacgacaa ctggcatacc | 300 |
| gatgtgacat ttattgaaac gccacccgca ggggcgattc tggcagctaa agagttacct | 360 |
| tcgaccggcg gtgatacgct ctggaccagc ggtattgcgg cctatgaggc gctctctgtt | 420 |
| cccttccgcc agctgctgag tgggctgcgt gcggagcatg atttccgtaa atcgttcccg | 480 |
| gaatacaaat accgcaaaac cgaggaggaa catcaacgct ggcgcgaggc ggtcgcgaaa | 540 |
| aacccgccgt tgctacatcc ggtggtgcga acgcatccgg tgagcggtaa acaggcgctg | 600 |
| tttgtgaatg aaggctttac tacgcgaatt gttgatgtga gcgagaaaga gagcgaagcc | 660 |
| tgttaagtt ttttgtttgc ccatatcacc aaaccggagt ttcaggtgcg ctggcgctgg | 720 |
| caaccaaatg atattgcgat ttgggataac cgcgtgaccc agcactatgc caatgccgat | 780 |
| tacctgccac agcgacggat aatgcatcgg gcgacgatcc ttggggataa accgttttat | 840 |
| cgggcggggt aa | 852 |

<210> SEQ ID NO 26
<211> LENGTH: 283
<212> TYPE: PRT
<213> ORGANISM: E. coli

<400> SEQUENCE: 26

Met Ser Glu Arg Leu Ser Ile Thr Pro Leu Gly Pro Tyr Ile Gly Ala
1               5                   10                  15

Gln Ile Ser Gly Ala Asp Leu Thr Arg Pro Leu Ser Asp Asn Gln Phe
            20                  25                  30

Glu Gln Leu Tyr His Ala Val Leu Arg His Gln Val Val Phe Leu Arg
        35                  40                  45

Asp Gln Ala Ile Thr Pro Gln Gln Arg Ala Leu Ala Gln Arg Phe
    50                  55                  60

Gly Glu Leu His Ile His Pro Val Tyr Pro His Ala Glu Gly Val Asp
65                  70                  75                  80

Glu Ile Ile Val Leu Asp Thr His Asn Asp Asn Pro Pro Asp Asn Asp
                85                  90                  95

Asn Trp His Thr Asp Val Thr Phe Ile Glu Thr Pro Ala Gly Ala
            100                 105                 110

Ile Leu Ala Ala Lys Glu Leu Pro Ser Thr Gly Gly Asp Thr Leu Trp
        115                 120                 125

Thr Ser Gly Ile Ala Ala Tyr Glu Ala Leu Ser Val Pro Phe Arg Gln
    130                 135                 140

Leu Leu Ser Gly Leu Arg Ala Glu His Asp Phe Arg Lys Ser Phe Pro
145                 150                 155                 160

-continued

Glu Tyr Lys Tyr Arg Lys Thr Glu Glu His Gln Arg Trp Arg Glu
            165                 170                 175
Ala Val Ala Lys Asn Pro Pro Leu Leu His Pro Val Val Arg Thr His
        180                 185                 190
Pro Val Ser Gly Lys Gln Ala Leu Phe Val Asn Glu Gly Phe Thr Thr
    195                 200                 205
Arg Ile Val Asp Val Ser Lys Glu Ser Glu Ala Leu Leu Ser Phe
210                 215                 220
Leu Phe Ala His Ile Thr Lys Pro Glu Phe Gln Val Arg Trp Arg Trp
225                 230                 235                 240
Gln Pro Asn Asp Ile Ala Ile Trp Asp Asn Arg Val Thr Gln His Tyr
            245                 250                 255
Ala Asn Ala Asp Tyr Leu Pro Gln Arg Arg Ile Met His Arg Ala Thr
        260                 265                 270
Ile Leu Gly Asp Lys Pro Phe Tyr Arg Ala Gly
    275                 280

<210> SEQ ID NO 27
<211> LENGTH: 32
<212> TYPE: DNA
<213> ORGANISM: Artificial Sequence
<220> FEATURE:
<223> OTHER INFORMATION: primer

<400> SEQUENCE: 27
ttttggtacc cacatttgca aaatgatgaa tg                                    32

<210> SEQ ID NO 28
<211> LENGTH: 41
<212> TYPE: DNA
<213> ORGANISM: Artificial Sequence
<220> FEATURE:
<223> OTHER INFORMATION: primer

<400> SEQUENCE: 28
catgacttca gtctgctcca tccaatctgg ttaccgcatt g                          41

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
atggagcaga ctgaagtcat g                                                21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
tcagttattc tcctgcgaga c                                                21

<210> SEQ ID NO 31
<211> LENGTH: 41
<212> TYPE: DNA
<213> ORGANISM: Artificial Sequence
<220> FEATURE:
<223> OTHER INFORMATION: primer -continued

<400> SEQUENCE: 31
gtctcgcagg agaataactg agctaccgag ctcgaatttc c         41

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
cacgacgttg taaaacgacg gc                              22

<210> SEQ ID NO 33
<211> LENGTH: 32
<212> TYPE: DNA
<213> ORGANISM: Artificial Sequence
<220> FEATURE:
<223> OTHER INFORMATION: primer

<400> SEQUENCE: 33
ttttggtacc gtttacatat ggagatgatg tc                   32

<210> SEQ ID NO 34
<211> LENGTH: 35
<212> TYPE: DNA
<213> ORGANISM: Artificial Sequence
<220> FEATURE:
<223> OTHER INFORMATION: primer

<400> SEQUENCE: 34
tttttttcct agagatctag taacatagat gacac                35

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
caatgcctaa taatgtctag c                               21

<210> SEQ ID NO 36
<211> LENGTH: 43
<212> TYPE: DNA
<213> ORGANISM: Artificial Sequence
<220> FEATURE:
<223> OTHER INFORMATION: primer

<400> SEQUENCE: 36
catgacttca gtctgctcca tgccgtttga ttttgaattt gag       43

<210> SEQ ID NO 37
<211> LENGTH: 32
<212> TYPE: DNA
<213> ORGANISM: Artificial Sequence
<220> FEATURE:
<223> OTHER INFORMATION: primer

<400> SEQUENCE: 37
ttttcccggg attcttgaat tacgattgta cc                   32

<210> SEQ ID NO 38

```
<211> LENGTH: 46
<212> TYPE: DNA
<213> ORGANISM: Artificial Sequence
<220> FEATURE:
<223> OTHER INFORMATION: primer

<400> SEQUENCE: 38
cagcttccca tcagactcgt ccatgccgtt tgattttgaa tttgag        46

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
atggacgagt ctgatgggaa gctg                                24

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
tcatagatcc ttcccgagtt tc                                  22

<210> SEQ ID NO 41
<211> LENGTH: 42
<212> TYPE: DNA
<213> ORGANISM: Artificial Sequence
<220> FEATURE:
<223> OTHER INFORMATION: primer

<400> SEQUENCE: 41
gaaactcggg aaggatctat gagctaccga gctcgaattt cc            42

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
aaaaatctag aattcttgaa ttacgattgt acc                      33

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43
tttttttgtc gacgatctag taacatagat gacac                    35

<210> SEQ ID NO 44
<211> LENGTH: 43
<212> TYPE: DNA
<213> ORGANISM: Artificial Sequence
<220> FEATURE:
<223> OTHER INFORMATION: primer

<400> SEQUENCE: 44
```
cgttacttgc ttcttatcca tgccgtttga ttttgaattt gag                43

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
atggataaga agcaagtaac g                                       21

<210> SEQ ID NO 46
<211> LENGTH: 22
<212> TYPE: DNA
<213> ORGANISM: Artificial Sequence
<220> FEATURE:
<223> OTHER INFORMATION: primer

<400> SEQUENCE: 46
tcaggtatgt ttaaagctgt tc                                      22

<210> SEQ ID NO 47
<211> LENGTH: 42
<212> TYPE: DNA
<213> ORGANISM: Artificial Sequence
<220> FEATURE:
<223> OTHER INFORMATION: primer

<400> SEQUENCE: 47
gaacagcttt aaacatacct gagctaccga gctcgaattt cc                42

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
accaaaggat accctgattt g                                       21

<210> SEQ ID NO 49
<211> LENGTH: 44
<212> TYPE: DNA
<213> ORGANISM: Artificial Sequence
<220> FEATURE:
<223> OTHER INFORMATION: primer

<400> SEQUENCE: 49
gattttctgg actgtggaag tcatcacgga gatgagagag agag              44

<210> SEQ ID NO 50
<211> LENGTH: 24
<212> TYPE: DNA
<213> ORGANISM: Artificial Sequence
<220> FEATURE:
<223> OTHER INFORMATION: primer

<400> SEQUENCE: 50
atgacttcca cagtccagaa aatc                                    24

<210> SEQ ID NO 51
<211> LENGTH: 19
<212> TYPE: DNA

<213> ORGANISM: Artificial Sequence
<220> FEATURE:
<223> OTHER INFORMATION: primer

<400> SEQUENCE: 51
tcagagggtc actttaggc                                            19

<210> SEQ ID NO 52
<211> LENGTH: 39
<212> TYPE: DNA
<213> ORGANISM: Artificial Sequence
<220> FEATURE:
<223> OTHER INFORMATION: primer

<400> SEQUENCE: 52
gcctaaagtg accctctgag ctaccgagct cgaatttcc                      39

<210> SEQ ID NO 53
<211> LENGTH: 32
<212> TYPE: DNA
<213> ORGANISM: Artificial Sequence
<220> FEATURE:
<223> OTHER INFORMATION: primer

<400> SEQUENCE: 53
aaaaaggtac cgatatttga gcaaaactgt gg                             32

<210> SEQ ID NO 54
<211> LENGTH: 22
<212> TYPE: DNA
<213> ORGANISM: Artificial Sequence
<220> FEATURE:
<223> OTHER INFORMATION: primer

<400> SEQUENCE: 54
tcttaccttg tcctgcaacg ag                                        22

<210> SEQ ID NO 55
<211> LENGTH: 41
<212> TYPE: DNA
<213> ORGANISM: Artificial Sequence
<220> FEATURE:
<223> OTHER INFORMATION: primer

<400> SEQUENCE: 55
cattgaaatt gccgtccatc tttgtttctg tttagtgaaa g                   41

<210> SEQ ID NO 56
<211> LENGTH: 19
<212> TYPE: DNA
<213> ORGANISM: Artificial Sequence
<220> FEATURE:
<223> OTHER INFORMATION: primer

<400> SEQUENCE: 56
atggacggca atttcaatg                                            19

<210> SEQ ID NO 57
<211> LENGTH: 21
<212> TYPE: DNA
<213> ORGANISM: Artificial Sequence
<220> FEATURE:
<223> OTHER INFORMATION: primer

<400> SEQUENCE: 57
ttagccgaaa acgcgcgaca g                                         21

<210> SEQ ID NO 58
<211> LENGTH: 41
<212> TYPE: DNA
<213> ORGANISM: Artificial Sequence
<220> FEATURE:
<223> OTHER INFORMATION: primer

<400> SEQUENCE: 58
ctgtcgcgcg ttttcggcta agctaccgag ctcgaatttc c           41

<210> SEQ ID NO 59
<211> LENGTH: 32
<212> TYPE: DNA
<213> ORGANISM: Artificial Sequence
<220> FEATURE:
<223> OTHER INFORMATION: primer

<400> SEQUENCE: 59
ttttggtacc ctctttcgga acgagcttca ac                      32

<210> SEQ ID NO 60
<211> LENGTH: 41
<212> TYPE: DNA
<213> ORGANISM: Artificial Sequence
<220> FEATURE:
<223> OTHER INFORMATION: primer

<400> SEQUENCE: 60
cttcagtggt cattttcatc tttgtttctg tttagtgaaa g           41

<210> SEQ ID NO 61
<211> LENGTH: 19
<212> TYPE: DNA
<213> ORGANISM: Artificial Sequence
<220> FEATURE:
<223> OTHER INFORMATION: primer

<400> SEQUENCE: 61
atgaaaatga ccactgaag                                     19

<210> SEQ ID NO 62
<211> LENGTH: 19
<212> TYPE: DNA
<213> ORGANISM: Artificial Sequence
<220> FEATURE:
<223> OTHER INFORMATION: primer

<400> SEQUENCE: 62
tcagacagtc tgtggacgc                                     19

<210> SEQ ID NO 63
<211> LENGTH: 39
<212> TYPE: DNA
<213> ORGANISM: Artificial Sequence
<220> FEATURE:
<223> OTHER INFORMATION: primer

<400> SEQUENCE: 63
gcgtccacag actgtctgag ctaccgagct cgaatttcc               39

<210> SEQ ID NO 64
<211> LENGTH: 30
<212> TYPE: DNA
<213> ORGANISM: Artificial Sequence
<220> FEATURE:

<223> OTHER INFORMATION: primer

<400> SEQUENCE: 64
tttttctaga gaacgagctt caacgtagcc                              30

<210> SEQ ID NO 65
<211> LENGTH: 33
<212> TYPE: DNA
<213> ORGANISM: Artificial Sequence
<220> FEATURE:
<223> OTHER INFORMATION: primer

<400> SEQUENCE: 65
aaaaaaagct tgatctagta acatagatga cac                          33

<210> SEQ ID NO 66
<211> LENGTH: 24
<212> TYPE: DNA
<213> ORGANISM: Artificial Sequence
<220> FEATURE:
<223> OTHER INFORMATION: primer

<400> SEQUENCE: 66
gatcatacat attcatactt gatg                                    24

<210> SEQ ID NO 67
<211> LENGTH: 47
<212> TYPE: DNA
<213> ORGANISM: Artificial Sequence
<220> FEATURE:
<223> OTHER INFORMATION: primer

<400> SEQUENCE: 67
gagctgtcag tgttttggtc atataatttc ttgtatagct ctgtaac           47

<210> SEQ ID NO 68
<211> LENGTH: 22
<212> TYPE: DNA
<213> ORGANISM: Artificial Sequence
<220> FEATURE:
<223> OTHER INFORMATION: primer

<400> SEQUENCE: 68
atgaccaaaa cactgacagc tc                                      22

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
ttaagccttg aagggcgggc                                         20

<210> SEQ ID NO 70
<211> LENGTH: 40
<212> TYPE: DNA
<213> ORGANISM: Artificial Sequence
<220> FEATURE:
<223> OTHER INFORMATION: primer

<400> SEQUENCE: 70
gcccgccctt caaggcttaa gctaccgagc tcgaatttcc                   40

<210> SEQ ID NO 71
<211> LENGTH: 30
<212> TYPE: DNA
<213> ORGANISM: Artificial Sequence
<220> FEATURE:
<223> OTHER INFORMATION: primer

<400> SEQUENCE: 71
ttttggtacc cgaagctcaa tcgtctcgag                              30

<210> SEQ ID NO 72
<211> LENGTH: 46
<212> TYPE: DNA
<213> ORGANISM: Artificial Sequence
<220> FEATURE:
<223> OTHER INFORMATION: primer

<400> SEQUENCE: 72
gtgctttggt ctatgtggca tataatttct tgtatagctc tgtaac            46

<210> SEQ ID NO 73
<211> LENGTH: 21
<212> TYPE: DNA
<213> ORGANISM: Artificial Sequence
<220> FEATURE:
<223> OTHER INFORMATION: primer

<400> SEQUENCE: 73
atgccacata gaccaaagca c                                       21

<210> SEQ ID NO 74
<211> LENGTH: 21
<212> TYPE: DNA
<213> ORGANISM: Artificial Sequence
<220> FEATURE:
<223> OTHER INFORMATION: primer

<400> SEQUENCE: 74
tcagagaatt tcatcgcgaa g                                       21

<210> SEQ ID NO 75
<211> LENGTH: 41
<212> TYPE: DNA
<213> ORGANISM: Artificial Sequence
<220> FEATURE:
<223> OTHER INFORMATION: primer

<400> SEQUENCE: 75
cttcgcgatg aaattctctg agctaccgag ctcgaatttc c                 41

<210> SEQ ID NO 76
<211> LENGTH: 31
<212> TYPE: DNA
<213> ORGANISM: Artificial Sequence
<220> FEATURE:
<223> OTHER INFORMATION: primer

<400> SEQUENCE: 76
aaaaatctag acgaagctca atcgtctcga g                            31

<210> SEQ ID NO 77
<211> LENGTH: 19
<212> TYPE: DNA
<213> ORGANISM: Artificial Sequence
<220> FEATURE:
<223> OTHER INFORMATION: primer

```
<400> SEQUENCE: 77
tcacaatcga tggactctc                                                19

<210> SEQ ID NO 78
<211> LENGTH: 43
<212> TYPE: DNA
<213> ORGANISM: Artificial Sequence
<220> FEATURE:
<223> OTHER INFORMATION: primer

<400> SEQUENCE: 78
gtaatgctca gacgttcact cattgctatg tgtgttttgt agc                     43

<210> SEQ ID NO 79
<211> LENGTH: 23
<212> TYPE: DNA
<213> ORGANISM: Artificial Sequence
<220> FEATURE:
<223> OTHER INFORMATION: primer

<400> SEQUENCE: 79
atgagtgaac gtctgagcat tac                                           23

<210> SEQ ID NO 80
<211> LENGTH: 20
<212> TYPE: DNA
<213> ORGANISM: Artificial Sequence
<220> FEATURE:
<223> OTHER INFORMATION: primer

<400> SEQUENCE: 80 ttacccgcc cgataaaacg                                                20

<210> SEQ ID NO 81
<211> LENGTH: 40
<212> TYPE: DNA
<213> ORGANISM: Artificial Sequence
<220> FEATURE:
<223> OTHER INFORMATION: primer

<400> SEQUENCE: 81
cgttttatcg ggcggggtaa gctaccgagc tcgaatttcc                         40

<210> SEQ ID NO 82
<211> LENGTH: 31
<212> TYPE: DNA
<213> ORGANISM: Artificial Sequence
<220> FEATURE:
<223> OTHER INFORMATION: primer

<400> SEQUENCE: 82
ttttggtacc ctatattggt gtcattttgc c                                  31

<210> SEQ ID NO 83
<211> LENGTH: 46
<212> TYPE: DNA
<213> ORGANISM: Artificial Sequence
<220> FEATURE:
<223> OTHER INFORMATION: primer

<400> SEQUENCE: 83
gagcgtctcg caggagaata acatggacga gtctgatggg aagctg                  46

<210> SEQ ID NO 84
<211> LENGTH: 85
```

<212> TYPE: DNA
<213> ORGANISM: Artificial Sequence
<220> FEATURE:
<223> OTHER INFORMATION: primer

<400> SEQUENCE: 84
gagcgtctcg caggagaata acagtactga aggcgaagtt aacgcggaag aagaaggctt    60
tatggacgag tctgatggga agctg    85

<210> SEQ ID NO 85
<211> LENGTH: 79
<212> TYPE: DNA
<213> ORGANISM: Artificial Sequence
<220> FEATURE:
<223> OTHER INFORMATION: primer

<400> SEQUENCE: 85
gaaactcggg aaggatctaa gtactgaagg cgaagttaac gcggaagaag aaggctttat    60
ggagcagact gaagtcatg    79

<210> SEQ ID NO 86
<211> LENGTH: 43
<212> TYPE: DNA
<213> ORGANISM: Artificial Sequence
<220> FEATURE:
<223> OTHER INFORMATION: primer

<400> SEQUENCE: 86
gagcgtctcg caggagaata acatggataa gaagcaagta acg    43

<210> SEQ ID NO 87
<211> LENGTH: 82
<212> TYPE: DNA
<213> ORGANISM: Artificial Sequence
<220> FEATURE:
<223> OTHER INFORMATION: primer

<400> SEQUENCE: 87
gagcgtctcg caggagaata acagtactga aggcgaagtt aacgcggaag aagaaggctt    60
tatggataag aagcaagtaa cg    82

<210> SEQ ID NO 88
<211> LENGTH: 79
<212> TYPE: DNA
<213> ORGANISM: Artificial Sequence
<220> FEATURE:
<223> OTHER INFORMATION: primer

<400> SEQUENCE: 88
gaacagcttt aaacatacca gtactgaagg cgaagttaac gcggaagaag aaggctttat    60
ggagcagact gaagtcatg    79

<210> SEQ ID NO 89
<211> LENGTH: 38
<212> TYPE: DNA
<213> ORGANISM: Artificial Sequence
<220> FEATURE:
<223> OTHER INFORMATION: primer

<400> SEQUENCE: 89
catgcgtcca cagactgtca tggacggcaa tttcaatg    38

<210> SEQ ID NO 90

-continued

```
<211> LENGTH: 77
<212> TYPE: DNA
<213> ORGANISM: Artificial Sequence
<220> FEATURE:
<223> OTHER INFORMATION: primer

<400> SEQUENCE: 90
catgcgtcca cagactgtca gtactgaagg cgaagttaac gcggaagaag aaggctttat    60
ggacggcaat ttcaatg                                                  77

<210> SEQ ID NO 91
<211> LENGTH: 78
<212> TYPE: DNA
<213> ORGANISM: Artificial Sequence
<220> FEATURE:
<223> OTHER INFORMATION: primer

<400> SEQUENCE: 91
cgctgtcgcg cgttttcggc agtactgaag gcgaagttaa cgcggaagaa gaaggcttta    60
tgaaaatgac cactgaag                                                 78

<210> SEQ ID NO 92
<211> LENGTH: 38
<212> TYPE: DNA
<213> ORGANISM: Artificial Sequence
<220> FEATURE:
<223> OTHER INFORMATION: primer

<400> SEQUENCE: 92
gcccgccctt caaggctatg ccacatagac caaagcac                           38

<210> SEQ ID NO 93
<211> LENGTH: 77
<212> TYPE: DNA
<213> ORGANISM: Artificial Sequence
<220> FEATURE:
<223> OTHER INFORMATION: primer

<400> SEQUENCE: 93
gcccgccctt caaggctagt actgaaggcg aagttaacgc ggaagaagaa ggctttatgc    60
cacatagacc aaagcac                                                  77

<210> SEQ ID NO 94
<211> LENGTH: 79
<212> TYPE: DNA
<213> ORGANISM: Artificial Sequence
<220> FEATURE:
<223> OTHER INFORMATION: primer

<400> SEQUENCE: 94
cttcgcgatg aaattctcag tactgaaggc gaagttaacg cggaagaaga aggctttatg    60
accaaaacac tgacagctc                                                79

<210> SEQ ID NO 95
<211> LENGTH: 606
<212> TYPE: DNA
<213> ORGANISM: Xenopus tropicalis
<220> FEATURE:
<221> NAME/KEY: CDS
<222> LOCATION: (1)..(606)

<400> SEQUENCE: 95 atg gag cag act gaa gtg cta aag ccc aac acc ctg gat gag ctg atc    48
Met Glu Gln Thr Glu Val Leu Lys Pro Asn Thr Leu Asp Glu Leu Ile
```

```
                1               5                      10                      15
    cag atc ctg cat gag ata ttt gcc agt gat aaa gtg aat ata gag gag        96
    Gln Ile Leu His Glu Ile Phe Ala Ser Asp Lys Val Asn Ile Glu Glu
                 20                      25                      30 gtg cag gct ata gtg gag tcc tat gaa agc aac cca agg gaa tgg atg       144
    Val Gln Ala Ile Val Glu Ser Tyr Glu Ser Asn Pro Arg Glu Trp Met
                     35                      40                      45 aaa ttt gcc aag ttt gac cag tac agg tac acc cga aat ctt gtg gat       192
    Lys Phe Ala Lys Phe Asp Gln Tyr Arg Tyr Thr Arg Asn Leu Val Asp
     50                      55                      60 gag gga aat gga aag ttc aat cta atg atc ctg tgc tgg gga gaa gga       240
    Glu Gly Asn Gly Lys Phe Asn Leu Met Ile Leu Cys Trp Gly Glu Gly
     65                      70                      75                      80 cat ggc agc agt atc cat gac cat gcc aac tcc cac tgc ttc ttg aaa       288
    His Gly Ser Ser Ile His Asp His Ala Asn Ser His Cys Phe Leu Lys
                         85                      90                      95 atc ctt cag gga agc ctc aaa gaa act ctg tat gag tgg ccc aag aaa       336
    Ile Leu Gln Gly Ser Leu Lys Glu Thr Leu Tyr Glu Trp Pro Lys Lys
                        100                     105                     110 aaa agt aac act gaa atg gtg aag aag gca gaa ggt gta ttg aag ctg       384
    Lys Ser Asn Thr Glu Met Val Lys Lys Ala Glu Gly Val Leu Lys Leu
                    115                     120                     125 aat caa tgt gcc tat att aat gat tct att ggc ctc cat cgt gta gag       432
    Asn Gln Cys Ala Tyr Ile Asn Asp Ser Ile Gly Leu His Arg Val Glu
                130                     135                     140 aac ccg agc cat aca gag cct gct gta agc ctc cat tta tac agc cct       480
    Asn Pro Ser His Thr Glu Pro Ala Val Ser Leu His Leu Tyr Ser Pro
    145                     150                     155                     160 cca ttt aat gag tgc cac aca ttc gat cag agg act gga cac aca aat       528
    Pro Phe Asn Glu Cys His Thr Phe Asp Gln Arg Thr Gly His Thr Asn
                        165                     170                     175 tca gtg aaa atg act ttt tgg agc aag tat gga gac aga act cct ttt       576
    Ser Val Lys Met Thr Phe Trp Ser Lys Tyr Gly Asp Arg Thr Pro Phe
                    180                     185                     190 gca att gca cag tcg cag gaa aat aac taa                               606
    Ala Ile Ala Gln Ser Gln Glu Asn Asn
                    195                     200
```

<210> SEQ ID NO 96
<211> LENGTH: 201
<212> TYPE: PRT
<213> ORGANISM: Xenopus tropicalis

<400> SEQUENCE: 96

```
Met Glu Gln Thr Glu Val Leu Lys Pro Asn Thr Leu Asp Glu Leu Ile
  1               5                  10                  15

Gln Ile Leu His Glu Ile Phe Ala Ser Asp Lys Val Asn Ile Glu Glu
             20                  25                  30

Val Gln Ala Ile Val Glu Ser Tyr Glu Ser Asn Pro Arg Glu Trp Met
         35                  40                  45

Lys Phe Ala Lys Phe Asp Gln Tyr Arg Tyr Thr Arg Asn Leu Val Asp
     50                  55                  60

Glu Gly Asn Gly Lys Phe Asn Leu Met Ile Leu Cys Trp Gly Glu Gly
 65                  70                  75                  80

His Gly Ser Ser Ile His Asp His Ala Asn Ser His Cys Phe Leu Lys
                 85                  90                  95

Ile Leu Gln Gly Ser Leu Lys Glu Thr Leu Tyr Glu Trp Pro Lys Lys
            100                 105                 110
```

```
Lys Ser Asn Thr Glu Met Val Lys Ala Glu Gly Val Leu Lys Leu
            115                 120                 125

Asn Gln Cys Ala Tyr Ile Asn Asp Ser Ile Gly Leu His Arg Val Glu
        130                 135                 140

Asn Pro Ser His Thr Glu Pro Ala Val Ser Leu His Leu Tyr Ser Pro
145                 150                 155                 160

Pro Phe Asn Glu Cys His Thr Phe Asp Gln Arg Thr Gly His Thr Asn
                165                 170                 175

Ser Val Lys Met Thr Phe Trp Ser Lys Tyr Gly Asp Arg Thr Pro Phe
                180                 185                 190

Ala Ile Ala Gln Ser Gln Glu Asn Asn
        195                 200

<210> SEQ ID NO 97
<211> LENGTH: 645
<212> TYPE: DNA
<213> ORGANISM: Cimex lectularis
<220> FEATURE:
<221> NAME/KEY: CDS
<222> LOCATION: (1)..(645)

<400> SEQUENCE: 97 atg cta cca gag atg aca tct tta agc gtt aag aag cca gag acg ttg        48
Met Leu Pro Glu Met Thr Ser Leu Ser Val Lys Lys Pro Glu Thr Leu
1               5                   10                  15 gaa gaa ctg aaa gaa ggg ctt agg cag gcc ttc agc ggc gac aag gtg        96
Glu Glu Leu Lys Glu Gly Leu Arg Gln Ala Phe Ser Gly Asp Lys Val
                20                  25                  30 aac att gaa ttt gta agc gac ctt cta aaa tcc tac acc agt aat cca       144
Asn Ile Glu Phe Val Ser Asp Leu Leu Lys Ser Tyr Thr Ser Asn Pro
            35                  40                  45 cag gaa tgg aaa aag ttt gca aaa ttc gac aga tac agg tac acg aga       192
Gln Glu Trp Lys Lys Phe Ala Lys Phe Asp Arg Tyr Arg Tyr Thr Arg
        50                  55                  60 aat tta att gac gaa ggg aac gga aaa tac aac ctg atg tta ctt tgt       240
Asn Leu Ile Asp Glu Gly Asn Gly Lys Tyr Asn Leu Met Leu Leu Cys
65                  70                  75                  80 tgg ggt gaa ggg cac ggg tca gct atc cac gac cac gcc gat gct cat       288
Trp Gly Glu Gly His Gly Ser Ala Ile His Asp His Ala Asp Ala His
                85                  90                  95 tgt ttc atg aaa att ctc gaa ggg aag ctg agc gaa gtg cgg ttt gcc       336
Cys Phe Met Lys Ile Leu Glu Gly Lys Leu Ser Glu Val Arg Phe Ala
                100                 105                 110 tgg cca gac gaa aaa gag gtg tat ata gct gat gac gag tac aac ccg       384
Trp Pro Asp Glu Lys Glu Val Tyr Ile Ala Asp Asp Glu Tyr Asn Pro
            115                 120                 125 atg aaa gaa acc gga cga aca acg ctg agg acg aat gaa gtc tgc tat       432
Met Lys Glu Thr Gly Arg Thr Thr Leu Arg Thr Asn Glu Val Cys Tyr
        130                 135                 140 ata aat gac agc ttg gga ctt cac cgt gtg gaa aat ccg agt tct tca       480
Ile Asn Asp Ser Leu Gly Leu His Arg Val Glu Asn Pro Ser Ser Ser
145                 150                 155                 160 gag ccg gca gtg agc ctt cac ttg tac tgt ccc cct ttc gac cag tgc       528
Glu Pro Ala Val Ser Leu His Leu Tyr Cys Pro Pro Phe Asp Gln Cys
                165                 170                 175 cac gtc ttt aac cag cag acc ggt cac aag tct gta gcc aaa gtt acc       576
His Val Phe Asn Gln Gln Thr Gly His Lys Ser Val Ala Lys Val Thr
                180                 185                 190 ttt tgg tca aaa tac gga agc aaa ccg gac ccg aaa ata caa gat gaa       624
Phe Trp Ser Lys Tyr Gly Ser Lys Pro Asp Pro Lys Ile Gln Asp Glu
```

```
                    195                 200                 205
agg gca cct gag gac aat taa                                              645
Arg Ala Pro Glu Asp Asn
    210
```

<210> SEQ ID NO 98
<211> LENGTH: 214
<212> TYPE: PRT
<213> ORGANISM: Cimex lectularis

<400> SEQUENCE: 98

```
Met Leu Pro Glu Met Thr Ser Leu Ser Val Lys Lys Pro Glu Thr Leu
1               5                   10                  15

Glu Glu Leu Lys Glu Gly Leu Arg Gln Ala Phe Ser Gly Asp Lys Val
            20                  25                  30

Asn Ile Glu Phe Val Ser Asp Leu Leu Lys Ser Tyr Thr Ser Asn Pro
        35                  40                  45

Gln Glu Trp Lys Lys Phe Ala Lys Phe Asp Arg Tyr Arg Tyr Thr Arg
    50                  55                  60

Asn Leu Ile Asp Glu Gly Asn Gly Lys Tyr Asn Leu Met Leu Leu Cys
65                  70                  75                  80

Trp Gly Glu Gly His Gly Ser Ala Ile His Asp Ala Asp Ala His
                85                  90                  95

Cys Phe Met Lys Ile Leu Glu Gly Lys Leu Ser Glu Val Arg Phe Ala
                100                 105                 110

Trp Pro Asp Glu Lys Glu Val Tyr Ile Ala Asp Glu Tyr Asn Pro
            115                 120                 125

Met Lys Glu Thr Gly Arg Thr Thr Leu Arg Thr Asn Glu Val Cys Tyr
    130                 135                 140

Ile Asn Asp Ser Leu Gly Leu His Arg Val Glu Asn Pro Ser Ser Ser
145                 150                 155                 160

Glu Pro Ala Val Ser Leu His Leu Tyr Cys Pro Pro Phe Asp Gln Cys
                165                 170                 175

His Val Phe Asn Gln Gln Thr Gly His Lys Ser Val Ala Lys Val Thr
                180                 185                 190

Phe Trp Ser Lys Tyr Gly Ser Lys Pro Asp Pro Lys Ile Gln Asp Glu
            195                 200                 205

Arg Ala Pro Glu Asp Asn
    210
```

<210> SEQ ID NO 99
<211> LENGTH: 489
<212> TYPE: DNA
<213> ORGANISM: Bacillus atroophaeus
<220> FEATURE:
<221> NAME/KEY: CDS
<222> LOCATION: (1)..(489)

<400> SEQUENCE: 99

```
atg gaa cta cat gag tgt att cat gaa att ttt agc ggg ttg aag aac       48
Met Glu Leu His Glu Cys Ile His Glu Ile Phe Ser Gly Leu Lys Asn
1               5                   10                  15 cca ttg gtt aaa gat ttg gca act tct tta aaa caa att ccg aac gca       96
Pro Leu Val Lys Asp Leu Ala Thr Ser Leu Lys Gln Ile Pro Asn Ala
            20                  25                  30 tca aaa ttg agt caa cct tat att aag gaa cca gac caa tac gct tac      144
Ser Lys Leu Ser Gln Pro Tyr Ile Lys Glu Pro Asp Gln Tyr Ala Tyr
        35                  40                  45
```

```
ggc cga aat gta atc tac aga aac aat gaa ttg gaa att atc gtt ata      192
Gly Arg Asn Val Ile Tyr Arg Asn Asn Glu Leu Glu Ile Ile Val Ile
    50                  55                  60 aac att ccg cca aac aag gag aca aca gtc cac gat cat ggt caa tcc      240
Asn Ile Pro Pro Asn Lys Glu Thr Thr Val His Asp His Gly Gln Ser
65                  70                  75                  80 att ggt tgc gca atg gtg tta gaa gga gaa ctt ctc aat tct att tat      288
Ile Gly Cys Ala Met Val Leu Glu Gly Glu Leu Leu Asn Ser Ile Tyr
                85                  90                  95 cgc tca aac gac gat cat gta gaa ctc tcc tct tct tac ttt gtt cgc      336
Arg Ser Asn Asp Asp His Val Glu Leu Ser Ser Ser Tyr Phe Val Arg
            100                 105                 110 gag gga gag tgc ctt gtt tca agt aaa ggt tta att cac aaa atg tcc      384
Glu Gly Glu Cys Leu Val Ser Ser Lys Gly Leu Ile His Lys Met Ser
        115                 120                 125 aat cct acc tcc gaa aga gtg gtg tct ctt cat gtc tac tca ccc cct      432
Asn Pro Thr Ser Glu Arg Val Val Ser Leu His Val Tyr Ser Pro Pro
130                 135                 140 ttg gaa gac atg act gtc ttt gag gaa caa agt ggt gta ttg cga aac      480
Leu Glu Asp Met Thr Val Phe Glu Glu Gln Ser Gly Val Leu Arg Asn
145                 150                 155                 160 tgt aca tga                                                          489
Cys Thr <210> SEQ ID NO 100
<211> LENGTH: 162
<212> TYPE: PRT
<213> ORGANISM: Bacillus atroophaeus

<400> SEQUENCE: 100

Met Glu Leu His Glu Cys Ile His Glu Ile Phe Ser Gly Leu Lys Asn
1               5                   10                  15

Pro Leu Val Lys Asp Leu Ala Thr Ser Leu Lys Gln Ile Pro Asn Ala
            20                  25                  30

Ser Lys Leu Ser Gln Pro Tyr Ile Lys Glu Pro Asp Gln Tyr Ala Tyr
        35                  40                  45

Gly Arg Asn Val Ile Tyr Arg Asn Asn Glu Leu Glu Ile Ile Val Ile
    50                  55                  60

Asn Ile Pro Pro Asn Lys Glu Thr Thr Val His Asp His Gly Gln Ser
65                  70                  75                  80

Ile Gly Cys Ala Met Val Leu Glu Gly Glu Leu Leu Asn Ser Ile Tyr
                85                  90                  95

Arg Ser Asn Asp Asp His Val Glu Leu Ser Ser Ser Tyr Phe Val Arg
            100                 105                 110

Glu Gly Glu Cys Leu Val Ser Ser Lys Gly Leu Ile His Lys Met Ser
        115                 120                 125

Asn Pro Thr Ser Glu Arg Val Val Ser Leu His Val Tyr Ser Pro Pro
130                 135                 140

Leu Glu Asp Met Thr Val Phe Glu Glu Gln Ser Gly Val Leu Arg Asn
145                 150                 155                 160

Cys Thr

<210> SEQ ID NO 101
<211> LENGTH: 693
<212> TYPE: DNA
<213> ORGANISM: Chlorella sorokiniana
<220> FEATURE:
<221> NAME/KEY: CDS
<222> LOCATION: (1)..(693)
```

<400> SEQUENCE: 101

| | | | | | | | | | | | | | | | | |
|---|---|---|---|---|---|---|---|---|---|---|---|---|---|---|---|---|
| atg | ttt | gac | acc | ctg | gca | gac | gct | ttc | gca | gca | gag | cgc | gca | gcg | ggg | 48 |
| Met | Phe | Asp | Thr | Leu | Ala | Asp | Ala | Phe | Ala | Ala | Glu | Arg | Ala | Ala | Gly | |
| 1 | | | | 5 | | | | | 10 | | | | | 15 | | |
| tgc | acc | atc | ggc | agc | cac | cag | ccg | ccc | cag | tcg | gcg | gca | cgg | ctg | gac | 96 |
| Cys | Thr | Ile | Gly | Ser | His | Gln | Pro | Pro | Gln | Ser | Ala | Ala | Arg | Leu | Asp | |
| | | | 20 | | | | | 25 | | | | | 30 | | | |
| gcg | gcg | gtt | cgg | gca | gcc | gtg | cag | gca | tac | gtt | gcc | gct | ggg | cac | cag | 144 |
| Ala | Ala | Val | Arg | Ala | Ala | Val | Gln | Ala | Tyr | Val | Ala | Ala | Gly | His | Gln | |
| | | 35 | | | | | 40 | | | | | 45 | | | | |
| gac | tgg | cgg | gcg | ctg | gcc | aag | ttc | aac | gac | tcg | cac | tac | gtg | cgg | cac | 192 |
| Asp | Trp | Arg | Ala | Leu | Ala | Lys | Phe | Asn | Asp | Ser | His | Tyr | Val | Arg | His | |
| 50 | | | | | 55 | | | | | 60 | | | | | | |
| ctg | gtg | gac | gag | aac | ggc | gac | ttt | gag | atg | att | ctc | atc | tgt | tgg | aag | 240 |
| Leu | Val | Asp | Glu | Asn | Gly | Asp | Phe | Glu | Met | Ile | Leu | Ile | Cys | Trp | Lys | |
| 65 | | | | 70 | | | | | 75 | | | | | 80 | | |
| caa | ggc | cag | gcc | agc | cgc | gtg | cac | aac | cat | gcg | cag | tcg | cac | tgc | tgg | 288 |
| Gln | Gly | Gln | Ala | Ser | Arg | Val | His | Asn | His | Ala | Gln | Ser | His | Cys | Trp | |
| | | | | 85 | | | | | 90 | | | | | 95 | | |
| ctc | aac | gtg | ctg | agc | ggc | ggc | gtg | gag | gag | ctg | cgg | tac | acc | aca | ggc | 336 |
| Leu | Asn | Val | Leu | Ser | Gly | Gly | Val | Glu | Glu | Leu | Arg | Tyr | Thr | Thr | Gly | |
| | | | 100 | | | | | 105 | | | | | 110 | | | |
| gac | acg | ccg | gag | ggg | gtg | gag | ccg | gct | gtg | gcg | ccc | cgc | ctg | ccc | ggc | 384 |
| Asp | Thr | Pro | Glu | Gly | Val | Glu | Pro | Ala | Val | Ala | Pro | Arg | Leu | Pro | Gly | |
| | | 115 | | | | | 120 | | | | | 125 | | | | |
| gtc | atc | tca | gcc | agc | gca | ccc | tgc | ccg | ctg | ctg | atg | ccg | gca | ggc | gtg | 432 |
| Val | Ile | Ser | Ala | Ser | Ala | Pro | Cys | Pro | Leu | Leu | Met | Pro | Ala | Gly | Val | |
| | | 130 | | | | | 135 | | | | | 140 | | | | |
| ggc | aag | gtg | ggg | ccg | ggc | ggc | acc | gcc | tac | atc | aac | gac | acc | att | gcg | 480 |
| Gly | Lys | Val | Gly | Pro | Gly | Gly | Thr | Ala | Tyr | Ile | Asn | Asp | Thr | Ile | Ala | |
| 145 | | | | | 150 | | | | | 155 | | | | | 160 | |
| ctg | cac | gca | gtg | cgg | tgt | gac | gac | gcg | gcg | tgt | gag | gct | gcg | ggc | gag | 528 |
| Leu | His | Ala | Val | Arg | Cys | Asp | Asp | Ala | Ala | Cys | Glu | Ala | Ala | Gly | Glu | |
| | | | | 165 | | | | | 170 | | | | | 175 | | |
| gag | ggc | gct | gtc | agc | ctg | cac | gtg | tat | gcg | ccg | ccc | atc | cgg | cgc | gtg | 576 |
| Glu | Gly | Ala | Val | Ser | Leu | His | Val | Tyr | Ala | Pro | Pro | Ile | Arg | Arg | Val | |
| | | | 180 | | | | | 185 | | | | | 190 | | | |
| aag | ctg | tac | gag | caa | gag | gag | aac | agg | gtg | act | gtg | cgc | gcc | ccc | ggc | 624 |
| Lys | Leu | Tyr | Glu | Gln | Glu | Glu | Asn | Arg | Val | Thr | Val | Arg | Ala | Pro | Gly | |
| | | 195 | | | | | 200 | | | | | 205 | | | | |
| ttt | gcc | acg | atc | cgg | ggc | gtg | gtg | gat | gca | gac | ctg | cag | gat | ctg | agc | 672 |
| Phe | Ala | Thr | Ile | Arg | Gly | Val | Val | Asp | Ala | Asp | Leu | Gln | Asp | Leu | Ser | |
| | | 210 | | | | | 215 | | | | | 220 | | | | |
| cgc | ctc | agc | tcc | tcg | ctg | tga | | | | | | | | | | 693 |
| Arg | Leu | Ser | Ser | Ser | Leu | | | | | | | | | | | |
| 225 | | | | 230 | | | | | | | | | | | | |

<210> SEQ ID NO 102
<211> LENGTH: 230
<212> TYPE: PRT
<213> ORGANISM: Chlorella sorokiniana

<400> SEQUENCE: 102

Met Phe Asp Thr Leu Ala Asp Ala Phe Ala Ala Glu Arg Ala Ala Gly
1               5                   10                  15

Cys Thr Ile Gly Ser His Gln Pro Pro Gln Ser Ala Ala Arg Leu Asp
            20                  25                  30

Ala Ala Val Arg Ala Ala Val Gln Ala Tyr Val Ala Ala Gly His Gln
        35                  40                  45

```
Asp Trp Arg Ala Leu Ala Lys Phe Asn Asp Ser His Tyr Val Arg His
             50                  55                  60

Leu Val Asp Glu Asn Gly Asp Phe Glu Met Ile Leu Ile Cys Trp Lys
 65                  70                  75                  80

Gln Gly Gln Ala Ser Arg Val His Asn His Ala Gln Ser His Cys Trp
                 85                  90                  95

Leu Asn Val Leu Ser Gly Gly Val Glu Glu Leu Arg Tyr Thr Thr Gly
                100                 105                 110

Asp Thr Pro Glu Gly Val Glu Pro Ala Val Ala Pro Arg Leu Pro Gly
                115                 120                 125

Val Ile Ser Ala Ser Ala Pro Cys Pro Leu Leu Met Pro Ala Gly Val
            130                 135                 140

Gly Lys Val Gly Pro Gly Gly Thr Ala Tyr Ile Asn Asp Thr Ile Ala
145                 150                 155                 160

Leu His Ala Val Arg Cys Asp Asp Ala Ala Cys Glu Ala Ala Gly Glu
                165                 170                 175

Glu Gly Ala Val Ser Leu His Val Tyr Ala Pro Pro Ile Arg Arg Val
                180                 185                 190

Lys Leu Tyr Glu Gln Glu Glu Asn Arg Val Thr Val Arg Ala Pro Gly
                195                 200                 205

Phe Ala Thr Ile Arg Gly Val Val Asp Ala Asp Leu Gln Asp Leu Ser
            210                 215                 220

Arg Leu Ser Ser Ser Leu
225                 230

<210> SEQ ID NO 103
<211> LENGTH: 810
<212> TYPE: DNA
<213> ORGANISM: Chlamydomonas reinhardtii
<220> FEATURE:
<221> NAME/KEY: CDS
<222> LOCATION: (1)..(810)

<400> SEQUENCE: 103 atg tct tct atc atc gct atg cct atc aac gag gac ggt gtc gtt gtg    48
Met Ser Ser Ile Ile Ala Met Pro Ile Asn Glu Asp Gly Val Val Val
 1               5                  10                  15 gtc gac cgc aag ctg ctg ggc aac gag gtc gag agc aag gcc cgc tgc    96
Val Asp Arg Lys Leu Leu Gly Asn Glu Val Glu Ser Lys Ala Arg Cys
            20                  25                  30 gcg gac acc gcc tgc acc gcg gct gcg ccc gcc ccg ccc gcc acg gcg   144
Ala Asp Thr Ala Cys Thr Ala Ala Ala Pro Ala Pro Pro Ala Thr Ala
        35                  40                  45 gcc gcg ccc acc tcc atg ccg gag ctg ttg cag gcg ttg cag cgc gcc   192
Ala Ala Pro Thr Ser Met Pro Glu Leu Leu Gln Ala Leu Gln Arg Ala
    50                  55                  60 att gac gag gag aag gcc act ggc cag gtc gcc atc aac gct gtg gac   240
Ile Asp Glu Glu Lys Ala Thr Gly Gln Val Ala Ile Asn Ala Val Asp
 65                  70                  75                  80 cag acg ccc gag tcc gct gcg cgg ctg agc gcc cgc gtg cag gct cta   288
Gln Thr Pro Glu Ser Ala Ala Arg Leu Ser Ala Arg Val Gln Ala Leu
                 85                  90                  95 ctc tcg gcc tac acc agc tcc aac tcg ggc gac tgg cga cgc tac gcc   336
Leu Ser Ala Tyr Thr Ser Ser Asn Ser Gly Asp Trp Arg Arg Tyr Ala
                100                 105                 110 atg ttc aac gac atc cac tac gtg cgc aac ctg gtg gat gcc aat gag   384
Met Phe Asn Asp Ile His Tyr Val Arg Asn Leu Val Asp Ala Asn Glu
                115                 120                 125
```

```
gac ttt gaa cta att gtt ctt tgt tgg aag cgc ggg caa gtc agc cgc    432
Asp Phe Glu Leu Ile Val Leu Cys Trp Lys Arg Gly Gln Val Ser Arg
    130                 135                 140 gtg cac aac cac gcc aac gcg cac tgc tgg ctg gcg gtg ctg gac ggc    480
Val His Asn His Ala Asn Ala His Cys Trp Leu Ala Val Leu Asp Gly
145                 150                 155                 160 gag atg cgc gag acg cag ttc cag cgc gcg tcc gcg ccg ccc ggc tgc    528
Glu Met Arg Glu Thr Gln Phe Gln Arg Ala Ser Ala Pro Pro Gly Cys
                165                 170                 175 ccc gcg ccc gcg gcc tcg gag cac gat ggc agc act gtg tac gtg gag    576
Pro Ala Pro Ala Ala Ser Glu His Asp Gly Ser Thr Val Tyr Val Glu
            180                 185                 190 ccc aca cag gtg tcc gac atg cga gtg ggt gac gcc ggc tac atc aac    624
Pro Thr Gln Val Ser Asp Met Arg Val Gly Asp Ala Gly Tyr Ile Asn
        195                 200                 205 gac tcc atg gcg ctg cac aac gtg ggg tgt tgc atg ccc gcc ctg gcc    672
Asp Ser Met Ala Leu His Asn Val Gly Cys Cys Met Pro Ala Leu Ala
    210                 215                 220 gct ggc gag gag ggc ccc gag ggc ggg gtg acg ctg cac tgc tac gcc    720
Ala Gly Glu Glu Gly Pro Glu Gly Gly Val Thr Leu His Cys Tyr Ala
225                 230                 235                 240 ccc ccg att cgc cgc gtc aag atc tat gag gac agc aag gtc acg gag    768
Pro Pro Ile Arg Arg Val Lys Ile Tyr Glu Asp Ser Lys Val Thr Glu
                245                 250                 255 cgc gtg ccc ggc tac tac tcc aag ggc gga gtg cgc gtt tga             810
Arg Val Pro Gly Tyr Tyr Ser Lys Gly Gly Val Arg Val
            260                 265

<210> SEQ ID NO 104
<211> LENGTH: 269
<212> TYPE: PRT
<213> ORGANISM: Chlamydomonas reinhardtii

<400> SEQUENCE: 104

Met Ser Ser Ile Ile Ala Met Pro Ile Asn Glu Asp Gly Val Val
1               5                   10                  15

Val Asp Arg Lys Leu Leu Gly Asn Glu Val Glu Ser Lys Ala Arg Cys
                20                  25                  30

Ala Asp Thr Ala Cys Thr Ala Ala Pro Ala Pro Pro Ala Thr Ala
            35                  40                  45

Ala Ala Pro Thr Ser Met Pro Glu Leu Leu Gln Ala Leu Gln Arg Ala
        50                  55                  60

Ile Asp Glu Glu Lys Ala Thr Gly Gln Val Ala Ile Asn Ala Val Asp
65                  70                  75                  80

Gln Thr Pro Glu Ser Ala Ala Arg Leu Ser Ala Arg Val Gln Ala Leu
                85                  90                  95

Leu Ser Ala Tyr Thr Ser Ser Asn Ser Gly Asp Trp Arg Arg Tyr Ala
            100                 105                 110

Met Phe Asn Asp Ile His Tyr Val Arg Asn Leu Val Asp Ala Asn Glu
        115                 120                 125

Asp Phe Glu Leu Ile Val Leu Cys Trp Lys Arg Gly Gln Val Ser Arg
    130                 135                 140

Val His Asn His Ala Asn Ala His Cys Trp Leu Ala Val Leu Asp Gly
145                 150                 155                 160

Glu Met Arg Glu Thr Gln Phe Gln Arg Ala Ser Ala Pro Pro Gly Cys
                165                 170                 175

Pro Ala Pro Ala Ala Ser Glu His Asp Gly Ser Thr Val Tyr Val Glu
```

|   |   |   | 180 |   |   |   | 185 |   |   |   | 190 |   |   |
|---|---|---|---|---|---|---|---|---|---|---|---|---|---|

Pro Thr Gln Val Ser Asp Met Arg Val Gly Asp Ala Gly Tyr Ile Asn
        195                 200                 205

Asp Ser Met Ala Leu His Asn Val Gly Cys Cys Met Pro Ala Leu Ala
    210                 215                 220

Ala Gly Glu Glu Gly Pro Glu Gly Gly Val Thr Leu His Cys Tyr Ala
225                 230                 235                 240

Pro Pro Ile Arg Arg Val Lys Ile Tyr Glu Asp Ser Lys Val Thr Glu
                245                 250                 255

Arg Val Pro Gly Tyr Tyr Ser Lys Gly Gly Val Arg Val
                260                 265

<210> SEQ ID NO 105
<211> LENGTH: 828
<212> TYPE: DNA
<213> ORGANISM: Tetrabaena socialis
<220> FEATURE:
<221> NAME/KEY: CDS
<222> LOCATION: (1)..(828)

<400> SEQUENCE: 105

```
atg gca agc gtg gta tgt agc ctc gac ggg gac ggc atg gtc cag att      48
Met Ala Ser Val Val Cys Ser Leu Asp Gly Asp Gly Met Val Gln Ile
1               5                   10                  15 gcg cgg aag acg gtc acc gag tcg gtg ggc aag ggg tgt cag gac acc      96
Ala Arg Lys Thr Val Thr Glu Ser Val Gly Lys Gly Cys Gln Asp Thr
            20                  25                  30 agc gcg gct gtc gtc cag ctt ggc gct gcc gcc agt gct gct gcg ggg     144
Ser Ala Ala Val Val Gln Leu Gly Ala Ala Ala Ser Ala Ala Ala Gly
        35                  40                  45 gtc ccc gag gtg ccg cgg ctg gag gac ctg ctg cag cag ctg cgc gac     192
Val Pro Glu Val Pro Arg Leu Glu Asp Leu Leu Gln Gln Leu Arg Asp
    50                  55                  60 gtc ttc gag cgg gaa aag gcg cag ggc atc acc ctc ggc agc cag cag     240
Val Phe Glu Arg Glu Lys Ala Gln Gly Ile Thr Leu Gly Ser Gln Gln
65                  70                  75                  80 cac cag cag cag ccc gag tcc ttc aag cgc atg aac gac ggc gtg cag     288
His Gln Gln Gln Pro Glu Ser Phe Lys Arg Met Asn Asp Gly Val Gln
                85                  90                  95 ggg ctg ctc agg gct tac gcg gcc tcc aac tcc ctc gac tgg cag aag     336
Gly Leu Leu Arg Ala Tyr Ala Ala Ser Asn Ser Leu Asp Trp Gln Lys
            100                 105                 110 tac gcg ctc ttc aat gac ctg cac tac gtg cgc aac ctg gtg gag gcg     384
Tyr Ala Leu Phe Asn Asp Leu His Tyr Val Arg Asn Leu Val Glu Ala
        115                 120                 125 aac gac gac ttt gag ctc atc gtg ctg tgc tgg aag acg ggc caa gtg     432
Asn Asp Asp Phe Glu Leu Ile Val Leu Cys Trp Lys Thr Gly Gln Val
    130                 135                 140 agc cgg gtt cac aat cac gcg gac agc cac tgc tgg ttg gcg gtg ctg     480
Ser Arg Val His Asn His Ala Asp Ser His Cys Trp Leu Ala Val Leu
145                 150                 155                 160 ggc ggc gag atg cgc gag gtg cag tac cag cag gcg ccc gcg cct ccc     528
Gly Gly Glu Met Arg Glu Val Gln Tyr Gln Gln Ala Pro Ala Pro Pro
                165                 170                 175 gcg gtc cac ggc gcc gcc gtc ccc gag gat gcg gcg tat gtc gag gcc     576
Ala Val His Gly Ala Ala Val Pro Glu Asp Ala Ala Tyr Val Glu Ala
            180                 185                 190 acc cac agc aca gag atg cgg gtg ggg gac tgc ggc tac atc aac gac     624
Thr His Ser Thr Glu Met Arg Val Gly Asp Cys Gly Tyr Ile Asn Asp
        195                 200                 205
```

| | | | | | | | | | | | | | | |
|---|---|---|---|---|---|---|---|---|---|---|---|---|---|---|
| ttc | ctg | gcg | ctg | cac | acc | gtc | ggg | tgc | tat | ggg | ccg | gag | gcg | gaa | cgg | 672 |
| Phe | Leu | Ala | Leu | His | Thr | Val | Gly | Cys | Tyr | Gly | Pro | Glu | Ala | Glu | Arg | |
| | | 210 | | | | 215 | | | | | 220 | | | | | |
| tgt | cgc | agt | gag | ggc | ggc | gcg | ggg | ccg | tac | gtg | ccg | cag | ggc | ggc | gtg | 720 |
| Cys | Arg | Ser | Glu | Gly | Gly | Ala | Gly | Pro | Tyr | Val | Pro | Gln | Gly | Gly | Val | |
| 225 | | | | | 230 | | | | | 235 | | | | | 240 | |
| acg | ctg | cac | ctg | tac | gcg | ccg | ccc | atc | aag | agg | gtc | aag | atc | tac | gac | 768 |
| Thr | Leu | His | Leu | Tyr | Ala | Pro | Pro | Ile | Lys | Arg | Val | Lys | Ile | Tyr | Asp | |
| | | | | 245 | | | | | 250 | | | | | 255 | | |
| aat | gac | acc | gtg | acg | gag | cgc | atc | ccg | ggc | ttc | tac | tcc | aag | ggt | ggt | 816 |
| Asn | Asp | Thr | Val | Thr | Glu | Arg | Ile | Pro | Gly | Phe | Tyr | Ser | Lys | Gly | Gly | |
| | | | 260 | | | | | 265 | | | | | 270 | | | |
| gtg | cgg | gtg | tag | | | | | | | | | | | | | 828 |
| Val | Arg | Val | | | | | | | | | | | | | | |
| | | 275 | | | | | | | | | | | | | | |

<210> SEQ ID NO 106
<211> LENGTH: 275
<212> TYPE: PRT
<213> ORGANISM: Tetrabaena socialis

<400> SEQUENCE: 106

Met Ala Ser Val Val Cys Ser Leu Asp Gly Asp Gly Met Val Gln Ile
1               5                   10                  15

Ala Arg Lys Thr Val Thr Glu Ser Val Gly Lys Gly Cys Gln Asp Thr
            20                  25                  30

Ser Ala Ala Val Val Gln Leu Gly Ala Ala Ser Ala Ala Ala Gly
        35                  40                  45

Val Pro Glu Val Pro Arg Leu Glu Asp Leu Leu Gln Gln Leu Arg Asp
    50                  55                  60

Val Phe Glu Arg Glu Lys Ala Gln Gly Ile Thr Leu Gly Ser Gln Gln
65                  70                  75                  80

His Gln Gln Gln Pro Glu Ser Phe Lys Arg Met Asn Asp Gly Val Gln
                85                  90                  95

Gly Leu Leu Arg Ala Tyr Ala Ala Ser Asn Ser Leu Asp Trp Gln Lys
            100                 105                 110

Tyr Ala Leu Phe Asn Asp Leu His Tyr Val Arg Asn Leu Val Glu Ala
        115                 120                 125

Asn Asp Asp Phe Glu Leu Ile Val Leu Cys Trp Lys Thr Gly Gln Val
    130                 135                 140

Ser Arg Val His Asn His Ala Asp Ser His Cys Trp Leu Ala Val Leu
145                 150                 155                 160

Gly Gly Glu Met Arg Glu Val Gln Tyr Gln Gln Ala Pro Ala Pro Pro
                165                 170                 175

Ala Val His Gly Ala Ala Val Pro Glu Asp Ala Ala Tyr Val Glu Ala
            180                 185                 190

Thr His Ser Thr Glu Met Arg Val Gly Asp Cys Gly Tyr Ile Asn Asp
        195                 200                 205

Phe Leu Ala Leu His Thr Val Gly Cys Tyr Gly Pro Glu Ala Glu Arg
    210                 215                 220

Cys Arg Ser Glu Gly Gly Ala Gly Pro Tyr Val Pro Gln Gly Gly Val
225                 230                 235                 240

Thr Leu His Leu Tyr Ala Pro Pro Ile Lys Arg Val Lys Ile Tyr Asp
                245                 250                 255

Asn Asp Thr Val Thr Glu Arg Ile Pro Gly Phe Tyr Ser Lys Gly Gly
            260                 265                 270

Val Arg Val
          275

<210> SEQ ID NO 107
<211> LENGTH: 816
<212> TYPE: DNA
<213> ORGANISM: Porphyra umbilicalis
<220> FEATURE:
<221> NAME/KEY: CDS
<222> LOCATION: (1)..(816)

<400> SEQUENCE: 107

| atg | gcc | aag | ctt | cct | tgc | tgc | ccc | ccc | ccc | ccc | gac | cgc | ccg | ctg | | 48 |
|---|---|---|---|---|---|---|---|---|---|---|---|---|---|---|---|---|
| Met | Ala | Lys | Leu | Pro | Cys | Cys | Pro | Pro | Pro | Pro | Asp | Arg | Pro | Leu | | |
| 1 | | | | 5 | | | | | 10 | | | | | 15 | | |

| gag | cgc | gcc | gac | ccc | gcc | ctg | gtg | gcc | gcc | ctg | gtg | gcg | ggg | gat | ggc | 96 |
|---|---|---|---|---|---|---|---|---|---|---|---|---|---|---|---|---|
| Glu | Arg | Ala | Asp | Pro | Ala | Leu | Val | Ala | Ala | Leu | Val | Ala | Gly | Asp | Gly | |
| | | | 20 | | | | | 25 | | | | | 30 | | | |

| gac | gcg | gtg | gcg | tcc | cgc | cta | gcc | ggc | gac | gac | atg | gtg | agc | ccc | gac | 144 |
|---|---|---|---|---|---|---|---|---|---|---|---|---|---|---|---|---|
| Asp | Ala | Val | Ala | Ser | Arg | Leu | Ala | Gly | Asp | Asp | Met | Val | Ser | Pro | Asp | |
| | 35 | | | | | 40 | | | | | 45 | | | | | |

| gcc | ctc | cgc | ccc | tac | atc | ttc | ttt | gac | ggc | caa | aag | ccc | tac | acc | cgc | 192 |
|---|---|---|---|---|---|---|---|---|---|---|---|---|---|---|---|---|
| Ala | Leu | Arg | Pro | Tyr | Ile | Phe | Phe | Asp | Gly | Gln | Lys | Pro | Tyr | Thr | Arg | |
| 50 | | | | | 55 | | | | | 60 | | | | | | |

| aac | gtc | gtc | acg | gtg | aac | gag | cac | tac | gcg | ctc | atc | gcc | atg | tgc | tgg | 240 |
|---|---|---|---|---|---|---|---|---|---|---|---|---|---|---|---|---|
| Asn | Val | Val | Thr | Val | Asn | Glu | His | Tyr | Ala | Leu | Ile | Ala | Met | Cys | Trp | |
| 65 | | | | 70 | | | | | 75 | | | | | 80 | | |

| tcc | ccc | ggc | cgc | tcg | tcg | ccg | gtg | cat | gac | cac | gcg | ggc | tcg | ggc | tgc | 288 |
|---|---|---|---|---|---|---|---|---|---|---|---|---|---|---|---|---|
| Ser | Pro | Gly | Arg | Ser | Ser | Pro | Val | His | Asp | His | Ala | Gly | Ser | Gly | Cys | |
| | | | | 85 | | | | | 90 | | | | | 95 | | |

| tgg | ctg | cgc | gtc | atc | agt | ggg | ggg | ctc | acc | gag | tcc | ctc | tac | agc | ggc | 336 |
|---|---|---|---|---|---|---|---|---|---|---|---|---|---|---|---|---|
| Trp | Leu | Arg | Val | Ile | Ser | Gly | Gly | Leu | Thr | Glu | Ser | Leu | Tyr | Ser | Gly | |
| | | | 100 | | | | | 105 | | | | | 110 | | | |

| ccg | tcg | gga | gag | ggc | ggg | gac | aag | gcc | ttc | cca | gac | gag | ccc | ctc | tcc | 384 |
|---|---|---|---|---|---|---|---|---|---|---|---|---|---|---|---|---|
| Pro | Ser | Gly | Glu | Gly | Gly | Asp | Lys | Ala | Phe | Pro | Asp | Glu | Pro | Leu | Ser | |
| | 115 | | | | | 120 | | | | | 125 | | | | | |

| tcg | tct | gac | ggg | gag | gcg | gat | gcg | gcc | gca | acg | acg | gcg | ccg | gcg | gtg | 432 |
|---|---|---|---|---|---|---|---|---|---|---|---|---|---|---|---|---|
| Ser | Ser | Asp | Gly | Glu | Ala | Asp | Ala | Ala | Ala | Thr | Thr | Ala | Pro | Ala | Val | |
| 130 | | | | | 135 | | | | | 140 | | | | | | |

| gac | tgt | tcc | gac | ggc | ggc | ggc | ggc | gtc | gcc | gcg | cac | acg | gac | cgc | gcg | 480 |
|---|---|---|---|---|---|---|---|---|---|---|---|---|---|---|---|---|
| Asp | Cys | Ser | Asp | Gly | Gly | Gly | Gly | Val | Ala | Ala | His | Thr | Asp | Arg | Ala | |
| 145 | | | | | 150 | | | | | 155 | | | | | 160 | |

| ttg | cgg | tta | gtg | tca | cgg | cgc | ccc | ctc | cgc | tct | ggt | agt | tgt | tcg | tac | 528 |
|---|---|---|---|---|---|---|---|---|---|---|---|---|---|---|---|---|
| Leu | Arg | Leu | Val | Ser | Arg | Arg | Pro | Leu | Arg | Ser | Gly | Ser | Cys | Ser | Tyr | |
| | | | | 165 | | | | | 170 | | | | | 175 | | |

| atg | gca | gac | gac | ctc | ggc | ctg | cac | gcg | gtg | agc | aac | gcg | tct | tcc | gtg | 576 |
|---|---|---|---|---|---|---|---|---|---|---|---|---|---|---|---|---|
| Met | Ala | Asp | Asp | Leu | Gly | Leu | His | Ala | Val | Ser | Asn | Ala | Ser | Ser | Val | |
| | | | 180 | | | | | 185 | | | | | 190 | | | |

| aca | ccc | gcc | gtg | tcc | ctc | cac | tgc | tat | gcg | ccg | ccg | ttt | gcg | tcg | tgc | 624 |
|---|---|---|---|---|---|---|---|---|---|---|---|---|---|---|---|---|
| Thr | Pro | Ala | Val | Ser | Leu | His | Cys | Tyr | Ala | Pro | Pro | Phe | Ala | Ser | Cys | |
| | 195 | | | | | 200 | | | | | 205 | | | | | |

| caa | gtc | ttt | ggg | cgc | gtc | cgc | gtc | ggc | ggc | ggc | att | gac | cgg | gcg | gcc | 672 |
|---|---|---|---|---|---|---|---|---|---|---|---|---|---|---|---|---|
| Gln | Val | Phe | Gly | Arg | Val | Arg | Val | Gly | Gly | Gly | Ile | Asp | Arg | Ala | Ala | |
| 210 | | | | | 215 | | | | | 220 | | | | | | |

| att | gag | cgc | gtc | ggc | aag | gag | gtg | cac | atg | acc | ttt | gat | tcg | gtg | gga | 720 |
|---|---|---|---|---|---|---|---|---|---|---|---|---|---|---|---|---|
| Ile | Glu | Arg | Val | Gly | Lys | Glu | Val | His | Met | Thr | Phe | Asp | Ser | Val | Gly | |
| 225 | | | | | 230 | | | | | 235 | | | | | 240 | |

| ggg | cag | gtg | ctc | ggc | gag | cgc | ggt | gat | gcg | ctc | atc | aag | agc | ttt | gtg | 768 |
|---|---|---|---|---|---|---|---|---|---|---|---|---|---|---|---|---|
| Gly | Gln | Val | Leu | Gly | Glu | Arg | Gly | Asp | Ala | Leu | Ile | Lys | Ser | Phe | Val | |
| | | | | 245 | | | | | 250 | | | | | 255 | | |

| | | | | | | | | | | | | | | | |
|---|---|---|---|---|---|---|---|---|---|---|---|---|---|---|---|
| ccg | ttg | gag | cgg | gag | ggt | ggg | gaa | gac | gtg | ctg | atg | tac | gac | att tga | 816 |
| Pro | Leu | Glu | Arg | Glu | Gly | Gly | Glu | Asp | Val | Leu | Met | Tyr | Asp | Ile | |
| | | 260 | | | | | 265 | | | | | 270 | | | |

<210> SEQ ID NO 108
<211> LENGTH: 271
<212> TYPE: PRT
<213> ORGANISM: Porphyra umbilicalis

<400> SEQUENCE: 108

Met Ala Lys Leu Pro Cys Cys Pro Pro Pro Pro Asp Arg Pro Leu
1               5                   10                  15

Glu Arg Ala Asp Pro Ala Leu Val Ala Ala Leu Val Ala Gly Asp Gly
        20                  25                  30

Asp Ala Val Ala Ser Arg Leu Ala Gly Asp Asp Met Val Ser Pro Asp
            35                  40                  45

Ala Leu Arg Pro Tyr Ile Phe Phe Asp Gly Gln Lys Pro Tyr Thr Arg
    50                  55                  60

Asn Val Val Thr Val Asn Glu His Tyr Ala Leu Ile Ala Met Cys Trp
65                  70                  75                  80

Ser Pro Gly Arg Ser Ser Pro Val His Asp His Ala Gly Ser Gly Cys
                85                  90                  95

Trp Leu Arg Val Ile Ser Gly Gly Leu Thr Glu Ser Leu Tyr Ser Gly
            100                 105                 110

Pro Ser Gly Glu Gly Gly Asp Lys Ala Phe Pro Asp Glu Pro Leu Ser
        115                 120                 125

Ser Ser Asp Gly Glu Ala Asp Ala Ala Thr Thr Ala Pro Ala Val
    130                 135                 140

Asp Cys Ser Asp Gly Gly Gly Val Ala Ala His Thr Asp Arg Ala
145                 150                 155                 160

Leu Arg Leu Val Ser Arg Arg Pro Leu Arg Ser Gly Ser Cys Ser Tyr
                165                 170                 175

Met Ala Asp Asp Leu Gly Leu His Ala Val Ser Asn Ala Ser Ser Val
            180                 185                 190

Thr Pro Ala Val Ser Leu His Cys Tyr Ala Pro Pro Phe Ala Ser Cys
        195                 200                 205

Gln Val Phe Gly Arg Val Arg Val Gly Gly Gly Ile Asp Arg Ala Ala
    210                 215                 220

Ile Glu Arg Val Gly Lys Glu Val His Met Thr Phe Asp Ser Val Gly
225                 230                 235                 240

Gly Gln Val Leu Gly Glu Arg Gly Asp Ala Leu Ile Lys Ser Phe Val
                245                 250                 255

Pro Leu Glu Arg Glu Gly Gly Glu Asp Val Leu Met Tyr Asp Ile
            260                 265                 270

<210> SEQ ID NO 109
<211> LENGTH: 1473
<212> TYPE: DNA
<213> ORGANISM: Xenopus laevis
<220> FEATURE:
<221> NAME/KEY: CDS
<222> LOCATION: (1)..(1473)

<400> SEQUENCE: 109

| | | | | | | | | | | | | | | | |
|---|---|---|---|---|---|---|---|---|---|---|---|---|---|---|---|
| atg | gat | gga | gga | att | tct | gca | ata | aaa | aca | gag | aac | tca | gga | gat gaa | 48 |
| Met | Asp | Gly | Gly | Ile | Ser | Ala | Ile | Lys | Thr | Glu | Asn | Ser | Gly | Asp Glu | |
| 1 | | | | 5 | | | | 10 | | | | | | 15 | |
| ttc | ttg | aaa | gaa | gct | ctt | gtt | att | cta | atg | cag | gat | gcg | gtg | caa aag | 96 |

```
Phe Leu Lys Glu Ala Leu Val Ile Leu Met Gln Asp Ala Val Gln Lys
         20                  25                  30 ggg aca gac agg ggc cac aag gtg tgt gag tgg atg gag cca gag aaa      144
Gly Thr Asp Arg Gly His Lys Val Cys Glu Trp Met Glu Pro Glu Lys
             35                  40                  45 ctt cat gaa atc ctg gac tta aaa cta cag aga aac ggc gaa tct cag      192
Leu His Glu Ile Leu Asp Leu Lys Leu Gln Arg Asn Gly Glu Ser Gln
         50                  55                  60 gaa gtg ctg ctg ggc tac tgc agg gac atc gtc agg ttt agt gtc aag      240
Glu Val Leu Leu Gly Tyr Cys Arg Asp Ile Val Arg Phe Ser Val Lys
65                  70                  75                  80 aca ggg cat cca cgg ttc ttc aac cag cta ttc tct gga tta gac cga      288
Thr Gly His Pro Arg Phe Phe Asn Gln Leu Phe Ser Gly Leu Asp Arg
                 85                  90                  95 cat gcg ctg act ggt cgc atc tta agt gag acc ttg aac act agt caa      336
His Ala Leu Thr Gly Arg Ile Leu Ser Glu Thr Leu Asn Thr Ser Gln
            100                 105                 110 tat acc tat gaa gtt gct cca gtc ttt gtt ctg atg gag gaa gaa gta      384
Tyr Thr Tyr Glu Val Ala Pro Val Phe Val Leu Met Glu Glu Glu Val
        115                 120                 125 ctc aca aca ctg agg cat tat gtc ggc tgg aca gca gga gat ggg att      432
Leu Thr Thr Leu Arg His Tyr Val Gly Trp Thr Ala Gly Asp Gly Ile
    130                 135                 140 ttc tgc cca ggg ggc tcc att tcc aac atg tac gct ata aat gtg gcc      480
Phe Cys Pro Gly Gly Ser Ile Ser Asn Met Tyr Ala Ile Asn Val Ala
145                 150                 155                 160 cga ttt cat cgc ttc cca cat gct aaa gag aag ggg ctg agt gca ctg      528
Arg Phe His Arg Phe Pro His Ala Lys Glu Lys Gly Leu Ser Ala Leu
                165                 170                 175 ccg agg atg act ata ttc aca aca cac gag agc cat tat tca gtc aga      576
Pro Arg Met Thr Ile Phe Thr Thr His Glu Ser His Tyr Ser Val Arg
            180                 185                 190 aag ggg gca gca ttc ctg ggc att gga aca gac aac atc atc ctt gta      624
Lys Gly Ala Ala Phe Leu Gly Ile Gly Thr Asp Asn Ile Ile Leu Val
        195                 200                 205 cag aca aac gac agg gga aaa atg ttg cct gaa gat tta gag aaa aaa      672
Gln Thr Asn Asp Arg Gly Lys Met Leu Pro Glu Asp Leu Glu Lys Lys
    210                 215                 220 att gag aaa tca aaa tct gag ggt gca gtc cct ttc ttg gtc agt gca      720
Ile Glu Lys Ser Lys Ser Glu Gly Ala Val Pro Phe Leu Val Ser Ala
225                 230                 235                 240 acc tgc gga aca aca gtt cta ggg gct ttt gat cct atc gca gac att      768
Thr Cys Gly Thr Thr Val Leu Gly Ala Phe Asp Pro Ile Ala Asp Ile
                245                 250                 255 gct gat gta tgt gaa cga cat ggc tta tgg cta cat gca gat gct gct      816
Ala Asp Val Cys Glu Arg His Gly Leu Trp Leu His Ala Asp Ala Ala
            260                 265                 270 ttt ggt ggc agt gcc ctc tta tcc agc aag cac aga cat ctt tta cat      864
Phe Gly Gly Ser Ala Leu Leu Ser Ser Lys His Arg His Leu Leu His
        275                 280                 285 ggc ata gaa agg gca aat tct gtc act tgg aat cct cat aaa atg ctg      912
Gly Ile Glu Arg Ala Asn Ser Val Thr Trp Asn Pro His Lys Met Leu
    290                 295                 300 gga gtt ggt ctg cag tgt tca gcc ttt ctc ctt ccg gac acg aca gga      960
Gly Val Gly Leu Gln Cys Ser Ala Phe Leu Leu Pro Asp Thr Thr Gly
305                 310                 315                 320 cta tta cag cga tgc cat gca gct aat gcc aca tat ctc ttc caa acg     1008
Leu Leu Gln Arg Cys His Ala Ala Asn Ala Thr Tyr Leu Phe Gln Thr
                325                 330                 335
```

```
gac aaa ttt tat gac ctt aag tat gac act gga gac aaa tca atc cag    1056
Asp Lys Phe Tyr Asp Leu Lys Tyr Asp Thr Gly Asp Lys Ser Ile Gln
            340                 345                 350 tgc ggt cga agg gtg gac tgc ttg aag ctt tgg ttg atg tgg aag gca    1104
Cys Gly Arg Arg Val Asp Cys Leu Lys Leu Trp Leu Met Trp Lys Ala
            355                 360                 365 ctc ggg tct caa ggt ttg gaa aag cga gtg gac aag gca ttg gaa caa    1152
Leu Gly Ser Gln Gly Leu Glu Lys Arg Val Asp Lys Ala Leu Glu Gln
    370                 375                 380 act aga tac ctg gtg gaa gaa atg aag gcg agg gag ggt ttt tgt cta    1200
Thr Arg Tyr Leu Val Glu Glu Met Lys Ala Arg Glu Gly Phe Cys Leu
385                 390                 395                 400 att atg gag cca gaa ttc gtg aac ctg tgt ttc tgg tat gtg cca ccc    1248
Ile Met Glu Pro Glu Phe Val Asn Leu Cys Phe Trp Tyr Val Pro Pro
                405                 410                 415 agc ctt cga gac cag cag gat tcc ccg gat tac tgg cag aga cta gga    1296
Ser Leu Arg Asp Gln Gln Asp Ser Pro Asp Tyr Trp Gln Arg Leu Gly
            420                 425                 430 aag gta gct ccg gta ata aag gag aga atg att aag aaa ggc tcc atg    1344
Lys Val Ala Pro Val Ile Lys Glu Arg Met Ile Lys Lys Gly Ser Met
            435                 440                 445 atg gtt gga tac cag ccc cat gga gac aga gta aac ttc ttt cgt caa    1392
Met Val Gly Tyr Gln Pro His Gly Asp Arg Val Asn Phe Phe Arg Gln
450                 455                 460 gtt ctt gtg aat cct gca cta act aag act gac ctg gat ttt ttc ctg    1440
Val Leu Val Asn Pro Ala Leu Thr Lys Thr Asp Leu Asp Phe Phe Leu
465                 470                 475                 480 gat gaa ata gaa cta tta gca gag gac ctc tga                        1473
Asp Glu Ile Glu Leu Leu Ala Glu Asp Leu
                485                 490

<210> SEQ ID NO 110
<211> LENGTH: 490
<212> TYPE: PRT
<213> ORGANISM: Xenopus laevis

<400> SEQUENCE: 110

Met Asp Gly Gly Ile Ser Ala Ile Lys Thr Glu Asn Ser Gly Asp Glu
1               5                   10                  15

Phe Leu Lys Glu Ala Leu Val Ile Leu Met Gln Asp Ala Val Gln Lys
            20                  25                  30

Gly Thr Asp Arg Gly His Lys Val Cys Glu Trp Met Glu Pro Glu Lys
        35                  40                  45

Leu His Glu Ile Leu Asp Leu Lys Leu Gln Arg Asn Gly Glu Ser Gln
    50                  55                  60

Glu Val Leu Leu Gly Tyr Cys Arg Asp Ile Val Arg Phe Ser Val Lys
65                  70                  75                  80

Thr Gly His Pro Arg Phe Phe Asn Gln Leu Phe Ser Gly Leu Asp Arg
                85                  90                  95

His Ala Leu Thr Gly Arg Ile Leu Ser Glu Thr Leu Asn Thr Ser Gln
            100                 105                 110

Tyr Thr Tyr Glu Val Ala Pro Val Phe Val Leu Met Glu Glu Glu Val
        115                 120                 125

Leu Thr Thr Leu Arg His Tyr Val Gly Trp Thr Ala Gly Asp Gly Ile
    130                 135                 140

Phe Cys Pro Gly Gly Ser Ile Ser Asn Met Tyr Ala Ile Asn Val Ala
145                 150                 155                 160

Arg Phe His Arg Phe Pro His Ala Lys Glu Lys Gly Leu Ser Ala Leu
```

```
                    165                 170                 175
Pro Arg Met Thr Ile Phe Thr Thr His Glu Ser His Tyr Ser Val Arg
                180                 185                 190

Lys Gly Ala Ala Phe Leu Gly Ile Gly Thr Asp Asn Ile Ile Leu Val
            195                 200                 205

Gln Thr Asn Asp Arg Gly Lys Met Leu Pro Glu Asp Leu Glu Lys Lys
        210                 215                 220

Ile Glu Lys Ser Lys Ser Glu Gly Ala Val Pro Phe Leu Val Ser Ala
225                 230                 235                 240

Thr Cys Gly Thr Thr Val Leu Gly Ala Phe Asp Pro Ile Ala Asp Ile
                245                 250                 255

Ala Asp Val Cys Glu Arg His Gly Leu Trp Leu His Ala Asp Ala Ala
                260                 265                 270

Phe Gly Gly Ser Ala Leu Leu Ser Ser Lys Arg His Leu Leu His
            275                 280                 285

Gly Ile Glu Arg Ala Asn Ser Val Thr Trp Asn Pro His Lys Met Leu
        290                 295                 300

Gly Val Gly Leu Gln Cys Ser Ala Phe Leu Leu Pro Asp Thr Thr Gly
305                 310                 315                 320

Leu Leu Gln Arg Cys His Ala Ala Asn Ala Thr Tyr Leu Phe Gln Thr
                325                 330                 335

Asp Lys Phe Tyr Asp Leu Lys Tyr Asp Thr Gly Asp Lys Ser Ile Gln
                340                 345                 350

Cys Gly Arg Arg Val Asp Cys Leu Lys Leu Trp Leu Met Trp Lys Ala
            355                 360                 365

Leu Gly Ser Gln Gly Leu Glu Lys Arg Val Asp Lys Ala Leu Glu Gln
        370                 375                 380

Thr Arg Tyr Leu Val Glu Glu Met Lys Ala Arg Glu Gly Phe Cys Leu
385                 390                 395                 400

Ile Met Glu Pro Glu Phe Val Asn Leu Cys Phe Trp Tyr Val Pro Pro
                405                 410                 415

Ser Leu Arg Asp Gln Gln Asp Ser Pro Asp Tyr Trp Gln Arg Leu Gly
                420                 425                 430

Lys Val Ala Pro Val Ile Lys Glu Arg Met Ile Lys Lys Gly Ser Met
            435                 440                 445

Met Val Gly Tyr Gln Pro His Gly Asp Arg Val Asn Phe Phe Arg Gln
        450                 455                 460

Val Leu Val Asn Pro Ala Leu Thr Lys Thr Asp Leu Asp Phe Phe Leu
465                 470                 475                 480

Asp Glu Ile Glu Leu Leu Ala Glu Asp Leu
                485                 490

<210> SEQ ID NO 111
<211> LENGTH: 1545
<212> TYPE: DNA
<213> ORGANISM: Drosophila melangaster
<220> FEATURE:
<221> NAME/KEY: CDS
<222> LOCATION: (1)..(1545)

<400> SEQUENCE: 111 atg ttg gcc aac gcc gcc aac aat aat aat aat aat aac aac atc        48
Met Leu Ala Asn Ala Ala Asn Asn Asn Asn Asn Asn Asn Asn Ile
1               5                   10                  15 acg agc acc aag gat gat cta tcc agc ttt gtg gcc agc cat ccg gcg    96
Thr Ser Thr Lys Asp Asp Leu Ser Ser Phe Val Ala Ser His Pro Ala
```

```
                    20                      25                      30
gca gag ttc gag ggc ttc atc cgc gct tgc gtc gac gag atc atc aag     144
Ala Glu Phe Glu Gly Phe Ile Arg Ala Cys Val Asp Glu Ile Ile Lys
         35                      40                      45 ctg gcc gtc ttc cag ggc acc aat cgc tcg aag gtc gtc gag tgg         192
Leu Ala Val Phe Gln Gly Thr Asn Arg Ser Ser Lys Val Val Glu Trp
 50                      55                      60 cac gag cca gct gag ctg cga cag ctc ttt gac ttc cag ctg cgg gag     240
His Glu Pro Ala Glu Leu Arg Gln Leu Phe Asp Phe Gln Leu Arg Glu
 65                      70                      75                      80 cag ggc gaa tcg cag gac aag ctg cgc gag ctg ctg cgg gaa acg att     288
Gln Gly Glu Ser Gln Asp Lys Leu Arg Glu Leu Leu Arg Glu Thr Ile
                 85                      90                      95 cga ttc tcc gtg aag aca gga cat ccg tac ttc atc aat cag ttg tac     336
Arg Phe Ser Val Lys Thr Gly His Pro Tyr Phe Ile Asn Gln Leu Tyr
             100                     105                     110 tcg ggt gtg gat cca tac gcg ctg gta ggt caa tgg ctc acc gat gcc     384
Ser Gly Val Asp Pro Tyr Ala Leu Val Gly Gln Trp Leu Thr Asp Ala
         115                     120                     125 ctc aat ccc agc gtg tac acg tac gag gtg gct cca ctc ttt acg ctg     432
Leu Asn Pro Ser Val Tyr Thr Tyr Glu Val Ala Pro Leu Phe Thr Leu
130                     135                     140 atg gag gag cag gtg ttg gcc gag atg cga cgc att gtg ggc ttc ccc     480
Met Glu Glu Gln Val Leu Ala Glu Met Arg Arg Ile Val Gly Phe Pro
145                     150                     155                     160 aat ggc ggc cag ggt gat ggc atc ttc tgt ccc ggc ggc tcg ata gcc     528
Asn Gly Gly Gln Gly Asp Gly Ile Phe Cys Pro Gly Gly Ser Ile Ala
                 165                     170                     175 aac ggt tat gca atc agc tgc gcc cgc tac aga cac tcg ccc gag tcc     576
Asn Gly Tyr Ala Ile Ser Cys Ala Arg Tyr Arg His Ser Pro Glu Ser
             180                     185                     190 aag aaa aac gga ctc ttt aat gcc aag ccg ctg att atc ttc acc tcg     624
Lys Lys Asn Gly Leu Phe Asn Ala Lys Pro Leu Ile Ile Phe Thr Ser
         195                     200                     205 gag gac gcg cac tac tcc gtg gag aag ctg gcc atg ttc atg ggc ttc     672
Glu Asp Ala His Tyr Ser Val Glu Lys Leu Ala Met Phe Met Gly Phe
210                     215                     220 ggc agc gat cat gtg cgc aag ata gcc acc aac gag gtg ggc aag atg     720
Gly Ser Asp His Val Arg Lys Ile Ala Thr Asn Glu Val Gly Lys Met
225                     230                     235                     240 cgg ctg agc gac ctg gag aaa cag gtg aag ctg tgc ctg gag aac ggc     768
Arg Leu Ser Asp Leu Glu Lys Gln Val Lys Leu Cys Leu Glu Asn Gly
                 245                     250                     255 tgg cag ccg ctg atg gta tcg gcc aca gcg ggt acc act gtg ctg ggc     816
Trp Gln Pro Leu Met Val Ser Ala Thr Ala Gly Thr Thr Val Leu Gly
             260                     265                     270 gcc ttc gat gat ctg gct gga atc tcg gag gtg tgc aag aag tac aac     864
Ala Phe Asp Asp Leu Ala Gly Ile Ser Glu Val Cys Lys Lys Tyr Asn
         275                     280                     285 atg tgg atg cac gtg gat gcg gct tgg ggt ggc ggt gcg ctc atg tcc     912
Met Trp Met His Val Asp Ala Ala Trp Gly Gly Gly Ala Leu Met Ser
290                     295                     300 aag aag tat cgc cat ctg ctc aat ggc atc gaa cgg gct gat tcg gtc     960
Lys Lys Tyr Arg His Leu Leu Asn Gly Ile Glu Arg Ala Asp Ser Val
305                     310                     315                     320 act tgg aat cca cac aag ctg ctg gct gcc tcg caa cag tgt tcc acc    1008
Thr Trp Asn Pro His Lys Leu Leu Ala Ala Ser Gln Gln Cys Ser Thr
                 325                     330                     335 ttc ctg acg cgt cac cag cag gtg ctg gcc cag tgc cat tcg acc aat    1056
```

```
Phe Leu Thr Arg His Gln Gln Val Leu Ala Gln Cys His Ser Thr Asn
                340                 345                 350 gcg aca tac ttg ttc cag aag gac aag ttc tat gac aca tcc ttc gac      1104
Ala Thr Tyr Leu Phe Gln Lys Asp Lys Phe Tyr Asp Thr Ser Phe Asp
            355                 360                 365 acc ggc gac aag cac atc cag tgc ggc cga cga gcg gat gtc ttc aag      1152
Thr Gly Asp Lys His Ile Gln Cys Gly Arg Arg Ala Asp Val Phe Lys
370                 375                 380 ttc tgg ttc atg tgg aag gcg aag ggc acc cag ggt ctg gag gcg cat      1200
Phe Trp Phe Met Trp Lys Ala Lys Gly Thr Gln Gly Leu Glu Ala His
385                 390                 395                 400 gtc gag aag gtc ttc cgc atg gcc gag ttc ttc acg gcc aag gtg agg      1248
Val Glu Lys Val Phe Arg Met Ala Glu Phe Phe Thr Ala Lys Val Arg
            405                 410                 415 gag cgt cct gga ttc gag ctc gtc ctc gag agt ccc gag tgc acc aac      1296
Glu Arg Pro Gly Phe Glu Leu Val Leu Glu Ser Pro Glu Cys Thr Asn
            420                 425                 430 att agc ttc tgg tat gtg ccg ccc ggt ctg cgg gaa atg gag cgc aat      1344
Ile Ser Phe Trp Tyr Val Pro Pro Gly Leu Arg Glu Met Glu Arg Asn
            435                 440                 445 cgc gag ttc tac gac cgt ctg cat aag gtg gcg ccg aag gtc aag gag      1392
Arg Glu Phe Tyr Asp Arg Leu His Lys Val Ala Pro Lys Val Lys Glu
450                 455                 460 ggc atg atc aag aag ggc tcc atg atg atc acg tac cag ccg ttg cgc      1440
Gly Met Ile Lys Lys Gly Ser Met Met Ile Thr Tyr Gln Pro Leu Arg
465                 470                 475                 480 cag ctg ccc aac ttc ttt cgc ctg gtg ctg cag aac tcc tgc ctg gag      1488
Gln Leu Pro Asn Phe Phe Arg Leu Val Leu Gln Asn Ser Cys Leu Glu
            485                 490                 495 gag tcg gac atg gtc tac ttt ctg gac gag atc gaa tcg ctc gcc caa      1536
Glu Ser Asp Met Val Tyr Phe Leu Asp Glu Ile Glu Ser Leu Ala Gln
            500                 505                 510 aac ttg taa                                                           1545
Asn Leu <210> SEQ ID NO 112
<211> LENGTH: 514
<212> TYPE: PRT
<213> ORGANISM: Drosophila melangaster

<400> SEQUENCE: 112

Met Leu Ala Asn Ala Ala Asn Asn Asn Asn Asn Asn Asn Asn Asn Ile
1               5                   10                  15

Thr Ser Thr Lys Asp Asp Leu Ser Ser Phe Val Ala Ser His Pro Ala
            20                  25                  30

Ala Glu Phe Glu Gly Phe Ile Arg Ala Cys Val Asp Glu Ile Ile Lys
        35                  40                  45

Leu Ala Val Phe Gln Gly Thr Asn Arg Ser Ser Lys Val Val Glu Trp
    50                  55                  60

His Glu Pro Ala Glu Leu Arg Gln Leu Phe Asp Phe Gln Leu Arg Glu
65                  70                  75                  80

Gln Gly Glu Ser Gln Asp Lys Leu Arg Glu Leu Leu Arg Glu Thr Ile
            85                  90                  95

Arg Phe Ser Val Lys Thr Gly His Pro Tyr Phe Ile Asn Gln Leu Tyr
            100                 105                 110

Ser Gly Val Asp Pro Tyr Ala Leu Val Gly Gln Trp Leu Thr Asp Ala
        115                 120                 125

Leu Asn Pro Ser Val Tyr Thr Tyr Glu Val Ala Pro Leu Phe Thr Leu
```

-continued

```
            130                 135                 140
Met Glu Glu Gln Val Leu Ala Glu Met Arg Arg Ile Val Gly Phe Pro
145                 150                 155                 160

Asn Gly Gly Gln Gly Asp Gly Ile Phe Cys Pro Gly Gly Ser Ile Ala
                165                 170                 175

Asn Gly Tyr Ala Ile Ser Cys Ala Arg Tyr Arg His Ser Pro Glu Ser
            180                 185                 190

Lys Lys Asn Gly Leu Phe Asn Ala Lys Pro Leu Ile Ile Phe Thr Ser
        195                 200                 205

Glu Asp Ala His Tyr Ser Val Glu Lys Leu Ala Met Phe Met Gly Phe
    210                 215                 220

Gly Ser Asp His Val Arg Lys Ile Ala Thr Asn Glu Val Gly Lys Met
225                 230                 235                 240

Arg Leu Ser Asp Leu Glu Lys Gln Val Lys Leu Cys Leu Glu Asn Gly
                245                 250                 255

Trp Gln Pro Leu Met Val Ser Ala Thr Ala Gly Thr Thr Val Leu Gly
            260                 265                 270

Ala Phe Asp Asp Leu Ala Gly Ile Ser Glu Val Cys Lys Lys Tyr Asn
        275                 280                 285

Met Trp Met His Val Asp Ala Ala Trp Gly Gly Ala Leu Met Ser
    290                 295                 300

Lys Lys Tyr Arg His Leu Leu Asn Gly Ile Glu Arg Ala Asp Ser Val
305                 310                 315                 320

Thr Trp Asn Pro His Lys Leu Leu Ala Ala Ser Gln Gln Cys Ser Thr
                325                 330                 335

Phe Leu Thr Arg His Gln Val Leu Ala Gln Cys His Ser Thr Asn
            340                 345                 350

Ala Thr Tyr Leu Phe Gln Lys Asp Lys Phe Tyr Asp Thr Ser Phe Asp
        355                 360                 365

Thr Gly Asp Lys His Ile Gln Cys Gly Arg Arg Ala Asp Val Phe Lys
    370                 375                 380

Phe Trp Phe Met Trp Lys Ala Lys Gly Thr Gln Gly Leu Glu Ala His
385                 390                 395                 400

Val Glu Lys Val Phe Arg Met Ala Glu Phe Thr Ala Lys Val Arg
                405                 410                 415

Glu Arg Pro Gly Phe Glu Leu Val Leu Glu Ser Pro Glu Cys Thr Asn
            420                 425                 430

Ile Ser Phe Trp Tyr Val Pro Pro Gly Leu Arg Glu Met Glu Arg Asn
        435                 440                 445

Arg Glu Phe Tyr Asp Arg Leu His Lys Val Ala Pro Lys Val Lys Glu
    450                 455                 460

Gly Met Ile Lys Lys Gly Ser Met Met Ile Thr Tyr Gln Pro Leu Arg
465                 470                 475                 480

Gln Leu Pro Asn Phe Phe Arg Leu Val Leu Gln Asn Ser Cys Leu Glu
                485                 490                 495

Glu Ser Asp Met Val Tyr Phe Leu Asp Glu Ile Glu Ser Leu Ala Gln
            500                 505                 510

Asn Leu
```

<210> SEQ ID NO 113
<211> LENGTH: 1518
<212> TYPE: DNA
<213> ORGANISM: Nannocystis exedens
<220> FEATURE:

<221> NAME/KEY: CDS
<222> LOCATION: (1)..(1518)

<400> SEQUENCE: 113

```
atg gcg ctc gtg ggg ccg ggg ccg cgc ttg acc gcg ccg gcc tcg ccc       48
Met Ala Leu Val Gly Pro Gly Pro Arg Leu Thr Ala Pro Ala Ser Pro
1               5                   10                  15 gca aaa gtg cct cgc gtg gac ctc gac gcg ctc gtg cga ccg atc ctc       96
Ala Lys Val Pro Arg Val Asp Leu Asp Ala Leu Val Arg Pro Ile Leu
            20                  25                  30 gat ctc ctg cgg cgg gcc gac cag cgc gac gtc cgg atc acc gac ctc      144
Asp Leu Leu Arg Arg Ala Asp Gln Arg Asp Val Arg Ile Thr Asp Leu
        35                  40                  45 gcg ggc ccc gag gcc cac gcc gac gcc ttc gcc gcc atc ggc gct ccc      192
Ala Gly Pro Glu Ala His Ala Asp Ala Phe Ala Ala Ile Gly Ala Pro
    50                  55                  60 ctg tct ctc ggg cca ggt gac gca ccg ctc gat ctc acg acc ctg acg      240
Leu Ser Leu Gly Pro Gly Asp Ala Pro Leu Asp Leu Thr Thr Leu Thr
65                  70                  75                  80 cgg gcg atc gag gcg gtc atc gcc cgc tcg gtg cgg acg ctg cac ccg      288
Arg Ala Ile Glu Ala Val Ile Ala Arg Ser Val Arg Thr Leu His Pro
                85                  90                  95 cgc ttc ttc aac cag aac ttc gcc ggc gcc gac ccg gtc gcc gtc gtc      336
Arg Phe Phe Asn Gln Asn Phe Ala Gly Ala Asp Pro Val Ala Val Val
            100                 105                 110 ggt gat ttt ctc ggc gcc gcg ctc aac acc acc atg gcc acc tac gag      384
Gly Asp Phe Leu Gly Ala Ala Leu Asn Thr Thr Met Ala Thr Tyr Glu
        115                 120                 125 gcc gcg ccg gtg ttc acc ctg atc gag cgc gag gtg ctg gcg cgc ctg      432
Ala Ala Pro Val Phe Thr Leu Ile Glu Arg Glu Val Leu Ala Arg Leu
    130                 135                 140 gcc gcg ctg gcc ggc tgg ccc gcg cac gag ggc gtg ttc gtg ccc ggc      480
Ala Ala Leu Ala Gly Trp Pro Ala His Glu Gly Val Phe Val Pro Gly
145                 150                 155                 160 ggc tcg gtc tcc aac ctc tac gcg ctg cag ctc gcg cgc ctg cgg gtc      528
Gly Ser Val Ser Asn Leu Tyr Ala Leu Gln Leu Ala Arg Leu Arg Val
                165                 170                 175 gac ccc gag gcg cgc gag cgc ggg cac gac ggc gtc ccg ctg gtc gcc      576
Asp Pro Glu Ala Arg Glu Arg Gly His Asp Gly Val Pro Leu Val Ala
            180                 185                 190 ttc gcc tcg acg cac gcc cac tac tcc ttc gaa aaa tcg gtc gtg ctg      624
Phe Ala Ser Thr His Ala His Tyr Ser Phe Glu Lys Ser Val Val Leu
        195                 200                 205 ctc ggc ctc ggc cgg cgt gct ctg atc aaa gtc gca tgc gac gag cgc      672
Leu Gly Leu Gly Arg Arg Ala Leu Ile Lys Val Ala Cys Asp Glu Arg
    210                 215                 220 ggc cgc atg cgc ccc gac gct ctg gcc gcc gcc atc gac gcc gcc ctc      720
Gly Arg Met Arg Pro Asp Ala Leu Ala Ala Ala Ile Asp Ala Ala Leu
225                 230                 235                 240 gct cgc ggg cag cgg ccg ttc ttc gtc ggc gcc acc gcc ggc acc acc      768
Ala Arg Gly Gln Arg Pro Phe Phe Val Gly Ala Thr Ala Gly Thr Thr
                245                 250                 255 gtg ctc ggc ggc ttc gac ccg ttg ccc gcg ctc gcc gat ctc gcc gag      816
Val Leu Gly Gly Phe Asp Pro Leu Pro Ala Leu Ala Asp Leu Ala Glu
            260                 265                 270 cgc cac cgc ctg tgg ctg cac gtc gac ggc agc ttc ggc gcc tcg gcg      864
Arg His Arg Leu Trp Leu His Val Asp Gly Ser Phe Gly Ala Ser Ala
        275                 280                 285 ctg ttc tcc tcg ggg cag gcg cag ctc atg gcc ggc gtc gcc cgg gcc      912
Leu Phe Ser Ser Gly Gln Ala Gln Leu Met Ala Gly Val Ala Arg Ala
```

```
                290                 295                 300
gac tcg ctg gcg tgg aac ctc cat aag atg ctc ggg gtc acc cag cag       960
Asp Ser Leu Ala Trp Asn Leu His Lys Met Leu Gly Val Thr Gln Gln
305                 310                 315                 320 tgc gca gcc ttc ctg gtc cga ggg aca ggt gcc ttg cgg gcc gcg ttc      1008
Cys Ala Ala Phe Leu Val Arg Gly Thr Gly Ala Leu Arg Ala Ala Phe
                325                 330                 335 gcc acc ggc gcc agc tac ctg ttc cag ccc gac aag ccg cac gcc gag      1056
Ala Thr Gly Ala Ser Tyr Leu Phe Gln Pro Asp Lys Pro His Ala Glu
            340                 345                 350 ctc gac agc ggc gac gcc acc ttt cag tgc gcc cgg cgg gtc gac gcg      1104
Leu Asp Ser Gly Asp Ala Thr Phe Gln Cys Ala Arg Arg Val Asp Ala
        355                 360                 365 ctc aag gcc tgg ctc gtc tgg aag ttc cgc ggc gag gcc ggc ttc gcc      1152
Leu Lys Ala Trp Leu Val Trp Lys Phe Arg Gly Glu Ala Gly Phe Ala
370                 375                 380 gcg cgc atc gac cac gcc gtc ggc ctc gcc gac cac tgc gcc gcg cgg      1200
Ala Arg Ile Asp His Ala Val Gly Leu Ala Asp His Cys Ala Ala Arg
385                 390                 395                 400 atc gcc ggc gac ccg cgg ttt tac ctg gcc gcc ccc tcg tgg gtc          1248
Ile Ala Gly Asp Pro Arg Phe Tyr Leu Ala Ala Pro Pro Ser Trp Val
                405                 410                 415 aac gtg tgt ttt tgg tgg atc ccc ccg gac ctg cgg ccc ttc gcc ggc      1296
Asn Val Cys Phe Trp Trp Ile Pro Pro Asp Leu Arg Pro Phe Ala Gly
            420                 425                 430 cgc acc ccc gag gtc gac gcg acg ctg cac gcc ctg gcc ccg cgg ctc      1344
Arg Thr Pro Glu Val Asp Ala Thr Leu His Ala Leu Ala Pro Arg Leu
        435                 440                 445 aag gcc gcc atg ctg cgc cgc ggc gag gcg atg ctc ggc ttt cag ccg      1392
Lys Ala Ala Met Leu Arg Arg Gly Glu Ala Met Leu Gly Phe Gln Pro
450                 455                 460 gtc gac ggc ggg ccg aac tgc ttc cgc ctg ctg ttc atc aac ccg gcc      1440
Val Asp Gly Gly Pro Asn Cys Phe Arg Leu Leu Phe Ile Asn Pro Ala
465                 470                 475                 480 acg acg atc gcg gac gtc gac gcg acg ctc gag ctc gtc gac gcc tgc      1488
Thr Thr Ile Ala Asp Val Asp Ala Thr Leu Glu Leu Val Asp Ala Cys
                485                 490                 495 ggc cgc gag gcg ctg gcg tca ggc gat tga                              1518
Gly Arg Glu Ala Leu Ala Ser Gly Asp
            500                 505

<210> SEQ ID NO 114
<211> LENGTH: 505
<212> TYPE: PRT
<213> ORGANISM: Nannocystis exedens

<400> SEQUENCE: 114

Met Ala Leu Val Gly Pro Gly Pro Arg Leu Thr Ala Pro Ala Ser Pro
1               5                   10                  15

Ala Lys Val Pro Arg Val Asp Leu Asp Ala Leu Val Arg Pro Ile Leu
            20                  25                  30

Asp Leu Leu Arg Arg Ala Asp Gln Arg Asp Val Arg Ile Thr Asp Leu
        35                  40                  45

Ala Gly Pro Glu Ala His Ala Asp Ala Phe Ala Ala Ile Gly Ala Pro
    50                  55                  60

Leu Ser Leu Gly Pro Gly Asp Ala Pro Leu Asp Leu Thr Thr Leu Thr
65                  70                  75                  80

Arg Ala Ile Glu Ala Val Ile Ala Arg Ser Val Arg Thr Leu His Pro
                85                  90                  95
```

```
Arg Phe Phe Asn Gln Asn Phe Ala Gly Ala Asp Pro Val Ala Val
            100                 105                 110
Gly Asp Phe Leu Gly Ala Ala Leu Asn Thr Thr Met Ala Thr Tyr Glu
            115                 120                 125
Ala Ala Pro Val Phe Thr Leu Ile Glu Arg Glu Val Leu Ala Arg Leu
130                 135                 140
Ala Ala Leu Ala Gly Trp Pro Ala His Glu Gly Val Phe Val Pro Gly
145                 150                 155                 160
Gly Ser Val Ser Asn Leu Tyr Ala Leu Gln Leu Ala Arg Leu Arg Val
                165                 170                 175
Asp Pro Glu Ala Arg Glu Arg Gly His Asp Gly Val Pro Leu Val Ala
            180                 185                 190
Phe Ala Ser Thr His Ala His Tyr Ser Phe Glu Lys Ser Val Val Leu
            195                 200                 205
Leu Gly Leu Gly Arg Arg Ala Leu Ile Lys Val Ala Cys Asp Glu Arg
    210                 215                 220
Gly Arg Met Arg Pro Asp Ala Leu Ala Ala Ile Asp Ala Ala Leu
225                 230                 235                 240
Ala Arg Gly Gln Arg Pro Phe Phe Val Gly Ala Thr Ala Gly Thr Thr
            245                 250                 255
Val Leu Gly Gly Phe Asp Pro Leu Pro Ala Leu Ala Asp Leu Ala Glu
        260                 265                 270
Arg His Arg Leu Trp Leu His Val Asp Gly Ser Phe Gly Ala Ser Ala
    275                 280                 285
Leu Phe Ser Ser Gly Gln Ala Gln Leu Met Ala Gly Val Ala Arg Ala
    290                 295                 300
Asp Ser Leu Ala Trp Asn Leu His Lys Met Leu Gly Val Thr Gln Gln
305                 310                 315                 320
Cys Ala Ala Phe Leu Val Arg Gly Thr Gly Ala Leu Arg Ala Ala Phe
            325                 330                 335
Ala Thr Gly Ala Ser Tyr Leu Phe Gln Pro Asp Lys Pro His Ala Glu
            340                 345                 350
Leu Asp Ser Gly Asp Ala Thr Phe Gln Cys Ala Arg Arg Val Asp Ala
        355                 360                 365
Leu Lys Ala Trp Leu Val Trp Lys Phe Arg Gly Glu Ala Gly Phe Ala
    370                 375                 380
Ala Arg Ile Asp His Ala Val Gly Leu Ala Asp His Cys Ala Ala Arg
385                 390                 395                 400
Ile Ala Gly Asp Pro Arg Phe Tyr Leu Ala Ala Pro Pro Ser Trp Val
                405                 410                 415
Asn Val Cys Phe Trp Trp Ile Pro Pro Asp Leu Arg Pro Phe Ala Gly
            420                 425                 430
Arg Thr Pro Glu Val Asp Ala Thr Leu His Ala Leu Ala Pro Arg Leu
        435                 440                 445
Lys Ala Ala Met Leu Arg Arg Gly Glu Ala Met Leu Gly Phe Gln Pro
    450                 455                 460
Val Asp Gly Gly Pro Asn Cys Phe Arg Leu Leu Phe Ile Asn Pro Ala
465                 470                 475                 480
Thr Thr Ile Ala Asp Val Asp Ala Thr Leu Glu Leu Val Asp Ala Cys
                485                 490                 495
Gly Arg Glu Ala Leu Ala Ser Gly Asp
            500                 505
```

<210> SEQ ID NO 115
<211> LENGTH: 2958
<212> TYPE: DNA
<213> ORGANISM: Micromonas pusilla CCMP1545
<220> FEATURE:
<221> NAME/KEY: CDS
<222> LOCATION: (1)..(2958)

<400> SEQUENCE: 115

| | | | | | | | | | | | | | | | | |
|---|---|---|---|---|---|---|---|---|---|---|---|---|---|---|---|---|
| atg | tcc | gcg | gcg | acg | gga | tca | tta | tcc | cta | ccc | cta | ctc | ggg | cat | ctc | 48 |
| Met | Ser | Ala | Ala | Thr | Gly | Ser | Leu | Ser | Leu | Pro | Leu | Leu | Gly | His | Leu | |
| 1 | | | | 5 | | | | | 10 | | | | | 15 | | |
| gcg | acc | tcg | cgt | aac | gca | cgc | gcg | cgt | cgg | aac | cgc | gcc | gcc | gcg | gcc | 96 |
| Ala | Thr | Ser | Arg | Asn | Ala | Arg | Ala | Arg | Arg | Asn | Arg | Ala | Ala | Ala | Ala | |
| | | | 20 | | | | | 25 | | | | | 30 | | | |
| atc | ccc | ggc | gtc | tcc | ctc | ggg | aaa | tcg | acc | tcg | gtt | ttc | act | ccg | cga | 144 |
| Ile | Pro | Gly | Val | Ser | Leu | Gly | Lys | Ser | Thr | Ser | Val | Phe | Thr | Pro | Arg | |
| | | 35 | | | | | 40 | | | | | 45 | | | | |
| ggt | cct | aag | cgc | atc | gcg | cgc | gtc | gtc | acc | tcg | aag | gcg | ggc | ccg | cat | 192 |
| Gly | Pro | Lys | Arg | Ile | Ala | Arg | Val | Val | Thr | Ser | Lys | Ala | Gly | Pro | His | |
| | 50 | | | | | 55 | | | | | 60 | | | | | |
| tcg | aac | cct | ccg | agg | gcg | ata | tcg | acc | gtc | gac | gac | gtc | ctc | gcg | ttc | 240 |
| Ser | Asn | Pro | Pro | Arg | Ala | Ile | Ser | Thr | Val | Asp | Asp | Val | Leu | Ala | Phe | |
| 65 | | | | | 70 | | | | | 75 | | | | | 80 | |
| acc | gtg | ccc | acc | gac | gag | ccc | gcg | gcc | gag | acc | gcc | tcc | ccc | gcc | gac | 288 |
| Thr | Val | Pro | Thr | Asp | Glu | Pro | Ala | Ala | Glu | Thr | Ala | Ser | Pro | Ala | Asp | |
| | | | | 85 | | | | | 90 | | | | | 95 | | |
| agc | gac | tgc | gaa | ggc | gag | ttc | tgc | gac | atg | aag | gag | agc | tcg | tgc | acg | 336 |
| Ser | Asp | Cys | Glu | Gly | Glu | Phe | Cys | Asp | Met | Lys | Glu | Ser | Ser | Cys | Thr | |
| | | | 100 | | | | | 105 | | | | | 110 | | | |
| acg | agg | gac | ctc | atc | ggc | agc | acg | ccg | ctg | ctc | gat | ctg | agc | gcg | tac | 384 |
| Thr | Arg | Asp | Leu | Ile | Gly | Ser | Thr | Pro | Leu | Leu | Asp | Leu | Ser | Ala | Tyr | |
| | | 115 | | | | | 120 | | | | | 125 | | | | |
| tcc | ctg | aac | ccc | acc | gtg | aag | atc | ctc | gcg | aag | tgc | gag | tac | ctc | aac | 432 |
| Ser | Leu | Asn | Pro | Thr | Val | Lys | Ile | Leu | Ala | Lys | Cys | Glu | Tyr | Leu | Asn | |
| | 130 | | | | | 135 | | | | | 140 | | | | | |
| ccg | tcc | ggg | tcc | atc | aaa | gac | cgc | atc | gcg | acg | cac | atc | ctg | gac | aag | 480 |
| Pro | Ser | Gly | Ser | Ile | Lys | Asp | Arg | Ile | Ala | Thr | His | Ile | Leu | Asp | Lys | |
| 145 | | | | | 150 | | | | | 155 | | | | | 160 | |
| gcg | atc | aag | agc | ggc | gat | ctc | aag | ccc | ggg | atg | acc | gtc | gtc | gcg | gcg | 528 |
| Ala | Ile | Lys | Ser | Gly | Asp | Leu | Lys | Pro | Gly | Met | Thr | Val | Val | Ala | Ala | |
| | | | | 165 | | | | | 170 | | | | | 175 | | |
| acg | tcc | ggg | aac | acc | ggc | gcc | gcg | atc | gcg | atg | gcg | tgc | gcg | ttg | cgc | 576 |
| Thr | Ser | Gly | Asn | Thr | Gly | Ala | Ala | Ile | Ala | Met | Ala | Cys | Ala | Leu | Arg | |
| | | | 180 | | | | | 185 | | | | | 190 | | | |
| ggg | tac | gac | tac | atc | gtc | atc | acc | aac | gag | aag | acg | tcc | aag | gag | aag | 624 |
| Gly | Tyr | Asp | Tyr | Ile | Val | Ile | Thr | Asn | Glu | Lys | Thr | Ser | Lys | Glu | Lys | |
| | | 195 | | | | | 200 | | | | | 205 | | | | |
| gtg | gac | gcg | atg | aga | gcg | tac | ggc | ggc | gag | gtg | atc | gtc | tcc | ccg | tcc | 672 |
| Val | Asp | Ala | Met | Arg | Ala | Tyr | Gly | Gly | Glu | Val | Ile | Val | Ser | Pro | Ser | |
| | 210 | | | | | 215 | | | | | 220 | | | | | |
| ggg | gtg | tcc | ccg | gac | gac | cca | cag | cac | tac | cag | aac | atc | gag | aac | aag | 720 |
| Gly | Val | Ser | Pro | Asp | Asp | Pro | Gln | His | Tyr | Gln | Asn | Ile | Glu | Asn | Lys | |
| 225 | | | | | 230 | | | | | 235 | | | | | 240 | |
| ctg | tgc | gag | gag | aac | ccc | ggg | acg | tac | tac | ggc | gtg | gat | cag | tat | aac | 768 |
| Leu | Cys | Glu | Glu | Asn | Pro | Gly | Thr | Tyr | Tyr | Gly | Val | Asp | Gln | Tyr | Asn | |
| | | | | 245 | | | | | 250 | | | | | 255 | | |
| aac | ccg | tac | aac | gcg | gac | gcg | tac | gag | gcg | acg | ctc | ggg | ccg | gag | att | 816 |
| Asn | Pro | Tyr | Asn | Ala | Asp | Ala | Tyr | Glu | Ala | Thr | Leu | Gly | Pro | Glu | Ile | |
| | | | 260 | | | | | 265 | | | | | 270 | | | |

-continued

```
tgg cgt cag agc gtg ggc gcg gtg acg cac ttc atc gtc ggc ggc agc      864
Trp Arg Gln Ser Val Gly Ala Val Thr His Phe Ile Val Gly Gly Ser
    275                 280                 285 acc ggc ggc acg gtc agc ggc acg ggg agg tac ttg aag caa gag aac      912
Thr Gly Gly Thr Val Ser Gly Thr Gly Arg Tyr Leu Lys Gln Glu Asn
290                 295                 300 ccg gac gtg agg atc gtc ctc gcg gac ccg aga ggg agc gtg ttc tgg      960
Pro Asp Val Arg Ile Val Leu Ala Asp Pro Arg Gly Ser Val Phe Trp
305                 310                 315                 320 gac cac gtc gtc aac ggc gtc gcc gcc gac gac gtc aag gtg tcc aag     1008
Asp His Val Val Asn Gly Val Ala Ala Asp Asp Val Lys Val Ser Lys
                325                 330                 335 tcg tgg gag acg gag ggc gtc ggc aag gat tcc atc ccc ggg tgc ctc     1056
Ser Trp Glu Thr Glu Gly Val Gly Lys Asp Ser Ile Pro Gly Cys Leu
            340                 345                 350 gac gtc tcg atc gtg gac ggg atg gtg cgc gcg acg gac gag cag gcg     1104
Asp Val Ser Ile Val Asp Gly Met Val Arg Ala Thr Asp Glu Gln Ala
        355                 360                 365 ttc ggc gtg tgc cgc gag ctc gcg agc agc gac ggc ctc ctc gtc ggc     1152
Phe Gly Val Cys Arg Glu Leu Ala Ser Ser Asp Gly Leu Leu Val Gly
370                 375                 380 ggc agc agc ggt ctg aac ctc cac gcc tcg cgc gtg tta tcc ggc gac     1200
Gly Ser Ser Gly Leu Asn Leu His Ala Ser Arg Val Leu Ser Gly Asp
385                 390                 395                 400 gtc gcg gac gac agc gtc atc gtc acg gtg ttc ccg gac aac ggc gtg     1248
Val Ala Asp Asp Ser Val Ile Val Thr Val Phe Pro Asp Asn Gly Val
                405                 410                 415 aag tac ctg tcg aag att tac aac gac gac tgg ctc gac tcg aag aag     1296
Lys Tyr Leu Ser Lys Ile Tyr Asn Asp Asp Trp Leu Asp Ser Lys Lys
            420                 425                 430 atg ggc ggc gca aag aac tcg gac ggg aac gcg gag aga gcc gcg gag     1344
Met Gly Gly Ala Lys Asn Ser Asp Gly Asn Ala Glu Arg Ala Ala Glu
        435                 440                 445 tgc gag gtg tac tgg cgc ccg gac gcg ctc tcg ttc gcg gag cga aag     1392
Cys Glu Val Tyr Trp Arg Pro Asp Ala Leu Ser Phe Ala Glu Arg Lys
450                 455                 460 gcg gcg gcg gac gcc gcc gcc gcc gcc gcc gtc gag ggc gac aac ctc     1440
Ala Ala Ala Asp Ala Ala Ala Ala Ala Ala Val Glu Gly Asp Asn Leu
465                 470                 475                 480 tgg ccc gag gac gag acc gag cgc gag ctc aag ttc ctg gag gaa ctc     1488
Trp Pro Glu Asp Glu Thr Glu Arg Glu Leu Lys Phe Leu Glu Glu Leu
                485                 490                 495 gcg ccg aag ctg acg cag tac cac aga gac tcc atc aag ggc gac gag     1536
Ala Pro Lys Leu Thr Gln Tyr His Arg Asp Ser Ile Lys Gly Asp Glu
            500                 505                 510 cgc gtg cac agc aag ctc cag tcc ccg gag gag ctc gcg gcg acg ttc     1584
Arg Val His Ser Lys Leu Gln Ser Pro Glu Glu Leu Ala Ala Thr Phe
        515                 520                 525 gcc gcc gcg ggg gcg ccc atc gac ctc gcg gag ggc gac gcc ccc gcg     1632
Ala Ala Ala Gly Ala Pro Ile Asp Leu Ala Glu Gly Asp Ala Pro Ala
530                 535                 540 acg gag gag caa ctc gcg ctc gcg gtg cag gcg gtc atg gac aac tcg     1680
Thr Glu Glu Gln Leu Ala Leu Ala Val Gln Ala Val Met Asp Asn Ser
545                 550                 555                 560 gtc cgc tcc tcg cac ccg atg ttc ttg aac cag ctg tac gcc ggc gtc     1728
Val Arg Ser Ser His Pro Met Phe Leu Asn Gln Leu Tyr Ala Gly Val
                565                 570                 575 gac gtc gtc gcg ctc gcg ggg gag tgg acc gcg agc gcg ttg aac gcc     1776
Asp Val Val Ala Leu Ala Gly Glu Trp Thr Ala Ser Ala Leu Asn Ala
            580                 585                 590
```

-continued

```
aac gtg cac acg ttt gaa gtc gcg ccg gtg ctc acg gag att gag aaa         1824
Asn Val His Thr Phe Glu Val Ala Pro Val Leu Thr Glu Ile Glu Lys
        595                 600                 605 gcc gtc ctc gcg aaa acc gcg cgg atg tgg ctg aac aag ccc ggg tct         1872
Ala Val Leu Ala Lys Thr Ala Arg Met Trp Leu Asn Lys Pro Gly Ser
610                 615                 620 aag acg acg ccg ccg cac gac ggt ctg ctc gtc ccc ggc ggg tcc ctg         1920
Lys Thr Thr Pro Pro His Asp Gly Leu Leu Val Pro Gly Gly Ser Leu
625                 630                 635                 640 gcg aac atg tac tcg atg atc ctc gcg cgc gat cgc gcg gag ccg gag         1968
Ala Asn Met Tyr Ser Met Ile Leu Ala Arg Asp Arg Ala Glu Pro Glu
                645                 650                 655 gcg aag acc aag ggc gcg agc ggc aac ctc gtc gcg ttt tgc tcg gag         2016
Ala Lys Thr Lys Gly Ala Ser Gly Asn Leu Val Ala Phe Cys Ser Glu
    660                 665                 670 cag tcg cac tac tcg tac aaa aag tcc gcg atg gtc atg ggc ctc ggg         2064
Gln Ser His Tyr Ser Tyr Lys Lys Ser Ala Met Val Met Gly Leu Gly
        675                 680                 685 atg gac aac atg atc aag gtg aag tgc gac cag tcc ggc gcg atg atc         2112
Met Asp Asn Met Ile Lys Val Lys Cys Asp Gln Ser Gly Ala Met Ile
690                 695                 700 ccg gcg gag ctc gag aag gcg gtt cag gag gcc aag tcc cgg ggc aag         2160
Pro Ala Glu Leu Glu Lys Ala Val Gln Glu Ala Lys Ser Arg Gly Lys
705                 710                 715                 720 gtg ccg ttc tac gtc ggc acc acc gcg ggg tcc acc gtg ctc ggc gcc         2208
Val Pro Phe Tyr Val Gly Thr Thr Ala Gly Ser Thr Val Leu Gly Ala
                725                 730                 735 ttt gac gac tac gaa ggc tgc gcg gac gtc tgc gaa aag cac gac atg         2256
Phe Asp Asp Tyr Glu Gly Cys Ala Asp Val Cys Glu Lys His Asp Met
    740                 745                 750 tgg atg cac gtc gac ggc gcg tgg ggc ggc gcc gcg gcg ctg tcc ccg         2304
Trp Met His Val Asp Gly Ala Trp Gly Gly Ala Ala Ala Leu Ser Pro
        755                 760                 765 acg aga agg cac aat ctc cag ggc gcg aac aga gcg gac tcg ttc tgc         2352
Thr Arg Arg His Asn Leu Gln Gly Ala Asn Arg Ala Asp Ser Phe Cys
770                 775                 780 tgg aac ccg cac aag atg ctc ggg ttg ccg ctc cag tgc tcc atc ttc         2400
Trp Asn Pro His Lys Met Leu Gly Leu Pro Leu Gln Cys Ser Ile Phe
785                 790                 795                 800 gtg acg aag caa ccc ggg gcg ctg tcc aag gcg aac gcc gcg cag gcg         2448
Val Thr Lys Gln Pro Gly Ala Leu Ser Lys Ala Asn Ala Ala Gln Ala
                805                 810                 815 gac tac ttg ttc cag ccg gac aag aac aac gcc gcc gcg gac ctc ggc         2496
Asp Tyr Leu Phe Gln Pro Asp Lys Asn Asn Ala Ala Ala Asp Leu Gly
    820                 825                 830 gac cgc acg att cag tgc gga cgc aag gcg gac gcc ctc aag atc tgg         2544
Asp Arg Thr Ile Gln Cys Gly Arg Lys Ala Asp Ala Leu Lys Ile Trp
        835                 840                 845 ctc gcg tgg aag gcg cgc gga gac gaa ggc tgg gcg aat ctc gtg gac         2592
Leu Ala Trp Lys Ala Arg Gly Asp Glu Gly Trp Ala Asn Leu Val Asp
850                 855                 860 cgc tcc ttt ggc ctc gcg gag tac gtc gag gcg tcg gtg cgc gag cgg         2640
Arg Ser Phe Gly Leu Ala Glu Tyr Val Glu Ala Ser Val Arg Glu Arg
865                 870                 875                 880 tgc gaa aaa gac ggc tcg ttc gtc ctc gcc gcg ccc gcg cag tgc gcg         2688
Cys Glu Lys Asp Gly Ser Phe Val Leu Ala Ala Pro Ala Gln Cys Ala
                885                 890                 895 aac atc ggg ttc tgg tac gtg ccc ccg cgc ctg agg ccg ttc gat gtc         2736
Asn Ile Gly Phe Trp Tyr Val Pro Pro Arg Leu Arg Pro Phe Asp Val
```

```
                900             905             910
gag tcc gcg acc gcg gac cag ctc acg gag att ggg ttc gtc gcc ccg      2784
Glu Ser Ala Thr Ala Asp Gln Leu Thr Glu Ile Gly Phe Val Ala Pro
    915                 920                 925 aag ctg aag gac cgg atg caa cgg acc ggg gac gcg atg atc ggg ttc      2832
Lys Leu Lys Asp Arg Met Gln Arg Thr Gly Asp Ala Met Ile Gly Phe
930                 935                 940 cag ccg atc gac tcg atg aac ctt cca aac ttt ttc cga ctc gtg ctt      2880
Gln Pro Ile Asp Ser Met Asn Leu Pro Asn Phe Phe Arg Leu Val Leu
945                 950                 955                 960 cca aac tcg agg cac ctg tcg aag aac gcg ctc gac gct atg ctc gat      2928
Pro Asn Ser Arg His Leu Ser Lys Asn Ala Leu Asp Ala Met Leu Asp
                965                 970                 975 cgc atg gac gac atg ggc aaa gac ctg tga                              2958
Arg Met Asp Asp Met Gly Lys Asp Leu
            980                 985
```

<210> SEQ ID NO 116
<211> LENGTH: 985
<212> TYPE: PRT
<213> ORGANISM: Micromonas pusilla CCMP1545

<400> SEQUENCE: 116

```
Met Ser Ala Ala Thr Gly Ser Leu Ser Leu Pro Leu Leu Gly His Leu
1               5                   10                  15

Ala Thr Ser Arg Asn Ala Arg Ala Arg Arg Asn Arg Ala Ala Ala Ala
            20                  25                  30

Ile Pro Gly Val Ser Leu Gly Lys Ser Thr Ser Val Phe Thr Pro Arg
        35                  40                  45

Gly Pro Lys Arg Ile Ala Arg Val Val Thr Ser Lys Ala Gly Pro His
    50                  55                  60

Ser Asn Pro Pro Arg Ala Ile Ser Thr Val Asp Asp Val Leu Ala Phe
65                  70                  75                  80

Thr Val Pro Thr Asp Glu Pro Ala Ala Glu Thr Ala Ser Pro Ala Asp
                85                  90                  95

Ser Asp Cys Glu Gly Glu Phe Cys Asp Met Lys Glu Ser Ser Cys Thr
            100                 105                 110

Thr Arg Asp Leu Ile Gly Ser Thr Pro Leu Leu Asp Leu Ser Ala Tyr
        115                 120                 125

Ser Leu Asn Pro Thr Val Lys Ile Leu Ala Lys Cys Glu Tyr Leu Asn
    130                 135                 140

Pro Ser Gly Ser Ile Lys Asp Arg Ile Ala Thr His Ile Leu Asp Lys
145                 150                 155                 160

Ala Ile Lys Ser Gly Asp Leu Lys Pro Gly Met Thr Val Val Ala Ala
                165                 170                 175

Thr Ser Gly Asn Thr Gly Ala Ala Ile Ala Met Ala Cys Ala Leu Arg
            180                 185                 190

Gly Tyr Asp Tyr Ile Val Ile Thr Asn Glu Lys Thr Ser Lys Glu Lys
        195                 200                 205

Val Asp Ala Met Arg Ala Tyr Gly Gly Glu Val Ile Val Ser Pro Ser
    210                 215                 220

Gly Val Ser Pro Asp Asp Pro Gln His Tyr Gln Asn Ile Glu Asn Lys
225                 230                 235                 240

Leu Cys Glu Glu Asn Pro Gly Thr Tyr Tyr Gly Val Asp Gln Tyr Asn
                245                 250                 255

Asn Pro Tyr Asn Ala Asp Ala Tyr Glu Ala Thr Leu Gly Pro Glu Ile
```

```
                260             265             270
Trp Arg Gln Ser Val Gly Ala Val Thr His Phe Ile Val Gly Gly Ser
        275             280             285
Thr Gly Gly Thr Val Ser Gly Thr Gly Arg Tyr Leu Lys Gln Glu Asn
        290             295             300
Pro Asp Val Arg Ile Val Leu Ala Asp Pro Arg Gly Ser Val Phe Trp
305             310             315             320
Asp His Val Val Asn Gly Val Ala Ala Asp Val Lys Val Ser Lys
                325             330             335
Ser Trp Glu Thr Glu Gly Val Gly Lys Asp Ser Ile Pro Gly Cys Leu
        340             345             350
Asp Val Ser Ile Val Asp Gly Met Val Arg Ala Thr Asp Glu Gln Ala
        355             360             365
Phe Gly Val Cys Arg Glu Leu Ala Ser Ser Asp Gly Leu Leu Val Gly
        370             375             380
Gly Ser Ser Gly Leu Asn Leu His Ala Ser Arg Val Leu Ser Gly Asp
385             390             395             400
Val Ala Asp Asp Ser Val Ile Val Thr Val Phe Pro Asp Asn Gly Val
                405             410             415
Lys Tyr Leu Ser Lys Ile Tyr Asn Asp Asp Trp Leu Asp Ser Lys Lys
        420             425             430
Met Gly Gly Ala Lys Asn Ser Asp Gly Asn Ala Glu Arg Ala Ala Glu
        435             440             445
Cys Glu Val Tyr Trp Arg Pro Asp Ala Leu Ser Phe Ala Glu Arg Lys
        450             455             460
Ala Ala Ala Asp Ala Ala Ala Ala Ala Val Glu Gly Asp Asn Leu
465             470             475             480
Trp Pro Glu Asp Glu Thr Glu Arg Glu Leu Lys Phe Leu Glu Glu Leu
                485             490             495
Ala Pro Lys Leu Thr Gln Tyr His Arg Asp Ser Ile Lys Gly Asp Glu
        500             505             510
Arg Val His Ser Lys Leu Gln Ser Pro Glu Glu Leu Ala Ala Thr Phe
        515             520             525
Ala Ala Ala Gly Ala Pro Ile Asp Leu Ala Glu Gly Asp Ala Pro Ala
        530             535             540
Thr Glu Glu Gln Leu Ala Leu Ala Val Gln Ala Val Met Asp Asn Ser
545             550             555             560
Val Arg Ser Ser His Pro Met Phe Leu Asn Gln Leu Tyr Ala Gly Val
                565             570             575
Asp Val Val Ala Leu Ala Gly Glu Trp Thr Ala Ser Ala Leu Asn Ala
        580             585             590
Asn Val His Thr Phe Glu Val Ala Pro Val Leu Thr Glu Ile Glu Lys
        595             600             605
Ala Val Leu Ala Lys Thr Ala Arg Met Trp Leu Asn Lys Pro Gly Ser
        610             615             620
Lys Thr Thr Pro Pro His Asp Gly Leu Leu Val Pro Gly Gly Ser Leu
625             630             635             640
Ala Asn Met Tyr Ser Met Ile Leu Ala Arg Asp Arg Ala Glu Pro Glu
                645             650             655
Ala Lys Thr Lys Gly Ala Ser Gly Asn Leu Val Ala Phe Cys Ser Glu
        660             665             670
Gln Ser His Tyr Ser Tyr Lys Lys Ser Ala Met Val Met Gly Leu Gly
        675             680             685
```

```
Met Asp Asn Met Ile Lys Val Lys Cys Asp Gln Ser Gly Ala Met Ile
            690                 695                 700

Pro Ala Glu Leu Glu Lys Ala Val Gln Glu Ala Lys Ser Arg Gly Lys
705                 710                 715                 720

Val Pro Phe Tyr Val Gly Thr Thr Ala Gly Ser Thr Val Leu Gly Ala
                725                 730                 735

Phe Asp Asp Tyr Glu Gly Cys Ala Asp Val Cys Glu Lys His Asp Met
                740                 745                 750

Trp Met His Val Asp Gly Ala Trp Gly Gly Ala Ala Ala Leu Ser Pro
            755                 760                 765

Thr Arg Arg His Asn Leu Gln Gly Ala Asn Arg Ala Asp Ser Phe Cys
770                 775                 780

Trp Asn Pro His Lys Met Leu Gly Leu Pro Leu Gln Cys Ser Ile Phe
785                 790                 795                 800

Val Thr Lys Gln Pro Gly Ala Leu Ser Lys Ala Asn Ala Ala Gln Ala
                805                 810                 815

Asp Tyr Leu Phe Gln Pro Asp Lys Asn Asn Ala Ala Ala Asp Leu Gly
                820                 825                 830

Asp Arg Thr Ile Gln Cys Gly Arg Lys Ala Asp Ala Leu Lys Ile Trp
            835                 840                 845

Leu Ala Trp Lys Ala Arg Gly Asp Glu Gly Trp Ala Asn Leu Val Asp
850                 855                 860

Arg Ser Phe Gly Leu Ala Glu Tyr Val Glu Ala Ser Val Arg Glu Arg
865                 870                 875                 880

Cys Glu Lys Asp Gly Ser Phe Val Leu Ala Ala Pro Ala Gln Cys Ala
                885                 890                 895

Asn Ile Gly Phe Trp Tyr Val Pro Pro Arg Leu Arg Pro Phe Asp Val
                900                 905                 910

Glu Ser Ala Thr Ala Asp Gln Leu Thr Glu Ile Gly Phe Val Ala Pro
            915                 920                 925

Lys Leu Lys Asp Arg Met Gln Arg Thr Gly Asp Ala Met Ile Gly Phe
930                 935                 940

Gln Pro Ile Asp Ser Met Asn Leu Pro Asn Phe Phe Arg Leu Val Leu
945                 950                 955                 960

Pro Asn Ser Arg His Leu Ser Lys Asn Ala Leu Asp Ala Met Leu Asp
                965                 970                 975

Arg Met Asp Asp Met Gly Lys Asp Leu
            980                 985

<210> SEQ ID NO 117
<211> LENGTH: 1629
<212> TYPE: DNA
<213> ORGANISM: Guillardia theta CCMP2712
<220> FEATURE:
<221> NAME/KEY: CDS
<222> LOCATION: (1)..(1629)

<400> SEQUENCE: 117 atg gtg ccc ccc gcc ttg cat gaa ggg ttc tgc agc cct cga ggc agg      48
Met Val Pro Pro Ala Leu His Glu Gly Phe Cys Ser Pro Arg Gly Arg
1               5                   10                  15 act tgt tgc tct cag gtg gga cac gtg gag ttg ttg gag agc tgg gaa      96
Thr Cys Cys Ser Gln Val Gly His Val Glu Leu Leu Glu Ser Trp Glu
            20                  25                  30 acg cag ggg aac aag ctg aga tgc gag caa gac ctc ctg ctg gcc aag     144
Thr Gln Gly Asn Lys Leu Arg Cys Glu Gln Asp Leu Leu Leu Ala Lys
```

```
                35                  40                  45
gtt ccc tct cgc ttc cac cac ctt gag gaa gtg gcc gag ctg gat gat       192
Val Pro Ser Arg Phe His His Leu Glu Glu Val Ala Glu Leu Asp Asp
    50                  55                  60 atc ttc agg gag gtg tat cct ctg atc cgg cag tac gag acg gag aac       240
Ile Phe Arg Glu Val Tyr Pro Leu Ile Arg Gln Tyr Glu Thr Glu Asn
65                  70                  75                  80 gcg cta gca gac gag cac aag gtg ctg gag ttc agg acg cca gcg gag       288
Ala Leu Ala Asp Glu His Lys Val Leu Glu Phe Arg Thr Pro Ala Glu
                85                  90                  95 ctg aag gag gag gtg gac gtg ggg ctg cct gag gag gga tct gtg gag       336
Leu Lys Glu Glu Val Asp Val Gly Leu Pro Glu Glu Gly Ser Val Glu
            100                 105                 110 aaa ttt gtc gag gga tgc aga agc tct atg aag tac agc gtc cga acg       384
Lys Phe Val Glu Gly Cys Arg Ser Ser Met Lys Tyr Ser Val Arg Thr
        115                 120                 125 agt cac ccg cgc ttc atg aac cag ctc tat gct ggc agc gac ccg gca       432
Ser His Pro Arg Phe Met Asn Gln Leu Tyr Ala Gly Ser Asp Pro Ala
    130                 135                 140 ggg cag gtg gca gag ctg ctc agt gct gtg ctg aac acc acc atc cac       480
Gly Gln Val Ala Glu Leu Leu Ser Ala Val Leu Asn Thr Thr Ile His
145                 150                 155                 160 acg tac ggg gca gct ccc ttc ttc tcc gtg ctg gag cgg cag gtg atc       528
Thr Tyr Gly Ala Ala Pro Phe Phe Ser Val Leu Glu Arg Gln Val Ile
                165                 170                 175 gag aag ctg ggg agg atg ctg ggg ttt cag gag cat gtc gac ggc gtc       576
Glu Lys Leu Gly Arg Met Leu Gly Phe Gln Glu His Val Asp Gly Val
            180                 185                 190 ttt gcc ccc gga ggc tcg tac gcg aac atg gtg gcg ctg ata gtt gcg       624
Phe Ala Pro Gly Gly Ser Tyr Ala Asn Met Val Ala Leu Ile Val Ala
        195                 200                 205 agg aac cag cac ttc cct cat gtg cgg gag cat ggc tgg agg agc gac       672
Arg Asn Gln His Phe Pro His Val Arg Glu His Gly Trp Arg Ser Asp
    210                 215                 220 gac aaa cct gtt atc ttc act tct tcc cat gct cac tac tct gtc gcc       720
Asp Lys Pro Val Ile Phe Thr Ser Ser His Ala His Tyr Ser Val Ala
225                 230                 235                 240 aag gct gcc atg atc acg ggg atg ggg tcg aat caa gtg gtc gct gtg       768
Lys Ala Ala Met Ile Thr Gly Met Gly Ser Asn Gln Val Val Ala Val
                245                 250                 255 cct acg gac gag cag gga aga atg cag cct gca gcg ctg gag gag gag       816
Pro Thr Asp Glu Gln Gly Arg Met Gln Pro Ala Ala Leu Glu Glu Glu
            260                 265                 270 att atg cga gca aag gag agc gga cgg aag cct ttc tac gtg agc tgc       864
Ile Met Arg Ala Lys Glu Ser Gly Arg Lys Pro Phe Tyr Val Ser Cys
        275                 280                 285 acg gca ggg acg aca gtg act ggg gcg ttt gac ccg att gac gag atc       912
Thr Ala Gly Thr Thr Val Thr Gly Ala Phe Asp Pro Ile Asp Glu Ile
    290                 295                 300 tgt cag ata tgt aga agg cat gag atg tgg ctg cac acg gat ggc gcg       960
Cys Gln Ile Cys Arg Arg His Glu Met Trp Leu His Thr Asp Gly Ala
305                 310                 315                 320 tgg gga gga gct gca ata ttc tcg gag gag cac aga aat ctt cta cga      1008
Trp Gly Gly Ala Ala Ile Phe Ser Glu Glu His Arg Asn Leu Leu Arg
                325                 330                 335 gga gtt gag ggc gtc gat agc ttc tgc ttg aat ccg cac aag atg ctg      1056
Gly Val Glu Gly Val Asp Ser Phe Cys Leu Asn Pro His Lys Met Leu
            340                 345                 350 ggg gtc ccg atg cag tgc tcc gtg ctc atc ctc aac aac cac gag ggg      1104
```

```
Gly Val Pro Met Gln Cys Ser Val Leu Ile Leu Asn Asn His Glu Gly
        355                 360                 365 cgc tcg aga gga gca aca gag gaa gag agc ttg gat ctc ggg cag aag      1152
Arg Ser Arg Gly Ala Thr Glu Glu Glu Ser Leu Asp Leu Gly Gln Lys
        370                 375                 380 tcg ctg cag tgc gga agg aaa cct gat tgc cta aag ctc tgg ctc tgc      1200
Ser Leu Gln Cys Gly Arg Lys Pro Asp Cys Leu Lys Leu Trp Leu Cys
385                 390                 395                 400 tgg aag cga cat gga acc cgc ggg ttt gca agg agg gta gat cgc gcg      1248
Trp Lys Arg His Gly Thr Arg Gly Phe Ala Arg Arg Val Asp Arg Ala
                405                 410                 415 tat acc ttc tcg cag aag ttc gca gaa atg gtc aga agg gac ccc agg      1296
Tyr Thr Phe Ser Gln Lys Phe Ala Glu Met Val Arg Arg Asp Pro Arg
        420                 425                 430 ttc tac ctg ctg atg gac ccg atc tcc tgc aac gtc tgc ttc ttc tac      1344
Phe Tyr Leu Leu Met Asp Pro Ile Ser Cys Asn Val Cys Phe Phe Tyr
        435                 440                 445 ctc cct ccc tcc ctc cgg cag cag ctg gtg gac aga aac ctc aac gac      1392
Leu Pro Pro Ser Leu Arg Gln Gln Leu Val Asp Arg Asn Leu Asn Asp
450                 455                 460 ttg gaa aag gag gag gcg cag cgg cag ctc aag gag ttc cat gct cga      1440
Leu Glu Lys Glu Glu Ala Gln Arg Gln Leu Lys Glu Phe His Ala Arg
465                 470                 475                 480 ctc ggt cag gtt act cag atc atc tac agg agg atg cag aaa gac ggc      1488
Leu Gly Gln Val Thr Gln Ile Ile Tyr Arg Arg Met Gln Lys Asp Gly
                485                 490                 495 aag atg ctc atc aac ttc agc cct ctt aaa gac aga gat ctg cct cac      1536
Lys Met Leu Ile Asn Phe Ser Pro Leu Lys Asp Arg Asp Leu Pro His
        500                 505                 510 ttc ttc cga gcc gtc atg atc cag cag aga gta acg gaa gac gat ctt      1584
Phe Phe Arg Ala Val Met Ile Gln Gln Arg Val Thr Glu Asp Asp Leu
        515                 520                 525 gtt ttc atc ctc gat cat ttt gaa cat ctg gga aag gac ctc tag          1629
Val Phe Ile Leu Asp His Phe Glu His Leu Gly Lys Asp Leu
530                 535                 540

<210> SEQ ID NO 118
<211> LENGTH: 542
<212> TYPE: PRT
<213> ORGANISM: Guillardia theta CCMP2712

<400> SEQUENCE: 118

Met Val Pro Pro Ala Leu His Glu Gly Phe Cys Ser Pro Arg Gly Arg
1               5                   10                  15

Thr Cys Cys Ser Gln Val Gly His Val Glu Leu Leu Glu Ser Trp Glu
            20                  25                  30

Thr Gln Gly Asn Lys Leu Arg Cys Glu Gln Asp Leu Leu Leu Ala Lys
        35                  40                  45

Val Pro Ser Arg Phe His His Leu Glu Glu Val Ala Glu Leu Asp Asp
    50                  55                  60

Ile Phe Arg Glu Val Tyr Pro Leu Ile Arg Gln Tyr Glu Thr Glu Asn
65                  70                  75                  80

Ala Leu Ala Asp Glu His Lys Val Leu Glu Phe Arg Thr Pro Ala Glu
                85                  90                  95

Leu Lys Glu Glu Val Asp Val Gly Leu Pro Glu Glu Gly Ser Val Glu
            100                 105                 110

Lys Phe Val Glu Gly Cys Arg Ser Ser Met Lys Tyr Ser Val Arg Thr
        115                 120                 125
```

```
Ser His Pro Arg Phe Met Asn Gln Leu Tyr Ala Gly Ser Asp Pro Ala
    130                 135                 140

Gly Gln Val Ala Glu Leu Leu Ser Ala Val Leu Asn Thr Thr Ile His
145                 150                 155                 160

Thr Tyr Gly Ala Ala Pro Phe Phe Ser Val Leu Glu Arg Gln Val Ile
                165                 170                 175

Glu Lys Leu Gly Arg Met Leu Gly Phe Gln Glu His Val Asp Gly Val
            180                 185                 190

Phe Ala Pro Gly Gly Ser Tyr Ala Asn Met Val Ala Leu Ile Val Ala
        195                 200                 205

Arg Asn Gln His Phe Pro His Val Arg Glu His Gly Trp Arg Ser Asp
210                 215                 220

Asp Lys Pro Val Ile Phe Thr Ser Ser His Ala His Tyr Ser Val Ala
225                 230                 235                 240

Lys Ala Ala Met Ile Thr Gly Met Gly Ser Asn Gln Val Val Ala Val
                245                 250                 255

Pro Thr Asp Glu Gln Gly Arg Met Gln Pro Ala Ala Leu Glu Glu Glu
            260                 265                 270

Ile Met Arg Ala Lys Glu Ser Gly Arg Lys Pro Phe Tyr Val Ser Cys
        275                 280                 285

Thr Ala Gly Thr Thr Val Thr Gly Ala Phe Asp Pro Ile Asp Glu Ile
    290                 295                 300

Cys Gln Ile Cys Arg Arg His Glu Met Trp Leu His Thr Asp Gly Ala
305                 310                 315                 320

Trp Gly Gly Ala Ala Ile Phe Ser Glu Glu His Arg Asn Leu Leu Arg
                325                 330                 335

Gly Val Glu Gly Val Asp Ser Phe Cys Leu Asn Pro His Lys Met Leu
            340                 345                 350

Gly Val Pro Met Gln Cys Ser Val Leu Ile Leu Asn Asn His Glu Gly
        355                 360                 365

Arg Ser Arg Gly Ala Thr Glu Glu Ser Leu Asp Leu Gly Gln Lys
370                 375                 380

Ser Leu Gln Cys Gly Arg Lys Pro Asp Cys Leu Lys Leu Trp Leu Cys
385                 390                 395                 400

Trp Lys Arg His Gly Thr Arg Gly Phe Ala Arg Arg Val Asp Arg Ala
                405                 410                 415

Tyr Thr Phe Ser Gln Lys Phe Ala Glu Met Val Arg Arg Asp Pro Arg
            420                 425                 430

Phe Tyr Leu Leu Met Asp Pro Ile Ser Cys Asn Val Cys Phe Phe Tyr
        435                 440                 445

Leu Pro Pro Ser Leu Arg Gln Gln Leu Val Asp Arg Asn Leu Asn Asp
450                 455                 460

Leu Glu Lys Glu Glu Ala Gln Arg Gln Leu Lys Glu Phe His Ala Arg
465                 470                 475                 480

Leu Gly Gln Val Thr Gln Ile Ile Tyr Arg Arg Met Gln Lys Asp Gly
                485                 490                 495

Lys Met Leu Ile Asn Phe Ser Pro Leu Lys Asp Arg Asp Leu Pro His
            500                 505                 510

Phe Phe Arg Ala Val Met Ile Gln Gln Arg Val Thr Glu Asp Asp Leu
        515                 520                 525

Val Phe Ile Leu Asp His Phe Glu His Leu Gly Lys Asp Leu
530                 535                 540
```

```
<210> SEQ ID NO 119
<211> LENGTH: 1413
<212> TYPE: DNA
<213> ORGANISM: Moorea producens
<220> FEATURE:
<221> NAME/KEY: CDS
<222> LOCATION: (1)..(1413)

<400> SEQUENCE: 119
```

| | | | | | | | | | | | | | | | |
|---|---|---|---|---|---|---|---|---|---|---|---|---|---|---|---|
| atg | atc | gag | ttt | gaa | aaa | ata | atc | aac | tta | act | gtt | gat | aaa | ctc | ctt | 48 |
| Met | Ile | Glu | Phe | Glu | Lys | Ile | Ile | Asn | Leu | Thr | Val | Asp | Lys | Leu | Leu | |
| 1 | | | | 5 | | | | | 10 | | | | | 15 | | |
| aac | tat | ttg | cag | gaa | aat | aaa | aat | acc | gac | acc | aag | gta | ata | gat | tac | 96 |
| Asn | Tyr | Leu | Gln | Glu | Asn | Lys | Asn | Thr | Asp | Thr | Lys | Val | Ile | Asp | Tyr | |
| | | | 20 | | | | | 25 | | | | | 30 | | | |
| aaa | agc | cct | caa | gcc | ctt | aag | gaa | aaa | ctc | gat | tta | agc | tta | cca | gaa | 144 |
| Lys | Ser | Pro | Gln | Ala | Leu | Lys | Glu | Lys | Leu | Asp | Leu | Ser | Leu | Pro | Glu | |
| 35 | | | | | 40 | | | | | 45 | | | | | | |
| aac | gga | gtt | ccc | tta | gcc | gat | tta | att | ccg | att | att | gaa | tcg | tat | ctc | 192 |
| Asn | Gly | Val | Pro | Leu | Ala | Asp | Leu | Ile | Pro | Ile | Ile | Glu | Ser | Tyr | Leu | |
| | 50 | | | | | 55 | | | | | 60 | | | | | |
| gac | cac | agc | gtg | cgg | act | agt | agc | cat | aag | ttt | ttc | aac | cag | ctt | tgg | 240 |
| Asp | His | Ser | Val | Arg | Thr | Ser | Ser | His | Lys | Phe | Phe | Asn | Gln | Leu | Trp | |
| 65 | | | | | 70 | | | | | 75 | | | | | 80 | |
| ggt | gga | ttt | gag | ata | act | gga | tta | tta | gca | gaa | atg | gta | act | agt | act | 288 |
| Gly | Gly | Phe | Glu | Ile | Thr | Gly | Leu | Leu | Ala | Glu | Met | Val | Thr | Ser | Thr | |
| | | | | 85 | | | | | 90 | | | | | 95 | | |
| gct | aat | act | tct | atg | tat | acc | tat | gaa | gtt | gct | cca | gta | gcc | acg | ctg | 336 |
| Ala | Asn | Thr | Ser | Met | Tyr | Thr | Tyr | Glu | Val | Ala | Pro | Val | Ala | Thr | Leu | |
| | | | 100 | | | | | 105 | | | | | 110 | | | |
| atc | gag | att | aaa | ttg | att | gag | gct | ctc | aag | gac | ttg | atc | ggt | ttt | cct | 384 |
| Ile | Glu | Ile | Lys | Leu | Ile | Glu | Ala | Leu | Lys | Asp | Leu | Ile | Gly | Phe | Pro | |
| | | 115 | | | | | 120 | | | | | 125 | | | | |
| caa | ggt | gag | ggg | ttg | atg | gtg | aca | gga | ggc | agt | aat | gct | aat | ctg | atc | 432 |
| Gln | Gly | Glu | Gly | Leu | Met | Val | Thr | Gly | Gly | Ser | Asn | Ala | Asn | Leu | Ile | |
| | 130 | | | | | 135 | | | | | 140 | | | | | |
| gcc | atg | ctt | tgt | gcc | cga | cac | aaa | ctt | cta | ccc | gaa | gcc | aaa | aac | aag | 480 |
| Ala | Met | Leu | Cys | Ala | Arg | His | Lys | Leu | Leu | Pro | Glu | Ala | Lys | Asn | Lys | |
| 145 | | | | | 150 | | | | | 155 | | | | | 160 | |
| gga | ttg | gga | aat | cac | cag | cta | gta | gca | ttc | atc | tcc | gat | cag | gct | cac | 528 |
| Gly | Leu | Gly | Asn | His | Gln | Leu | Val | Ala | Phe | Ile | Ser | Asp | Gln | Ala | His | |
| | | | | 165 | | | | | 170 | | | | | 175 | | |
| tat | tcc | ttt | ttc | aaa | gca | gca | aat | ttg | ttg | ggc | atg | ggg | ata | gac | aat | 576 |
| Tyr | Ser | Phe | Phe | Lys | Ala | Ala | Asn | Leu | Leu | Gly | Met | Gly | Ile | Asp | Asn | |
| | | | 180 | | | | | 185 | | | | | 190 | | | |
| gta | gtc | aaa | gtc | aaa | tcc | gat | ggc | gat | cag | cgc | atg | tgc | ccg | caa | caa | 624 |
| Val | Val | Lys | Val | Lys | Ser | Asp | Gly | Asp | Gln | Arg | Met | Cys | Pro | Gln | Gln | |
| | | 195 | | | | | 200 | | | | | 205 | | | | |
| tta | gaa | gct | gct | att | caa | caa | agc | cta | agg | gaa | gga | aaa | aca | cct | ttc | 672 |
| Leu | Glu | Ala | Ala | Ile | Gln | Gln | Ser | Leu | Arg | Glu | Gly | Lys | Thr | Pro | Phe | |
| | 210 | | | | | 215 | | | | | 220 | | | | | |
| ttt | gtt | aca | gct | act | gcg | ggc | act | acc | gtt | gcc | ggt | gca | ttc | gat | ccg | 720 |
| Phe | Val | Thr | Ala | Thr | Ala | Gly | Thr | Thr | Val | Ala | Gly | Ala | Phe | Asp | Pro | |
| 225 | | | | | 230 | | | | | 235 | | | | | 240 | |
| ttg | ccc | tca | att | gca | gaa | att | acc | agc | aaa | tat | gga | ctc | tgg | cta | cat | 768 |
| Leu | Pro | Ser | Ile | Ala | Glu | Ile | Thr | Ser | Lys | Tyr | Gly | Leu | Trp | Leu | His | |
| | | | | 245 | | | | | 250 | | | | | 255 | | |
| gtg | gat | ggg | tct | tgg | ggt | gct | ccg | gtt | ttg | ttc | agc | aac | cag | cac | aag | 816 |
| Val | Asp | Gly | Ser | Trp | Gly | Ala | Pro | Val | Leu | Phe | Ser | Asn | Gln | His | Lys | |
| | | | 260 | | | | | 265 | | | | | 270 | | | |
| cat | ctg | ttg | gaa | ggt | agc | tcc | tta | gca | gat | tct | ttt | acc | tgg | gat | gct | 864 |

```
                His Leu Leu Glu Gly Ser Ser Leu Ala Asp Ser Phe Thr Trp Asp Ala
                        275                 280                 285 cac aaa ctc atg ggc gtg ccc ttg att tgt tca gct att cta gtc aaa       912
His Lys Leu Met Gly Val Pro Leu Ile Cys Ser Ala Ile Leu Val Lys
        290                 295                 300 caa cca ggg act tta ttg gag gct tgt tct agt caa ggt act cac tat       960
Gln Pro Gly Thr Leu Leu Glu Ala Cys Ser Ser Gln Gly Thr His Tyr
305                 310                 315                 320 atc ttc cac gat gat gaa gat agt gcc tat aat ctt gga act atg tcc      1008
Ile Phe His Asp Asp Glu Asp Ser Ala Tyr Asn Leu Gly Thr Met Ser
                325                 330                 335 ttg cag tgt ggg cgg aaa gta gat gcc ctt aag ctg tgg cta gcc tgg      1056
Leu Gln Cys Gly Arg Lys Val Asp Ala Leu Lys Leu Trp Leu Ala Trp
            340                 345                 350 aaa tac tac ggc aaa aat ggt tat gaa gca agg gtt gac cgc tta ttt      1104
Lys Tyr Tyr Gly Lys Asn Gly Tyr Glu Ala Arg Val Asp Arg Leu Phe
                355                 360                 365 gaa ctc gct agc tac gcg gcg gat tat att cgc aat tgt gag aat tta      1152
Glu Leu Ala Ser Tyr Ala Ala Asp Tyr Ile Arg Asn Cys Glu Asn Leu
    370                 375                 380 gaa ttg ata gtt caa cca aca ttt ttg aat atc tgt ttt cgc tat aat      1200
Glu Leu Ile Val Gln Pro Thr Phe Leu Asn Ile Cys Phe Arg Tyr Asn
385                 390                 395                 400 ccc agg gat aac agt ctg tct aat cat ggt tta gat cag cta aat ctg      1248
Pro Arg Asp Asn Ser Leu Ser Asn His Gly Leu Asp Gln Leu Asn Leu
                405                 410                 415 gag ata cgt gag caa tta atg cgc tct ggt caa gca tta gtc aat tac      1296
Glu Ile Arg Glu Gln Leu Met Arg Ser Gly Gln Ala Leu Val Asn Tyr
            420                 425                 430 tct cag tat caa gaa cag att gta att cgc ttc att ctc agc aat cca      1344
Ser Gln Tyr Gln Glu Gln Ile Val Ile Arg Phe Ile Leu Ser Asn Pro
                435                 440                 445 gaa att aac gaa gca gat ata gat agt ttt ttg gat aac ttt atc aaa      1392
Glu Ile Asn Glu Ala Asp Ile Asp Ser Phe Leu Asp Asn Phe Ile Lys
    450                 455                 460 att ggt aat agt tta tta tag                                          1413
Ile Gly Asn Ser Leu Leu
465                 470

<210> SEQ ID NO 120
<211> LENGTH: 470
<212> TYPE: PRT
<213> ORGANISM: Moorea producens

<400> SEQUENCE: 120

Met Ile Glu Phe Glu Lys Ile Ile Asn Leu Thr Val Asp Lys Leu Leu
1               5                   10                  15

Asn Tyr Leu Gln Glu Asn Lys Asn Thr Asp Thr Lys Val Ile Asp Tyr
            20                  25                  30

Lys Ser Pro Gln Ala Leu Lys Glu Lys Leu Asp Leu Ser Leu Pro Glu
        35                  40                  45

Asn Gly Val Pro Leu Ala Asp Leu Ile Pro Ile Ile Glu Ser Tyr Leu
    50                  55                  60

Asp His Ser Val Arg Thr Ser His Lys Phe Phe Asn Gln Leu Trp
65                  70                  75                  80

Gly Gly Phe Glu Ile Thr Gly Leu Leu Ala Glu Met Val Thr Ser Thr
            85                  90                  95

Ala Asn Thr Ser Met Tyr Thr Tyr Glu Val Ala Pro Val Ala Thr Leu
        100                 105                 110
```

```
Ile Glu Ile Lys Leu Ile Glu Ala Leu Lys Asp Leu Ile Gly Phe Pro
            115                 120                 125

Gln Gly Glu Gly Leu Met Val Thr Gly Gly Ser Asn Ala Asn Leu Ile
130                 135                 140

Ala Met Leu Cys Ala Arg His Lys Leu Leu Pro Glu Ala Lys Asn Lys
145                 150                 155                 160

Gly Leu Gly Asn His Gln Leu Val Ala Phe Ile Ser Asp Gln Ala His
                165                 170                 175

Tyr Ser Phe Phe Lys Ala Ala Asn Leu Leu Gly Met Gly Ile Asp Asn
            180                 185                 190

Val Val Lys Val Lys Ser Asp Gly Asp Gln Arg Met Cys Pro Gln Gln
        195                 200                 205

Leu Glu Ala Ala Ile Gln Gln Ser Leu Arg Glu Gly Lys Thr Pro Phe
    210                 215                 220

Phe Val Thr Ala Thr Ala Gly Thr Thr Val Ala Gly Ala Phe Asp Pro
225                 230                 235                 240

Leu Pro Ser Ile Ala Glu Ile Thr Ser Lys Tyr Gly Leu Trp Leu His
                245                 250                 255

Val Asp Gly Ser Trp Gly Ala Pro Val Leu Phe Ser Asn Gln His Lys
            260                 265                 270

His Leu Leu Glu Gly Ser Ser Leu Ala Asp Ser Phe Thr Trp Asp Ala
        275                 280                 285

His Lys Leu Met Gly Val Pro Leu Ile Cys Ser Ala Ile Leu Val Lys
    290                 295                 300

Gln Pro Gly Thr Leu Leu Glu Ala Cys Ser Ser Gln Gly Thr His Tyr
305                 310                 315                 320

Ile Phe His Asp Asp Glu Asp Ser Ala Tyr Asn Leu Gly Thr Met Ser
                325                 330                 335

Leu Gln Cys Gly Arg Lys Val Asp Ala Leu Lys Leu Trp Leu Ala Trp
            340                 345                 350

Lys Tyr Tyr Gly Lys Asn Gly Tyr Glu Ala Arg Val Asp Arg Leu Phe
        355                 360                 365

Glu Leu Ala Ser Tyr Ala Ala Asp Tyr Ile Arg Asn Cys Glu Asn Leu
    370                 375                 380

Glu Leu Ile Val Gln Pro Thr Phe Leu Asn Ile Cys Phe Arg Tyr Asn
385                 390                 395                 400

Pro Arg Asp Asn Ser Leu Ser Asn His Gly Leu Asp Gln Leu Asn Leu
                405                 410                 415

Glu Ile Arg Glu Gln Leu Met Arg Ser Gly Gln Ala Leu Val Asn Tyr
            420                 425                 430

Ser Gln Tyr Gln Glu Gln Ile Val Ile Arg Phe Ile Leu Ser Asn Pro
        435                 440                 445

Glu Ile Asn Glu Ala Asp Ile Asp Ser Phe Leu Asp Asn Phe Ile Lys
    450                 455                 460

Ile Gly Asn Ser Leu Leu
465                 470

<210> SEQ ID NO 121
<211> LENGTH: 1425
<212> TYPE: DNA
<213> ORGANISM: Moorea bouillonii
<220> FEATURE:
<221> NAME/KEY: CDS
<222> LOCATION: (1)..(1425)
```

-continued

```
<400> SEQUENCE: 121 atg aac cat aga aaa aca acc ctg act aaa gcc ttt acc ata att ctc      48
Met Asn His Arg Lys Thr Thr Leu Thr Lys Ala Phe Thr Ile Ile Leu
1               5                   10                  15 aac tat tta gac ggt aat ttg gaa ccc gag ccc aaa gtc gtt aat tat      96
Asn Tyr Leu Asp Gly Asn Leu Glu Pro Glu Pro Lys Val Val Asn Tyr
            20                  25                  30 caa acc gct aat gat ctt aag gaa aaa ctc gat tta acc tta ccc gat     144
Gln Thr Ala Asn Asp Leu Lys Glu Lys Leu Asp Leu Thr Leu Pro Asp
        35                  40                  45 gag gga gta gcg tta gaa gcg tta att cct ata gta gaa tct tac ctg     192
Glu Gly Val Ala Leu Glu Ala Leu Ile Pro Ile Val Glu Ser Tyr Leu
    50                  55                  60 aac tat agc gtt aga acc ggt agc act caa ttt ttt aat cta ctt ttt     240
Asn Tyr Ser Val Arg Thr Gly Ser Thr Gln Phe Phe Asn Leu Leu Phe
65                  70                  75                  80 agt ggg tct agt att ccg gga ata ata gcc gac atg gtg acc agt gcc     288
Ser Gly Ser Ser Ile Pro Gly Ile Ile Ala Asp Met Val Thr Ser Ala
                85                  90                  95 acg aat act acc atg cac acc tat gat gtc gcc cca gta gcc acc ctg     336
Thr Asn Thr Thr Met His Thr Tyr Asp Val Ala Pro Val Ala Thr Leu
            100                 105                 110 atg gaa ata gaa ttg att aaa aaa ttg acc agt tta gtg gga ttt aat     384
Met Glu Ile Glu Leu Ile Lys Lys Leu Thr Ser Leu Val Gly Phe Asn
        115                 120                 125 cca ggt gaa gga ttg atg gta act gga gga agt aat gct aat ctg atc     432
Pro Gly Glu Gly Leu Met Val Thr Gly Gly Ser Asn Ala Asn Leu Ile
    130                 135                 140 gga atg ctt tgt gga cga cat caa gtt tta cca gaa gct aaa ttg cag     480
Gly Met Leu Cys Gly Arg His Gln Val Leu Pro Glu Ala Lys Leu Gln
145                 150                 155                 160 gga ttg ggt aat cat cag tta gtc gcc ttt gtt tcc gat caa gct cat     528
Gly Leu Gly Asn His Gln Leu Val Ala Phe Val Ser Asp Gln Ala His
                165                 170                 175 tat tcc tat tta aaa gct gcc aat ttg tta ggg att ggt atc aaa aat     576
Tyr Ser Tyr Leu Lys Ala Ala Asn Leu Leu Gly Ile Gly Ile Lys Asn
            180                 185                 190 tta gtc aag gtt aag tct gat gtt gat ggc aaa atg att ccc gaa gca     624
Leu Val Lys Val Lys Ser Asp Val Asp Gly Lys Met Ile Pro Glu Ala
        195                 200                 205 cta gaa gct gcg att caa cag agc tta tca gaa gaa aaa aca ccg ttc     672
Leu Glu Ala Ala Ile Gln Gln Ser Leu Ser Glu Glu Lys Thr Pro Phe
    210                 215                 220 ttt gtg ggt gca act gcc ggt aca act gtt tta gga gcc ttc gat ccg     720
Phe Val Gly Ala Thr Ala Gly Thr Thr Val Leu Gly Ala Phe Asp Pro
225                 230                 235                 240 tta cca acc ctt gcc gaa att act agg aaa tat ggc ttg tgg ctg cat     768
Leu Pro Thr Leu Ala Glu Ile Thr Arg Lys Tyr Gly Leu Trp Leu His
                245                 250                 255 gtg gat gct gct tgg ggt ggg ccg gtt tta ttt agt gaa aaa cac cag     816
Val Asp Ala Ala Trp Gly Gly Pro Val Leu Phe Ser Glu Lys His Gln
            260                 265                 270 cat ttg tta gca gga agt gag tta ttt gat tcc ttt act tgg gat gct     864
His Leu Leu Ala Gly Ser Glu Leu Phe Asp Ser Phe Thr Trp Asp Ala
        275                 280                 285 cat aag tta atg gga gtt cct tta att tgt tcg gct att tta gtc aaa     912
His Lys Leu Met Gly Val Pro Leu Ile Cys Ser Ala Ile Leu Val Lys
    290                 295                 300 gaa aaa gga ata ttg tca gag gct tgt tct ggg gga ggt acc gat tat     960
```

```
Glu Lys Gly Ile Leu Ser Glu Ala Cys Ser Gly Gly Thr Asp Tyr
305                 310                 315                 320 cta ttc cat gat gat gaa aat gat tta tat aat tta gga act aaa tcg         1008
Leu Phe His Asp Asp Glu Asn Asp Leu Tyr Asn Leu Gly Thr Lys Ser
                    325                 330                 335 tta caa tgt ggt cgg aga gta gat gca ctt aaa tta tgg ctg tgt tgg         1056
Leu Gln Cys Gly Arg Arg Val Asp Ala Leu Lys Leu Trp Leu Cys Trp
                340                 345                 350 aaa tac tat ggt aaa aaa ggt tat gag cag ctg gtc aat cat tta ttt         1104
Lys Tyr Tyr Gly Lys Lys Gly Tyr Glu Gln Leu Val Asn His Leu Phe
            355                 360                 365 gac cta gct aat tat gcc acc gag tat atc cgc agt tgc gat aat tta         1152
Asp Leu Ala Asn Tyr Ala Thr Glu Tyr Ile Arg Ser Cys Asp Asn Leu
        370                 375                 380 gaa tta atc gct gaa cca caa ttt ttg aat att tgt ttc cgt tat atc         1200
Glu Leu Ile Ala Glu Pro Gln Phe Leu Asn Ile Cys Phe Arg Tyr Ile
385                 390                 395                 400 ccc aaa gat gaa ccg ctt gac gct act ggg tta gac cag ctg aat cta         1248
Pro Lys Asp Glu Pro Leu Asp Ala Thr Gly Leu Asp Gln Leu Asn Leu
                405                 410                 415 gac ata cgc aac cga tta ttt cat tcg gga aca gct ttt gta aac tat         1296
Asp Ile Arg Asn Arg Leu Phe His Ser Gly Thr Ala Phe Val Asn Tyr
            420                 425                 430 gct cat tat caa ggt ctg gtt atg att cgg tta att ctc gct aac cct         1344
Ala His Tyr Gln Gly Leu Val Met Ile Arg Leu Ile Leu Ala Asn Pro
        435                 440                 445 gaa ctg caa aaa gcc gat cta gaa atc ttt ttc cat aat tta ctt gat         1392
Glu Leu Gln Lys Ala Asp Leu Glu Ile Phe Phe His Asn Leu Leu Asp
450                 455                 460 gct ggt aaa cta tgt gaa gct gtt aaa gga tag                             1425
Ala Gly Lys Leu Cys Glu Ala Val Lys Gly
465                 470

<210> SEQ ID NO 122
<211> LENGTH: 474
<212> TYPE: PRT
<213> ORGANISM: Moorea bouillonii

<400> SEQUENCE: 122

Met Asn His Arg Lys Thr Thr Leu Thr Lys Ala Phe Thr Ile Ile Leu
1               5                   10                  15

Asn Tyr Leu Asp Gly Asn Leu Glu Pro Glu Pro Lys Val Val Asn Tyr
                20                  25                  30

Gln Thr Ala Asn Asp Leu Lys Glu Lys Leu Asp Leu Thr Leu Pro Asp
            35                  40                  45

Glu Gly Val Ala Leu Glu Ala Leu Ile Pro Ile Val Glu Ser Tyr Leu
        50                  55                  60

Asn Tyr Ser Val Arg Thr Gly Ser Thr Gln Phe Phe Asn Leu Leu Phe
65                  70                  75                  80

Ser Gly Ser Ser Ile Pro Gly Ile Ile Ala Asp Met Val Thr Ser Ala
                85                  90                  95

Thr Asn Thr Thr Met His Thr Tyr Asp Val Ala Pro Val Ala Thr Leu
            100                 105                 110

Met Glu Ile Glu Leu Ile Lys Lys Leu Thr Ser Leu Val Gly Phe Asn
        115                 120                 125

Pro Gly Glu Gly Leu Met Val Thr Gly Gly Ser Asn Ala Asn Leu Ile
    130                 135                 140

Gly Met Leu Cys Gly Arg His Gln Val Leu Pro Glu Ala Lys Leu Gln
```

```
                145                 150                 155                 160
Gly Leu Gly Asn His Gln Leu Val Ala Phe Val Ser Asp Gln Ala His
                165                 170                 175

Tyr Ser Tyr Leu Lys Ala Ala Asn Leu Leu Gly Ile Gly Ile Lys Asn
            180                 185                 190

Leu Val Lys Val Lys Ser Asp Val Asp Gly Lys Met Ile Pro Glu Ala
        195                 200                 205

Leu Glu Ala Ala Ile Gln Gln Ser Leu Ser Glu Lys Thr Pro Phe
    210                 215                 220

Phe Val Gly Ala Thr Ala Gly Thr Thr Val Leu Gly Ala Phe Asp Pro
225                 230                 235                 240

Leu Pro Thr Leu Ala Glu Ile Thr Arg Lys Tyr Gly Leu Trp Leu His
                245                 250                 255

Val Asp Ala Ala Trp Gly Gly Pro Val Leu Phe Ser Glu Lys His Gln
            260                 265                 270

His Leu Leu Ala Gly Ser Glu Leu Phe Asp Ser Phe Thr Trp Asp Ala
        275                 280                 285

His Lys Leu Met Gly Val Pro Leu Ile Cys Ser Ala Ile Leu Val Lys
    290                 295                 300

Glu Lys Gly Ile Leu Ser Glu Ala Cys Ser Gly Gly Thr Asp Tyr
305                 310                 315                 320

Leu Phe His Asp Asp Glu Asn Asp Leu Tyr Asn Leu Gly Thr Lys Ser
                325                 330                 335

Leu Gln Cys Gly Arg Arg Val Asp Ala Leu Lys Leu Trp Leu Cys Trp
            340                 345                 350

Lys Tyr Tyr Gly Lys Lys Gly Tyr Glu Gln Leu Val Asn His Leu Phe
        355                 360                 365

Asp Leu Ala Asn Tyr Ala Thr Glu Tyr Ile Arg Ser Cys Asp Asn Leu
    370                 375                 380

Glu Leu Ile Ala Glu Pro Gln Phe Leu Asn Ile Cys Phe Arg Tyr Ile
385                 390                 395                 400

Pro Lys Asp Glu Pro Leu Asp Ala Thr Gly Leu Asp Gln Leu Asn Leu
                405                 410                 415

Asp Ile Arg Asn Arg Leu Phe His Ser Gly Thr Ala Phe Val Asn Tyr
            420                 425                 430

Ala His Tyr Gln Gly Leu Val Met Ile Arg Leu Ile Leu Ala Asn Pro
        435                 440                 445

Glu Leu Gln Lys Ala Asp Leu Glu Ile Phe Phe His Asn Leu Leu Asp
    450                 455                 460

Ala Gly Lys Leu Cys Glu Ala Val Lys Gly
465                 470

<210> SEQ ID NO 123
<211> LENGTH: 1398
<212> TYPE: DNA
<213> ORGANISM: Synechococcus sp PCC7502
<220> FEATURE:
<221> NAME/KEY: CDS
<222> LOCATION: (1)..(1398)

<400> SEQUENCE: 123 atg ccc aac aat ttt tta gat tcc caa ttc agt agt caa ttt aat agt        48
Met Pro Asn Asn Phe Leu Asp Ser Gln Phe Ser Ser Gln Phe Asn Ser
1               5                   10                  15 caa tta aac agc caa ttt att aag cca gat ggt tcc aat cga gaa gtg        96
Gln Leu Asn Ser Gln Phe Ile Lys Pro Asp Gly Ser Asn Arg Glu Val
```

```
                   20                  25                  30
atc cgc caa atg ggt tat gcg ttt gtg gac tta att acg gat gag gtg         144
Ile Arg Gln Met Gly Tyr Ala Phe Val Asp Leu Ile Thr Asp Glu Val
         35                  40                  45 ttg gct aat cag tcc caa gat ttt gtg aag gat gcc tcg gta tta aaa         192
Leu Ala Asn Gln Ser Gln Asp Phe Val Lys Asp Ala Ser Val Leu Lys
 50                  55                  60 tta gat att ccc aag gtg ggt atg gat tgg caa gat ttg ctc cta gaa         240
Leu Asp Ile Pro Lys Val Gly Met Asp Trp Gln Asp Leu Leu Leu Glu
 65                  70                  75                  80 gtg cga tcg cag gta tta ccc cgt agt ctt aac ctt aac aat ccc cgt         288
Val Arg Ser Gln Val Leu Pro Arg Ser Leu Asn Leu Asn Asn Pro Arg
                 85                  90                  95 tat atg gga cac atg gat agc gta cct tta gca att acg att tgg gcg         336
Tyr Met Gly His Met Asp Ser Val Pro Leu Ala Ile Thr Ile Trp Ala
                100                 105                 110 gat gct tta gcc agt gcc att aat aac aat atg ctt agt agt gag ttg         384
Asp Ala Leu Ala Ser Ala Ile Asn Asn Asn Met Leu Ser Ser Glu Leu
            115                 120                 125 gct cca cta ttt acc cgc att gag gca gat tta atg tca tgg ttt gga         432
Ala Pro Leu Phe Thr Arg Ile Glu Ala Asp Leu Met Ser Trp Phe Gly
130                 135                 140 cag tta ttt ggt ttg ggc gat tgc agt ttc ggc aca tta acc agt ggt         480
Gln Leu Phe Gly Leu Gly Asp Cys Ser Phe Gly Thr Leu Thr Ser Gly
145                 150                 155                 160 ggc agt ttg gcg aat att acg gca ttg tta ata gca cgc aat cat aaa         528
Gly Ser Leu Ala Asn Ile Thr Ala Leu Leu Ile Ala Arg Asn His Lys
                165                 170                 175 ctt cct gaa att aaa tcc gat ggg att aag aat agt att aat gat aaa         576
Leu Pro Glu Ile Lys Ser Asp Gly Ile Lys Asn Ser Ile Asn Asp Lys
            180                 185                 190 tta gtc gct ttt att tcc gat gct gcc cat act tcc ttt gat aag ggc         624
Leu Val Ala Phe Ile Ser Asp Ala Ala His Thr Ser Phe Asp Lys Gly
        195                 200                 205 atg aac gtg att gga ctg ggt agt aaa aat ttg atc agg gtc gaa act         672
Met Asn Val Ile Gly Leu Gly Ser Lys Asn Leu Ile Arg Val Glu Thr
    210                 215                 220 aat gct tca gga cag gtt aag cca gat att tta gag gca aag att caa         720
Asn Ala Ser Gly Gln Val Lys Pro Asp Ile Leu Glu Ala Lys Ile Gln
225                 230                 235                 240 gag cag tta aag tta ggt aat att cct ttt ttg gtc ggg gcg atc gca         768
Glu Gln Leu Lys Leu Gly Asn Ile Pro Phe Leu Val Gly Ala Ile Ala
                245                 250                 255 ggt aca acg att aca ggg gta gta gat cat att caa tca gtt gga gaa         816
Gly Thr Thr Ile Thr Gly Val Val Asp His Ile Gln Ser Val Gly Glu
            260                 265                 270 atc gct cgg aaa tat aat tgt tgg ttt cat gtg gat gcc gcc tac gga         864
Ile Ala Arg Lys Tyr Asn Cys Trp Phe His Val Asp Ala Ala Tyr Gly
        275                 280                 285 gga gcc gca atc ctt tcc ccc aaa tgg caa cat tta tta tct ggc ata         912
Gly Ala Ala Ile Leu Ser Pro Lys Trp Gln His Leu Leu Ser Gly Ile
    290                 295                 300 gaa caa gca gac tct att acc ttt aat ccc caa aaa tgg atg tgg att         960
Glu Gln Ala Asp Ser Ile Thr Phe Asn Pro Gln Lys Trp Met Trp Ile
305                 310                 315                 320 gcc cgc acc tgt gcc atg ctc ttg gtt aac gat cga cag cac tta att        1008
Ala Arg Thr Cys Ala Met Leu Leu Val Asn Asp Arg Gln His Leu Ile
                325                 330                 335 gat ggc ttt gat cat aca ctg ccc tat atg gcg gat aat tcc tta aat        1056
Asp Gly Phe Asp His Thr Leu Pro Tyr Met Ala Asp Asn Ser Leu Asn
```

```
Asp Gly Phe Asp His Thr Leu Pro Tyr Met Ala Asp Asn Ser Leu Asn
            340                 345                 350 ttt ggt aat ttt aac ttg cag gga aca agg cgc acg gat agt tta aaa    1104
Phe Gly Asn Phe Asn Leu Gln Gly Thr Arg Arg Thr Asp Ser Leu Lys
            355                 360                 365 ctc tgg ctg gcg ttg cga tcg cta ggt tta gat ggt tac gct caa ctt    1152
Leu Trp Leu Ala Leu Arg Ser Leu Gly Leu Asp Gly Tyr Ala Gln Leu
    370                 375                 380 ata gat aac tcc atg cac aaa gct cag gca tta aga gtg tgg gtt gat    1200
Ile Asp Asn Ser Met His Lys Ala Gln Ala Leu Arg Val Trp Val Asp
385                 390                 395                 400 aat tct gct gat ttg gaa cta gtt tgt gaa ccg acg atg aat att gtc    1248
Asn Ser Ala Asp Leu Glu Leu Val Cys Glu Pro Thr Met Asn Ile Val
                405                 410                 415 tgt ata cga tcg ctt aat ccc gat cta gat aat agg aaa ctc cgc caa    1296
Cys Ile Arg Ser Leu Asn Pro Asp Leu Asp Asn Arg Lys Leu Arg Gln
            420                 425                 430 caa tgg att gat cag ggt aag tta tgg tta tct tta cca cta tgg cag    1344
Gln Trp Ile Asp Gln Gly Lys Leu Trp Leu Ser Leu Pro Leu Trp Gln
        435                 440                 445 gga gaa cgc att ctt aaa gct gta gtt ctg cat ccc tat gct cag tgg    1392
Gly Glu Arg Ile Leu Lys Ala Val Val Leu His Pro Tyr Ala Gln Trp
450                 455                 460 gat taa                                                              1398
Asp
465

<210> SEQ ID NO 124
<211> LENGTH: 465
<212> TYPE: PRT
<213> ORGANISM: Synechococcus sp PCC7502

<400> SEQUENCE: 124

Met Pro Asn Asn Phe Leu Asp Ser Gln Phe Ser Ser Gln Phe Asn Ser
1               5                   10                  15

Gln Leu Asn Ser Gln Phe Ile Lys Pro Asp Gly Ser Asn Arg Glu Val
            20                  25                  30

Ile Arg Gln Met Gly Tyr Ala Phe Val Asp Leu Ile Thr Asp Glu Val
        35                  40                  45

Leu Ala Asn Gln Ser Gln Asp Phe Val Lys Asp Ala Ser Val Leu Lys
    50                  55                  60

Leu Asp Ile Pro Lys Val Gly Met Asp Trp Gln Asp Leu Leu Leu Glu
65                  70                  75                  80

Val Arg Ser Gln Val Leu Pro Arg Ser Leu Asn Leu Asn Asn Pro Arg
                85                  90                  95

Tyr Met Gly His Met Asp Ser Val Pro Leu Ala Ile Thr Ile Trp Ala
            100                 105                 110

Asp Ala Leu Ala Ser Ala Ile Asn Asn Asn Met Leu Ser Ser Glu Leu
        115                 120                 125

Ala Pro Leu Phe Thr Arg Ile Glu Ala Asp Leu Met Ser Trp Phe Gly
    130                 135                 140

Gln Leu Phe Gly Leu Gly Asp Cys Ser Phe Gly Thr Leu Thr Ser Gly
145                 150                 155                 160

Gly Ser Leu Ala Asn Ile Thr Ala Leu Leu Ile Ala Arg Asn His Lys
                165                 170                 175

Leu Pro Glu Ile Lys Ser Asp Gly Ile Lys Asn Ser Ile Asn Asp Lys
            180                 185                 190
```

```
Leu Val Ala Phe Ile Ser Asp Ala His Thr Ser Phe Asp Lys Gly
            195                 200                 205

Met Asn Val Ile Gly Leu Gly Ser Lys Asn Leu Ile Arg Val Glu Thr
    210                 215                 220

Asn Ala Ser Gly Gln Val Lys Pro Asp Ile Leu Glu Ala Lys Ile Gln
225                 230                 235                 240

Glu Gln Leu Lys Leu Gly Asn Ile Pro Phe Leu Val Gly Ala Ile Ala
                245                 250                 255

Gly Thr Thr Ile Thr Gly Val Val Asp His Ile Gln Ser Val Gly Glu
                260                 265                 270

Ile Ala Arg Lys Tyr Asn Cys Trp Phe His Val Asp Ala Ala Tyr Gly
                275                 280                 285

Gly Ala Ala Ile Leu Ser Pro Lys Trp Gln His Leu Leu Ser Gly Ile
            290                 295                 300

Glu Gln Ala Asp Ser Ile Thr Phe Asn Pro Gln Lys Trp Met Trp Ile
305                 310                 315                 320

Ala Arg Thr Cys Ala Met Leu Leu Val Asn Asp Arg Gln His Leu Ile
                325                 330                 335

Asp Gly Phe Asp His Thr Leu Pro Tyr Met Ala Asp Asn Ser Leu Asn
                340                 345                 350

Phe Gly Asn Phe Asn Leu Gln Gly Thr Arg Arg Thr Asp Ser Leu Lys
            355                 360                 365

Leu Trp Leu Ala Leu Arg Ser Leu Gly Leu Asp Gly Tyr Ala Gln Leu
            370                 375                 380

Ile Asp Asn Ser Met His Lys Ala Gln Ala Leu Arg Val Trp Val Asp
385                 390                 395                 400

Asn Ser Ala Asp Leu Glu Leu Val Cys Glu Pro Thr Met Asn Ile Val
                405                 410                 415

Cys Ile Arg Ser Leu Asn Pro Asp Leu Asp Asn Arg Lys Leu Arg Gln
                420                 425                 430

Gln Trp Ile Asp Gln Gly Lys Leu Trp Leu Ser Leu Pro Leu Trp Gln
            435                 440                 445

Gly Glu Arg Ile Leu Lys Ala Val Val Leu His Pro Tyr Ala Gln Trp
    450                 455                 460

Asp
465

<210> SEQ ID NO 125
<211> LENGTH: 1833
<212> TYPE: DNA
<213> ORGANISM: Cyanidioschyzon merolae strain 10D
<220> FEATURE:
<221> NAME/KEY: CDS
<222> LOCATION: (1)..(1833)

<400> SEQUENCE: 125 atg gaa acc cgg aat gct ccc ggt agt gcg acc aac aaa cta aaa gaa      48
Met Glu Thr Arg Asn Ala Pro Gly Ser Ala Thr Asn Lys Leu Lys Glu
1               5                   10                  15 gtg ggt ttt ggg ggt gag ata gag ttt gcg cga gag ctc cag gaa ctg      96
Val Gly Phe Gly Gly Glu Ile Glu Phe Ala Arg Glu Leu Gln Glu Leu
                20                  25                  30 ctc ggg atc gtc gag cga aaa ctg gga ctc tgc acg tca agc gac gcg     144
Leu Gly Ile Val Glu Arg Lys Leu Gly Leu Cys Thr Ser Ser Asp Ala
            35                  40                  45 ggc agt gaa aat ggt gtg gaa cgg aca ccc gag gcg cag ttg ccg ctc     192
Gly Ser Glu Asn Gly Val Glu Arg Thr Pro Glu Ala Gln Leu Pro Leu
```

```
            50                  55                  60
gtg tac gta cca cca agt gct att tgg cga cag ctt gat cac tat gta       240
Val Tyr Val Pro Pro Ser Ala Ile Trp Arg Gln Leu Asp His Tyr Val
 65                  70                  75                  80 caa tgt gtt atc agc ggg gag agt gca ggt tcg cgc gac ttg ctg gaa       288
Gln Cys Val Ile Ser Gly Glu Ser Ala Gly Ser Arg Asp Leu Leu Glu
                     85                  90                  95 cag ttt ctc gaa gac ctt ctt cgg tat tcg gta cgg acg aag cac gcc       336
Gln Phe Leu Glu Asp Leu Leu Arg Tyr Ser Val Arg Thr Lys His Ala
                100                 105                 110 ttc ttt ttg cac cgt ctc tac ggc ggc tcg gat cca gta gga caa ata       384
Phe Phe Leu His Arg Leu Tyr Gly Gly Ser Asp Pro Val Gly Gln Ile
                115                 120                 125 gct gac ctc atc tgc tcg gtg tta aac aac tct gcg gat acg ttt tcc       432
Ala Asp Leu Ile Cys Ser Val Leu Asn Asn Ser Ala Asp Thr Phe Ser
130                 135                 140 gct gcg ccg tat ctg gtg ctt ctc gaa cga cgg gtt att gaa gcg ctg       480
Ala Ala Pro Tyr Leu Val Leu Leu Glu Arg Arg Val Ile Glu Ala Leu
145                 150                 155                 160 agt tcg tgc atc ggc tgg aag aca ccg ctg cag ggt gat ggt atc ttc       528
Ser Ser Cys Ile Gly Trp Lys Thr Pro Leu Gln Gly Asp Gly Ile Phe
                165                 170                 175 tgt cct ggc ggc agc tat gcg aac ctt att gca ctg acg aca gcg cgc       576
Cys Pro Gly Gly Ser Tyr Ala Asn Leu Ile Ala Leu Thr Thr Ala Arg
                180                 185                 190 cac gtg ttt caa atg aat gcc agg cga ccg cag aca aag cgt acc cag       624
His Val Phe Gln Met Asn Ala Arg Arg Pro Gln Thr Lys Arg Thr Gln
                195                 200                 205 cgc cat cac tgc aac gag cgg cga atg ggg atc ttc acg tcg gtc caa       672
Arg His His Cys Asn Glu Arg Arg Met Gly Ile Phe Thr Ser Val Gln
                210                 215                 220 ggc cac tac agc gtt cga cgg aat gcg gcc atg ctc ggg ttc tgt gat       720
Gly His Tyr Ser Val Arg Arg Asn Ala Ala Met Leu Gly Phe Cys Asp
225                 230                 235                 240 gca ccc ggt gag gac tgc tcg gat gtc gtg ctg gtg ccc tgt gac gag       768
Ala Pro Gly Glu Asp Cys Ser Asp Val Val Leu Val Pro Cys Asp Glu
                245                 250                 255 caa ggc cgc atg gac ccg gag gcg ttg cgt cga ctc att cac tgc ttt       816
Gln Gly Arg Met Asp Pro Glu Ala Leu Arg Arg Leu Ile His Cys Phe
                260                 265                 270 cgc aac acc cgg ccg ctt tcc agc gta ttc gtg aac gtg aca gcg ggt       864
Arg Asn Thr Arg Pro Leu Ser Ser Val Phe Val Asn Val Thr Ala Gly
                275                 280                 285 acg act gtt ttg agt gcg ttc gac cct ctg ccc gaa atc tgg aca gtt       912
Thr Thr Val Leu Ser Ala Phe Asp Pro Leu Pro Glu Ile Trp Thr Val
                290                 295                 300 ctg gca gag gca ttt cca ttg aat tcc gta gag tca gcg tca gca gag       960
Leu Ala Glu Ala Phe Pro Leu Asn Ser Val Glu Ser Ala Ser Ala Glu
305                 310                 315                 320 ctg gaa cag cgc ctt gag gca gac acc atg att cgg gag cgc ttg cct      1008
Leu Glu Gln Arg Leu Glu Ala Asp Thr Met Ile Arg Glu Arg Leu Pro
                325                 330                 335 cag ccg acg ttt tgg gtg cac gtg gac gga gcc tta ggc ggc tct ttc      1056
Gln Pro Thr Phe Trp Val His Val Asp Gly Ala Leu Gly Gly Ser Phe
                340                 345                 350 tta ttt tcg gag aga ttt cgt ccg gtg gcg ctg gct ggg ctt gaa aaa      1104
Leu Phe Ser Glu Arg Phe Arg Pro Val Ala Leu Ala Gly Leu Glu Lys
                355                 360                 365 tac gca aat tcg ttt gtg ctg aat gct cat aag cta ctc aat gca ccg      1152
```

```
                Tyr Ala Asn Ser Phe Val Leu Asn Ala His Lys Leu Leu Asn Ala Pro
                    370                 375                 380 ctg cag tgc tcg att ctg tta gtt cgg gag cgc ggt ttg ctt cag gcc      1200
Leu Gln Cys Ser Ile Leu Leu Val Arg Glu Arg Gly Leu Leu Gln Ala
385                 390                 395                 400 gcg cac gct gcg cga gca ccg tat ctg ttt cac gac gac ctc gat acc      1248
Ala His Ala Ala Arg Ala Pro Tyr Leu Phe His Asp Asp Leu Asp Thr
                405                 410                 415 gat gcg cag tac gat att ggc gac atg acg ctg acg tgt agc cgc cgc      1296
Asp Ala Gln Tyr Asp Ile Gly Asp Met Thr Leu Thr Cys Ser Arg Arg
            420                 425                 430 tct gat gcg ctc aag ttc tgg ctg atg tgg atg tgg cgt ggc agt gct      1344
Ser Asp Ala Leu Lys Phe Trp Leu Met Trp Met Trp Arg Gly Ser Ala
        435                 440                 445 ggt ttc ggg gcc cgc gtg gaa gcc gct gct cgc aac gca cgc gct att      1392
Gly Phe Gly Ala Arg Val Glu Ala Ala Ala Arg Asn Ala Arg Ala Ile
    450                 455                 460 gct gag gcc atg gcg aag cga ccg tgc ttc ctc ctg gta cac tgg ccg      1440
Ala Glu Ala Met Ala Lys Arg Pro Cys Phe Leu Leu Val His Trp Pro
465                 470                 475                 480 ctt gat cgg tct tat cct gcg acg aat gtt tgc ttt tat tac ctg cca      1488
Leu Asp Arg Ser Tyr Pro Ala Thr Asn Val Cys Phe Tyr Tyr Leu Pro
                485                 490                 495 tcg gac atg cga gaa agc att cgg aac ctg gca gac atc aag gcg gaa      1536
Ser Asp Met Arg Glu Ser Ile Arg Asn Leu Ala Asp Ile Lys Ala Glu
                500                 505                 510 aca gcc gct cag ctg ctg ggt agc atc agc gtc cgg ctg tgt cga gcg      1584
Thr Ala Ala Gln Leu Leu Gly Ser Ile Ser Val Arg Leu Cys Arg Ala
            515                 520                 525 ctg cag gtc agc ggc aag gcc ttg ctg aac tac tgc acg ctc gaa ggc      1632
Leu Gln Val Ser Gly Lys Ala Leu Leu Asn Tyr Cys Thr Leu Glu Gly
        530                 535                 540 aca gat ttg ccg att ttt ttg cgc ctt gcc ctg cat ggt ctt cac gta      1680
Thr Asp Leu Pro Ile Phe Leu Arg Leu Ala Leu His Gly Leu His Val
545                 550                 555                 560 tac gaa gag cag gaa att caa gat ctc ctg aac cgc att gaa gac tgt      1728
Tyr Glu Glu Gln Glu Ile Gln Asp Leu Leu Asn Arg Ile Glu Asp Cys
                565                 570                 575 ggc gat cac gca atc cgt ccc ggt aca cca gcg agc atc agc ggc aac      1776
Gly Asp His Ala Ile Arg Pro Gly Thr Pro Ala Ser Ile Ser Gly Asn
                580                 585                 590 gtc agc ggc gga gtg tcg ccc gta ggc gac gac ggc gct cat aat gcc      1824
Val Ser Gly Gly Val Ser Pro Val Gly Asp Asp Gly Ala His Asn Ala
            595                 600                 605 gtc ctc tag                                                          1833
Val Leu
    610

<210> SEQ ID NO 126
<211> LENGTH: 610
<212> TYPE: PRT
<213> ORGANISM: Cyanidioschyzon merolae strain 10D

<400> SEQUENCE: 126

Met Glu Thr Arg Asn Ala Pro Gly Ser Ala Thr Asn Lys Leu Lys Glu
1               5                   10                  15

Val Gly Phe Gly Gly Glu Ile Glu Phe Ala Arg Glu Leu Gln Glu Leu
            20                  25                  30

Leu Gly Ile Val Glu Arg Lys Leu Gly Leu Cys Thr Ser Ser Asp Ala
        35                  40                  45
```

```
Gly Ser Glu Asn Gly Val Glu Arg Thr Pro Glu Ala Gln Leu Pro Leu
 50                  55                  60

Val Tyr Val Pro Pro Ser Ala Ile Trp Arg Gln Leu Asp His Tyr Val
 65                  70                  75                  80

Gln Cys Val Ile Ser Gly Glu Ser Ala Gly Ser Arg Asp Leu Leu Glu
                 85                  90                  95

Gln Phe Leu Glu Asp Leu Leu Arg Tyr Ser Val Arg Thr Lys His Ala
            100                 105                 110

Phe Phe Leu His Arg Leu Tyr Gly Gly Ser Asp Pro Val Gly Gln Ile
        115                 120                 125

Ala Asp Leu Ile Cys Ser Val Leu Asn Asn Ser Ala Thr Phe Ser
130                 135                 140

Ala Ala Pro Tyr Leu Val Leu Leu Glu Arg Arg Val Ile Glu Ala Leu
145                 150                 155                 160

Ser Ser Cys Ile Gly Trp Lys Thr Pro Leu Gln Gly Asp Gly Ile Phe
                165                 170                 175

Cys Pro Gly Gly Ser Tyr Ala Asn Leu Ile Ala Leu Thr Thr Ala Arg
            180                 185                 190

His Val Phe Gln Met Asn Ala Arg Arg Pro Gln Thr Lys Arg Thr Gln
        195                 200                 205

Arg His His Cys Asn Glu Arg Arg Met Gly Ile Phe Thr Ser Val Gln
210                 215                 220

Gly His Tyr Ser Val Arg Arg Asn Ala Ala Met Leu Gly Phe Cys Asp
225                 230                 235                 240

Ala Pro Gly Glu Asp Cys Ser Asp Val Val Leu Val Pro Cys Asp Glu
            245                 250                 255

Gln Gly Arg Met Asp Pro Glu Ala Leu Arg Arg Leu Ile His Cys Phe
        260                 265                 270

Arg Asn Thr Arg Pro Leu Ser Ser Val Phe Val Asn Val Thr Ala Gly
        275                 280                 285

Thr Thr Val Leu Ser Ala Phe Asp Pro Leu Pro Glu Ile Trp Thr Val
290                 295                 300

Leu Ala Glu Ala Phe Pro Leu Asn Ser Val Glu Ser Ala Ser Ala Glu
305                 310                 315                 320

Leu Glu Gln Arg Leu Glu Ala Asp Thr Met Ile Arg Glu Arg Leu Pro
            325                 330                 335

Gln Pro Thr Phe Trp Val His Val Asp Gly Ala Leu Gly Gly Ser Phe
        340                 345                 350

Leu Phe Ser Glu Arg Phe Arg Pro Val Ala Leu Ala Gly Leu Glu Lys
        355                 360                 365

Tyr Ala Asn Ser Phe Val Leu Asn Ala His Lys Leu Leu Asn Ala Pro
370                 375                 380

Leu Gln Cys Ser Ile Leu Leu Val Arg Glu Arg Gly Leu Leu Gln Ala
385                 390                 395                 400

Ala His Ala Ala Arg Ala Pro Tyr Leu Phe His Asp Asp Leu Asp Thr
            405                 410                 415

Asp Ala Gln Tyr Asp Ile Gly Asp Met Thr Leu Thr Cys Ser Arg Arg
        420                 425                 430

Ser Asp Ala Leu Lys Phe Trp Leu Met Trp Met Trp Arg Gly Ser Ala
        435                 440                 445

Gly Phe Gly Ala Arg Val Glu Ala Ala Arg Asn Ala Arg Ala Ile
450                 455                 460
```

```
Ala Glu Ala Met Ala Lys Arg Pro Cys Phe Leu Leu Val His Trp Pro
465                 470                 475                 480

Leu Asp Arg Ser Tyr Pro Ala Thr Asn Val Cys Phe Tyr Leu Pro
            485                 490                 495

Ser Asp Met Arg Glu Ser Ile Arg Asn Leu Ala Asp Ile Lys Ala Glu
            500                 505                 510

Thr Ala Ala Gln Leu Leu Gly Ser Ile Ser Val Arg Leu Cys Arg Ala
            515                 520                 525

Leu Gln Val Ser Gly Lys Ala Leu Leu Asn Tyr Cys Thr Leu Glu Gly
    530                 535                 540

Thr Asp Leu Pro Ile Phe Leu Arg Leu Ala Leu His Gly Leu His Val
545                 550                 555                 560

Tyr Glu Glu Gln Glu Ile Gln Asp Leu Leu Asn Arg Ile Glu Asp Cys
                565                 570                 575

Gly Asp His Ala Ile Arg Pro Gly Thr Pro Ala Ser Ile Ser Gly Asn
            580                 585                 590

Val Ser Gly Gly Val Ser Pro Val Gly Asp Asp Gly Ala His Asn Ala
    595                 600                 605

Val Leu
    610

<210> SEQ ID NO 127
<211> LENGTH: 1419
<212> TYPE: DNA
<213> ORGANISM: Methylobacterium sp 17Sr1-28
<220> FEATURE:
<221> NAME/KEY: CDS
<222> LOCATION: (1)..(1419)

<400> SEQUENCE: 127 atg gac gac gag acg ttt cgg gcc tgg gcg cgc cgg gcc gcc gac tgg       48
Met Asp Asp Glu Thr Phe Arg Ala Trp Ala Arg Arg Ala Ala Asp Trp
1               5                   10                  15 tcg gtg gac tac ctc gcg ggc gtc ggc gag cgg ccg gtg cgg gcg cag       96
Ser Val Asp Tyr Leu Ala Gly Val Gly Glu Arg Pro Val Arg Ala Gln
            20                  25                  30 gtg gcg ccg ggc gag atc ttc cgc cag ctg ccg ccc gag ccg ccg gcc      144
Val Ala Pro Gly Glu Ile Phe Arg Gln Leu Pro Pro Glu Pro Pro Ala
        35                  40                  45 gcg ggc gag gcg atg gag gcc atc ttc gcc gac ctc gac cgg gtg gtg      192
Ala Gly Glu Ala Met Glu Ala Ile Phe Ala Asp Leu Asp Arg Val Val
    50                  55                  60 atg ccg ggc atg acc cac tgg cag cac ccg cgc ttc ttc gcc tac ttc      240
Met Pro Gly Met Thr His Trp Gln His Pro Arg Phe Phe Ala Tyr Phe
65                  70                  75                  80 ccg gcc aat gcc agc ccg ccc tcc ctg gtg gcg gag ttc gtc acc gcg      288
Pro Ala Asn Ala Ser Pro Pro Ser Leu Val Ala Glu Phe Val Thr Ala
                85                  90                  95 gcg ctc gcc gcc cag tgc atg ctc tgg cag acc tcg ccg gcg gcg acc      336
Ala Leu Ala Ala Gln Cys Met Leu Trp Gln Thr Ser Pro Ala Ala Thr
            100                 105                 110 gag ctc gag acc cgg gtg atg gac tgg ctg cgc cag atg atc ggc ctg      384
Glu Leu Glu Thr Arg Val Met Asp Trp Leu Arg Gln Met Ile Gly Leu
        115                 120                 125 ccc gac ggc ttc tcg ggc gtg atc cag gac tcg gcc tcg ggc gcg acg      432
Pro Asp Gly Phe Ser Gly Val Ile Gln Asp Ser Ala Ser Gly Ala Thr
    130                 135                 140 ctc gcc gcg ctg ctg acc gcc cgc gag cgg gcg ctc ggc ttc acc ggc      480
Leu Ala Ala Leu Leu Thr Ala Arg Glu Arg Ala Leu Gly Phe Thr Gly
```

```
                  145                 150                 155                 160
aac gcg aaa ggg ctc gcc ggc ggg cct gct tta cgg gtc tac gcc tcc          528
Asn Ala Lys Gly Leu Ala Gly Gly Pro Ala Leu Arg Val Tyr Ala Ser
                165                 170                 175 gag cag gtg cat tcc tcg gtc gac aag gcg gtg cgc atc gcc ggc atc          576
Glu Gln Val His Ser Ser Val Asp Lys Ala Val Arg Ile Ala Gly Ile
            180                 185                 190 ggc gat gcc aac ctg gtg cgg atc ccc gtg gcc ggc cct ctc cac ggc          624
Gly Asp Ala Asn Leu Val Arg Ile Pro Val Ala Gly Pro Leu His Gly
        195                 200                 205 atg gac ccg ggc gcc ctc gac gcg gcg atc cgg gcc gac cgc gag gcg          672
Met Asp Pro Gly Ala Leu Asp Ala Ala Ile Arg Ala Asp Arg Glu Ala
    210                 215                 220 ggg ctg agg cct gcc gcg atc gtc gcc tgc ctc ggc ggc acc ggg atc          720
Gly Leu Arg Pro Ala Ala Ile Val Ala Cys Leu Gly Gly Thr Gly Ile
225                 230                 235                 240 ggc gcc tgc gac ccg atc gag gcc gtc gcc gcg gtg gcg cgt cgt cac          768
Gly Ala Cys Asp Pro Ile Glu Ala Val Ala Ala Val Ala Arg Arg His
                245                 250                 255 gac gtc ttc ctc cac gtc gac gcc gcc tgg gcc ggc agc gcg atg atc          816
Asp Val Phe Leu His Val Asp Ala Ala Trp Ala Gly Ser Ala Met Ile
            260                 265                 270 tgc ccc gag ttc cgc gac ctg atg cgg ggc gcc gaa cag gcc gac agc          864
Cys Pro Glu Phe Arg Asp Leu Met Arg Gly Ala Glu Gln Ala Asp Ser
        275                 280                 285 ctg gtg ttc aac ccg cac aag tgg ctg ttc acc cat ttc gac tgc tcg          912
Leu Val Phe Asn Pro His Lys Trp Leu Phe Thr His Phe Asp Cys Ser
    290                 295                 300 gcc cat ttc gtg cgc gac ccg aag gcg ctc acc gac acg ctc ggc ctt          960
Ala His Phe Val Arg Asp Pro Lys Ala Leu Thr Asp Thr Leu Gly Leu
305                 310                 315                 320 cgc ccc tcc tac ctg cgc acg ctc ggc cac gac ggc gtc gtc gac tac         1008
Arg Pro Ser Tyr Leu Arg Thr Leu Gly His Asp Gly Val Val Asp Tyr
                325                 330                 335 aac gag tgg tcg atc ccc ctc ggg cgc cgc ttc cgg gcg ctg aag ctg         1056
Asn Glu Trp Ser Ile Pro Leu Gly Arg Arg Phe Arg Ala Leu Lys Leu
            340                 345                 350 tgg ttc gtg atc cgc tcc tac ggc gtc gag gcg ctg cgg ggc atg atc         1104
Trp Phe Val Ile Arg Ser Tyr Gly Val Glu Ala Leu Arg Gly Met Ile
        355                 360                 365 cgc gac cac gtc gcc tgg gcg cgg gag ctc gcc ggg ctc atc gag gcc         1152
Arg Asp His Val Ala Trp Ala Arg Glu Leu Ala Gly Leu Ile Glu Ala
    370                 375                 380 gag ccc gac ttc gag ctg acc tcg gcg ccg atc ctg tcc ctg ttc agc         1200
Glu Pro Asp Phe Glu Leu Thr Ser Ala Pro Ile Leu Ser Leu Phe Ser
385                 390                 395                 400 ttc cgc ttt gcg ccc gca ggg atc gac gac ctc gac gcg ctc aac gcc         1248
Phe Arg Phe Ala Pro Ala Gly Ile Asp Asp Leu Asp Ala Leu Asn Ala
                405                 410                 415 cgc ctc gtc gag cgc atc aac gac gac ggc cgc acc tac ctg acc cag         1296
Arg Leu Val Glu Arg Ile Asn Asp Asp Gly Arg Thr Tyr Leu Thr Gln
            420                 425                 430 acc cgg cac gat ggc cgc ttc gtc atc cgc ttc cag gtc ggc cag acc         1344
Thr Arg His Asp Gly Arg Phe Val Ile Arg Phe Gln Val Gly Gln Thr
        435                 440                 445 acc acg acg cgg gcg gac gtg atg atg gcg tgg gac gcg gtg cgg gag         1392
Thr Thr Thr Arg Ala Asp Val Met Met Ala Trp Asp Ala Val Arg Glu
    450                 455                 460 atc gcg gcg ggg ttg cgg gcg ggg tga                                      1419
```

Ile Ala Ala Gly Leu Arg Ala Gly
465                 470

<210> SEQ ID NO 128
<211> LENGTH: 472
<212> TYPE: PRT
<213> ORGANISM: Methylobacterium sp 17Sr1-28

<400> SEQUENCE: 128

Met Asp Asp Glu Thr Phe Arg Ala Trp Ala Arg Arg Ala Ala Asp Trp
1               5                   10                  15

Ser Val Asp Tyr Leu Ala Gly Val Gly Glu Arg Pro Val Arg Ala Gln
            20                  25                  30

Val Ala Pro Gly Glu Ile Phe Arg Gln Leu Pro Pro Glu Pro Pro Ala
        35                  40                  45

Ala Gly Glu Ala Met Glu Ala Ile Phe Ala Asp Leu Asp Arg Val Val
    50                  55                  60

Met Pro Gly Met Thr His Trp Gln His Pro Arg Phe Phe Ala Tyr Phe
65                  70                  75                  80

Pro Ala Asn Ala Ser Pro Pro Ser Leu Val Ala Glu Phe Val Thr Ala
                85                  90                  95

Ala Leu Ala Ala Gln Cys Met Leu Trp Gln Thr Ser Pro Ala Ala Thr
            100                 105                 110

Glu Leu Glu Thr Arg Val Met Asp Trp Leu Arg Gln Met Ile Gly Leu
        115                 120                 125

Pro Asp Gly Phe Ser Gly Val Ile Gln Asp Ser Ala Ser Gly Ala Thr
    130                 135                 140

Leu Ala Ala Leu Leu Thr Ala Arg Glu Arg Ala Leu Gly Phe Thr Gly
145                 150                 155                 160

Asn Ala Lys Gly Leu Ala Gly Gly Pro Ala Leu Arg Val Tyr Ala Ser
                165                 170                 175

Glu Gln Val His Ser Ser Val Asp Lys Ala Val Arg Ile Ala Gly Ile
            180                 185                 190

Gly Asp Ala Asn Leu Val Arg Ile Pro Val Ala Gly Pro Leu His Gly
        195                 200                 205

Met Asp Pro Gly Ala Leu Asp Ala Ala Ile Arg Ala Asp Arg Glu Ala
    210                 215                 220

Gly Leu Arg Pro Ala Ala Ile Val Ala Cys Leu Gly Gly Thr Gly Ile
225                 230                 235                 240

Gly Ala Cys Asp Pro Ile Glu Ala Val Ala Val Ala Arg Arg His
                245                 250                 255

Asp Val Phe Leu His Val Asp Ala Ala Trp Ala Gly Ser Ala Met Ile
            260                 265                 270

Cys Pro Glu Phe Arg Asp Leu Met Arg Gly Ala Glu Gln Ala Asp Ser
        275                 280                 285

Leu Val Phe Asn Pro His Lys Trp Leu Phe Thr His Phe Asp Cys Ser
    290                 295                 300

Ala His Phe Val Arg Asp Pro Lys Ala Leu Thr Asp Thr Leu Gly Leu
305                 310                 315                 320

Arg Pro Ser Tyr Leu Arg Thr Leu Gly His Asp Gly Val Val Asp Tyr
                325                 330                 335

Asn Glu Trp Ser Ile Pro Leu Gly Arg Arg Phe Arg Ala Leu Lys Leu
            340                 345                 350

Trp Phe Val Ile Arg Ser Tyr Gly Val Glu Ala Leu Arg Gly Met Ile
        355                 360                 365

```
Arg Asp His Val Ala Trp Ala Arg Glu Leu Ala Gly Leu Ile Glu Ala
    370             375             380

Glu Pro Asp Phe Glu Leu Thr Ser Ala Pro Ile Leu Ser Leu Phe Ser
385                 390             395                     400

Phe Arg Phe Ala Pro Ala Gly Ile Asp Asp Leu Asp Ala Leu Asn Ala
                405             410                 415

Arg Leu Val Glu Arg Ile Asn Asp Asp Gly Arg Thr Tyr Leu Thr Gln
            420             425             430

Thr Arg His Asp Gly Arg Phe Val Ile Arg Phe Gln Val Gly Gln Thr
        435             440             445

Thr Thr Thr Arg Ala Asp Val Met Met Ala Trp Asp Ala Val Arg Glu
    450             455             460

Ile Ala Ala Gly Leu Arg Ala Gly
465             470
```

METHODS FOR THE BIOSYNTHESIS OF TAURINE OR HYPOTAURINE IN CELLS

CROSS-REFERENCE TO RELATED APPLICATIONS

This application is a continuation-in-part of U.S. patent application Ser. No. 14/993,519 filed 12 Jan. 2016, which in turn is a continuation of U.S. patent application Ser. No. 13/505,415 filed 1 May 2012, now U.S. Pat. No. 9,267,148, which in turn is a national stage filing under 35 U.S.C. § 371 of PCT/US2010/054664 filed 29 Oct. 2010 which in turn is related to and claims the benefit of and U.S. Patent Application Ser. No. 61/263,548 filed 23 Nov. 2009 and U.S. Patent Application Ser. No. 61/257,240 filed 2 Nov. 2009. Each application is incorporated herein in its entirety by reference.

SEQUENCE LISTING

The present application is being filed along with a Sequence Listing in electronic format. The Sequence Listing is entitled 3834116CIPSequenceListing.txt, created on 8 Oct. 2018 and is 234 kb in size. The information in the electronic format of the Sequence Listing is incorporated herein by reference in its entirety.

FIELD OF THE INVENTION

The present invention is in the field of recombinant production of taurine.

BACKGROUND OF THE INVENTION

Taurine as a Plant Growth Stimulator

Exogenous application of taurine has been reported to increase crop harvest, yield, and biomass (1). Applications of taurine by foliar spray, soil and roots application, and seed immersion increase crop production and seedling growth (1). Exogenous applications of taurine have also been shown to increase photosynthetic capacity of isolated plant cells (protoplasts and chloroplasts) (1). Increased taurine production in plants can enhance plant growth and development, yield, or tolerance to biotic and/or abiotic stresses. Increased yield, growth, or biomass may be a result of increased nitrogen flow, sensing, uptake, storage, transport or nitrogen use efficiency. Increased yield, growth or biomass may also be a result of increased carbon metabolism due to increased photosynthesis or increased carbohydrate metabolism by increased sucrose production and/or transport or increase biosynthesis or mobilization of starch, or oil. Increased yield, growth or biomass may also be associated with increased phosphorus uptake, transport or utilization. Increased yield, growth or biomass may also be associated with increased sulfur or sulfate uptake, transport or utilization. Increased yield, growth or biomass may also be associated with increased water uptake, transport, utilization or water-use-efficiency. Increased yield, growth or biomass may also be due to changes in the cell cycle modifications that improve growth rates and may increase early vigor and accelerate maturation leading to improved yield. Increased yield, growth or biomass may also be due to changes in the production of hormones or signaling molecules that regulate and improve plant growth and development leading to improvements in yield and biotic or abiotic stress tolerance. Increases in carbon, nitrogen, phosphorus, or sulfate flow, sensing, uptake, storage, transport or efficiency may improve seed quality for starch, oil or protein content. Increased yield, growth or biomass may also be a result of increased tolerance to abiotic stress such as changes in osmotic conditions, oxidative damage, drought, salt, cold, freezing, heat, UV light or light intensity. Increased yield, growth or biomass may also be a result of increased tolerance to biotic stress such as challenges, infection or insult from pests, pathogens, bacteria, microbes, viruses, viroids, microorganisms, invertebrates, insects, nematodes, or vertebrate. Increased yield, growth or biomass may be a result of increased tolerance to abiotic stresses such as changes in osmotic conditions or light intensity, oxidative damage, drought, salt, cold, freezing, heat, or UV radiation.

Taurine is an Essential Compound for Animals

Taurine is essential for human neonatal development (2) and plays an important role in brain development (3, 4). Taurine is involved in the modulation of intracellular calcium homeostasis (5, 6) and may balance glutamate activity, protecting neurons against glutamate excitotoxicity (7, 8). Taurine is also an osmoregulator (9). Taurine is essential for heart function (10), protects the integrity of hepatic tissue (11), and plays a role in photoprotection (12).

Taurine as a Pharmaceutical or Therapeutic

Taurine is used as a pharmaceutical and therapeutic. Taurine has been used in the treatment of cardiovascular diseases (13, 14), elevated blood pressure (15), seizure disorders (16), hepatic disorders (17), and alcoholism (18) and may be useful in the treatment of diabetes (19), Alzheimer's disease (20), and ocular disorders (21). Taurine has been shown to prevent obesity (22) and control cholesterol (23, 24). Taurine acts as an antioxidant and protects against toxicity of various substances (25-27). Taurine has been shown to prevent oxidative stress induced by exercise (28), and is used in energy drinks to improve performance (29). Taurine can also be used in topical applications to treat dermatological conditions (30).

Taurine as a Dietary Supplement

Taurine is biosynthesized in most animals and can be found in meat and seafood. Those who do not eat these foods regularly (e.g., vegetarians) or do not produce sufficient levels of taurine, e.g., cats (31), must acquire it through dietary supplement. Trout that are fed all-plant protein diets must acquire dietary taurine for normal growth (32).

Metabolic Pathways that Synthesize Taurine

With few exceptions (33, 34), taurine is found in plants only in low levels (35), and the metabolic pathway for taurine and hypotaurine has not yet been identified in plants. Several metabolic pathways that synthesize taurine and hypotaurine have been identified in animals and bacteria (FIG. 1). In animals, cysteine and oxygen are converted into 3-sulfinoalanine by cysteine dioxygenase (CDO). 3-sulfinoalanine is converted into hypotaurine by sulfinoalanine decarboxylase (SAD) or glutamate decarboxylase (GAD). Hypotaurine is converted into taurine either by the activity of hypotaurine dehydrogenase (HTDeHase) or by a spontaneous conversion. Cysteamine (2-aminoethanethiol) and oxygen are converted into hypotaurine by cysteamine dioxygenase (ADO), and hypotaurine is converted into taurine. Alternatively cysteine and sulfite are converted into cysteate and hydrogen sulfide by cysteine lyase (cysteine sulfite lyase or cysteine hydrogen-sulfide-lyase). Cysteate is converted into taurine by SAD or GAD. In bacteria, the compound 2-sulfoacetaldehyde is synthesized from acetyl phosphate and sulfite by sulfoacetaldehyde acetyltransferase (SA). Alanine and 2-sulfoacetaldehyde are converted into taurine and pyruvate by taurine-pyruvate aminotransferase (TPAT). In addition, sulfoacetaldehyde and ammonia (or ammonium)

are converted into taurine and water in the presence of ferrocytochrome C by taurine dehydrogenase. Sulfite, aminoacetaldehyde, carbon dioxide and succinate are converted into taurine, 2-oxoglutarate and oxygen by taurine dioxygenase (TDO).

SUMMARY OF THE INVENTION

The invention provides methods and compositions for taurine or taurine precursor production in organisms. More particularly, the invention encompasses the use of polynucleotides that encode in plants functional (1) cysteine dioxygenase (CDO), (2) CDO and sulfinoalanine decarboxylase (SAD) or glutamate decarboxylase (GAD), (3) cysteamine dioxygenase (ADO), (4) taurine-pyruvate aminotransferase (TPAT), (5) TPAT and sulfoacetaldehyde acetyltransferase (SA), (6) taurine dehydrogenase (TDeHase) or (7) taurine dioxygenase (TDO). The invention provides methods for transforming plants and constructing vector constructs and other nucleic acid molecules for use therein. The transgenic plants will have increased levels of taurine or taurine-precursors for enhanced plant growth and development, yield, or tolerance to biotic and/or abiotic stresses and can be used to provide nutraceuticals or pharmaceuticals for improving physical or mental performance, antioxidative activity, or therapeutic compounds in the treatment of conditions including congestive heart failure, high blood pressure, hepatitis, high cholesterol, diabetes, fibrosis, epilepsy, autism, attention deficit-hyperactivity disorder, retinal disorders, alcoholism, or as a food supplement in animal feed.

The invention provides isolated cells comprising exogenous DNA which expresses enzymes of taurine biosynthetic pathways. In one embodiment, an isolated cell comprises two separate expression cassettes. A first expression cassette comprises a first promoter operably linked to a first polynucleotide, and a second expression cassette comprises a second promoter operably linked to a second polynucleotide. In some embodiments, the first polynucleotide encodes cysteine dioxygenase (CDO) and the second polynucleotide encodes sulfinoalanine decarboxylase (SAD). In other embodiments the first polynucleotide encodes cysteine dioxygenase (CDO) and the second polynucleotide encodes glutamate decarboxylase (GAD). In still other embodiments, the first polynucleotide encodes taurine-pyruvate aminotransferase (TPAT) and the second polynucleotide encodes sulfoacetaldehyde acetyltransferase (SA). In yet other embodiments the first polynucleotide encodes a small subunit of taurine dehydrogenase (ssTDeHase) and the second polynucleotide encodes a large subunit of taurine dehydrogenase (lsTDeHase).

Some isolated cells of the invention comprise exogenous DNA which comprises a single expression cassette. The single expression cassette comprises a promoter operably linked to a polynucleotide which encodes (i) CDO and SAD; (ii) CDO and GAD; (iii) TPAT; (iv) TPAT and SA; or (v) ssTDeHase and lsTDeHase.

Other isolated cells of the invention are plant cells which comprise exogenous DNA which comprises a promoter operably linked to a polynucleotide. The polynucleotide encodes CDO, ADO, or taurine dioxygenase (TDO).

The invention also provides plant storage organs comprising isolated cells of the invention; transgenic seeds with a genome comprising exogenous DNA encoding one or more of CDO, SAD, GAD, ADO, TPAT, SA, TDO, or TDeHase, and transgenic plants grown from the transgenic seeds.

The invention provides methods of altering a property of a transgenic plant of the invention by contacting the transgenic plant with an agent which increases sulfur or nitrogen concentration in cells of the transgenic plant.

The invention also provides pharmaceutical compositions and nutritional supplements comprising an extract of a transgenic plant of the invention, and feeds comprising a component, which can be one or more of the plant storage organs, transgenic seeds, and transgenic plants of the invention.

In one embodiment of the invention polynucleotides encoding functional CDO and SAD or GAD enzymes are used to transform plant cells or to transform plants. Inventive methods produce plants that have advantages of enhanced taurine production, that result in plants with enhanced plant growth characteristics, survival characteristics and/or tolerance to environmental or other plant stresses and increase nutritional, pharmaceutical, or therapeutic value. Plants are genetically modified in accordance with the invention to introduce into the plant a polynucleotide that encodes a CDO enzyme and/or a polynucleotide that encodes a SAD or GAD that functions in the formation of hypotaurine or taurine in the plant.

Another embodiment of the invention describes the use of ADO, TPAT, TDeHase, or TDO to produce hypotaurine or taurine in plants.

Another embodiment of the invention describes the use of TPAT and SA to produce taurine in plants.

Another embodiment of the invention describes the use of polynucleotides that encode polypeptides for functional CDO, CDO and SAD or GAD, ADO, TPAT, SA, TDeHase or TDO expressed in eukaryotes or prokaryotes or in eukaryotic or prokaryotic cells, for hypotaurine or taurine production.

BRIEF DESCRIPTION OF THE FIGURE

FIG. 1 shows taurine biosynthetic pathways.

DETAILED DESCRIPTION OF THE INVENTION

The present invention provides methods and materials for the production of taurine (2-aminoethanesulfonic acid) in cells and living organisms. In preferred embodiments, the invention provides methods for the genetic transformation of organisms, preferably plants, with genes that encode proteins that catalyze the conversion of cysteine to taurine, methionine to taurine, cysteamine to taurine, or alanine to taurine. The invention also provides methods of using plants with increased levels of endogenous taurine or taurine derivatives such as hypotaurine to improve plant growth, development and performance, that is to increase plant size, biomass, yield or tolerance to biotic or abiotic stress. The invention also provides methods of using plants with elevated levels of endogenous taurine or taurine derivatives such as hypotaurine as a food- or feed-supplement, dietary supplement, or as a component of a health supplement or therapy.

The present invention describes the methods for the synthesis of DNA constructs for taurine or taurine precursor production from polynucleotides and vectors and the methods for making transformed organisms including plants, photosynthetic organisms, microbes, invertebrates, and vertebrates. The present invention is unique in that it describes a method to produce plants that have advantages of enhanced taurine production and that result in plants with enhanced plant growth characteristics, survival characteristics and/or tolerance to environmental or other plant stresses and increased nutritional, pharmaceutical, or therapeutic value.

The present invention describes the insertion of the taurine biosynthetic pathway in organisms where the pathway does not exist or has not clearly been identified. The invention describes methods for the use of polynucleotides that encode functional cysteine dioxygenase (CDO) and sulfinoalanine decarboxylase (SAD) or glutamate decarboxylase (GAD), cysteamine dioxygenase (ADO), taurine-pyruvate aminotransferase (TPAT), TPAT and sulfoacetaldehyde acetyltransferase (SA), taurine dehydrogenase (TDeHase) or taurine dioxygenase (TDO) in plants. The preferred embodiment of the invention is in plants but other organisms may be used.

Enzymes of Taurine Biosynthetic Pathways

Examples of amino acid sequences of enzymes of taurine biosynthetic pathways are provided in the sequence listing: SEQ ID NO:3 and SEQ ID NO:4 (CDO); SEQ ID NO:7 and SEQ ID NO:8 (SAD); SEQ ID NO:11 and SEQ ID NO:12 (GAD); SEQ ID NO:18 (TPAT); SEQ ID NO:20 (SA); SEQ ID NO:22 (ssTDeHase); SEQ ID NO:22 (lsTDeHase); SEQ ID NO:13 and SEQ ID NO:14 (ADO); and SEQ ID NO:26 (TDO). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for CDO, SAD, GAD, or ADO from zebra fish (*Danio rerio*) or TPAT, SA, ssTDeHase or lsTDeHase from *Roseobacter denitrificans* or TDO from *Escherichia coli* may differ to a certain degree from the amino acid sequences of CDO, SAD, GAD, ADO, TPAT, SA, ssTDeHase, lsTDeHase or TDO in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Another manner in which similarity may exist between two amino acid sequences is where there is conserved substitution between a given amino acid of one group, such as a non-polar amino acid, an uncharged polar amino acid, a charged polar acidic amino acid, or a charged polar basic amino acid, with an amino acid from the same amino acid group. For example, it is known that the uncharged polar amino acid serine may commonly be substituted with the uncharged polar amino acid threonine in a polypeptide without substantially altering the functionality of the polypeptide. Whether a given substitution will affect the functionality of the enzyme may be determined without undue experimentation using synthetic techniques and screening assays known to one with ordinary skill in the art.

One of ordinary skill in the art will recognize that changes in the amino acid sequences, such as individual substitutions, deletions or additions to a nucleic acid, peptide, polypeptide, or protein sequence which alters, adds or deletes a single amino acid or a small percentage of amino acids in the encoded sequence is "sufficiently similar" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, CDO, SAD, GAD, ADO, TPAT, SA, ssTDeHase, lsTDeHase or TDO activity is generally at least 40%, 50%, 60%, 70%, 80% or 90%, preferably 60-90% of the native protein for the native substrate. Tables of conserved substitution provide lists of functionally similar amino acids.

The following three groups each contain amino acids that are conserved substitutions for one another: (1) Alanine (A), Serine (S), Threonine (T); (2) Aspartic acid (D), Glutamic acid (E); and (3) Asparagine (N), Glutamine (Q);

Suitable Polynucleotides for CDO, SAD, GAD, ADO, TPAT, SA, TDO, ssTDeHase, and lsTDeHase As examples, suitable polynucleotides encoding enzymes of taurine biosynthetic pathways are described below. The invention is not limited to use of these sequences, however. In fact, any nucleotide sequence which encodes an enzyme of a taurine biosynthetic pathway can be used in an expression vector to produce that enzyme recombinantly.

Suitable polynucleotides for CDO are provided in SEQ ID NO:1 and SEQ ID NO:2 Other suitable polynucleotides for use in accordance with the invention may be obtained by the identification of polynucleotides that selectively hybridize to the polynucleotides of SEQ ID NO:1 or SEQ ID NO:2 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:1 or SEQ ID NO:2 when it used as a reference for sequence comparison or polynucleotides that encode polypeptides that have substantial identity to amino acid sequence of SEQ ID NO:3 or SEQ ID NO:4 when it used as a reference for sequence comparison.

Suitable polynucleotides for SAD are provided in SEQ ID NO:5 and SEQ ID NO:6. Other suitable polynucleotides for use in accordance with the invention may be obtained by the identification of polynucleotides that selectively hybridize to the polynucleotides of SEQ ID NO:5 or SEQ ID NO:6 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:5 or SEQ ID NO:6 when it used as a reference for sequence comparison or polynucleotides that encode polypeptides that have substantial identity to amino acid sequence of SEQ ID NO:7 or SEQ ID NO:8 when it is used as a reference for sequence comparison.

Suitable polynucleotides for GAD are provided in SEQ ID NO:9 and SEQ ID NO:10. Other suitable polynucleotides for use in accordance with the invention may be obtained by the identification of polynucleotides that selectively hybridize to the polynucleotides of SEQ ID NO:9 or SEQ ID NO:10 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:9 or SEQ ID NO:10 when it used as a reference for sequence comparison or polynucleotides that encode polypeptides that have substantial identity to amino acid sequence of SEQ ID NO:11 or SEQ ID NO:12 when it used as a reference for sequence comparison.

Suitable polynucleotides for ADO are provided in SEQ ID NO:13 and SEQ ID NO:14. Other suitable polynucleotides for use in accordance with the invention may be obtained by the identification of polynucleotides that selectively hybridize to the polynucleotides of SEQ ID NO:13 or SEQ ID NO:14 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:13 or SEQ ID NO:14 when it used as a reference for sequence comparison or polynucleotides that encode polypeptides that have substantial identity to amino acid sequence of SEQ ID NO:15 or SEQ ID NO:16 when it used as a reference for sequence comparison.

A suitable polynucleotide for TPAT is provided in SEQ ID NO:17. Other suitable polynucleotides for use in accordance with the invention may be obtained by the identification of polynucleotides that selectively hybridize to the polynucleotides of SEQ ID NO:17 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:17 when it used as a reference for sequence comparison or polynucleotides that encode polypeptides that have substantial identity to amino acid sequence of SEQ ID NO:18 when it used as a reference for sequence comparison.

A suitable polynucleotide for SA is provided in SEQ ID NO:19. Other suitable polynucleotides for use in accordance with the invention may be obtained by the identification of polynucleotides that selectively hybridize to the polynucleotides of SEQ ID NO:19 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:19 when it used as a reference for sequence comparison or polynucleotides that encode polypeptides that have substantial identity to amino acid sequence of SEQ ID NO:20 when it used as a reference for sequence comparison.

A suitable polynucleotide for ssTDeHase is provided in SEQ ID NO:21. Other suitable polynucleotides for use in accordance with the invention may be obtained by the identification of polynucleotides that selectively hybridize to the polynucleotides of SEQ ID NO:21 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:21 when it used as a reference for sequence comparison or polynucleotides that encode polypeptides that have substantial identity to amino acid sequence of SEQ ID NO:22 when it used as a reference for sequence comparison.

A suitable polynucleotide for lsTDeHase is provided in SEQ ID NO:23. Other suitable polynucleotides for use in accordance with the invention may be obtained by the identification of polynucleotides that selectively hybridize to the polynucleotides of SEQ ID NO:23 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:23 when it used as a reference for sequence comparison or polynucleotides that encode polypeptides that have substantial identity to amino acid sequence of SEQ ID NO:24 when it used as a reference for sequence comparison.

A suitable polynucleotide for TDO is provided in SEQ ID NO:25. Other suitable polynucleotides for use in accordance with the invention may be obtained by the identification of polynucleotides that selectively hybridize to the polynucleotides of SEQ ID NO:25 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:25 when it used as a reference for sequence comparison or polynucleotides that encode polypeptides that have substantial identity to amino acid sequence of SEQ ID NO:26 when it used as a reference for sequence comparison.

Another embodiment of the invention is a polynucleotide (e.g., a DNA construct) that encodes a protein that functions as a CDO, SAD, GAD, ADO, TPAT, SA, ssTDeHase, lsTDeHase or TDO and selectively hybridizes to either SEQ ID NO:1, SEQ ID NO:2, SEQ ID NO:5, SEQ ID NO:6, SEQ ID NO:9, SEQ ID NO:10, SEQ ID NO:13, SEQ ID NO:14, SEQ ID NO:17, SEQ ID NO:19, SEQ ID NO:21, SEQ ID NO:23, or SEQ ID NO:25 respectively. Selectively hybridizing sequences typically have at least 40% sequence identity, preferably 60-90% sequence identity, and most preferably 100% sequence identity with each other.

Another embodiment of the invention is a polynucleotide that encodes a polypeptide that has substantial identity to the amino acid sequence of SEQ ID NO:3, SEQ ID NO:4, SEQ ID NO:7, SEQ ID NO:8, SEQ ID NO:11, SEQ ID NO:12, SEQ ID NO:15, SEQ ID NO:16, SEQ ID NO:18, SEQ ID NO:20, SEQ ID NO:22, SEQ ID NO:24, or SEQ ID NO:26. Substantial identity of amino acid sequences for these purposes normally means sequence identity of between 50-100%, preferably at least 55%, preferably at least 60%, more preferably at least 70%, 80%, 90%, and most preferably at least 95%.

The process of encoding a specific amino acid sequence may involve DNA sequences having one or more base changes (i.e., insertions, deletions, substitutions) that do not cause a change in the encoded amino acid, or which involve base changes which may alter one or more amino acids, but do not eliminate the functional properties of the polypeptide encoded by the DNA sequence.

It is therefore understood that the invention encompasses more than the specific polynucleotides encoding the proteins described herein. For example, modifications to a sequence, such as deletions, insertions, or substitutions in the sequence, which produce "silent" changes that do not substantially affect the functional properties of the resulting polypeptide are expressly contemplated by the present invention. Furthermore, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill in the art will recognize that each amino acid has more than one codon, except for methionine and tryptophan that ordinarily have the codons AUG and UGG, respectively. It is known by those of ordinary skill in the art, "universal" code is not completely universal. Some mitochondrial and bacterial genomes diverge from the universal code, e.g., some termination codons in the universal code specify amino acids in the mitochondria or bacterial codes. Thus each silent variation of a nucleic acid, which encodes a polypeptide of the present invention, is implicit in each described polypeptide sequence and incorporated in the descriptions of the invention.

It is understood that alterations in a nucleotide sequence, which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product.

Nucleotide changes which result in alteration of the amino-terminal and carboxy-terminal portions of the encoded polypeptide molecule would also not generally be expected to alter the activity of the polypeptide. In some cases, it may in fact be desirable to make mutations in the sequence in order to study the effect of alteration on the biological activity of the polypeptide. Each of the proposed modifications is well within the routine skill in the art.

When the nucleic acid is prepared or altered synthetically, one of ordinary skill in the art can take into account the known codon preferences for the intended host where the nucleic acid is to be expressed. For example, although nucleic acid sequences of the present invention may be expressed in both monocotyledonous and dicotyledonous plant species, sequences can be modified to account for the specific codon preferences and GC-content preferences of monocotyledonous plants or dicotyledonous plants, as these preferences have been shown to differ (36). An alternative approach to the generation of variants of the sequences is to use random recombination techniques such as "DNA shuffling" (37). An alternative method to modify the sequences is by rapid molecular evolution methods such as a staggered extension process (38).

Cloning Techniques

For purposes of promoting an understanding of the principles of the invention, reference will now be made to particular embodiments of the invention and specific language will be used to describe the same. The materials, methods and examples are illustrative only and not limiting. Unless mentioned otherwise, the techniques employed or contemplated herein are standard methodologies well known to one of ordinary skill in the art. Specific terms, while employed below and defined at the end of this section, are used in a descriptive sense only and not for purposes of limitation. The practice of the present invention will employ, unless otherwise indicated, conventional techniques of botany, microbiology, tissue culture, molecular biology, chemistry, biochemistry and recombinant DNA technology, which are within the skill of the art (39-46).

A suitable polynucleotide for use in accordance with the invention may be obtained by cloning techniques using cDNA or genomic libraries, DNA, or cDNA from bacteria which are available commercially or which may be constructed using standard methods known to persons of ordinary skill in the art. Suitable nucleotide sequences may be isolated from DNA libraries obtained from a wide variety of species by means of nucleic acid hybridization or amplification methods, such as polymerase chain reaction (PCR) procedures, using as probes or primers nucleotide sequences selected in accordance with the invention.

Furthermore, nucleic acid sequences may be constructed or amplified using chemical synthesis. The product of amplification is termed an amplicon. Moreover, if the particular nucleic acid sequence is of a length that makes chemical synthesis of the entire length impractical, the sequence may be broken up into smaller segments that may be synthesized and ligated together to form the entire desired sequence by methods known in the art. Alternatively, individual components or DNA fragments may be amplified by PCR and adjacent fragments can be amplified together using fusion-PCR (47), overlap-PCR (48) or chemical (de novo) synthesis (49-53) by methods known in the art.

A suitable polynucleotide for use in accordance with the invention may be constructed by recombinant DNA technology, for example, by cutting or splicing nucleic acids using restriction enzymes and mixing with a cleaved (cut with a restriction enzyme) vector with the cleaved insert (DNA of the invention) and ligated using DNA ligase. Alternatively amplification techniques, such as PCR, can be used, where restriction sites are incorporated in the primers that otherwise match the nucleotide sequences (especially at the 3' ends) selected in accordance with the invention. The desired amplified recombinant molecule is cut or spliced using restriction enzymes and mixed with a cleaved vector and ligated using DNA ligase. In another method, after amplification of the desired recombinant molecule, DNA linker sequences are ligated to the 5' and 3' ends of the desired nucleotide insert with ligase, the DNA insert is cleaved with a restriction enzyme that specifically recognizes sequences present in the linker sequences and the desired vector. The cleaved vector is mixed with the cleaved insert, and the two fragments are ligated using DNA ligase. In yet another method, the desired recombinant molecule is amplified with primers that have recombination sites (e.g. Gateway) incorporated in the primers, that otherwise match the nucleotide sequences selected in accordance with the invention. The desired amplified recombinant molecule is mixed with a vector containing the recombination site and recombinase, the two molecules are ligated together by recombination.

The recombinant expression cassette or DNA construct includes a promoter that directs transcription in a plant cell, operably linked to the polynucleotide encoding a CDO, SAD, GAD, ADO, TPAT, SA, ssTDeHase or lsTDeHase. In various aspects of the invention described herein, a variety of different types of promoters are described and used. As used herein, a polynucleotide is "operably linked" to a promoter or other nucleotide sequence when it is placed into a functional relationship with the promoter or other nucleotide sequence. The functional relationship between a promoter and a desired polynucleotide insert typically involves the polynucleotide and the promoter sequences being contiguous such that transcription of the polynucleotide sequence will be facilitated. Two nucleic acid sequences are further said to be operably linked if the nature of the linkage between the two sequences does not (1) result in the introduction of a frame-shift mutation; (2) interfere with the ability of the promoter region sequence to direct the transcription of the desired nucleotide sequence, or (3) interfere with the ability of the desired nucleotide sequence to be transcribed by the promoter sequence region. Typically, the promoter element is generally upstream (i.e., at the 5' end) of the nucleic acid insert coding sequence.

While a promoter sequence can be ligated to a coding sequence prior to insertion into a vector, in other embodiments, a vector is selected that includes a promoter operable in the host cell into which the vector is to be inserted. In addition, certain preferred vectors have a region that codes a ribosome binding site positioned between the promoter and the site at which the DNA sequence is inserted so as to be operatively associated with the DNA sequence of the invention to produce the desired polypeptide, i.e., the DNA sequence of the invention in-frame.

Suitable Promoters

A wide variety of promoters are known to those of ordinary skill in the art as are other regulatory elements that can be used alone or in combination with promoters. A wide variety of promoters that direct transcription in plants cells can be used in connection with the present invention. For purposes of describing the present invention, promoters are divided into two types, namely, constitutive promoters and non-constitutive promoters. Constitutive promoters are classified as providing for a range of constitutive expression. Thus, some are weak constitutive promoters, and others are strong constitutive promoters. Non-constitutive promoters include tissue-preferred promoters, tissue-specific promoters, cell-type specific promoters, and inducible-promoters.

Of particular interest in certain embodiments of the present invention are inducible-promoters that respond to various forms of environmental stresses, or other stimuli, including, for example, mechanical shock, heat, cold, salt, flooding, drought, salt, anoxia, pathogens, such as bacteria, fungi, and viruses, and nutritional deprivation, including deprivation during times of flowering and/or fruiting, and other forms of plant stress. For example, the promoter selected in alternate forms of the invention, can be a promoter is induced by one or more, but not limiting to one of the following, abiotic stresses such as wounding, cold, dessication, ultraviolet-B (54), heat shock (55) or other heat stress, drought stress or water stress. The promoter may further be one induced by biotic stresses including pathogen stress, such as stress induced by a virus (56) or fungi (57, 58), stresses induced as part of the plant defense pathway (59) or by other environmental signals, such as light (60), carbon dioxide (61, 62), hormones or other signaling molecules such as auxin, hydrogen peroxide and salicylic acid (63, 64), sugars and gibberellin (65) or abscissic acid and ethylene (66).

In other embodiments of the invention, tissue-specific promoters are used. Tissue-specific expression patterns as controlled by tissue- or stage-specific promoters that include, but is not limited to, fiber-specific, green tissue-specific, root-specific, stem-specific, and flower-specific. Examples of the utilization of tissue-specific expression includes, but is not limited to, the expression in leaves of the desired peptide for the protection of plants against foliar pathogens, the expression in roots of the desired peptide for the protection of plants against root pathogens, and the expression in roots or seedlings of the desired peptide for the protection of seedlings against soil-borne pathogens. In many cases, however, protection against more than one type of pathogen may be sought, and expression in multiple tissues will be desirable.

Although many promoters from dicotyledons have been shown to be operational in monocotyledons and vice versa, ideally dicotyledonous promoters are selected for expression in dicotyledons, and monocotyledonous promoters are selected for expression in monocotyledons. There are also promoters that control expression of genes in green tissue or for genes involved in photosynthesis from both monocotyledons and dicotyledons such as the maize from the phosphenol carboxylase gene (67). There are suitable promoters for root specific expression (68, 69). A promoter selected can be an endogenous promoter, i.e. a promoter native to the species and or cell type being transformed. Alternatively, the promoter can be a foreign promoter, which promotes transcription of a length of DNA of viral, microbes, bacterial or eukaryotic origin, invertebrates, vertebrates including those from plants and plant viruses. For example, in certain preferred embodiments, the promoter may be of viral origin, including a cauliflower mosaic virus promoter (CaMV), such as CaMV 35S or 19S, a figwort mosaic virus promoter (FMV 35S), or the coat protein promoter of tobacco mosaic virus (TMV). The promoter may further be, for example, a promoter for the small subunit of ribulose-1,3-biphosphate carboxylase. Promoters of bacterial origin (microbe promoters) include the octopine synthase promoter, the nopaline synthase promoter and other promoters derived from native Ti plasmids (70).

The promoters may further be selected such that they require activation by other elements known to those of ordinary skill in the art, so that production of the protein encoded by the nucleic acid sequence insert may be regulated as desired. In one embodiment of the invention, a DNA construct comprising a non-constitutive promoter operably linked to a polynucleotide encoding the desired polypeptide of the invention is used to make a transformed plant that selectively increases the level of the desired polypeptide of the invention in response to a signal. The term "signal" is used to refer to a condition, stress or stimulus that results in or causes a non-constitutive promoter to direct expression of a coding sequence operably linked to it. To make such a plant in accordance with the invention, a DNA construct is provided that includes a non-constitutive promoter operably linked to a polynucleotide encoding the desired polypeptide of the invention. The construct is incorporated into a plant genome to provide a transformed plant that expresses the polynucleotide in response to a signal.

In alternate embodiments of the invention, the selected promoter is a tissue-preferred promoter, a tissue-specific promoter, a cell-type-specific promoter, an inducible promoter or other type of non-constitutive promoter. It is readily apparent that such a DNA construct causes a plant transformed thereby to selectively express the gene for the desired polypeptide of the invention. Therefore under specific conditions or in certain tissue- or cell-types the desired polypeptide will be expressed. The result of this expression in the plant depends upon the activity of the promoter and in some cases the conditions of the cell or cells in which it is expressed.

It is understood that the non-constitutive promoter does not continuously produce the transcript or RNA of the invention. But in this embodiment the selected promoter for inclusion of the invention advantageously induces or increases transcription of gene for the desired polypeptide of the invention in response to a signal, such as an environmental cue or other stress signal including biotic and/or abiotic stresses or other conditions.

In another embodiment of the invention, a DNA construct comprising a plant GAD promoter operably linked to polynucleotides that encode the desired polypeptide of the invention is used to make a transformed plant that selectively increases the transcript or RNA of the desired polypeptide of the invention in the same cells, tissues, and under the environmental conditions that express a plant glutamate decarboxylase. It is understood to those of ordinary skill in the art that the regulatory sequences that comprise a plant promoter driven by RNA polymerase II reside in the region approximately 2900 to 1200 basepairs up-stream (5') of the translation initiation site or start codon (ATG). For example, the full-length promoter for the nodule-enhanced PEP carboxylase from alfalfa is 1277 basepairs prior to the start codon (71), the full-length promoter for cytokinin oxidase from orchid is 2189 basepairs prior to the start codon (72), the full-length promoter for ACC oxidase from peach is 2919 basepairs prior to the start codon (73), full-length promoter for cytokinin oxidase from orchid is 2189 basepairs prior to the start codon, full-length promoter for glutathione peroxidase1 from *Citrus sinensis* is 1600 basepairs prior to the start codon (74), and the full-length promoter for glucuronosyltransferase from cotton is 1647 basepairs prior to the start codon (75). Most full-length promoters are 1700 basepairs prior to the start codon. The accepted convention is to describe this region (promoter) as −1700 to −1, where the numbers designate the number of basepairs prior to the "A" in the start codon. In this embodiment of the invention that the region of −2000 to −1 basepairs 5' to a plant GAD is operably linked to a polynucleotide for the said encoded peptide to make a transformed plant that selectively expresses the polynucleotide or increases the level of the said protein where the plant GAD is expressed or accumulates. A plant GAD promoter is the −2000 to −1 basepair region genes that include, but is not limited to, the five *Arabidopsis thaliana* GADs (AtGAD) (76), petunia GAD (77), tomato GAD (78), tobacco GAD (79), rice (80), barely, poplar, soybean, mustard, orange, *Medicago truncatula*, grape and pine. Those of ordinary skill in the art can either digest the desired region using restriction enzymes and ligase to clone the plant GAD promoters or use amplification, such as PCR, techniques with the incorporation of restriction or recombination sites to clone the plant GAD promoters 5' to the desired polynucleotide. A plant GAD promoter for these purposes normally means the following regions upstream (5') to the start codon between −200 to −1 basepairs, preferably at least between −500 to −1 basepairs, preferably at least between −1000 to −1 basepairs, more preferably at least between −1500 to −1 basepairs, and most preferably at −2000 to −1 basepairs.

In another embodiment of the invention, a DNA construct comprising a plant glutamate receptor promoter operably linked to polynucleotides that encode the desired polypeptide of the invention is used to make a transformed plant that selectively increases the transcript or RNA of the desired polypeptide of the invention in the same cells, tissues, and under the environmental conditions that express a plant glutamate receptor. It is understood to those of ordinary skill in the art that the regulatory sequences that comprise a plant promoter driven by RNA polymerase II reside in the region approximately 2900 to 1200 basepairs up-stream (5') of the translation initiation site or start codon (ATG). A plant glutamate receptor promoter is the −2000 to −1 basepair region genes that include, but is not limited to, the 20 *Arabidopsis thaliana* glutamate receptors (AtGLRs or AtGluRs) and 23 rice glutamate receptors. The promoters for the following AtGLRs genes, 1.1, 2.1, 3.1 (81), 3.2 (note this is designated as GLR2 in the manuscript; (82), and 3.4 (83) have been shown to control specific cell-type, tissue-type, developmental and environmental expression patterns in plants. Those of ordinary skill in the art can either digest the desired region using restriction enzymes and ligase to clone the plant glutamate promoters or use amplification, such as PCR, techniques with the incorporation of restriction or recombination sites to clone the plant glutamate receptor promoters 5' to the desired polynucleotide. A plant glutamate receptor promoter for these purposes normally means the following regions upstream (5') to the start codon between −200 to −1 basepairs, preferably at least between −500 to −1 basepairs, preferably at least between −1000 to −1 basepairs, more preferably at least between −1500 to −1 basepairs, and most preferably at −2000 to −1 basepairs.

In another embodiment of the invention, a DNA construct comprising a plant sulphate transporter promoter operably linked to polynucleotides that encode the desired polypeptide of the invention is used to make a transformed plant that selectively increases the transcript or RNA of the desired polypeptide of the invention in the same cells, tissues, and under the environmental conditions that express a plant sulphate transporter. It is understood to those of ordinary skill in the art that the regulatory sequences that comprise a plant promoter driven by RNA polymerase II reside in the region approximately 2900 to 1200 basepairs up-stream (5') of the translation initiation site or start codon (ATG). A plant sulphate transporter promoter is the −2000 to −1 basepair region genes that include, but is not limited to, the *Arabidopsis thaliana* sulphate transporters (SULTR or AtSULTR). The promoters for the following SULTR genes, SULTR1;1, SULTR1;2 (84), SULTR 1;3; (85), SULTR2;1 (86), and SULTR3;5 (87) have been shown to control specific cell-type, tissue-type, developmental and environmental expression patterns in plants. Those of ordinary skill in the art can either digest the desired region using restriction enzymes and ligase to clone the plant glutamate promoters or use amplification, such as PCR, techniques with the incorporation of restriction or recombination sites to clone the plant sulphate transporter promoters 5' to the desired polynucleotide. A plant sulphate transporter promoter for these purposes normally means the following regions upstream (5') to the start codon between −200 to −1 basepairs, preferably at least between −500 to −1 basepairs, preferably at least between −1000 to −1 basepairs, more preferably at least between −1500 to −1 basepairs, and most preferably at −2000 to −1 basepairs.

Suitable Vectors

A wide variety of vectors may be employed to transform a plant, plant cell or other cells with a construct made or selected in accordance with the invention, including high- or low-copy number plasmids, phage vectors and cosmids. Such vectors, as well as other vectors, are well known in the art. Representative T-DNA vector systems (70, 88) and numerous expression cassettes and vectors and in vitro culture methods for plant cell or tissue transformation and regeneration of plants are known and available (89). The vectors can be chosen such that operably linked promoter and polynucleotides that encode the desired polypeptide of the invention are incorporated into the genome of the plant. Although the preferred embodiment of the invention is expression in plants or plant cells, other embodiments may include expression in prokaryotic or eukaryotic photosynthetic organisms, microbes, invertebrates or vertebrates.

It is known by those of ordinary skill in the art that there exist numerous expression systems available for expression of a nucleic acid encoding a protein of the present invention. There are many commercially available recombinant vectors to transform a host plant or plant cell. Standard molecular and cloning techniques (43, 46, 90) are available to make a recombinant expression cassette that expresses the polynucleotide that encodes the desired polypeptide of the invention. No attempt to describe in detail the various methods known for the expression of proteins in prokaryotes or eukaryotes will be made. In brief, the expression of isolated nucleic acids encoding a protein of the present invention will typically be achieved by operably linking, for example, the DNA or cDNA to a promoter, followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high-level expression of a cloned gene, it is desirable to construct expression vectors that contain, at the minimum, a strong promoter, such as ubiquitin, to direct transcription, a ribosome-binding site for translational initiation, and a transcription/translation terminator.

One of ordinary skill to the art recognizes that modifications could be made to a protein of the present invention without diminishing its biological activity. Some modifications may be made to facilitate the cloning, expression, targeting or to direct the location of the polypeptide in the host, or for the purification or detection of the polypeptide by the addition of a "tag" as a fusion protein. Such modifications are well known to those of skill in the art and include, for example, a methionine added at the amino terminus to provide an initiation site, additional amino acids (tags) placed on either terminus to create a tag, additional nucleic acids to insert a restriction site or a termination.

In addition to the selection of a suitable promoter, the DNA constructs requires an appropriate transcriptional terminator to be attached downstream of the desired gene of the invention for proper expression in plants. Several such terminators are available and known to persons of ordinary skill in the art. These include, but are not limited to, the tml from CaMV and E9 from rbcS. Another example of a terminator sequence is the polyadenlyation sequence from the bovine growth hormone gene. A wide variety of available terminators known to function in plants can be used in the context of this invention. Vectors may also have other control sequence features that increase their suitability. These include an origin of replication, enhancer sequences, ribosome binding sites, RNA splice sites, polyadenylation sites, selectable markers and RNA stability signal. Origin of replication is a gene sequence that controls replication of the vector in the host cell. Enhancer sequences cooperate with the promoter to increase expression of the polynucleotide insert coding sequence. Enhancers can stimulate promoter activity in host cell. An example of specific polyadenylation sequence in higher eukaryotes is ATTTA. Examples of plant polyadenylation signal sequences are AATAAA or AATAAT. RNA splice sites are sequences that ensure accurate splicing of the transcript. Selectable markers usually confer resistance to an antibiotic, herbicide or chemical or provide color change, which aid the identification of transformed organisms. The vectors also include a RNA stability signal, which are 3'-regulatory sequence elements that increase the stability of the transcribed RNA (91, 92).

In addition, polynucleotides that encode a CDO, SAD, GAD, ADO, TPAT, SA, ssTDeHase, lsTDeHase or TDO can be placed in the appropriate plant expression vector used to transform plant cells. The polypeptide can then be isolated from plant callus or the transformed cells can be used to regenerate transgenic plants. Such transgenic plants can be harvested, and the appropriate tissues can be subjected to large-scale protein extraction and purification techniques.

The vectors may include another polynucleotide insert that encodes a peptide or polypeptide used as a "tag" to aid in purification or detection of the desired protein. The additional polynucleotide is positioned in the vector such that upon cloning and expression of the desired polynucleotide a fusion, or chimeric, protein is obtained. The tag may be incorporated at the amino or carboxy terminus. If the vector does not contain a tag, persons with ordinary skill in the art know that the extra nucleotides necessary to encode a tag can be added with the ligation of linkers, adaptors, or spacers or by PCR using designed primers. After expression of the peptide the tag can be used for purification using affinity chromatography, and if desired, the tag can be cleaved with an appropriate enzyme. The tag can also be maintained, not cleaved, and used to detect the accumulation of the desired polypeptide in the protein extracts from the host using western blot analysis. In another embodiment, a vector includes the polynucleotide for the tag that is fused in-frame to the polynucleotide that encodes a functional CDO, SAD, GAD, ADO, TPAT, SA, ssTDeHase, lsTDeHase or TDO to form a fusion protein. The tags that may be used include, but are not limited to, Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin (Trx-Tag). These are available from a variety of manufacturers Clontech Laboratories, Takara Bio Company GE Healthcare, Invitrogen, Novagen Promega and QIAGEN.

The vector may include another polynucleotide that encodes a signal polypeptide or signal sequence ("subcellular location sequence") to direct the desired polypeptide in the host cell, so that the polypeptide accumulates in a specific cellular compartment, subcellular compartment, or membrane. The specific cellular compartments include the apoplast, vacuole, plastids chloroplast, mitochondrion, peroxisomes, secretory pathway, lysosome, endoplasmic reticulum, nucleus or Golgi apparatus. A signal polypeptide or signal sequence is usually at the amino terminus and normally absent from the mature protein due to protease that removes the signal peptide when the polypeptide reaches its final destination. Signal sequences can be a primary sequence located at the N-terminus (93-96), C-terminus (97, 98) or internal (99-101) or tertiary structure (101). If a signal polypeptide or signal sequence to direct the polypeptide does not exist on the vector, it is expected that those of ordinary skill in the art can incorporate the extra nucleotides necessary to encode a signal polypeptide or signal sequence by the ligation of the appropriate nucleotides or by PCR. Those of ordinary skill in the art can identify the nucleotide sequence of a signal polypeptide or signal sequence using computational tools. There are numerous computational tools available for the identification of targeting sequences or signal sequence. These include, but are not limited to, TargetP (102, 103), iPSORT (104), SignalP (105), PrediSi (106), ELSpred (107) HSLpred (108) and PSLpred (109), MultiLoc (110), SherLoc (111), ChloroP (112), MITOPROT (113), Predotar (114) and 3D-PSSM (115). Additional methods and protocols are discussed in the literature (110).

Fusion of Two Gene Products

Two gene products can be fused together to increase the efficiency of an enzymatic reaction conducted by two enzymes (116-118). The two genes can be fused in-frame to be expressed as a single gene product with or without a linker. The linker can be a sequence that encodes a "tag" or a peptide.

Transformation of Host Cells

Transformation of a plant can be accomplished in a wide variety of ways within the scope of a person of ordinary skill in the art. In one embodiment, a DNA construct is incorporated into a plant by (i) transforming a cell, tissue or organ from a host plant with the DNA construct; (ii) selecting a transformed cell, cell callus, somatic embryo, or seed which contains the DNA construct; (iii) regenerating a whole plant from the selected transformed cell, cell callus, somatic embryo, or seed; and (iv) selecting a regenerated whole plant that expresses the polynucleotide. Many methods of transforming a plant, plant tissue or plant cell for the construction of a transformed cell are suitable. Once transformed, these cells can be used to regenerate transgenic plants (119).

Those of ordinary skill in the art can use different plant gene transfer techniques found in references for, but not limited to, the electroporation (120-124), microinjection (125, 126), lipofection (127), liposome or spheroplast fusions (128-130), *Agrobacterium* (131), direct gene transfer (132), T-DNA mediated transformation of monocots (133), T-DNA mediated transformation of dicots); (134, 135), microprojectile bombardment or ballistic particle acceleration (136-139), chemical transfection including CaCl2 precipitation, polyvinyl alcohol, or poly-L-ornithine (140), silicon carbide whisker methods (141, 142), laser methods (143, 144), sonication methods (145-147), polyethylene glycol methods (148), and vacuum infiltration (149) and transbacter (150).

In one embodiment of the invention, a transformed host cell may be cultured to produce a transformed plant. In this regard, a transformed plant can be made, for example, by transforming a cell, tissue or organ from a host plant with an inventive DNA construct; selecting a transformed cell, cell callus, somatic embryo, or seed which contains the DNA construct; regenerating a whole plant from the selected transformed cell, cell callus, somatic embryo, or seed; and selecting a regenerated whole plant that expresses the polynucleotide.

A wide variety of host cells may be used in the invention, including prokaryotic and eukaryotic host cells. These cells or organisms may include microbes, invertebrate, vertebrates or photosynthetic organisms. Preferred host cells are eukaryotic, preferably plant cells, such as those derived from monocotyledons, such as duckweed, corn, rice, sugarcane, wheat, bent grass, rye grass, Bermuda grass, Blue grass, and Fescue, or dicotyledons, including canola, cotton, camelina, lettuce, rapeseed, radishes, cabbage, sugarbeet, peppers, broccoli, potatoes and tomatoes, and legumes such as soybeans and bush beans.

One embodiment of the invention is a method for the production of hypotaurine or taurine by the following steps:

1. operably link a promoter to the 5' end of the polynucleotide for a functional CDO gene product;
2. insert the polynucleotide construct (from step 1 above) into a vector;
3. transform the vector containing the CDO construct into a plant or plant cell;
4. operably link a promoter to the 5' end of the polynucleotide for the functional SAD gene product;
5. insert the polynucleotide construct (from step 4 above) into a vector; and
6. transform the vector containing the SAD construct into a plant or plant cell carrying a CDO construct or one that expresses a functional CDO gene product.

Another embodiment of the invention is a method for the production of hypotaurine or taurine by the following steps:

1. operably link a promoter to the 5' end of the polynucleotide for the functional CDO gene product;
2. insert the polynucleotide construct (from step 1 above) into a vector;
3. transform the vector containing the CDO construct into a plant or plant cell;
4. operably link a promoter to the 5' end of the polynucleotide for the functional SAD gene product;
5. insert the polynucleotide construct (from step 4 above) into a vector;
6. transform the vector containing the SAD construct into a plant or plant cell; and
7. Sexually cross a plant (or fuse cells) carrying a CDO construct or one that expresses a functional CDO with a plant (or cells) carrying a SAD construct or one that expresses a functional SAD gene product.

Another embodiment of the invention is a method for the production of hypotaurine or taurine by the following steps:

1. In the same vector, operably link a promoter to the 5' end of the polynucleotide for the functional CDO gene product;
2. operably link a promoter to the 5' end of the polynucleotide for the functional SAD gene product;
3. insert the two polynucleotides into the vector in such a manner that both polynucleotides are expressed by one promoter or each polynucleotide is expressed by one promoter; and
4. transform the vector containing the CDO and SAD constructs into a plant or plant cell.

Another embodiment of the invention is a method for the production of hypotaurine or taurine by the following steps:

1. operably link a promoter to the 5' end of the polynucleotide for a functional CDO gene product;
2. insert the polynucleotide construct (from step 1 above) into a vector;
3. transform the vector containing the CDO construct into a plant or plant cell;
4. operably link a promoter to the 5' end of the polynucleotide for the functional GAD gene product;
5. insert the polynucleotide construct (from step 4 above) into a vector; and
6. transform the vector containing the GAD construct into a plant or plant cell carrying a CDO construct or one that expresses a functional CDO gene product.

Another embodiment of the invention is a method for the production of hypotaurine or taurine by the following steps:

1. operably link a promoter to the 5' end of the polynucleotide for the functional CDO gene product;
2. insert the polynucleotide construct (from step 1 above) into a vector;
3. transform the vector containing the CDO construct into a plant or plant cell;
4. operably link a promoter to the 5' end of the polynucleotide for the functional GAD gene product;
5. insert the polynucleotide construct (from step 4 above) into a vector;
6. transform the vector containing the GAD construct into a plant or plant cell; and
7. Sexually cross a plant (or fuse cells) carrying a CDO construct or one that expresses a functional CDO with a plant (or cells) carrying a GAD construct or one that expresses a functional GAD gene product.

Another embodiment of the invention is a method for the production of hypotaurine or taurine by the following steps:
1. In the same vector, operably link a promoter to the 5' end of the polynucleotide for the functional CDO gene product;
2. operably link a promoter to the 5' end of the polynucleotide for the functional GAD gene product;
3. insert the two polynucleotides into the vector in such a manner that both polynucleotides are expressed by one promoter or each polynucleotide is expressed by one promoter; and
4. transform the vector containing the CDO and GAD constructs into a plant or plant cell.

Another embodiment of the invention is a method for the production of hypotaurine or taurine by the following steps:
1. operably link a promoter to the 5' end of the polynucleotide for a functional CDO gene product;
2. insert the polynucleotide construct (from step 1 above) into a vector; transform the vector containing the CDO construct into a plant or plant cell.

Another embodiment of the invention is a method for the production of taurine by the following steps:
1. operably link a promoter to the 5' end of the polynucleotide for a functional SAD gene product;
2. insert the polynucleotide construct (from step 1 above) into a vector; transform the vector containing the SAD construct into a plant or plant cell.

Another embodiment of the invention is a method for the production of hypotaurine or taurine by the following steps:
1. operably link a promoter to the 5' end of the polynucleotide for a functional ADO gene product;
2. insert the polynucleotide construct (from step 1 above) into a vector; transform the vector containing the ADO construct into a plant or plant cell.

Another embodiment of the invention is a method for the production of taurine by the following steps:
1. operably link a promoter to the 5' end of the polynucleotide for a functional TPAT gene product;
2. insert the polynucleotide construct (from step 1 above) into a vector; transform the vector containing the TPAT construct into a plant or plant cell.

One embodiment of the invention is a method for the production of taurine by the following steps:
1. operably link a promoter to the 5' end of the polynucleotide for a functional TPAT gene product;
2. insert the polynucleotide construct (from step 1 above) into a vector;
3. transform the vector containing the TPAT construct into a plant or plant cell;
4. operably link a promoter to the 5' end of the polynucleotide for the functional SA gene product;
5. insert the polynucleotide construct (from step 4 above) into a vector; and
6. transform the vector containing the TPAT construct into a plant or plant cell carrying a SA construct or one that expresses a functional SA gene product.

Another embodiment of the invention is a method for the production of taurine by the following steps:
1. operably link a promoter to the 5' end of the polynucleotide for the functional TPAT gene product;
2. insert the polynucleotide construct (from step 1 above) into a vector;
3. transform the vector containing the TPAT construct into a plant or plant cell;
4. operably link a promoter to the 5' end of the polynucleotide for the functional SA gene product;
5. insert the polynucleotide construct (from step 4 above) into a vector;
6. transform the vector containing the SA construct into a plant or plant cell; and
7. Sexually cross a plant (or fuse cells) carrying a TPAT construct or one that expresses a functional TPAT with a plant (or cells) carrying a SA construct or one that expresses a functional SA gene product.

Another embodiment of the invention is a method for the production of taurine by the following steps:
1. In the same vector, operably link a promoter to the 5' end of the polynucleotide for the functional TPAT gene product;
2. operably link a promoter to the 5' end of the polynucleotide for the functional SA gene product;
3. insert the two polynucleotides into the vector in such a manner that both polynucleotides are expressed by one promoter or each polynucleotide is expressed by one promoter; and
4. transform the vector containing the TPAT and SA construct into a plant or plant cell.

Another embodiment of the invention is a method for the production of taurine by the following steps:
1. operably link a promoter to the 5' end of the polynucleotide for a functional small subunit of TDeHase (ssTDeHase) gene product;
2. insert the polynucleotide construct (from step 1 above) into a vector;
3. transform the vector containing the ssTDeHase construct into a plant or plant cell;
4. operably link a promoter to the 5' end of the polynucleotide for the functional large subunit of TDeHase (lsTDeHase) gene product;
5. insert the polynucleotide construct (from step 4 above) into a vector; and
6. transform the vector containing the lsTDeHase construct into a plant or plant cell carrying a ssTDeHase construct or one that expresses a functional ssTDeHase gene product.

Another embodiment of the invention is a method for the production of taurine by the following steps:
1. operably link a promoter to the 5' end of the polynucleotide for the functional ssTDeHase gene product;
2. insert the polynucleotide construct (from step 1 above) into a vector;
3. transform the vector containing the ssTDeHase construct into a plant or plant cell;
4. operably link a promoter to the 5' end of the polynucleotide for the functional lsTDeHase gene product;
5. insert the polynucleotide construct (from step 4 above) into a vector;
6. transform the vector containing the lsTDeHase construct into a plant or plant cell; and
7. Sexually cross a plant (or fuse cells) carrying a ssTDeHase construct or one that expresses a functional ssTDeHase with a plant (or cells) carrying a lsTDeHase construct or one that expresses a functional lsTDeHase gene product.

Another embodiment of the invention is a method for the production of taurine by the following steps:
1. In the same vector, operably link a promoter to the 5' end of the polynucleotide for the functional ssTDeHase gene product;
2. operably link a promoter to the 5' end of the polynucleotide for the functional lsTDeHase gene product;

3. insert the two polynucleotides into the vector in such a manner that both polynucleotides are expressed by one promoter or each polynucleotide is expressed by one promoter; and 4. transform the vector containing the ssTDeHase and lsTDeHase construct into a plant or plant cell.

Another embodiment of the invention is a method for the production of taurine by the following steps:

1. operably link a promoter to the 5' end of the polynucleotide for a functional TDO gene product;

2. insert the polynucleotide construct (from step 1 above) into a vector; transform the vector containing the TDO construct into a plant or plant cell.

Another embodiment of the invention is a method for the production of hypotaurine or taurine by the following steps:

1. operably link a promoter to the 5' end of the polynucleotide for a functional CDO fused in-frame to a functional SAD gene product;

2. insert the polynucleotide construct (from step 1 above) into a vector; transform the vector containing the CDO-SAD construct into a plant or plant cell.

Another embodiment of the invention is a method for the production of hypotaurine or taurine by the following steps:

1. operably link a promoter to the 5' end of the polynucleotide for a functional CDO fused with a linker in-frame to a functional SAD gene product;

2. insert the polynucleotide construct (from step 1 above) into a vector; transform the vector containing the CDO-linker-SAD construct into a plant or plant cell.

Another embodiment of the invention is a method for the production of hypotaurine or taurine by the following steps:

1. operably link a promoter to the 5' end of the polynucleotide for a functional SAD fused in-frame to a functional CDO gene product;

2. insert the polynucleotide construct (from step 1 above) into a vector; transform the vector containing the SAD-CDO construct into a plant or plant cell.

Another embodiment of the invention is a method for the production of hypotaurine or taurine by the following steps:

1. operably link a promoter to the 5' end of the polynucleotide for a functional SAD fused with a linker in-frame to a functional CDO gene product;

2. insert the polynucleotide construct (from step 1 above) into a vector; transform the vector containing the SAD-linker-CDO construct into a plant or plant cell.

Another embodiment of the invention is a method for the production of hypotaurine or taurine by the following steps:

1. operably link a promoter to the 5' end of the polynucleotide for a functional CDO fused in-frame to a functional GAD gene product;

2. insert the polynucleotide construct (from step 1 above) into a vector; transform the vector containing the CDO-GAD construct into a plant or plant cell.

Another embodiment of the invention is a method for the production of hypotaurine or taurine by the following steps:

1. operably link a promoter to the 5' end of the polynucleotide for a functional CDO fused with a linker in-frame to a functional GAD gene product;

2. insert the polynucleotide construct (from step 1 above) into a vector; transform the vector containing the CDO-linker-GAD construct into a plant or plant cell.

Another embodiment of the invention is a method for the production of hypotaurine or taurine by the following steps:

1. operably link a promoter to the 5' end of the polynucleotide for a functional GAD fused in-frame to a functional CDO gene product;

2. insert the polynucleotide construct (from step 1 above) into a vector; transform the vector containing the GAD-CDO construct into a plant or plant cell.

Another embodiment of the invention is a method for the production of hypotaurine or taurine by the following steps:

1. operably link a promoter to the 5' end of the polynucleotide for a functional GAD fused with a linker in-frame to a functional CDO gene product;

2. insert the polynucleotide construct (from step 1 above) into a vector; transform the vector containing the GAD-linker-CDO construct into a plant or plant cell.

Another embodiment of the invention is a method for the production of hypotaurine or taurine by the following steps:

1. operably link a promoter to the 5' end of the polynucleotide for a functional TPAT fused in-frame to a functional SA gene product;

2. insert the polynucleotide construct (from step 1 above) into a vector; transform the vector containing the TPAT-SA construct into a plant or plant cell.

Another embodiment of the invention is a method for the production of hypotaurine or taurine by the following steps:

1. operably link a promoter to the 5' end of the polynucleotide for a functional TPAT fused with a linker in-frame to a functional SA gene product;

2. insert the polynucleotide construct (from step 1 above) into a vector; transform the vector containing the TPAT-linker-SA construct into a plant or plant cell.

Another embodiment of the invention is a method for the production of hypotaurine or taurine by the following steps:

1. operably link a promoter to the 5' end of the polynucleotide for a functional SA fused in-frame to a functional TPAT gene product;

2. insert the polynucleotide construct (from step 1 above) into a vector; transform the vector containing the SA-TPAT construct into a plant or plant cell.

Another embodiment of the invention is a method for the production of hypotaurine or taurine by the following steps:

1. operably link a promoter to the 5' end of the polynucleotide for a functional SA fused with a linker in-frame to a functional TPAT gene product;

2. insert the polynucleotide construct (from step 1 above) into a vector; transform the vector containing the SA-linker-TPAT construct into a plant or plant cell.

Another embodiment of the invention is a method for the production of hypotaurine or taurine by the following steps:

1. operably link a promoter to the 5' end of the polynucleotide for a functional ssTDeHase fused in-frame to a functional lsTDeHase gene product;

2. insert the polynucleotide construct (from step 1 above) into a vector; transform the vector containing the ssTDeHase-lsTDeHase construct into a plant or plant cell.

Another embodiment of the invention is a method for the production of hypotaurine or taurine by the following steps:

1. operably link a promoter to the 5' end of the polynucleotide for a functional ssTDeHase fused with a linker in-frame to a functional lsTDeHase gene product;

2. insert the polynucleotide construct (from step 1 above) into a vector; transform the vector containing the ssTDeHase-linker-lsTDeHase construct into a plant or plant cell.

Another embodiment of the invention is a method for the production of hypotaurine or taurine by the following steps:

1. operably link a promoter to the 5' end of the polynucleotide for a functional lsTDeHase fused in-frame to a functional ssTDeHase gene product;

2. insert the polynucleotide construct (from step 1 above) into a vector; transform the vector containing the lsTDeHase-ssTDeHase construct into a plant or plant cell.

Another embodiment of the invention is a method for the production of hypotaurine or taurine by the following steps:

1. operably link a promoter to the 5' end of the polynucleotide for a functional lsTDeHase fused with a linker in-frame to a functional ssTDeHase gene product;
2. insert the polynucleotide construct (from step 1 above) into a vector; transform the vector containing the lsTDe-Hase-linker-ssTDeHase construct into a plant or plant cell.

Suitable Plants

The methods described above may be applied to transform a wide variety of plants, including decorative or recreational plants or crops, but are particularly useful for treating commercial and ornamental crops. Examples of plants that may be transformed in the present invention include, but are not limited to, Acacia, alfalfa, algae, aneth, apple, apricot, artichoke, arugula, asparagus, avocado, banana, barley, beans, beech, beet, Bermuda grass, bent grass, blackberry, blueberry, Blue grass, broccoli, Brussels sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jicama, kiwifruit, lettuce, leeks, lemon, lime, Loblolly pine, maize, mango, melon, mushroom, nectarine, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, seaweed, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini. Other suitable hosts include bacteria, fungi, algae and other photosynthetic organisms, and animals including vertebrate and invertebrates.

Once transformed, the plant may be treated with other "active agents" either prior to or during the exposure of the plant to stress to further decrease the effects of plant stress. "Active agent," as used herein, refers to an agent that has a beneficial effect on the plant or increases production of amino acid production by the plant. For example, the agent may have a beneficial effect on the plant with respect to nutrition, and the resistance against, or reduction of, the effects of plant stress. Some of these agents may be precursors of end products for reaction catalyzed by CDO, SAD, GAD, ADO, TPAT, SA, ssTDeHase or lsTDeHase. These compounds could promote growth, development, biomass and yield, and change in metabolism. In addition to the twenty amino acids that are involved in protein synthesis specifically sulfur containing amino acids methionine, and cysteine, other amino acids such as glutamate, glutamine, serine, alanine and glycine, sulfur containing compounds such as fertilizer, sulfite, sulfide, sulfate, taurine, hypotaurine, cysteate, 2-sulfacetaldehyde, homotaurine, homocysteine, cystathionine, N-acetyl thiazolidine 4 carboxylic acid (ATCA), glutathione, or bile, or other non-protein amino acids, such as GABA, citrulline and ornithine, or other nitrogen containing compounds such as polyamines may also be used to activate CDO, SAD, GAD, ADO, TPAT, SA, ssTDeHase, lsTDeHase or TDO. Depending on the type of gene construct or recombinant expression cassette, other metabolites and nutrients may be used to activate CDO, SAD, GAD, ADO, TPAT, SA, ssTDeHase, lsTDeHase, or TDO. These include, but are not limited to, sugars, carbohydrates, lipids, oligopeptides, mono- (glucose, arabinose, fructose, xylose, and ribose) di- (sucrose and trehalose) and polysaccharides, carboxylic acids (succinate, malate and fumarate) and nutrients such as phosphate, molybdate, or iron.

Accordingly, the active agent may include a wide variety of fertilizers, pesticides and herbicides known to those of ordinary skill in the art (151). Other greening agents fall within the definition of "active agent" as well, including minerals such as calcium, magnesium and iron. The pesticides protect the plant from pests or disease and may be either chemical or biological and include fungicides, bactericides, insecticides and anti-viral agents as known to those of ordinary skill in the art.

In some embodiments properties of a transgenic plant are altered using an agent which increases sulfur concentration in cells of the transgenic plant, such as fertilizer, sulfur, sulfite, sulfide, sulfate, taurine, hypotaurine, homotaurine, cysteate, 2-sulfacetaldehyde, N-acetyl thiazolidine 4 carboxylic acid (ATCA), glutathione, and bile. In other embodiments, the agent increases nitrogen concentration. Amino acids, either naturally occurring in proteins (e.g., cysteine, methionine, glutamate, glutamine, serine, alanine, or glycine) or which do not naturally occur in proteins (e.g., GABA, citrulline, or ornithine) and/or polyamines can be used for this purpose.

Expression in Prokaryotes

The use of prokaryotes as hosts includes strains of *E. coli*. However, other microbial strains including, but not limited to, *Bacillus* (152) and *Salmonella* may also be used. Commonly used prokaryotic control sequences include promoters for transcription initiation, optionally with an operator, along with ribosome binding site sequences. Commonly used prokaryotic promoters include the beta lactamase (153), lactose (153), and tryptophan (154) promoters. The vectors usually contain selectable markers to identify transfected or transformed cells. Some commonly used selectable markers include the genes for resistance to ampicillin, tetracycline, or chloramphenicol. The vectors are typically a plasmid or phage. Bacterial cells are transfected or transformed with the plasmid vector DNA. Phage DNA can be infected with phage vector particles or transfected with naked phage DNA. The plasmid and phage DNA for the vectors are commercially available from numerous vendors known to those of ordinary skill in the art.

Expression in Non Plant Eukaryotes

The present invention can be expressed in a variety of eukaryotic expression systems such as yeast, insect cell lines, and mammalian cells which are known to those of ordinary skill in the art. For each host system there are suitable vectors that are commercially available (e.g., Invitrogen, Startagene, GE Healthcare Life Sciences). The vectors usually have expression control sequences, such as promoters, an origin of replication, enhancer sequences, termination sequences, ribosome binding sites, RNA splice sites, polyadenylation sites, transcriptional terminator sequences, and selectable markers. Synthesis of heterologous proteins in yeast is well known to those of ordinary skill in the art (155, 156). The most widely used yeasts are *Saccharomyces cerevisiae* and *Pichia pastoris*. Insect cell lines that include, but are not limited to, mosquito larvae, silkworm, armyworm, moth, and *Drosophila* cell lines can be used to express proteins of the present invention using baculovirus-derived vectors. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines.

A protein of the present invention, once expressed in any of the non-plant eukaryotic systems can be isolated from the organism by lysing the cells and applying standard protein isolation techniques to the lysates or the pellets. The monitoring of the purification process can be accomplished by using western blot techniques or radioimmunoassay of other standard immunoassay techniques.

Pharmaceutical Compositions

The invention provides pharmaceutical compositions which comprise extracts of one or more transgenic plants described above. Plant extracts containing taurine and hypotaurine can be used to synthesize or manufacture homotaurine or other taurine derivatives (157, 158), taurine-conjugates (159) or taurine-polymers (160) that may have a wide range of commercial and medicinal applications (161). Some taurine derivatives can function as organogelators (162) or dyes (163) and can be used in nanosensor synthesis (164). Some taurine derivatives have anticonvulsant (157) or anti-cancer (165) properties. Other taurine derivatives are used in the treatment of alcoholism (166, 167). Taurine-conjugated carboxyethylester-polyrotaxanes increase anticoagulant activity (168). Taurine-containing polymers may increase wound healing (169, 170). Taurine linked polymers such as poly gamma-glutamic acid-sulfonates are biodegradable and may have applications in the development of drug delivery systems, environmental materials, tissue engineering, and medical materials (171). Extracts from taurine-containing plants may be used in pharmaceutical or medicinal compositions to deliver taurine, hypotaurine, taurine-conjugates, or taurine-polymers for use in the treatment of congestive heart failure, high blood pressure, hepatitis, high cholesterol, fibrosis, epilepsy, autism, attention deficit-hyperactivity disorder, retinal degeneration, diabetes, and alcoholism. It is also used to improve mental performance and as an antioxidant.

Pharmaceutically acceptable vehicles of taurine, taurine derivatives, taurine-conjugates, or taurine-polymers are tablets, capsules, gel, ointment, film, patch, powder or dissolved in liquid form.

Nutritional Supplements and Feeds

Transgenic plants containing taurine or hypotaurine may be consumed or used to make extracts for nutritional supplements. Transgenic plant parts that have elevated levels of taurine or hypotaurine may be used for human consumption. The plant parts may include but are not limited to leaves, stalks, stems, tubers, stolons, roots, petioles, cotyledons, seeds, fruits, grain, strover, nuts, flowers, petioles, pollen, buds, or pods. Extracts from transgenic plants containing taurine or hypotaurine may be used as nutritional supplements, as an antioxidant or to improve physical or mental performance. The extracts may be used in the form of a liquid, powder, capsule or tablet.

Transgenic plants containing taurine or hypotaurine may be used as fish or animal feed or used to make extracts for the supplementation of animal feed. Plant parts that have elevated levels of taurine or hypotaurine may be used as animal or fish feed include but are not limited to leaves, stalks, stems, tubers, stolons, roots, petioles, cotyledons, seeds, fruits, grain, strover, nuts, flowers, petioles, buds, pods, or husks. Extracts from transgenic plants containing taurine or hypotaurine may be used as feed supplements in the form of a liquid, powder, capsule or tablet.

Definitions

The term "polynucleotide" refers to a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "amplified" and "amplification" refer to the construction of multiple copies of a nucleic acid sequence or multiple copies complementary to the nucleic acid sequence using at least one of the nucleic acid sequences as a template. Amplification can be achieved by chemical synthesis using any of the following methods, such as solid-phase phosphoramidate technology or the polymerase chain reaction (PCR). Other amplification systems include the ligase chain reaction system, nucleic acid sequence based amplification, Q-Beta Replicase systems, transcription-based amplification system, and strand displacement amplification. The product of amplification is termed an amplicon.

As used herein "promoter" includes reference to a region of DNA upstream from the start of transcription and involved in recognition and binding of RNA polymerase, either I, II or III, and other proteins to initiate transcription. Promoters include necessary nucleic acid sequences near the start site of transcription, such as, in the case of a polymerase II type promoter, a TATA element. A promoter also optionally includes distal enhancer or repressor elements, which can be located as far as several thousand base pairs from the start site of transcription.

The term "plant promoter" refers to a promoter capable of initiating transcription in plant cells.

The term "microbe promoter" refers to a promoter capable of initiating transcription in microbes.

The term "foreign promoter" refers to a promoter, other than the native, or natural, promoter, which promotes transcription of a length of DNA of viral, bacterial or eukaryotic origin, including those from microbes, plants, plant viruses, invertebrates or vertebrates.

The term "microbe" refers to any microorganism (including both eukaryotic and prokaryotic microorganisms), such as fungi, yeast, bacteria, actinomycetes, algae and protozoa, as well as other unicellular structures.

The term "plant" includes whole plants, and plant organs, and progeny of same. Plant organs comprise, e.g., shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like). The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "plant storage organ" includes roots, seeds, tubers, fruits, and specialized stems.

The term "constitutive" refers to a promoter that is active under most environmental and developmental conditions, such as, for example, but not limited to, the CaMV 35S promoter and the nopaline synthase terminator.

The term "tissue-preferred promoter" refers to a promoter that is under developmental control or a promoter that preferentially initiates transcription in certain tissues.

The term "tissue-specific promoter" refers to a promoter that initiates transcription only in certain tissues.

The term "cell-type specific promoter" refers to a promoter that primarily initiates transcription only in certain cell types in one or more organs.

The term "inducible promoter" refers to a promoter that is under environmental control.

The terms "encoding" and "coding" refer to the process by which a polynucleotide, through the mechanisms of transcription and translation, provides the information to a cell from which a series of amino acids can be assembled into a specific amino acid sequence to produce a functional polypeptide, such as, for example, an active enzyme or ligand binding protein.

The terms "polypeptide," "peptide," "protein" and "gene product" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

The terms "residue," "amino acid residue," and "amino acid" are used interchangeably herein to refer to an amino acid that is incorporated into a protein, polypeptide, or peptide. The amino acid may be a naturally occurring amino acid and may encompass known analogs of natural amino acids that can function in a similar manner as the naturally occurring amino acids.

The terms "cysteine dioxygenase" and "CDO" refer to the protein (EC:1.13.11.20) that catalyzes the following reaction:

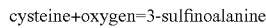
cysteine+oxygen=3-sulfinoalanine

NOTE: 3-sulfinoalanine is another name for cysteine sulfinic acid, cysteine sulfinate, 3-sulphino-L-alanine, 3-sulfino-alanine, 3-sulfino-L-alanine, L-cysteine sulfinic acid, L-cysteine sulfinic acid, cysteine hydrogen sulfite ester or alanine 3-sulfinic acid The terms "sulfinoalanine decarboxylase" and "SAD" refer to the protein (4.1.1.29) that catalyzes the following reaction:

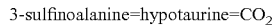
3-sulfinoalanine=hypotaurine=CO₂

NOTE: SAD is another name for cysteine-sulfinate decarboxylase, L-cysteine sulfinic acid decarboxylase, cysteine-sulfinate decarboxylase, CADCase/CSADCase, CSAD, cysteic decarboxylase, cysteine sulfinic acid decarboxylase, cysteine sulfinate decarboxylase, sulfoalanine decarboxylase, sulphinoalanine decarboxylase, and 3-sulfino-L-alanine carboxy-lyase.

NOTE: the SAD reaction is also catalyzed by GAD (4.1.1.15) (glutamic acid decarboxylase or glutamate decarboxylase).

Other names for hypotaurine are 2-aminoethane sulfinate, 2-aminoethylsulfinic acid, and 2-aminoethanesulfinic acid Other names for taurine are 2-aminoethane sulfonic acid, aminoethanesulfonate, L-taurine, taurine ethyl ester, and taurine ketoisocaproic acid 2-aminoethane sulfinate.

The terms "cysteamine dioxygenase" and "ADO" refer to the protein (EC 1.13.11.19) that catalyzes the following reaction:

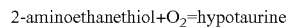
2-aminoethanethiol+O₂=hypotaurine

ADO is another name for 2-aminoethanethiol:oxygen oxidoreductase, persulfurase, cysteamine oxygenase, and cysteamine:oxygen oxidoreductase.

Other names for 2-aminoethanethiol are cysteamine or 2-aminoethane-1-thiol, b-mercaptoethylamine, 22-mercaptoethylamine, decarboxycysteine, and thioethanolamine.

The terms "taurine-pyruvate aminotransferase" and "TPAT" refer to the protein (EC 2.6.1.77) that catalyzes the following reaction:

L-alanine+2-sulfoacetaldehyde=taurine+pyruvate

TPAT is another name for taurine transaminase or Tpa

The terms "sulfoacetaldehyde acetyltransferase" and "SA" refer to the protein (EC:2.3.3.15) that catalyzes the following reaction:

acetyl phosphate+sulfite=sulfoacetaldehyde+orthophosphate

SA is another name for acetyl-phosphate:sulfite S-acetyltransferase or Xsc

The terms "taurine dehydrogenase" and "TDeHase" refer to the protein (EC:1.4.2.-) that catalyzes the following reaction:

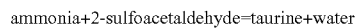
ammonia+2-sulfoacetaldehyde=taurine+water

TDeHase is another name for taurine:oxidoreductase, taurine:ferricytochrome-c oxidoreductase, tauX or tauY The terms "taurine dioxygenase" and "TDO" refer to the protein (EC:1.14.11.17) that catalyzes the following reaction:

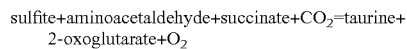
sulfite+aminoacetaldehyde+succinate+CO₂=taurine+ 2-oxoglutarate+O₂

TDO is another name for 2-aminoethanesulfonate dioxygenase, alpha-ketoglutarate-dependent taurine dioxygenase, taurine, 2-oxoglutarate:O2 oxidoreductase or tauD 2-oxoglutarate is another name for alpha-ketoglutarate The term "functional" with reference to CDO, SAD, GAD, ADO, TPAT, SA, ssTDeHase, lsTDeHase or TDO refers to peptides, proteins or enzymes that catalyze the CDO, SAD, GAD, ADO, TPAT, SA, TDeHase or TDO reactions, respectively.

The term "recombinant" includes reference to a cell or vector that has been modified by the introduction of a heterologous nucleic acid. Recombinant cells express genes that are not normally found in that cell or express native genes that are otherwise abnormally expressed, underexpressed, or not expressed at all as a result of deliberate human intervention, or expression of the native gene may have reduced or eliminated as a result of deliberate human intervention.

The term "recombinant expression cassette" refers to a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "transgenic plant" includes reference to a plant, which comprises within its genome a heterologous polynucleotide. Generally, the heterologous polynucleotide is integrated within the genome such that the polynucleotide is passed on to successive generations. The heterologous polynucleotide may be integrated into the genome alone or as part of a recombinant expression cassette. "Transgenic" is also used to include any cell, cell line, callus, tissue, plant part or plant, the genotype of which has been altered by the presence of heterologous nucleic acid including those transgenic plants altered or created by sexual crosses or asexual propagation from the initial transgenic plant. The term "transgenic" does not encompass the alteration of the genome by conventional plant breeding methods or by naturally occurring events such as random cross-fertilization, non-recombinant viral infection, non-recombinant bacterial transformation, non-recombinant transposition, or spontaneous mutation.

The term "vector" includes reference to a nucleic acid used in transfection or transformation of a host cell and into which can be inserted a polynucleotide.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" and "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt solution. Low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Moderate stringency conditions include hybridization in 40 to 45% formamide, 1 M NaCl, 1% SDS at 37° C., and a wash in 0.5× to 1×SSC at 55 to 60° C. High stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated (172), where the $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill in the art will understand that variations in the stringency of hybridization and/or wash solutions are inherently described. An extensive guide to the hybridization of nucleic acids is found in the scientific literature (90, 173). Unless otherwise stated, in the present application high stringency is defined as hybridization in 4×SSC, 5×Denhardt solution (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or polynucleotides or polypeptides: "reference sequence," "comparison window," "sequence identity," "percentage of sequence identity," and "substantial identity."

The term "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "comparison window" includes reference to a contiguous and specified segment of a polynucleotide sequence, where the polynucleotide sequence may be compared to a reference sequence and the portion of the polynucleotide sequence in the comparison window may comprise additions or deletions (i.e., gaps) when it is compared to the reference sequence for optimal alignment. The comparison window is usually at least 20 contiguous nucleotides in length, and optionally can be 30, 40, 50, 100 or longer. Those of ordinary skill in the art understand that the inclusion of gaps in a polynucleotide sequence alignment introduces a gap penalty, and it is subtracted from the number of matches.

Methods of alignment of nucleotide and amino acid sequences for comparison are well known to those of ordinary skill in the art. The local homology algorithm, BESTFIT, (174) can perform an optimal alignment of sequences for comparison using a homology alignment algorithm called GAP (175), search for similarity using Tfasta and Fasta (176), by computerized implementations of these algorithms widely available on-line or from various vendors (Intelligenetics, Genetics Computer Group). CLUSTAL allows for the alignment of multiple sequences (177-179) and program PileUp can be used for optimal global alignment of multiple sequences (180). The BLAST family of programs can be used for nucleotide or protein database similarity searches. BLASTN searches a nucleotide database using a nucleotide query. BLASTP searches a protein database using a protein query. BLASTX searches a protein database using a translated nucleotide query that is derived from a six-frame translation of the nucleotide query sequence (both strands). TBLASTN searches a translated nucleotide database using a protein query that is derived by reverse-translation. TBLASTX search a translated nucleotide database using a translated nucleotide query.

GAP (175) maximizes the number of matches and minimizes the number of gaps in an alignment of two complete sequences. GAP considers all possible alignments and gap positions and creates the alignment with the largest number of matched bases and the fewest gaps. It also calculates a gap penalty and a gap extension penalty in units of matched bases. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (181).

Unless otherwise stated, sequence identity or similarity values refer to the value obtained using the BLAST 2.0 suite of programs using default parameters (182). As those of ordinary skill in the art understand that BLAST searches assume that proteins can be modeled as random sequences and that proteins comprise regions of nonrandom sequences, short repeats, or enriched for one or more amino acid residues, called low-complexity regions. These low-complexity regions may be aligned between unrelated proteins even though other regions of the protein are entirely dissimilar. Those of ordinary skill in the art can use low-complexity filter programs to reduce number of low-complexity regions that are aligned in a search. These filter programs include, but are not limited to, the SEG (183, 184) and XNU (185).

The terms "sequence identity" and "identity" are used in the context of two nucleic acid or polypeptide sequences and include reference to the residues in the two sequences, which are the same when aligned for maximum correspondence over a specified comparison window. When the percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conserved substitutions, the percent sequence identity may be adjusted upwards to correct for the conserved nature of the substitution. Sequences, which differ by such conservative substitutions, are said to have "sequence similarity" or "similarity." Scoring for a conservative substitution allows for a partial rather than a full mismatch (186), thereby increasing the percentage sequence similarity.

The term "percentage of sequence identity" means the value determined by comparing two optimally aligned sequences over a comparison window, wherein the portion of the polynucleotide sequence in the comparison window may comprise gaps (additions or deletions) when compared to the reference sequence for optimal alignment. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of ordinary skill in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 50-100%. Another indication that nucleotide sequences are substantially identical is if two molecules hybridize to each low stringency conditions, moderate stringency conditions or high stringency conditions. Yet another indication that two nucleic acid sequences are substantially identical is if the two polypeptides immunologically cross-react with the same antibody in a western blot, immunoblot or ELISA assay.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm (175). Thus, a peptide is substantially identical to a second peptide, for example, where the two peptides differ only by a conserved substitution. Another indication that amino acid sequences are substantially identical is if two polypeptides immunologically cross-react with the same antibody in a western blot, immunoblot or ELISA assay. In addition, a peptide can be substantially identical to a second peptide when they differ by a non-conservative change if the epitope that the antibody recognizes is substantially identical.

REFERENCES

1. Suzuki et al., 1989. U.S. Pa. No. 4877447.
2. Sturman 1988. "Taurine in development." J Nutr, 118: 1169-1176.
3. Sturman et al., 1980. "The biology of taurine in nutrition and development." Adv Nutr Res, 3: 231-299.
4. Chen et al., 1998. "Effect of taurine on human fetal neuron cells: Proliferation and differentiation." Adv Exp Med Biol, 442: 397-403.

5. El Idrissi et al., 1999. "Growth factors and taurine protect against excitotoxicity by stabilizing calcium homeostasis and energy metabolism." J Neurosci, 19: 9459-9468.
6. El Idrissi et al., 2003. "Taurine regulates mitochondrial calcium homeostasis." Adv Exp Med Biol, 526: 527-536.
7. Trenkner 1990. "Possible role of glutamate with taurine in neuron-glia interaction during cerebellar development." Prog Clin Biol Res, 351: 133-140.
8. Wu et al., 2005. "Mode of action of taurine as a neuroprotector." Brain Res, 1038: 123-131.
9. Schaffer et al., 2000. "Role of osmoregulation in the actions of taurine." Amino Acids, 19: 527-546.
10. Chapman et al., 1993. "Taurine and the heart." Cardiovasc Res, 27: 358-363.
11. Tabassuma et al., 2006. "Attenuation of tamoxifen-induced hepatotoxicity by taurine in mice." Clin Chim Acta, 370: 129-136.
12. Rocket et al., 2007. "The osmolyte taurine protects against ultraviolet B radiation-induced immunosuppression." J Immunol, 179: 3604-3612.
13. Milei et al., 1992. "Reduction of reperfusion injury with preoperative rapid intravenous infusion of taurine during myocardial revascularization." Am Heart J, 123: 339-345.
14. Militante et al., 2002. "Treatment of hypertension with oral taurine." Endocrinology, 147: 3276-3284.
15. Fujita et al., 1987. "Effects of increased adrenomedullary activity and taurine in young patients with borderline hypertension." Circulation, 75: 525-532.
16. McCown et al., 1987. "Amino acid influences on seizures elicited within the inferior colliculus." J Pharmacol Exp Ther, 243: 603-608.
17. Matsuyama et al., 1983. "The effect of taurine administration on patients with acute hepatitis." Prog Clin Biol Res, 125: 461-468.
18. Ikeda 1977. "Effects of taurine on alcohol withdrawal." Lancet, 2: 509.
19. Franconi et al., 2004. "Is taurine beneficial in reducing risk factors for diabetes mellitus?" Neurochem Res, 29: 143-150.
20. Paula-Lima et al., 2005. "Activation of GABAA receptors by taurine and muscimol blocks the neurotoxicity of [beta]-amyloid in rat hippocampal and cortical neurons." Neuropharmacology, 49: 1140-1148.
21. Nakamori et al., 1993. "Quantitative evaluation of the effectiveness of taurine in protecting the ocular surface against oxidant." Chem Pharm Bull, 41: 335-338.
22. Zhang et al., 2004. "Beneficial effects of taurine on serum lipids in overweight or obese non-diabetic subjects." Amino Acids, 26: 267-271.
23. Yokogoshi et al., 1999. "Dietary taurine enhances cholesterol degradation and reduces serum and liver cholesterol concentrations in rats fed a high-cholesterol diet." J Nutr, 129: 1705-1712.
24. Yamamoto et al., 2000. "Dietary taurine decreases hepatic secretion of cholesterol ester in rats fed a high-cholesterol diet." Pharmacology, 60: 27-33.
25. Green et al., 1991. "Antioxidant role and subcellular location of hypotaurine and taurine in human neutrophils." Biochim Biophys Acta, 1073: 91-97.
26. Gürer et al., 2001. "Antioxidant effect of taurine against lead-induced oxidative stress." Arch Environ Contam Toxicol, 41: 397-402.
27. Das et al., 2008. "Taurine provides antioxidant defense against NaF-induced cytotoxicity in murine hepatocytes." Pathophysiology, 15: 181-190.
28. Zhang et al., 2004. "Role of taurine supplementation to prevent exercise-induced oxidative stress in healthy young men." Amino Acids, 26: 203-207.
29. Williams 2005. "Dietary supplements and sports performance: Amino acids." Journal of the International Society of Sports Nutrition, 2: 63-67.
30. da Silva et al., 2008. "Penetration profile of taurine in the human skin and its distribution in skin layers." Pharm Res, 25: 1846-1850.
31. Knopf et al., 1978. "Taurine: An essential nutrient for the cat." J Nutr, 108: 773-778.
32. Gibson et al., 2007. "Supplementation of taurine and methionine to all-plant protein diets for rainbow trout (Oncorhynchus mykiss)." Aquaculture, 269: 514-524.
33. Schweigen 1967. "Low-molecular-weight compounds in Macrocystis pyrifera, a marine algae." Arch Biochem Biophys, 118: 383-387.
34. Huxtable 1992. "Physiological actions of taurine." Physiol Rev, 72: 101-163.
35. Kataoka et al., 1986. "Occurrence of taurine in plants." Agric Biol Chem, 50: 1887-1888.
36. Murray et al., 1989. "Codon usage in plant genes." Nucleic Acids Research, 17: 477-498.
37. Stemmer 1997. U.S. Pat. No. 5,605,793.
38. Short 1999. U.S. Pat. No. 5,965,408.
39. Langenheim et al., 1982. Botany: Plant Biology and its Relation to Human Affairs. New York: John Wiley & Sons Inc.
40. Vasil 1984. Cell Culture and Somatic Cell Genetics of Plants: Laboraory Procedures and Their Applications. Orlando: Academic Press.
41. Stanier et al., 1986. The Microbial World. New Jersey: Prentice-Hall.
42. Dhringra et al., 1985. Basic plant pathology methods. Boca Raton, Fla.: CRC Press.
43. Maniatis et al., 1985. Molecular Cloning: A Laboratory Manual: DNA Cloning. New York: Cold Spring Harbor.
44. Gait 1984. Oligonucleotide Synthesis-A Practical Approach. Washington, D.C.: IRL Press.
45. Hames et al., 1984. Nucleic Acid Hybridization: A Practical Approach. Washington D.C.: IRL Press.
46. Watson et al., 1992. Recombinant DNA. New York: Scientific American Books.
47. Szewczyk et al., 2006. "Fusion PCR and gene targeting in *Aspergillus nidulans*." Nat Protoc, 1: 3111-3121.
48. Ho et al., 1989. "Site-directed mutagenesis by overlap extension using the polymerase chain reaction." Gene, 77: 51-59.
49. Fuhrmann et al., 1999. "A synthetic gene coding for the green fluorescent protein (GFP) is a versatile reporter in *Chlamydomonas reinhardtii*." Plant J, 19: 353-361.
50. Mandecki et al., 1988. "FokI method of gene synthesis." Gene, 68: 101-107.
51. Stemmer 1995. "Single-step assembly of a gene and entire plasmid from large numbers of oligodeoxyribonucleotides." Gene, 164: 49-53.
52. Gao et al., 2003. "Thermodynamically balanced inside-out (TBIO) PCR-based gene synthesis: a novel method of primer design for high-fidelity assembly of longer gene sequences." Nucleic Acids Res, 31: e143.
53. Young et al., 2004. "Two-step total gene synthesis method." Nucleic Acids Res, 32: e59.
54. van Der Krol et al., 1999. "Developmental and wound-, cold-, desiccation-, ultraviolet-B-stress-induced modulations in the expression of the petunia zinc finger transcription factor gene ZPT2-2." Plant Physiol, 121: 1153-62.

55. Shinmyo et al., 1998. "Metabolic engineering of cultured tobacco cells." Biotechnol Bioeng, 58: 329-32.
56. Sohal et al., 1999. "The promoter of a *Brassica napus* lipid transfer protein gene is active in a range of tissues and stimulated by light and viral infection in transgenic *Arabidopsis*." Plant Mol Biol, 41: 75-87.
57. Cormack et al., 2002. "Leucine zipper-containing WRKY proteins widen the spectrum of immediate early elicitor-induced WRKY transcription factors in parsley." Biochim Biophys Acta, 1576: 92-100.
58. Eulgem et al., 1999. "Early nuclear events in plant defence signalling: rapid gene activation by WRKY transcription factors." EMBO (Eur Mol Biol Organ) J, 18: 4689-99.
59. Lebel et al., 1998. "Functional analysis of regulatory sequences controlling PR-1 gene expression in *Arabidopsis*." Plant J, 16: 223-33.
60. Ngai et al., 1997. "Light-induced transcriptional repression of the pea AS1 gene: identification of cis-elements and transfactors." Plant J, 12: 1021-34.
61. Kucho et al., 1999. "CO(2)-responsive transcriptional regulation of CAH1 encoding carbonic anhydrase is mediated by enhancer and silencer regions in *Chlamydomonas reinhardtii*." Plant Physiol, 121: 1329-38.
62. Kucho et al., 2003. "Cis-acting elements and DNA-binding proteins involved in CO2-responsive transcriptional activation of Cah1 encoding a periplasmic carbonic anhydrase in *Chlamydomonas reinhardtii*." Plant Physiol, 133: 783-93.
63. Chen et al., 1996. "The promoter of a H2O2-inducible, *Arabidopsis* glutathione 5-transferase gene contains closely linked OBF- and OBP1-binding sites." Plant J, 10: 955-66.
64. Chen et al., 1999. "The auxin, hydrogen peroxide and salicylic acid induced expression of the *Arabidopsis* GST6 promoter is mediated in part by an ocs element." Plant J, 19: 667-77.
65. Lu et al., 1998. "Sugar response sequence in the promoter of a rice alpha-amylase gene serves as a transcriptional enhancer." J Biol Chem, 273: 10120-31.
66. Leubner-Metzger et al., 1998. "Ethylene-responsive element binding protein (EREBP) expression and the transcriptional regulation of class I beta-1,3-glucanase during tobacco seed germination." Plant Mol Biol, 38: 785-95.
67. Hudspeth et al., 1992. "Expression of maize phosphoenolpyruvate carboxylase in transgenic tobacco: Effects on biochemistry and physiology." Plant Physiol, 98: 458-464.
68. de Framond 1991. "A metallothionein-like gene from maize (*Zea mays*). Cloning and characterization." FEBS Lett, 290: 103-6.
69. Hudspeth et al., 1996. "Characterization and expression of metallothionein-like genes in cotton." Plant Mol Biol, 31: 701-5.
70. Herrera-Estrella et al., 1983. "Expression of chimaeric genes transferred into plant cells using a Ti-plasmid-derived vector." Nature, 303: 209-213.
71. Pathirana et al., 1997. "Analyses of phosphoenolpyruvate carboxylase gene structure and expression in alfalfa nodules." Plant J, 12: 293-304.
72. Yang et al., 2002. "Isolation and characterization of the orchid cytokinin oxidase DSCKX1 promoter." J Exp Bot, 53: 1899-1907.
73. Moon et al., 2004. "Developmental regulation of peach ACC oxidase promoter-GUS fusions in transgenic tomato fruits." J Exp Bot, 55: 1519-1528.
74. Avsian-Kretchmer et al., 2004. "The salt-stress signal transduction pathway that activates the gpx1 promoter is mediated by intracellular H2O2, different from the pathway induced by extracellular H2O2." Plant Physiol, 135: 1685-96.
75. Wu et al., 2007. "Functional analysis of a cotton glucuronosyltransferase promoter in transgenic tobaccos." Cell Res, 17: 174-183.
76. Shelp et al., 1999. "Metabolism and functions of gamma-aminobutyric acid." Trends Plant Sci, 41: 446-452.
77. Baum et al., 1993. "A plant glutamate decarboxylase containing a calmodulin binding domain. Cloning, sequence, and functional analysis." J Biol Chem, 268: 19610-19617.
78. Gallego et al., 1995. "A role for glutamate decarboxylase during tomato ripening: the characterisation of a cDNA encoding a putative glutamate decarboxylase with a calmodulin-binding site." Plant Mol Biol, 27: 1143-1151.
79. Yun et al., 1998. "Cloning and characterization of tobacco cDNA encoding calcium/calmodulin-dependent glutamate decarboxylase." Mol Cell, 8: 125-129.
80. Oh et al., 2005. "Cloning and characterization of a rice cDNA encoding glutamate decarboxylase." J Biochem Mol Biol, 38: 595-601.
81. Chiu et al., 2002. "Phylogenetic and expression analysis of the glutamate-receptor-like gene family in *Arabidopsis thaliana*." Mol Biol Evol, 19: 1066-1082.
82. Kim et al., 2001. "Overexpression of the AtGluR2 gene encoding an *Arabidopsis* homolog of mammalian glutamate receptors impairs calcium utilization and sensitivity to ionic stress in transgenic plants." Plant Cell Physiol, 42: 74-84.
83. Meyerhoff et al., 2005. "AtGLR3.4, a glutamate receptor channel-like gene is sensitive to touch and cold." Planta, 222: 418-27.
84. Maruyama-Nakashita et al., 2004. "Regulation of high-affinity sulphate transporters in plants towards systematic analysis of sulphur signalling and regulation." J Exp Bot, 55: 1843-1849.
85. Yoshimoto et al., 2003. "Phloem-localizing sulfate transporter, Sultr1;3, mediates re-distribution of sulfur from source to sink organs in *Arabidopsis*." Plant Physiol, 131: 1511-1517.
86. Awazuhara et al., 2005. "The function of SULTR2;1 sulfate transporter during seed development in *Arabidopsis thaliana*." Physiol Plant, 125: 95-105.
87. Kataoka et al., 2004. "Root-to-shoot transport of sulfate in *Arabidopsis*: Evidence for the role of SULTR3;5 as a component of low-affinity sulfate transport system in the root vasculature." Plant Physiol, 136: 4198-4204.
88. An et al., 1985. "New cloning vehicles for transformation of higher plants." EMBO (Eur Mol Biol Organ) J, 4: 277-284.
89. Gruber et al., 1993. Vectors for plant transformation. In Glick B R & J E Thompson, editors. Methods in Plant Molecular Biology and Biotechnology 89-119. Baco Raton, Fla.: CRC Press.
90. Ausubel et al., 1995. Current Protocols in Molecular Biology. New York: Greene Publishing and Wiley-Interscience.
91. Newman et al., 1993. "DST sequences, highly conserved among plant SAUR genes, target reporter transcripts for rapid decay in tobacco." Plant Cell, 5: 701-14.
92. Ohme-Takagi et al., 1993. "The effect of sequences with high AU content on mRNA stability in tobacco." Proc Natl Acad Sci USA, 90: 11811-5.

93. von Heijne 1986. "Mitochondrial targeting sequences may form amphiphilic helices." EMBO (Eur Mol Biol Organ) J, 5: 1335-1342.
94. Swinkels et al., 1991. "A novel, cleavable peroxisomal targeting signal at the amino-terminus of the rat 3-ketoacyl-CoA thiolase." EMBO (Eur Mol Biol Organ) J, 10: 3255-62.
95. Rusch et al., 1995. "Protein transport via amino-terminal targeting sequences: Common themes in diverse systems." Mol Membr Biol, 12: 295-307.
96. Soll et al., 1998. "Protein translocation into and across the chloroplastic envelope membranes." Plant Mol Biol, 38: 191-207.
97. Gould et al., 1988. "Identification of peroxisomal targeting signals located at the carboxy terminus of four peroxisomal proteins." J Cell Biol, 107: 897-905.
98. Gould et al., 1989. "A conserved tripeptide sorts proteins to peroxisomes." J Cell Biol, 108: 1657-64.
99. McCammon et al., 1994. "An internal region of the peroxisomal membrane protein PMP47 is essential for sorting to peroxisomes." J Cell Biol, 124: 915-25.
100. Cokol et al., 2000. "Finding nuclear localization signals." EMBO Rep, 1: 411-5.
101. Helenius et al., 2001. "Intracellular functions of N-linked glycans." Science, 291: 2364-9.
102. Emanuelsson et al., 2007. "Locating proteins in the cell using TargetP, SignalP and related tools." Nat Protoc, 2: 953-971.
103. Emanuelsson et al., 2000. "Predicting subcellular localization of proteins based on their N-terminal amino acid sequence." J Mol Biol, 300: 1005-1016.
104. Bannai et al., 2002. "Extensive feature detection of N-terminal protein sorting signals." Bioinformatics, 18: 298-305.
105. Bendtsen et al., 2004. "Improved prediction of signal peptides: SignalP 3.0." J Mol Biol, 340: 783-95.
106. Hiller et al., 2004. "PrediSi: prediction of signal peptides and their cleavage positions." Nucleic Acids Res, 32: W375-9.
107. Bhasin et al., 2004. "ESLpred: SVM-based method for subcellular localization of eukaryotic proteins using dipeptide composition and PSI-BLAST." Nucleic Acids Res, 32: W414-9.
108. Garg et al., 2005. "Support vector machine-based method for subcellular localization of human proteins using amino acid compositions, their order, and similarity search." J Biol Chem, 280: 14427-32.
109. Bhasin et al., 2005. "PSLpred: prediction of subcellular localization of bacterial proteins." Bioinformatics, 21: 2522-4.
110. Hoglund et al., 2006. "MultiLoc: prediction of protein subcellular localization using N-terminal targeting sequences, sequence motifs and amino acid composition." Bioinformatics, 22: 1158-65.
111. Shatkay et al., 2007. "SherLoc: high-accuracy prediction of protein subcellular localization by integrating text and protein sequence data." Bioinformatics, 23: 1410-7.
112. Emanuelsson et al., 1999. "ChloroP, a neural network-based method for predicting chloroplast transit peptides and their cleavage sites." Protein Sci, 8: 978-984.
113. Claros et al., 1996. "Computational method to predict mitochondrially imported proteins and their targeting sequences." Eur J Biochem, 241: 779-86.
114. Small et al., 2004. "Predotar: A tool for rapidly screening proteomes for N-terminal targeting sequences." Proteomics, 4: 1581-1590.
115. Kelley et al., 2000. "Enhanced genome annotation using structural profiles in the program 3D-PSSM." J Mol Biol, 299: 499-520.
116. Bilow et al., 1991. "Multienzyme systems obtained by gene fusion." Trends Biotechnol, 9: 226-231.
117. Seo et al., 2000. "Characterization of a bifunctional enzyme fusion of trehalose-6-phosphate synthetase and trehalose-6-phosphate phosphatase of *Escherichia coli*." Appl Environ Microbiol, 66: 2484-2490.
118. Honjoh et al., 2009. "Enhancement of menadione stress tolerance in yeast by accumulation of hypotaurine and taurine: co-expression of cDNA clones, from *Cyprinus carpio*, for cysteine dioxygenase and cysteine sulfinate decarboxylase in *Saccharomyces cerevisiae*." Amino Acids, [Epub ahead of print].
119. Shahin 1985. "Totipotency of tomato protoplasts." Theor Appl Genet, 69: 235-240.
120. Fromm et al., 1985. "Expression of genes transferred into monocot and dicot plant cells by electroporation." Proc Natl Acad Sci USA, 82: 5824-5828.
121. Fromm et al., 1986. "Stable transformation of maize after gene transfer by electroporation." Nature, 319: 791-3.
122. Riggs et al., 1986. "Stable transformation of tobacco by electroporation: evidence for plasmid concatenation." Proc Natl Acad Sci USA, 83: 5602-5606.
123. D'Halluin et al., 1992. "Transgenic maize plants by tissue electroporation." Plant Cell, 4: 1495-1505.
124. Laursen et al., 1994. "Production of fertile transgenic maize by electroporation of suspension culture cells" Plant Mol Biol, 24: 51-61
125. Crossway et al., 1986. "Integration of foreign DNA following microinjection of tobacco mesophyll protoplasts." Mol Gen Genet, 202: 179-185.
126. Griesbach 1983. "Protoplast microinjection." Plant Mol Biol Report, 1: 32-37.
127. Sporlein et al., 1991. "Lipofectin: direct gene transfer to higher plants using cationic liposomes." Theor Appl Genet, 83: 1-5.
128. Ohgawara et al., 1983. "Uptake of liposome-encapsulated plasmid DNA by plant protoplasts and molecular fate of foreign DNA" Protoplasma, 116: 145-148.
129. Deshayes et al., 1985. "Liposome-mediated transformation of tobacco mesophyll protoplasts by an *Escherichia coli* plasmid." EMBO (Eur Mol Biol Organ) J, 4: 2731-7.
130. Christou et al., 1987. "Stable transformation of soybean by electroporation and root formation from transformed callus." Proc Natl Acad Sci USA, 84: 3962-3966.
131. Horsch et al., 1985. "A simple and general method for transferring genes into plants." Science, 227: 1229-1231.
132. Paszkowski et al., 1984. "Direct gene transfer to plants." Embo J, 3: 2717-2722.
133. Hooykaas-Van Slogteren et al., 1984. "Expression of Ti plasmid genes in monocotyledonous plants infected with *Agrobacterium tumefaciens*." Nature, 311: 763-764.
134. Rogers 1986. "Gene transfer in plants: Production of transformed plants using Ti-plasmid vectors." Methods Enzymol, 118: 627-640.
135. Bevan et al., 1982. "T-DNA of the *Agrobacterium* Ti and Ri plasmids." Annu Rev Genet, 16: 357-384.
136. Klein et al., 1988. "Transfer of foreign genes into intact maize cells with high-velocity microprojectiles." Proc Natl Acad Sci USA, 85: 4305-4309.
137. Klein et al., 1988. "Factors influencing gene delivery into *Zea mays* cells by high-velocity microprojectiles." Biotechnology, 6: 559-563.

138. McCabe et al., 1988. "Stable transformation of soybean (*Glycine max*) by particle acceleration." Biotechnology, 6: 923-926.
139. Sanford et al., 1993. Optimizing the biolistic process for different biological application. In Wu R, editor. The Methods in Enzymology 483-509. Orlando: Academic Press.
140. Freeman et al., 1984. "A comparison of methods for plasmid delivery into plant protoplasts." Plant Cell Physiol, 25: 1353-1365.
141. Frame et al., 1994. "Production of fertile transgenic maize plants by silicon carbide whisker-mediated transformation." Plant J, 6: 941-948.
142. Thompson et al., 1995. "Maize transformation utilizing silicon carbide whiskers: a review." Euphytica, 85: 75-80.
143. Guo et al., 1995. "Laser-mediated gene transfer in rice." Physiol Plant, 93: 19-24.
144. Badr et al., 2005. "Production of fertile transgenic wheat plants by laser micropuncture." Photochem Photobiol Sci, 4: 803-807.
145. Bao et al., 1997. "Transfection of a reporter plasmid into cultured cells by sonoporation in vitro." Ultrasound in Medicine and Biology, 23: 953-959.
146. Finer et al., 2000. "Use of *Agrobacterium* expressing green fluorescent protein to evaluate colonization of sonication-assisted *Agrobacterium*-mediated transformation-treated soybean cotyledons." Lett Appl Microbiol, 30: 406-10.
147. Amoah et al., 2001. "Factors influencing *Agrobacterium*-mediated transient expression of uidA in wheat inflorescence tissue." J Exp Bot, 52: 1135-42.
148. Krens et al., 1982. "In Vitro transformation of plant protoplasts with Ti-plasmid DNA." Nature, 296: 72-74.
149. Bechtold et al., 1998. "In planta *Agrobacterium*-mediated transformation of adult *Arabidopsis thaliana* plants by vacuum infiltration." Methods Mol Biol, 82: 259-66.
150. Broothaerts et al., 2005. "Gene transfer to plants by diverse species of bacteria." Nature, 433: 629-633.
151. Kirk et al., 1993. Concise Encyclopedia of Chemical Technology: John Wiley & Sons.
152. Mosbach et al., 1983. "Formation of proinsulin by immobilized *Bacillus subtilis*." Nature, 302: 543-545.
153. Chan et al., 1974. "Structural uniqueness of lactose operator." Nature, 252: 205-209.
154. Goeddel et al., 1980. "Synthesis of human fibroblast interferon by *E. coli*" Nucleic Acids Res, 8: 4057-4074.
155. Sherman et al., 1982. Methods in Yeast Genetics. New York: Cold Spring Harbor Laboratory.
156. Sherman 1991. Getting started with yeast. In Guthrie C & G R Fink, editors. Methods in Enzymology, Guide to Yeast Genetics and Molecular Biology 3-21. New York: Acad. Press.
157. Andersen et al., 1984. "Synthesis and anticonvulsant properties of some 2-Aminoethanesulfonic acid (Taurine) derivatives." J Pharm Sci, 73: 106-108.
158. Herdeis et al., 1999. U.S. Pat. No. 5,889,183.
159. Tserng et al., 1977. "An improved procedure for the synthesis of glycine and taurine conjugates of bile acids." J Lipid Res, 18: 404-407.
160. Fong et al., 1992. U.S. Pat. No. 5,128,419.
161. Seeberger et al., 2007. "A new strategy for the synthesis of taurine derivatives using the 'safety-catch' principle for the protection of sulfonic acids." Org Biomol Chem, 5: 132-138.
162. Suzuki et al., 2006. "Fabrication of TiO2 using L-lysine-based organogelators as organic templates: control of the nanostructures." Chem Commun 377-379.
163. Mikhalenko et al., 2004. "Phthalocyanines and related compounds: XXXVIII. Synthesis of symmetric taurine- and choline-substituted phthalocyanines." Russ J Gen Chem, 74: 1775-1800.
164. Capone et al., 2007. "Designing nanosensors based on charged derivatives of Gramicidin A." J Am Chem Soc, 129: 9737-9745.
165. Gupta et al., 2005. "Taurine analogues; A new class of therapeutics: Retrospect and prospects" Curr Med Chem, 12: 2021-2039.
166. Johnson 2008. "Update on neuropharmacological treatments for alcoholism: Scientific basis and clinical findings." Biochem Pharmacol, 75: 34-56.
167. Tambour et al., 2007. "Preclinical and clinical pharmacology of alcohol dependence." Fundam Clin Pharmacol, 21: 9-28.
168. Joung et al., 2005. "Anticoagulant supramolecular-structured polymers: Synthesis and anticoagulant activity of taurine-conjugated carboxyethylester-polyrotaxanes." Sci Technol Adv Mater, 6: 484-490.
169. Özmeriç et al., 2000. "Chitosan film enriched with an antioxidant agent, taurine, in fenestration defects." J Biomed Mater Res A, 51: 500-503.
170. Degim et al., 2002. "An investigation on skin wound healing in mice with a taurinechitosan gel formulation." Amino Acids, 22: 187-198.
171. Matsusaki et al., 2002. "Novel functional biodegradable polymer: Synthesis and anticoagulant activity of poly(γ-Glutamic Acid)sulfonate (γ-PGA-sulfonate)." Bioconjugate Chem, 13: 23-28.
172. Meinkoth et al., 1984. "Hybridization of nucleic acids immobilized on solid supports." Anal Biochem, 138: 267-284.
173. Tijssen 1993. Overview of principles of hybridization and the strategy of nucleic acid probe assays. Laboratory Techniques in Biochemistry and Molecular Biology-Hybridization with Nucleic Acid Probes: Part I. New York: Elsevier.
174. Smith et al., 1981. "Comparison of biosequences." Adv Appl Math, 2: 482-489.
175. Needleman et al., 1970. "A general method applicable to the search for similarities in the amino acid sequence of two proteins." J Mol Biol, 48: 443-453.
176. Pearson et al., 1988. "Improved tools for biological sequence comparison." Proc Natl Acad Sci USA, 85: 2444-2448.
177. Higgins et al., 1989. "Fast and sensitive multiple sequence alignments on a microcomputer." Comput Appl Biosci, 5: 151-153.
178. Higgins et al., 1988. "CLUSTAL: a package for performing multiple sequence alignment on a microcomputer." Gene, 73: 237-244.
179. Higgins et al., 1992. "CLUSTAL V: improved software for multiple sequence alignment." Comput Appl Biosci, 8: 189-191.
180. Feng et al., 1987. "Progressive sequence alignment as a prerequisite to correct phylogenetic trees." J Mol Evol, 25: 351-360.
181. Henikoff et al., 1989. "Amino acid substitution matrices from protein blocks" Proc Natl Acad Sci USA, 89: 10915-10919.
182. Altschul et al., 1997. "Gapped BLAST and PSI-BLAST: a new generation of protein database search programs." Nucleic Acids Res, 25: 3389-3402.
183. Wootton et al., 1993. "Statistics of local complexity in amino acid sequences and sequence databases." Comput Chem, 17: 149-163.

184. Wootton et al., 1996. "Analysis of compositionally biased regions in sequence databases." Methods Enzymol, 266: 554-571.
185. Claverie et al., 1993. "Information enhancement methods for large scale sequence analysis." Comput Chem, 17: 191-201.
186. Myers et al., 1988. "Optimal alignments in linear-space." Comput Appl Biol Sci, 4: 11-17.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

Example 1

Development of a Transgenic Plant that Constitutively Expresses COD Using Fusion PCR Step 1: Make a DNA construct that contains an AtTUB5 promoter with a CDO gene and a NOS terminator in the following manner.

Step 1a. Use PCR to amplify the AtTUB5 promoter (−1851 to −1 bps) with a short overlap for the 5' end of CDO at the 3' end of the promoter using 500 ng of genomic DNA isolated from an *Arabidopsis thaliana* Col-0. Add 300 nM of the following primers: 5'KpnTub5prom (5'-ttttggtacccacat-ttgcaaaatgatgaatg-3'; SEQ ID NO:27) and Tub5CDO (5'-catgacttcagtctgctccatccaatctggttaccgcattg-3'; SEQ ID NO:28). Run the fusion PCR as described by Szewczyk et al. (45).

Step 1b: Use PCR to amplify the CDO gene from 500 ng of cDNA from a zebrafish (*Danio rerio*) cDNA library. Add 300 nM of the following primers: 5'CDO (5'-atggagcagact-gaagtcatg-3'; SEQ ID NO:29) and 3'CDO (5'-tcagttat-tctcctgcgagac-3'; SEQ ID NO:30). Run the fusion PCR as described by Szewczyk et al. (45).

Step 1c: Use PCR to amplify the NOS terminator with a short overlap for the 3' end of CDO at the 5' end of the terminator using 500 ng of pPV1. Add 300 nM of the following primers CDONOS (5'-gtctcgcaggagaataactgagc-taccgagctcgaatttcc-3'; SEQ ID NO:31) and 3'NOS (5'-cacgacgttgtaaaacgacggc-3'; SEQ ID NO:32). Run the fusion PCR as described by Szewczyk et al. (45).

Step 1d: Combine the amplified fragments from Example 3: steps 1a, 1b, and 1c and 300 nM of the following primers GP2 (5'-ttttggtaccgtttacatatggagatgatgtc-3'; SEQ ID NO:33) and GP5 (5'-ttttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1e. Transform *E. coli*, select for antibiotic resistance, conduct PCR identification of cloned DNA constructs in transformants, purify DNA and sequence. Digest the plasmid with Acc65I and XbaI, isolate DNA fragment and ligate into the vector pCAMBIA2300 that has been predigested with Acc65I and XbaI.

Step 1f. Transform the ligated vector containing the DNA construct by electroporation into *E. coli*. Select for kanamycin (50 μg/ml) resistance on LB plates. Confirm the presence of the DNA constructs in the selected colonies by PCR analysis with the GP2 and GP5 primers using the following program: 96° C. for 3 min followed by 25 cycles of 94° C. for 30 seconds, 55° C. for 30 seconds, 72° C. for 5 min, and 72° C. for 3 min. Grow a colony that contains the proper DNA construct overnight at 37° C. in 6 ml LB plus spectinomycin (100 μg/ml) or streptomycin (200 μg/ml). Isolate the plasmid DNA that contains the DNA construct by Wizard Plus SV Minipreps DNA Purification System (Promega Corporation, Madison, Wis., USA). Sequence the DNA insert to confirm its identity and the fidelity of the DNA construct.

Step 2: Transform *Agrobacterium tumefaciens*

Independently transform the vector construct into electrocompetent *Agrobacterium tumefaciens* EHA105, as described by the Green Lab Protocol (http://www.bch.ms-u.edu/pamgreen/green.htm). Select positive transformants using Terrific Broth plus kanamycin (50 μg/ml) on 1% agar plates. Confirm *Agrobacterium* colonies by PCR using the following primers: GP2 and GP5. Run the following PCR reaction: 96° C. for 5 min followed by 20 cycles of 94° C. for 45 seconds, 60° C. for 30 seconds, 70° C. for 5 min, and 72° C. for 3 min.

Step 3: Transform plant, *Arabidopsis thaliana*

Step 3a: Sow *Arabidopsis* (L.) Heynh. ecotype Columbia (Col-0) seeds in 248 cm² plastic pots with moistened soil (Promix HP, Premier Horticulture Inc., Redhill, Pa., Canada). Grow plants at 20-21° C., with 60-70% relative humidity, under cool white fluorescent lights (140 μmol m⁻² s⁻¹) with a 16 h light/8 h dark cycle. Water plants as needed by subirrigation. After two weeks, transfer five individual plants to smaller pots (72 cm²) for use in the transformation protocol. Grow the plants until the first floral buds and flowers form (2-3 additional weeks).

Step 3b: Grow *Agrobacterium*, the construct to be transformed, in 500 ml of Terrific Broth plus kanamycin (50 μg/ml) for 2 days at 29° C. Collect cells by centrifugation at 6000 rpm for 15 minutes, and resuspend cells in 5% sucrose plus 0.05% surfactant (Silwet L-77, Lehle Seeds, Round Rock, Tex., USA) solution.

Step 3c: Transform plants by the floral dip transformation (144). Keep the plants in sealed containers to maintain high humidity for 16 to 24 h and maintain plants as described in step 4a above. At 8 to 10 weeks, dry the plants, collect the seeds, and select for the marker in each line. Select for kanamycin resistance for the AtTUB5::CDO constructs in pCAMBIA2300 by incubating seeds on plates containing 4.418 g/L Murashige and Skoog Salt and Vitamin Mixture (MS medium, Life Technologies, Grand Island, N.Y., USA) plus kanamycin (50 μg/ml) and 0.8% (wt vol) Phytagar. Collect and transfer positively selected plants into pots containing soil and grow for 5 to 6 weeks. Allow the plants to self-pollinate. Collect the seeds and repeat the selection process until homozygotes are identified.

Example 2

Development of a Transgenic Plant that Constitutively Expresses (AtPHYB Promoter) CDO and SAD Using Fusion PCR Step 1: Make a DNA construct that contains an AtPHYB (Locus ID #At2g18790) promoter with a CDO gene and a NOS terminator in the following manner.

Step 1a: Use PCR to amplify the AtPHYB promoter (−1960 to −1 bps) with a short overlap for the 5' end of CDO at the 3' end using 500 ng of genomic DNA isolated from an *Arabidopsis thaliana* Col-0. Add 300 nM of the following primers: 5'AtPHYB (5'-caatgcctaataatgtctagc-3'; SEQ ID NO:35) and AtPHYBCDO (5'-catgacttcagtctgctccatgccgttt-gattttgaatttgag-3'; SEQ ID NO:36). Run the fusion PCR as described by Szewczyk et al. (45).

Step 1b: Use the CDO gene that was amplified in Example 1: Step 1b.

Step 1c: Use the NOS terminator with a short overlap for the 3' end of CDO at the 5' end of the NOS terminator that was amplified in Example 1: Step 1c.

Step 1d: Combine the PCR fragments (Example 2: 1a, 1b, and 1c) and 300 nM of the following primers HP2 (5'-ttttcccgggattcttgaattacgattgtacc-3'; SEQ ID NO:37) and GP5 (5'-ttttttttctagagatctagtaacatagatgacac-3'; SEQ ID NO:34). Run the fusion PCR as described by Szewczyk et al. (45). Clone into pCR4.0-TOPO as described by the manufacturer (Invitrogen).

Step 1e. Transform *E. coli*, select for antibiotic resistance, conduct PCR identification of cloned DNA constructs in transformants, purify DNA and sequence (described in Example 1: step 1e). Digest the plasmid with XmaI and XbaI, isolate DNA fragment and ligate into the vector pCAMBIA2300 that has been predigested with XmaI and XbaI.

Step 2: Make a DNA construct that contains an AtPHYB promoter with a SAD gene and a NOS terminator to in the following manner.

Step 2a: Use PCR to amplify the AtPHYB promoter (−1960 to −1 bps) with a short overlap for the 5' end of SAD at the 3' end using 500 ng of genomic DNA isolated from an *Arabidopsis thaliana* Col-0. Add 300 nM of the following primers: 5'AtPHYB (5'-caatgcctaataatgtctagc-3'; SEQ ID NO:35) and AtPHYBSAD (5'-cagcttcccatcagactcgtc-catgccgtttgattttgaatttgag-3'; SEQ ID NO:38). Run the fusion PCR as described by Szewczyk et al. (45).

Step 2b: Use PCR to amplify the SAD gene from 500 ng of cDNA from a zebrafish (*Danio rerio*) cDNA library. Add 300 nM of the following primers: 5'SAD (5'-atggacgagtct-gatgggaagctg-3'; SEQ ID NO:39) and 3'SAD (5'-tcata-gatccttcccgagtttc-3'; SEQ ID NO:40). Run the fusion PCR as described by Szewczyk et al. (45).

Step 2c: Use PCR to amplify the NOS terminator with a short overlap for the 3' end of SAD at the 5' end of the terminator using 500 ng of pPV1. Add 300 nM of the following primers SADNOS (5'-gaaactcgggaaggatctatgagc-taccgagctcgaatttcc-3'; SEQ ID NO:41) and 3'NOS (5'-cacgacgttgtaaaacgacggc-3'; SEQ ID NO:32). Run the fusion PCR as described by Szewczyk et al. (45).

Step 2d: Combine the PCR fragments (Example 2: 2a, 2b, and 2c) and 300 nM of the following primers IP2 (5'-aaaaatctagaattcttgaattacgattgtac-3'; SEQ ID NO:42) and IP5 (5'-ttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 2e: Transform *E. coli*, select for antibiotic resistance, conduct PCR identification of cloned DNA constructs in transformants, purify the plasmid that contains the DNA construct to confirm its identity and the fidelity of the sequence as described in Example 1: step 1e.purify. Digest the plasmid with XbaI and SalI, isolate DNA fragment and ligate into the vector pCAMBIA2300 that has been predigested with XbaI and SalI.

Step 3: Ligate the AtPHYB promoter-CDO-NOS terminator construct upstream of the AtPHYB promoter-SAD-NOS terminator construct into a plant expression vector.

Step 3a. Digest the pCambia2300-AtPHYB promoter-CDO-NOS terminator clone (from Example 4: Step 1e) with XmaI and XbaI, isolate DNA insert and ligate it into the vector pCambia2300-AtPHYB promoter-SAD-NOS terminator (from Example 4: Step 2e) that has been predigested with XmaI and XbaI. Transform the DNA construct into *E. coli*, select for antibiotic resistance and confirm the presence of the DNA construct with PCR or by restriction digest analysis.

Step 4: Transform *Agrobacterium tumefaciens*: Transform the DNA construct into *Agrobacterium tumefaciens*, select for antibiotic resistance and confirm the presence of the DNA construct as described in Example 1: Step 2.

Step 5: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 3

Development of a Transgenic Plant that Constitutively Expresses (AtPHYB Promoter) CDO and GAD Using Fusion PCR Step 1: Make a DNA construct that contains an AtPHYB (Locus ID #At2g18790) promoter with a CDO gene and a NOS terminator in the following manner.

Step 1a: Use the AtPHYB promoter with a short overlap for the 5' end of CDO at the 3' end that was amplified in Example 2: Step 1a Step 1b: Use the CDO gene that was amplified in Example 1: Step 1b.

Step 1c: Use the NOS terminator with a short overlap for the 3' end of CDO at the 5' end of the NOS terminator that was amplified in Example 1: Step 1c.

Step 1d: Combine the PCR fragments (Example 3: 1a, 1b, and 1c), run the PCR and the clone the amplified fragment as described in Example 2: Step 1d.

Step 1e. Transform *E. coli*, select for antibiotic resistance, conduct PCR identification of cloned DNA constructs in transformants, purify DNA and sequence (described in Example 1: step 1e). Digest the plasmid with XmaI and XbaI, isolate DNA fragment and ligate into the vector pCAMBIA2300 that has been predigested with XmaI and XbaI.

Step 2: Make a DNA construct that contains an AtPHYB promoter with a GAD gene and a NOS terminator to in the following manner.

Step 2a: Use PCR to amplify the AtPHYB promoter (−1960 to −1 bps) with a short overlap for the 5' end of GAD at the 3' end using 500 ng of genomic DNA isolated from an *Arabidopsis thaliana* Col-0. Add 300 nM of the following primers: 5'AtPHYB (5'-caatgcctaataatgtctagc-3'; SEQ ID NO:35) and AtPHYBGAD (5'-cgttacttgcttcttatccatgccgttt-gattttgaatttgag-3'; SEQ ID NO:44). Run the fusion PCR as described by Szewczyk et al. (45).

Step 2b: Use PCR to amplify the GAD gene from 500 ng of DNA from *E. coli* strain K12. Add 300 nM of the following primers: 5'GAD (5'-atggataagaagcaagtaacg-3'; SEQ ID NO:45) and 3'GAD (5'-tcaggtatgtttaaagctgttc-3'; SEQ ID NO:46). Run the fusion PCR as described by Szewczyk et al. (45).

Step 2c: Use PCR to amplify the NOS terminator with a short overlap for the 3' end of GAD at the 5' end of the terminator using 500 ng of pPV1. Add 300 nM of the following primers GADNOS (5'-gaacagctttaaacatacctgagc-taccgagctcgaatttcc-3'; SEQ ID NO:47) and 3'NOS (5'-cacgacgttgtaaaacgacggc-3'; SEQ ID NO:32). Run the fusion PCR as described by Szewczyk et al. (45).

Step 2d: Combine the PCR fragments (Example 3: 2a, 2b, and 2c) and 300 nM of the following primers IP2 (5'-aaaaatctagaattcttgaattacgattgtacc-3'; SEQ ID NO:42) and IP5 (5'-tttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 2e: Transform *E. coli*, select for antibiotic resistance, conduct PCR identification of cloned DNA constructs in transformants, purify the plasmid that contains the DNA construct to confirm its identity and the fidelity of the sequence as described in Example 1: step 1e.purify. Digest the plasmid with XbaI and SalI, isolate DNA fragment and ligate into the vector pCAMBIA2300 that has been predigested with XbaI and SalI.

Step 3: Ligate the AtPHYB promoter-CDO-NOS terminator construct upstream of the AtPHYB promoter-GAD-NOS terminator construct into a plant expression vector.

Step 3a. Digest the pCambia2300-AtPHYB promoter-CDO-NOS terminator clone (from Example 4: Step 1e) with XmaI and XbaI, isolate DNA insert and ligate it into the vector pCambia2300-AtPHYB promoter-GAD-NOS terminator (from Example 4: Step 2e) that has been predigested with XmaI and XbaI. Transform the DNA construct into *E. coli*, select for antibiotic resistance and confirm the presence of the DNA construct with PCR or by restriction digest analysis.

Step 4: Transform *Agrobacterium tumefaciens*: Transform the DNA construct into *Agrobacterium tumefaciens*, select for antibiotic resistance and confirm the presence of the DNA construct as described in Example 1: Step 2.

Step 5: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 4

Development of a Transgenic Plant that Non-Constitutively Expresses (AtGAD1 Promoter) ADO Using Fusion PCR Step 1: Make a DNA construct that contains an AtGAD1 (Locus ID #At5g17330) promoter with an ADO gene and a NOS terminator in the following manner.

Step 1a: Use PCR to amplify the AtGAD1 promoter (−1732 to −1 bps) with a short overlap for the 5' end of ADO at the 3' end of the promoter using 500 ng of genomic DNA isolated from an *Arabidopsis thaliana* Col-0. Add 300 nM of the following primers: 5'AtGAD1 (5'-accaaaggataccctgatttg-3'; SEQ ID NO:48) and AtGAD1ADO (5'-gattttctggactgtg-gaagtcatcacggagatgagagagagag-3'; SEQ ID NO:49). Run the fusion PCR as described by Szewczyk et al. (45).

Step 1b: Use PCR to amplify the ADO gene from 500 ng of cDNA from a zebrafish (*Danio rerio*) cDNA library. Add 300 nM of the following primers: 5'ADO (5'-atgacttc-cacagtccagaaaatc-3'; SEQ ID NO:50) and 3'ADO (5'-tcagagggtcactttaggc-3'; SEQ ID NO:51). Run the fusion PCR as described by Szewczyk et al. (45).

Step 1c: Use PCR to amplify the NOS terminator with a short overlap for the 3' end of ADO at the 5' end of the terminator using 500 ng of pPV1. Add 300 nM of the following primers ADONOS (5'-gcctaaagtgaccctctgagc-taccgagctcgaatttcc-3'; SEQ ID NO:52) and 3'NOS (5'-cacgacgttgtaaaacgacggc-3'; SEQ ID NO:32). Run the fusion PCR as described by Szewczyk et al. (45).

Step 1d: Combine the amplified fragments (Example 4: steps 1a, 1b, and 1c) and 300 nM of the following primers JP2 (5'-aaaaaggtaccgatatttgagcaaaactgtgg-3'; SEQ ID NO:30) and GP5 (5'-ttttttTCTAGAgatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1e. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens*: Transform the DNA construct into *Agrobacterium tumefaciens*, select for antibiotic resistance and confirm the presence of the DNA construct as described in Example 1: Step 2.

Step 4: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 5

Development of a Transgenic Plant that Non-Constitutively Expresses (AtGAD2 Promoter) TPAT Using Fusion PCR Step 1: Make a DNA construct that contains an AtGAD2 (Locus ID #At1g65960) promoter with a TPAT gene and a NOS terminator in the following manner.

Step 1a: Use PCR to amplify the AtGAD2 promoter (−1714 to −1 bps) with a short overlap for the 5' end of TPAT at the 3' end using 500 ng of genomic DNA isolated from an *Arabidopsis thaliana* Col-0. Add 300 nM of the following primers: 5'AtGAD2 (5'-tcttaccttgtcctgcaacgag-3'; SEQ ID NO:54) and AtGAD2TPAT (5'-cattgaaattgccgtc-catctttgtttctgtttagtgaaag-3'; SEQ ID NO:55). Run the fusion PCR as described by Szewczyk et al. (45).

Step 1b: Use PCR to amplify the TPAT gene from 500 ng of DNA from *Roseobacter denitrificans* strain. Add 300 nM of the following primers: 5'TPAT (5'-atggacggcaatttcaatg-3'; SEQ ID NO:56) and 3'TPAT (5'-ttagccgaaaacgcgcgacag-3'; SEQ ID NO:57). Run the fusion PCR as described by Szewczyk et al. (45).

Step 1c: Use PCR to amplify the NOS terminator with a short overlap for the 3' end of TPAT at the 5' end of the terminator using 500 ng of pPV1. Add 300 nM of the following primers TPATNOS (5'-ctgtcgcgcgttttcggctaagc-taccgagctcgaatttcc-3'; SEQ ID NO:58) and 3'NOS (5'-cacgacgttgtaaaacgacggc-3'; SEQ ID NO:32). Run the fusion PCR as described by Szewczyk et al. (45).

Step 1d: Combine the amplified fragments (Example 5: steps 1a, 1b, and 1c) and 300 nM of the following primers KP2 (5'-ttttggtaccctctttcggaacgagcttcaac-3'; SEQ ID NO:59) and GP5 (5'-ttttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1e. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens*: Transform the DNA construct into *Agrobacterium tumefaciens*, select for antibiotic resistance and confirm the presence of the DNA construct as described in Example 1: Step 2.

Step 4: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 6

Development of a Transgenic Plant that Non-Constitutively Expresses (AtGAD2 Promoter) TPAT and SA Using Fusion PCR Step 1: Make a DNA construct that contains an AtGAD2 (Locus ID #) promoter with a TPAT gene and a NOS terminator in the following manner.

Step 1a: Use the AtGAD2 promoter that was amplified in Example 5: Step 1b

Step 1b: Use the TPAT gene that was amplified in Example 5: Step 1b.

Step 1c: Use the NOS terminator with a short overlap for the 3' end of TPAT at the 5' end of the NOS terminator that was amplified in Example 5: Step 1c.

Step 1d: Combine the PCR fragments (Example 5: 1a, 1b, and 1c), run the PCR and the clone the amplified fragment as described in Example 5: Step 1d.

Step 1e. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2: Make a DNA construct that contains an AtGAD2 promoter with a SA gene and a NOS terminator to in the following manner.

Step 2a: Use PCR to amplify the AtGAD2 promoter (−1960 to −1 bps) with a short overlap for the 5' end of SA at the 3' end using 500 ng of genomic DNA isolated from an *Arabidopsis thaliana* Col-0. Add 300 nM of the following primers: 5'AtGAD2 (5'-cttaccttgtcctgcaacgag-3'; SEQ ID NO:54) and AtGAD2SA (5'-cttcagtggtcattttcatctttgtttctgtt-tagtgaaag-3'; SEQ ID NO:60). Run the fusion PCR as described by Szewczyk et al. (45).

Step 2b: Use PCR to amplify the SA gene from 500 ng of DNA from *Roseobacter denitrificans*. Add 300 nM of the following primers: 5'SA (5'-atgaaaatgaccactgaag-3'; SEQ ID NO:61) and 3'SA (5'-tcagacagtctgtggacgc-3'; SEQ ID NO:62). Run the fusion PCR as described by Szewczyk et al. (45).

Step 2c: Use PCR to amplify the NOS terminator with a short overlap for the 3' end of SA at the 5' end of the terminator using 500 ng of pPV1. Add 300 nM of the following primers SANOS (5'-gcgtccacagactgtctgagc-taccgagctcgaatttcc-3'; SEQ ID NO:63) and 3'NOS; 5'-cacgacgttgtaaaacgacggc-3' SEQ ID NO:32). Run the fusion PCR as described by Szewczyk et al. (45).

Step 2d: Combine the PCR fragments (Example 6: 2a, 2b, and 2c) and 300 nM of the following primers LP2 (5'-tttttctagagaacgagcttcaacgtagcc-3'; SEQ ID NO:64) and LP5 (5'-aaaaaaagcttgatctagtaacatagatgacac-3'; SEQ ID NO:65). Run the fusion PCR as described by Szewczyk et al. (45). Clone into pCR4.0-TOPO as described by the manufacturer (Invitrogen).

Step 2e: Transform *E. coli*, select for antibiotic resistance, conduct PCR identification of cloned DNA constructs in transformants, purify the plasmid that contains the DNA construct to confirm its identity and the fidelity of the sequence as described in Example 1: step 1e.purify. Digest the plasmid with XbaI and HindIII, isolate DNA fragment and ligate into the vector pCAMBIA2300 that has been predigested with XbaI and HindIII.

Step 3: Ligate the AtGAD2 promoter-TPAT-NOS terminator construct upstream of the AtGAD2 promoter-SA-NOS terminator construct into a plant expression vector.

Step 3a. Digest the pCambia2300-AtGAD2 promoter-TPAT-NOS terminator clone (from Example 4: Step 1e) with Acc65I and XbaI, isolate DNA insert and ligate it into the vector pCambia2300-AtGAD2 promoter-SA-NOS terminator (from Example 6: Step 2e) that has been predigested with Acc65I and XbaI. Transform the DNA construct into *E. coli*, select for antibiotic resistance and confirm the presence of the DNA construct with PCR or by restriction digest analysis.

Step 4: Transform *Agrobacterium tumefaciens*: Transform the DNA construct into *Agrobacterium tumefaciens*, select for antibiotic resistance and confirm the presence of the DNA construct as described in Example 1: Step 2.

Step 5: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 7

Development of a Transgenic Plant that that Non-Constitutively Expresses (AtGLR1.1 Promoter) ssTDeHase and lsTDeHase Using Fusion PCR Step 1: Make a DNA construct that contains an AtGLR1.1 (Locus ID #At3g04110) promoter with a ssTDeHase gene and a NOS terminator in the following manner.

Step 1a: Use PCR to amplify the glutamate receptor 1.1 promoter (−1400 to −1 bps) with a short overlap for the 5' end of ssTDeHase at the 3' end using 500 ng of genomic DNA isolated from an *Arabidopsis thaliana* Col-0. Add 300 nM of the following primers: 5'AtGLR1.1 (5'-gatcatacatat-tcatacttgatg-3'; SEQ ID NO:66) and AtGLR1.1ssTDeHase (5'-gagctgtcagtgttttggtcatataatttcttgtatagctctgtaac-3'; SEQ ID NO:67). Run the fusion PCR as described by Szewczyk et al. (45).

Step 1b: Use PCR to amplify the ssTDeHase gene from 500 ng of DNA from *Roseobacter denitrificans*. Add 300 nM of the following primers: 5'ssTDeHase (5'-atgac-caaaacactgacagctc-3'; SEQ ID NO:68) and 3'ssTDeHase (5'-ttaagccttgaagggcgggc-3'; SEQ ID NO:69). Run the fusion PCR as described by Szewczyk et al. (45).

Step 1c: Use PCR to amplify the NOS terminator with a short overlap for the 3' end of ssTDeHase at the 5' end of terminator using 500 ng of pPV1. Add 300 nM of the following primers ssTDeHaseNOS (5'-gcccgcccttcaaggct-taagctaccgagctcgaatttcc-3'; SEQ ID NO:70) and 3'NOS (5'- cacgacgttgtaaaacgacggc-3'; SEQ ID NO:32). Run the fusion PCR as described by Szewczyk et al. (45).

Step 1d: Combine the PCR fragments (Example 7: 1a, 1b, and 1c) and 300 nM of the following primers MP2 (5'-ttttggtacccgaagctcaatcgtctcgag-3'; SEQ ID NO:71) and GP5 (5'-ttttttttctagagatctagtaacatagatgacac-3'; SEQ ID NO:34). Run the fusion PCR as described by Szewczyk et al. (45). Clone into pCR4.0-TOPO as described by the manufacturer (Invitrogen).

Step 1e. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI Step 2: Make a DNA construct that contains an AtGLR1.1 promoter with a lsTDeHase gene and a NOS terminator to in the following manner.

Step 2a: Use PCR to amplify the AtGLR1.1 promoter (−1714 to −1 bps) with a short overlap for the 5' end of lsTDeHase at the 3' end of the promoter using 500 ng of genomic DNA isolated from an *Arabidopsis thaliana* Col-0. Add 300 nM of the following primers: 5'AtGLR1.1 (5'-gatcatacatattcatacttgatg-3'; SEQ ID NO:66) and AtGLR1.1-lsTDeHase (5'-gtgctttggtctatgtggcatataatttcttgtatagctctgtaac-3'; SEQ ID NO:72). Run the fusion PCR as described by Szewczyk et al. (45).

Step 2b: Use PCR to amplify the lsTDeHase gene from 500 ng of DNA from *Roseobacter denitrificans*. Add 300 nM of the following primers: 5'lsTDeHase (5'-atgccacatagac-caaagcac-3'; SEQ ID NO:73) and 3'lsTDeHase (5'-tcagagaatttcatcgcgaag-3'; SEQ ID NO:74). Run the fusion PCR as described by Szewczyk et al. (45).

Step 2c: Use PCR to amplify the NOS terminator with a short overlap for the 3' end of lsTDeHase at the 5' end of the terminator using 500 ng of pPV1. Add 300 nM of the following primers lsTDeHaseNOS (5'-cttcgcgatgaaattctct-gagctaccgagctcgaatttcc-3'; SEQ ID NO:75) and 3'NOS (5'-cacgacgttgtaaaacgacggc-3'; SEQ ID NO:32). Run the fusion PCR as described by Szewczyk et al. (45).

Step 2d: Combine the PCR fragments (Example 7: 2a, 2b, and 2c) and 300 nM of the following primers NP2 (5'-aaaaatctagacgaagctcaatcgtctcgag-3'; SEQ ID NO:76) and LP5 (5'-aaaaaaagcttgatctagtaacatagatgacac-3'; SEQ ID NO:65). Run the fusion PCR as described by Szewczyk et al. (45). Clone into pCR4.0-TOPO as described by the manufacturer (Invitrogen).

Step 2e: Transform *E. coli*, select for antibiotic resistance, conduct PCR identification of cloned DNA constructs in transformants, purify the plasmid that contains the DNA construct to confirm its identity and the fidelity of the sequence as described in Example 1: step 1e.purify. Digest the plasmid with XbaI and HindIII, isolate the DNA fragment and ligate into the vector pCAMBIA2300 that has been predigested with XbaI and HindIII.

Step 3: Ligate the AtGLR1.1 promoter-ssTDeHase-NOS terminator construct upstream of the AtGLR1.1 promoter-lsTDeHase-NOS terminator construct into a plant expression vector.

Step 3a. Digest the pCambia2300-AtGLR1.1 promoter-ssTDeHase-NOS terminator clone (from Example 4: Step 1e) with Acc65I and XbaI, isolate DNA insert and ligate it into the vector pCambia2300-AtGLR1.1 promoter-lsTDe-Hase-NOS terminator (from Example 4: Step 2e) that has been predigested with Acc65I and XbaI. Transform the DNA construct into *E. coli*, select for antibiotic resistance and confirm the presence of the DNA construct with PCR or by restriction digest analysis.

Step 4: Transform *Agrobacterium tumefaciens*: Transform the DNA construct into *Agrobacterium tumefaciens*, select for antibiotic resistance and confirm the presence of the DNA construct as described in Example 1: Step 2.

Step 5: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 8

Development of a Transgenic Plant that Non-Constitutively Expresses (AtSULTR1;3 Promoter) TDO Using Fusion PCR Step 1: Make a DNA construct that contains an 5'AtSULTR1;3 promoter with a TDO gene and a NOS terminator in the following manner.

Step 1a: Use PCR to amplify the AtSULTR1;3 promoter (−2406 to −1 bps) with a short overlap for the 5' end of TDO at the 3' end using 500 ng of genomic DNA isolated from an *Arabidopsis thaliana* Col-0. Add 300 nM of the following primers: 5'AtSULTR1;3 (5'-tcacaatcgatggactctc-3'; SEQ ID NO:77) and 5'AtSULTR1;3 TDO (5'-gtaatgctcagacgttcact-cattgctatgtgtgttttgtagc-3'; SEQ ID NO:78). Run the fusion PCR as described by Szewczyk et al. (45).

Step 1b: Use PCR to amplify the TDO gene from 500 ng of DNA from *E. coli* strain K12. Add 300 nM of the following primers: 5'TDO (5'-atgagtgaacgtctgagcattac-3'; SEQ ID NO:79) and 3'TDO (5'-ttaccccgcccgataaaacg-3'; SEQ ID NO:80). Run the fusion PCR as described by Szewczyk et al. (45).

Step 1c: Use PCR to amplify the NOS terminator with a short overlap for the 3' end of ADO at the 5' end of the terminator using 500 ng of pPV1. Add 300 nM of the following primers TDONOS (5'-cgttttatcgggcggggtaagc-taccgagctcgaatttcc-3'; SEQ ID NO:81) and 3'NOS (5'-cacgacgttgtaaaacgacggc-3'; SEQ ID NO:32). Run the fusion PCR as described by Szewczyk et al. (45).

Step 1d: Combine the amplified fragments from Example 3: steps 1a, 1b, and 1c and 300 nM of the following primers OP2 (5'-ttttggtaccctatattggtgtcattttgcc-3'; SEQ ID NO:82) and GP5 (5'-ttttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1e. Transform *E. coli*, select for antibiotic resistance, conduct PCR identification of cloned DNA constructs in transformants, purify DNA and sequence (described in Example 1: step 1c). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens*: Transform the DNA construct into *Agrobacterium tumefaciens*, select for antibiotic resistance and confirm the presence of the DNA construct as described in Example 1: Step 2.

Step 4: Transform plant, *Arabidopsis thaliana*: Transform the construct into *Arabidopsis thaliana*, select for antibiotic

Example 9

Development of a Transgenic Plant that Constitutively Expresses (AtPHYB Promoter) CDO Fused in-Frame with SAD (without a Linker) Using Fusion PCR Step 1: Make a DNA construct that contains an AtPHYB (Locus ID #At2g18790) promoter with a CDO gene fused in-frame with a SAD gene and a NOS terminator in the following manner.

Step 1a: Use the AtPHYB promoter (−1960 to −1 bps) with a short overlap for the 5' end of CDO at the 3' end that was amplified in Example 2: Step 1a.

Step 1b: Use the CDO gene that was amplified in Example 1: Step 1b.

Step 1c: Use PCR to amplify the SAD gene with a short overlap for the 3' end of CDO at the 5' end using 500 ng of cDNA from a zebrafish (*Danio rerio*) cDNA library. Add 300 nM of the following primers:

```
CDO/SAD
(5'-gagcgtctcgcaggagaataacatggacgagtctgatgggaagct
g-3'; SEQ ID NO: 83)
and 3'SAD
(5'-tcatagatccttcccgagtttc-3'; SEQ ID NO: 40).
```

Run the fusion PCR as described by Szewczyk et al. (45).

Step 1d: Use the NOS terminator with a short overlap for the 3' end of SAD at the 5' end of the NOS terminator that was amplified in Example 2: Step 2c.

Step 1e: Combine the PCR fragments (Example 9: 1a, 1b, 1c, and 1d) and 300 nM of the following primers HP2 (5'-ttttcccgggattcttgaattacgattgtacc-3'; SEQ ID NO:37) and IP5 (5'-ttttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with XmaI and SalI, isolate DNA fragment and ligate into the vector pCAM-BIA2300 that has been predigested with XmaI and SalI. Transform the DNA construct into *E. coli*, select for antibiotic resistance and confirm the presence of the DNA construct with PCR or by restriction digest analysis.

Step 2: Transform *Agrobacterium tumefaciens*: Transform the DNA construct into *Agrobacterium tumefaciens*, select for antibiotic resistance and confirm the presence of the DNA construct as described in Example 1: Step 2.

Step 3: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 10

Development of a Transgenic Plant that Constitutively Expresses (AtPHYB Promoter) CDO Fused in-Frame with a Linker to SAD Using Fusion PCR Step 1: Make a DNA construct that contains an AtPHYB (Locus ID #At2g18790) promoter with a CDO gene fused in-frame with a linker and the SAD gene and a NOS terminator in the following manner.

Step 1a: Use the AtPHYB promoter (−1960 to −1 bps) with a short overlap for the 5' end of CDO at the 3' end that was amplified in Example 2: Step 1a.

Step 1b: Use the CDO gene that was amplified in Example 1: Step 1b.

Step 1c: Use PCR to amplify the SAD gene with a short overlap for the 3' end of CDO at the 5' end using 500 ng of cDNA from a zebrafish (*Danio rerio*) cDNA library. Add 300 nM of the following primers: CDOlinkerSAD (5'-gagcgtctcgcaggagaataacagtactgaaggcgaagttaacgcg-gaagaagaaggcttatggacgagtctgatgggaagctg-3'; SEQ ID NO:84) and 3'SAD (5'-tcatagatccttcccgagtttc-3'; SEQ ID NO:40). Run the fusion PCR as described by Szewczyk et al. (45).

Step 1d: Use the NOS terminator with a short overlap for the 3' end of SAD at the 5' end of the NOS terminator that was amplified in Example 2: Step 2c.

Step 1e: Combine the PCR fragments (Example 10: 1a, 1b, 1c, and 1d) and 300 nM of the following primers HP2 (5'-ttttcccgggattcttgaattacgattgtacc-3'; SEQ ID NO:37) and IP5 (5'-ttttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with XmaI and SalI, isolate DNA fragment and ligate into the vector pCAM-BIA2300 that has been predigested with XmaI and SalI. Transform the DNA construct into *E. coli*, select for antibiotic resistance and confirm the presence of the DNA construct with PCR or by restriction digest analysis.

Step 2: Transform *Agrobacterium tumefaciens*: Transform the DNA construct into *Agrobacterium tumefaciens*, select for antibiotic resistance and confirm the presence of the DNA construct as described in Example 1: Step 2.

Step 3: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 11

Development of a Transgenic Plant that Constitutively Expresses (AtPHYB Promoter) SAD Fused in-Frame with CDO with Linker Using Fusion PCR Step 1: Make a DNA construct that contains an AtPHYB (Locus ID #At2g18790) promoter with a SAD gene fused in-frame with a CDO gene with a linker and a NOS terminator in the following manner.

Step 1a: Use the AtPHYB promoter (−1960 to −1 bps) with a short overlap for the 5' end of SAD at the 3' end that was amplified in Example 2: Step 2a.

Step 1b: Step Use the SAD gene that was amplified in Example 2: Step 2b.

Step 1c: Use PCR to amplify the CDO gene with a linker and short overlap for the SAD at the 3' using 500 ng of cDNA from a zebrafish (*Danio rerio*) cDNA library. Add 300 nM of the following primers: SADlinkerCDO (5'-gaaactcgggaaggatctaagtactgaaggcgaagttaacgcg-gaagaagaaggctttatggagcagactgaagtcatg-3'; SEQ ID NO:85 and 3'CDO (5'-tcagttattctcctgcgagac-3'; SEQ ID NO:30). Run the fusion PCR as described by Szewczyk et al. (45).

Step 1d: Use the NOS terminator with a short overlap for the 3' end of CDO at the 5' end of the NOS terminator that was amplified in Example 1: step 1c.

Step 1e: Combine the PCR fragments (Example 11: 1a, 1b, 1c, and 1d) and 300 nM of the following primers HP2 (5'-ttttcccgggattcttgaattacgattgtacc-3'; SEQ ID NO:37) and GP5 (5'-ttttttttctagagatctagtaacatagatgacac-3'; SEQ ID NO:34). Run the fusion PCR as described by Szewczyk et al. (45). Clone into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1c). Digest the plasmid with XmaI and XbaI, isolate DNA fragment and ligate into the vector pCAMBIA2300 that has been predigested with XmaI and XbaI. Transform the DNA construct into *E. coli*, select for antibiotic resistance and confirm the presence of the DNA construct with PCR or by restriction digest analysis.

Step 2: Transform *Agrobacterium tumefaciens*: Transform the DNA construct into *Agrobacterium tumefaciens*, select for antibiotic resistance and confirm the presence of the DNA construct as described in Example 1: Step 2.

Step 3: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 12

Development of a Transgenic Plant that Constitutively Expresses (AtPHYB Promoter) CDO Fused in-Frame with GAD (without a Linker) Using Fusion PCR Step 1: Make a DNA construct that contains an AtPHYB (Locus ID #At2g18790) promoter with a CDO gene fused in-frame with a GAD gene and a NOS terminator in the following manner.

Step 1a: Use the AtPHYB promoter (−1960 to −1 bps) with a short overlap for the 5' end of CDO at the 3' end that was amplified in Example 2: Step 1a.

Step 1b: Use the CDO gene that was amplified in Example 1: Step 1b.

Step 1c: Use PCR to amplify the GAD gene with a short overlap for the 3' end of CDO at the 5' end using from 500 ng of DNA from *E. coli* strain K12. Add 300 nM of the following primers: CDO/GAD (5'-gagcgtctcgcaggagaataa-cAtggataagaagcaagtaacg-3'; SEQ ID NO:86) and 3'GAD (5'-tcaggtatgtttaaagctgttc-3'; SEQ ID NO:46). Run the fusion PCR as described by Szewczyk et al. (45).

Step 1d: Use the NOS terminator with a short overlap for the 3' end of GAD at the 5' end of the NOS terminator that was amplified in Example 3: Step 2c.

Step 1e: Combine the PCR fragments (Example 12: 1a, 1b, 1c, and 1d) and 300 nM of the following primers HP2 (5'-ttttcccgggattcttgaattacgattgtacc-3'; SEQ ID NO:37) and IP5 (5'-ttttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with XmaI and SalI, isolate DNA fragment and ligate into the vector pCAMBIA2300 that has been predigested with XmaI and SalI. Transform the DNA construct into *E. coli*, select for antibiotic resistance and confirm the presence of the DNA construct with PCR or by restriction digest analysis.

Step 2: Transform *Agrobacterium tumefaciens*: Transform the DNA construct into *Agrobacterium tumefaciens*, select for antibiotic resistance and confirm the presence of the DNA construct as described in Example 1: Step 2.

Step 3: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 13

Development of a Transgenic Plant that Constitutively Expresses (AtPHYB Promoter) CDO Fused in-Frame with a Linker to GAD Using Fusion PCR Step 1: Make a DNA construct that contains an AtPHYB (Locus ID #At2g18790) promoter with a CDO gene fused in-frame with a linker and the GAD gene and a NOS terminator in the following manner.

Step 1a: Use the AtPHYB promoter (−1960 to −1 bps) with a short overlap for the 5' end of CDO at the 3' end that was amplified in Example 2: Step 1a.

Step 1b: Use the CDO gene that was amplified in Example 1: Step 1b.

Step 1c: Use PCR to amplify the GAD gene with a short overlap for the 3' end of CDO at the 5' end using 500 ng of DNA from *E. coli* strain K12. Add 300 nM of the following primers: CDOlinkerGAD (5'-gagcgtctcgcag-gagaataacagtactgaaggcgaagttaacgcggaagaagaaggctttatgga-taagaagcaagtaacg-3'; SEQ ID NO:87) and 3'GAD (5'-tcaggtatgtttaaagctgttc-3'; SEQ ID NO:46). Run the fusion PCR as described by Szewczyk et al. (45).

Step 1d: Use the NOS terminator with a short overlap for the 3' end of GAD at the 5' end of the NOS terminator that was amplified in Example 3: Step 2c.

Step 1e: Combine the PCR fragments (Example 13: 1a, 1b, 1c, and 1d) and 300 nM of the following primers HP2 (5'-ttttcccgggattcttgaattacgattgtacc-3'; SEQ ID NO:37) and IP5 (5'-ttttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with XmaI and SalI, isolate DNA fragment and ligate into the vector pCAMBIA2300 that has been predigested with XmaI and SalI. Transform the DNA construct into *E. coli*, select for antibiotic resistance and confirm the presence of the DNA construct with PCR or by restriction digest analysis.

Step 2: Transform *Agrobacterium tumefaciens*: Transform the DNA construct into *Agrobacterium tumefaciens*, select for antibiotic resistance and confirm the presence of the DNA construct as described in Example 1: Step 2.

Step 3: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 14

Development of a Transgenic Plant that Constitutively Expresses (AtPHYB Promoter) GAD Fused in-Frame with a Linker to CDO Using Fusion PCR Step 1: Make a DNA construct that contains an AtPHYB (Locus ID #At2g18790) promoter with a GAD gene fused in-frame with a linker and the CDO gene and a NOS terminator in the following manner.

Step 1a: Use the AtPHYB promoter (−1960 to −1 bps) with a short overlap for the 5' end of GAD at the 3' end that was amplified in Example 3: Step 2a.

Step 1b: Step Use the GAD gene that was amplified in Example 3: Step 2b.

Step 1c: Use PCR to amplify the GAD gene with a linker and short overlap for the CDO at the 3' using 500 ng of cDNA from a zebrafish (*Danio rerio*) cDNA library. Add 300 nM of the following primers: GADlinkerCDO (5'-gaacagctttaaacataccagtactgaaggcgaagttaacgcg-gaagaagaaggctttatggagcagactgaagtcatg-3'; SEQ ID NO:88) and 3'GAD (5'-tcaggtatgtttaaagctgttc-3'; SEQ ID NO:46). Run the fusion PCR as described by Szewczyk et al. (45).

Step 1d: Use the NOS terminator with a short overlap for the 3' end of CDO at the 5' end of the NOS terminator that was amplified in Example 1: step 1c.

Step 1e: Combine the PCR fragments (Example 14: 1a, 1b, 1c, and 1d) and 300 nM of the following primers HP2 (5'-ttttcccgggattcttgaattacgattgtacc-3'; SEQ ID NO:37) and IP5 (5'-tttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with XmaI and SalI, isolate DNA fragment and ligate into the vector pCAMBIA2300 that has been predigested with XmaI and SalI. Transform the DNA construct into *E. coli*, select for antibiotic resistance and confirm the presence of the DNA construct with PCR or by restriction digest analysis.

Step 2: Transform *Agrobacterium tumefaciens*: Transform the DNA construct into *Agrobacterium tumefaciens*, select for antibiotic resistance and confirm the presence of the DNA construct as described in Example 1: Step 2.

Step 3: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 15

Development of a Transgenic Plant that Non-Constitutively Expresses (AtGAD2 Promoter) SA Fused in-Frame to TPAT Using Fusion PCR Step 1: Make a DNA construct that contains an AtGAD2 (Locus ID #At1g65960) promoter with a SA gene fused in-frame with a TPAT gene and a NOS terminator in the following manner.

Step 1a: Use the AtGAD2 promoter (−1714 to −1 bps) with a short overlap for the 5' end of SA at the 3' end that was amplified in Example 6: Step 2a.

Step 1b: Step Use the SA gene that was amplified in Example 6: Step 2b.

Step 1c: Use PCR to amplify the TPAT gene with a short overlap for the 3'end of SA at the 5'end using 500 ng of DNA from *Roseobacter denitrificans* strain. Add 300 nM of the following primers: SA/TPAT (5'-catgcgtccacagactgt-catggacggcaatttcaatg-3'; SEQ ID NO:89) and 3'TPAT (5'-ttagccgaaaacgcgcgacag-3'; SEQ ID NO:57). Run the fusion PCR as described by Szewczyk et al. (45).

Step 1d: Use the NOS terminator with a short overlap for the 3' end of TPAT at the 5' end of the NOS terminator that was amplified in Example 5: step 1c.

Step 1e: Combine the amplified fragments (Example 15: steps 1a, 1b, 1c and 1d) and 300 nM of the following primers KP2 (5'-ttttggtaccctcttcggaacgagcttcaac-3'; SEQ ID NO:59) and GP5 (5'-tttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens*: Transform the DNA construct into *Agrobacterium tumefaciens*, select for antibiotic resistance and confirm the presence of the DNA construct as described in Example 1: Step 2.

Step 4: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 16

Development of a Transgenic Plant that Non-Constitutively Expresses (AtGAD2 Promoter) SA Fused in-Frame with a Linker to TPAT Using Fusion PCR Step 1: Make a DNA construct that contains an AtGAD2 (Locus ID #At1g65960) promoter with a SA gene fused in-frame with a linker to a TPAT gene and a NOS terminator in the following manner.

Step 1a: Use the AtGAD2 promoter (−1714 to −1 bps) with a short overlap for the 5' end of SA at the 3' end that was amplified in Example 6: Step 2a.

Step 1b: Use the SA gene that was amplified in Example 6: Step 2b.

Step 1c: Use PCR to amplify the TPAT gene with a linker and short overlap for the 3'end of SA at the 5'end using 500 ng of DNA from *Roseobacter denitrificans* strain. Add 300 nM of the following primers: SAlinkerTPAT (5'-catgcgtc-cacagactgtcagtactgaaggcgaagttaacgcggaagaagaaggctt-tatggacggcaatttcaatg-3'; SEQ ID NO:90) and 3'TPAT (5'-ttagccgaaaacgcgcgacag-3'; SEQ ID NO:57). Run the fusion PCR as described by Szewczyk et al. (45).

Step 1d: Use the NOS terminator with a short overlap for the 3' end of TPAT at the 5' end of the NOS terminator that was amplified in Example 5: step 1c.

Step 1e: Combine the amplified fragments (Example 16: steps 1a, 1b, 1c and 1d) 300 nM of the following primers KP2 (5'-ttttggtaccctctttcggaacgagcttcaac-3'; SEQ ID NO:59) and GP5 (5'-ttttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens*: Transform the DNA construct into *Agrobacterium tumefaciens*, select for antibiotic resistance and confirm the presence of the DNA construct as described in Example 1: Step 2.

Step 4: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 17

Development of a Transgenic Plant that Non-Constitutively Expresses (AtGAD2 Promoter) TPAT Fused in-Frame with a Linker to a SA Gene Using Fusion PCR Step 1: Make a DNA construct that contains an AtGAD2 (Locus ID #At1g65960) promoter with a TPAT gene fused in-frame with a linker to a SA gene and a NOS terminator in the following manner.

Step 1a: Use the AtGAD2 promoter (−1714 to −1 bps) with a short overlap for the 5' end of TPAT at the 3' end that was amplified in Example 5: Step 1a.

Step 1b: Use the TPAT gene that was amplified in Example 5: Step 1b.

Step 1c: Use PCR to amplify the SA with a short overlap for the 3' end of TPAT with a linker at the 5' end using 500 ng of DNA from *Roseobacter denitrificans* strain. Add 300 nM of the following primers: TPATlinkerSA (5'-cgctgtcgcgcgttttcggcagtactgaaggcgaagttaacgcg-gaagaagaaggctttatgaaaatgaccactgaag-3'; SEQ ID NO:91) and 3'SA (5'-tcagacagtctgtggacgc-3'; SEQ ID NO:62). Run the fusion PCR as described by Szewczyk et al. (45).

Step 1d: Use PCR to amplify the NOS terminator with a short overlap for the 3' end of SA that was amplified in Example 6: Step 2c.

Step 1e: Combine the amplified fragments (Example 17: steps 1a, 1b, 1c and 1d) and 300 nM of the following primers KP2 (5'-ttttggtaccctctttcggaacgagcttcaac-3'; SEQ ID NO:59) and GP5 (5'-ttttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens*: Transform the DNA construct into *Agrobacterium tumefaciens*, select for antibiotic resistance and confirm the presence of the DNA construct as described in Example 1: Step 2.

Step 4: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 18

Development of a Transgenic Plant that Non-Constitutively Expresses (AtGLR1.1 Promoter) ssTDeHase Fused in-Frame with lsTDeHase (without a Linker) Using Fusion PCR Step 1: Make a DNA construct that contains an AtGLR1.1 (Locus ID #At3g04110) promoter with a ssTDeHase gene fused in-frame with a lsTDeHase gene and a NOS terminator in the following manner.

Step 1a: Use the AtGLR1.1 promoter (−1960 to −1 bps) with a short overlap for the 5' end of ssTDeHase at the 3' end that was amplified in Example 7: Step 1a.

Step 1b: Use the ssTDeHase gene that was amplified in Example 7: Step 1b.

Step 1c: Use PCR to amplify the lsTDeHase gene with a short overlap for the 3' end of ssTDeHase at the 5' end using of DNA from *Roseobacter denitrificans*. Add 300 nM of the following primers: ssTDeHase/lsTDeHase (5'-gcccgcccctt-caaggctatgccacatagaccaaagcac-3'; SEQ ID NO:92) and 3'lsTDeHase (5'-tcagagaatttcatcgcgaag-3'; SEQ ID NO:74). Run the fusion PCR as described by Szewczyk et al. (45).

Step 1d: Use the NOS terminator with a short overlap for the 3' end of lsTDeHase at the 5' end of the NOS terminator that was amplified in Example 7: Step 2c.

Step 1e: Combine the amplified fragments (Example 18: steps 1a, 1b, 1c and 1d) and 300 nM of the following primers KP2 (5'-ttttggtaccctctttcggaacgagcttcaac-3'; SEQ ID NO:59) and GP5 (5'-ttttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens*: Transform the DNA construct into *Agrobacterium tumefaciens*, select for antibiotic resistance and confirm the presence of the DNA construct as described in Example 1: Step 2.

Step 4: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 19

Development of a Transgenic Plant that Non-Constitutively Expresses (AtGLR1.1 Promoter) ssTDeHase Fused in-Frame with a Linker to lsTDeHase Using Fusion PCR Step 1: Make a DNA construct that contains an AtGLR1.1 (Locus ID #At3g04110) promoter with a ssTDeHase gene fused in-frame with a linker and the lsTDeHase gene and a NOS terminator in the following manner.

Step 1a: Use the AtGLR1.1 promoter (−1960 to −1 bps) with a short overlap for the 5' end of ssTDeHase at the 3' end that was amplified in Example 7: Step 1a.

Step 1b: Use the ssTDeHase gene that was amplified in Example 7: Step 1b.

Step 1c: Use PCR to amplify the lsTDeHase gene with a short overlap for the 3' end of ssTDeHase at the 5' end using of DNA from *Roseobacter denitrificans*. Add 300 nM of the following primers: ssTDeHaselinkerlsTDeHase (5'-gcccgcccttcaaggctagtactgaaggcgaagttaacgcg-gaagaagaaggctttatgccacatagaccaaagcac-3'; SEQ ID NO:93) and 3'lsTDeHase (5'-tcagagaatttcatcgcgaag-3'; SEQ ID NO:74). Run the fusion PCR as described by Szewczyk et al. (45).

Step 1d: Use the NOS terminator with a short overlap for the 3' end of lsTDeHase at the 5' end of the NOS terminator that was amplified in Example 7: Step 2c.

Step 1e: Combine the amplified fragments (Example 19: steps 1a, 1b, 1c and 1d) and 300 nM of the following primers KP2 (5'-ttttggtaccctctttcggaacgagcttcaac-3'; SEQ ID NO:59) and GP5 (5'-ttttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens*: Transform the DNA construct into *Agrobacterium tumefaciens*, select for antibiotic resistance and confirm the presence of the DNA construct as described in Example 1: Step 2.

Step 4: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 20

Development of a Transgenic Plant that Non-Constitutively Expresses (AtGLR1.1 Promoter) lsTDeHase Fused in-Frame with a Linker to ssTDeHase Using Fusion PCR Step 1: Make a DNA construct that contains an AtGLR1.1 (Locus ID #At3g04110) promoter with a lsTDeHase gene fused in-frame with a linker and the ssTDeHase gene and a NOS terminator in the following manner.

Step 1a: Use the AtGLR1.1 promoter (−1960 to −1 bps) with a short overlap for the 5' end of lsTDeHase at the 3' end that was amplified in Example 7: Step 2a.

Step 1b: Use the lsTDeHase gene that was amplified in Example 7: Step 2b.

Step 1c: Use PCR to amplify the lsTDeHase gene with a short overlap for the 3' end of ssTDeHase at the 5' end using of DNA from *Roseobacter denitrificans*. Add 300 nM of the following primers: lsTDeHaselinkerssTDeHase (5'-cttcgc-gatgaaattctcagtactgaaggcgaagttaacgcggaagaagaaggctt-tatgaccaaaacactgacagctc-3'; SEQ ID NO:94) and 3'ssTDe-Hase (5'-ttaagccttgaagggcgggc-3'; SEQ ID NO:69). Run the fusion PCR as described by Szewczyk et al. (45).

Step 1d: Use the NOS terminator with a short overlap for the 3' end of ssTDeHase at the 5' end of the NOS terminator that was amplified in Example 7: step 1c.

Step 1e: Combine the amplified fragments (Example 3: steps 1a, 1b, 1c and 1d) and 300 nM of the following primers KP2 (5'-ttttggtaccctctttcggaacgagcttcaac-3'; SEQ ID NO:59) and GP5 (5'-ttttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f: Combine the amplified fragments from Example 20: steps 1a, 1b, 1c and 1d and 300 nM of the following primers KP2 (5'-ttttggtaccctctttcggaacgagcttcaac-3'; SEQ ID NO:59) and GP5 (5'-ttttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1g. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens*: Transform the DNA construct into *Agrobacterium tumefaciens*, select for antibiotic resistance and confirm the presence of the DNA construct as described in Example 1: Step 2.

Step 4: Transform plant, *Arabidopsis thaliana*: Transform the construct into *Arabidopsis thaliana*, select for antibiotic resistance, select for homozygote plants and confirm the presence of the DNA constructs as described in Example 1: Step 3.

Example 21

Production of Taurine in Bacteria that Express Fish CDO and SAD Gene Products Zebrafish CDO (SEQ ID NO: 2) and SAD (SEQ ID NO: 6) genes were fused as described in Example 11 and expressed in bacteria, *E. coli*, using a bacterial vector with a lac promoter system. The resulting peptide corresponds to the zebrafish CDO peptide (SEQ ID NO: 4) fused with the fish SAD peptide (SEQ ID NO: 8). The transformed bacteria were grown in LB media and expression on the CDO/SAD gene was induced using glucose and lactose. The resulting supernatant and cell pellet were analyzed for taurine using HPLC. Taurine production was 35 pmol/mL in the transgenic bacterial cultures and zero in the empty vector controls and wild-type bacterial cultures.

Example 22

Identification of Divergent CDO and SAD Gene Products for Production of Taurine in Cells The existence of other CDO and SAD gene products were identified from genetically divergent organisms that produce "sufficiently similar" CDO and SAD peptides with at least 40% sequence similarity (identity and conservative amino acid substitution) with the bovine CDO peptide (SEQ ID NO: 3) or zebrafish CDO (SEQ ID NO: 4) and the horse SAD peptide (SEQ ID NO: 7) or zebrafish SAD peptide (SEQ ID NO: 8). Table 1 contains a representative list of the CDO peptides that could be used to make taurine in cells, and Table 2 contains a representative list of the SAD peptides that could be used to make taurine in cells.

TABLE 1

Suitable CDO Gene Products

| NCBI Reference Sequence Number (SEQ ID NO:) | % identity or similarity with respect to SEQ ID NO: 3 | | % identity or similarity with respect to SEQ ID NO: 4 | |
|---|---|---|---|---|
| | % Identity | % Similarity | % Identity | % Similarity |
| NP_989132.1 (96) | 75 | 88 | 75 | 88 |
| XP_024085479.1 (98) | 57 | 72 | 60 | 75 |
| ATO28835.1 (100) | 27 | 54 | 25 | 51 |
| PRW56884.1 (102) | 30 | 48 | 33 | 51 |
| XP_001703453.1 (104) | 31 | 46 | 30 | 45 |
| PNH00535.1 (106) | 28 | 45 | 29 | 43 |
| OSX74768.1 (108) | 32 | 45 | 31 | 44 |

Table 1 contains suitable CDO amino acid sequences having a degree of identity or similarity as described herein by NCBI Reference Sequence Number. The NCBI Reference Sequence Number identifies the CDO gene products. The listed NCBI Reference Sequence Numbers are representative. Other suitable sequences can be identified, for example, by doing a BLAST search using SEQ ID NO: 3 or 4 or any of the listed accession numbers. Thus, it is evident that any CDO gene product is contemplated for use in the present invention.

Table 2 contains suitable SAD amino acid sequences having a degree of identity or similarity as described herein by NCBI Reference Sequence Number. The NCBI Reference Sequence Number identifies the SAD gene products. The listed NCBI Reference Sequence Numbers are representative. Other suitable sequences can be identified, for example, by doing a BLAST search using SEQ ID NO: 7 or 8 or any of the listed accession numbers. Thus, it is evident that any SAD gene product is contemplated for use in the present invention.

TABLE 2

Suitable SAD Gene Products

| NCBI Reference Sequence Number (SEQ ID NO:) | % identity or similarity with respect to SEQ ID NO: 7 | | % identity or similarity with respect to SEQ ID NO: 8 | |
|---|---|---|---|---|
| | % Identity | % Similarity | % Identity | % Similarity |
| XP_018103069.1 (110) | 67 | 83 | 66 | 80 |
| NP_001285910.1 (112) | 53 | 72 | 49 | 67 |
| SFF03823.1 (114) | 47 | 61 | 42 | 59 |
| XP_003057449.1 (116) | 40 | 58 | 43 | 60 |
| XP_005821099.1 (118) | 38 | 58 | 39 | 57 |
| WP_070394797.1 (120) | 38 | 58 | 39 | 58 |
| WP_075902409.1 (122) | 40 | 58 | 40 | 57 |
| WP_015167305.1 (124) | 38 | 50 | 30 | 52 |
| XP_005537788.1 (126) | 38 | 50 | 39 | 50 |
| WP_109957770.1 (128) | 29 | 44 | 30 | 45 |

Example 23

Taurine Production in Cells Using Evolutionary Divergent CDO and SAD Gene Products To demonstrate that divergent CDO and SAD gene product sequences can be used to produce taurine in cells, the genes for the *Chlamydomonas reinhardtii* CDO (XP_001703453.1, Table 1) and *Micromonas pusilla* SAD (XP_003057449.1, Table 2) gene products were fused and expressed in bacteria as described in Example 21. The resulting supernatant and cell pellets were analyzed for taurine using HPLC. Taurine production was 50 pmol/mL in the transgenic bacterial cultures and zero in the empty vector controls and wild-type bacterial cultures.

Similar results are obtained with other combinations of evolutionary divergent CDO and SAD gene products.

---

What is claimed is:

1. A prokaryotic cell comprising a first exogenous DNA which comprises two separate expression cassettes, wherein a first expression cassette comprises a first promoter operably linked to a first polynucleotide and a second expression cassette comprises a second promoter operably linked to a second polynucleotide, wherein the first polynucleotide encodes cysteine dioxygenase (CDO); and the second polynucleotide encodes sulfinoalanine decarboxylase (SAD), wherein the polynucleotide encoding CDO encodes a protein having at least 27% identity to SEQ ID NO:3 or at least 25% identity to SEQ ID NO:4 each of which has CDO activity and wherein the polynucleotide encoding SAD encodes a protein having at least 29% identity to SEQ ID NO:7 or at least 30% identity to SEQ ID NO:8 each of which has SAD activity.

2. A prokaryotic cell comprising a first exogenous DNA which comprises a single expression cassette, wherein the single expression cassette comprises a promoter operably linked to a polynucleotide which encodes cysteine dioxygenase (CDO) and encodes sulfinoalanine decarboxylase (SAD).

3. The prokaryotic cell of claim 1, wherein:
the CDO comprises an amino acid sequence selected from the group consisting of the amino acid sequence set forth in SEQ ID NO:96, 98, 100, 102, 104, 106 and 108; and
the SAD comprises an amino acid sequence selected from the group consisting of the amino acid sequence set forth in SEQ ID NO:110, 112, 114, 116, 118, 120, 122, 124, 126 and 128.

4. The prokaryotic cell of claim 2, wherein:
the CDO comprises an amino acid sequence selected from the group consisting of the amino acid sequence set forth in SEQ ID NO:96, 98, 100, 102, 104, 106 and 108; and
the SAD comprises an amino acid sequence selected from the group consisting of the amino acid sequence set forth in SEQ ID NO:110, 112, 114, 116, 118, 120, 122, 124, 126 and 128.

5. The prokaryotic cell of claim 1 which is *E. coli*.

6. The prokaryotic cell of claim 2 which is *E. coli*.

7. The prokaryotic cell of claim 3 which is *E. coli*.

8. The prokaryotic cell of claim 4 which is *E. coli*.

9. A method of producing taurine or hypotaurine, comprising growing the prokaryotic cell of claim 1 under conditions which permit expression of the first and second polynucleotides, thereby producing taurine or hypotaurine.

10. A method of producing taurine or hypotaurine, comprising growing the prokaryotic cell of claim 2 under conditions which permit expression of the polynucleotide, thereby producing taurine or hypotaurine.

11. A method of altering a property of transgenic prokaryotic cells with an agent which increases sulfur or nitrogen concentration in prokaryotic cells, wherein the property is selected from the group consisting of increased taurine, hypotaurine, cysteine and methionine and wherein the transgenic prokaryotic cells comprise an exogenous DNA encoding a cysteine dioxygenase (CDO) and a sulfinoalanine decarboxylase (SAD).

12. The method of claim 11, wherein the agent increases sulfur concentration and the agent is sulfur containing molecule that could be selected from the group consisting of sulfur, sulfite, sulfide, sulfate, hydrogen sulfide, mercaptoethanol (2-mercaptoethanol), cysteine, cystine, cyteiene, methionine, taurine, hypotaurine, homotaurine, cysteate, 2-sulfacetaldehyde, N-acetyl thiazolidine 4 carboxylic acid (ATCA), glutathione, and bile.

13. The method of claim 11, wherein the agent increases nitrogen concentration and the agent is nitrogen-containing molecule that could be selected from the group consisting of ammonia, nitrate, nitrite and an amino acid.

14. The method of claim 11, wherein the agent increases nitrogen concentration and the agent is selected from the group consisting of an non-protein amino acids.

15. The method of claim 14, wherein the non-protein amino acid is GABA, citrulline, ornithine or a polyamine.

* * * * *